US012577246B2

(12) United States Patent
Lu et al.

(10) Patent No.: US 12,577,246 B2
(45) Date of Patent: Mar. 17, 2026

(54) INDOLINE COMPOUND

(71) Applicant: Zhejiang Yangli Pharmaceutical Technology Co., Ltd., Zhejiang (CN)

(72) Inventors: Jianyu Lu, Shanghai (CN); Charles Z. Ding, Shanghai (CN); Huijun He, Shanghai (CN); Lihong Hu, Shanghai (CN); Yuanyuan Huang, Shanghai (CN); Jian Li, Shanghai (CN); Shuhui Chen, Shanghai (CN)

(73) Assignee: Zhejiang Yangli Pharmaceutical Technology Co., Ltd., Zhejiang (CN)

( * ) Notice: Subject to any disclaimer, the term of this patent is extended or adjusted under 35 U.S.C. 154(b) by 411 days.

(21) Appl. No.: 18/275,457

(22) PCT Filed: Feb. 8, 2022

(86) PCT No.: PCT/CN2022/075562

§ 371 (c)(1),
(2) Date: Aug. 2, 2023

(87) PCT Pub. No.: WO2022/166991

PCT Pub. Date: Aug. 11, 2022

(65) Prior Publication Data

US 2024/0132491 A1 Apr. 25, 2024

(30) Foreign Application Priority Data

Feb. 8, 2021 (CN) ......................... 202110172933.9
Aug. 13, 2021 (CN) ......................... 202110934819.5
Sep. 14, 2021 (CN) ......................... 202111076891.5
Oct. 15, 2021 (CN) ......................... 202111204272.X
Dec. 23, 2021 (CN) ......................... 202111593525.7

(51) Int. Cl.
*C07D 471/04* (2006.01)
*A61P 35/00* (2006.01)
*C07D 519/00* (2006.01)

(52) U.S. Cl.
CPC ............ *C07D 471/04* (2013.01); *A61P 35/00* (2018.01); *C07D 519/00* (2013.01)

(58) Field of Classification Search
CPC .. C07D 471/04; C07D 519/00; C07D 498/04; C07D 513/04; A61P 35/00; A61K 31/44; A61K 31/519
See application file for complete search history.

(56) References Cited

U.S. PATENT DOCUMENTS

2021/0040118 A1* 2/2021 Wang .................. C07D 513/08

FOREIGN PATENT DOCUMENTS

| | | | |
|---|---|---|---|
| CN | 106674209 | A | 5/2017 |
| CN | 108774219 | A | 11/2018 |
| CN | 108863963 | A | 11/2018 |
| CN | 109096219 | A | 12/2018 |
| CN | 109776377 | A | 5/2019 |
| CN | 110128415 | A | 8/2019 |
| WO | WO-2017118762 | A1 | 7/2017 |
| WO | WO-2018119224 | A1 | 6/2018 |

OTHER PUBLICATIONS

Apr. 26, 2022 International Search Report issued in International Patent Application No. PCT/CN2022/075562.
Apr. 26, 2022 Written Opinion of the International Searching Authority issued in International Patent Application No. PCT/CN2022/075562.

* cited by examiner

*Primary Examiner* — Joseph K McKane
*Assistant Examiner* — Meghan C Heasley
(74) *Attorney, Agent, or Firm* — Harness, Dickey & Pierce, P.L.C.

(57) ABSTRACT

An indoline compound. Specifically disclosed is an application of a compound represented by formula (I) and pharmaceutically acceptable salts thereof in the preparation of drugs for treating related diseases.

(I)

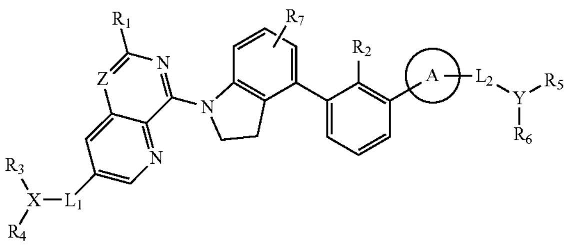

19 Claims, 3 Drawing Sheets

INDOLINE COMPOUND

CROSS-REFERENCE TO RELATED APPLICATIONS

The present application is a U.S. National Phase Application under 35 U.S.C. 371 of International Application No. PCT/CN2022/075562, filed on Feb. 8, 2022, which claims the right of priorities of Chinese patent application numbers CN202110172933.9, application date: Feb. 8, 2021; CN202110934819.5, application date Aug. 13, 2021; CN202111076891.5, application date: Sep. 14, 2021; CN202111204272.X, application date: Oct. 15, 2021; and CN202111593525.7, application date: Dec. 23, 2021. The entire disclosures of the aforementioned Chinese patent applications are incorporated herein by reference.

TECHNICAL FIELD

The present disclosure relates to a new class of indoline compounds, specifically to a use of a compound of formula (I) and a pharmaceutically acceptable salt thereof in the manufacture of a medicament for treating related diseases.

BACKGROUND

PD-1 stands for programmed death receptor 1, also known as programmed death 1, which is an important immunosuppressive molecule and a member of CD28 superfamily. PD-L1 stands for programmed death receptor-ligand 1, also known as programmed cell death-ligand 1, is a 40 kD transmembrane protein encoded by CD274 gene. PD-L1 may be induced to express on the surface of T cells, B cells, dendritic cells, macrophages, mesenchymal stem cells, bone marrow-derived mast cells, and non-hematopoietic cells, and may be rapidly upregulated in tumor tissues and other tissues in response to the simulation by interferon and other inflammatory factors. After activation of the PD-1/PD-L1 pathway, the immune system is suppressed on occasions like cancer, pregnancy, tissue transplantation, and autoimmune diseases. In addition, PD-L1 may also bind to CD80, thereby competitively inhibiting the T cell activation pathway of CD80 binding to ligand, and serving as another mechanism for PD-L1 to suppress T cell activity.

Under normal circumstances, the PD-1/PD-L1 signaling pathway can prevent excessive inflammation and autoimmune diseases induced by the immune system's over-attack on tissues. Whereas in abnormal conditions, such as tumor tissues and chronic HBV-infected tissue, there is an overexpression of PD-L1. Overexpression of PD-1/PD-L1 and activation of signaling pathways inhibit the activation and proliferation of functional T cells, inhibit anti-tumor immune responses, causing the immune system to lose its inhibitory effect on tumor development, thereby accelerating tumor progression and deterioration. Several medicaments have already been approved for this pathway. Among them, PD-L1 monoclonal antibody, such as Atezolizumab, has already been approved for indications in urothelial carcinoma and non-small cell lung cancer, and more clinical studies are underway for other tumor-related indications. However, compared with small molecules, macromolecule medicaments have obvious disadvantages in aspects such as tissue penetration, pharmacokinetic properties, cost, and administration methods. Therefore, the development of small molecule medicaments targeting the PD-1/PD-L1 signaling pathway remains an unmet clinical need with broad market prospects.

Currently, Bristol-Myers Squibb Company, Incyte Corporation, and Gilead Sciences, Inc. have reported small molecule PD-1/PD-L1 inhibitors. Incyte Corporation's patent WO2018119224 reports that this series of compounds demonstrated good cellular activity, and put compound INCB086550 into clinical practice. Despite that, there is still much room for improvement in the pharmacological properties (such as in vitro activity and in vivo tumor growth inhibition activity) of the aforementioned small molecule compound series. Therefore, in the development of small molecule inhibitors targeting the PD-1/PD-L1 signaling pathway, there is an even greater potential and prospect.

CONTENT OF THE PRESENT INVENTION

The present disclosure provides a compound of formula (I) or a pharmaceutically acceptable salt thereof, (I)

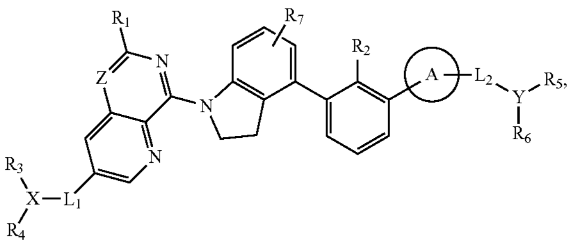

wherein ring A is selected from

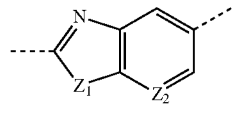

and

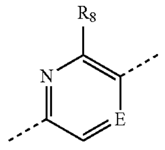

;

$L_1$ and $L_2$ are each independently selected from $—CH_2—$ and $—CH_2—NH—CH_2—$;

Z and E are each independently selected from CH and N;

$Z_1$ selected from O and S;

$Z_2$ selected from N and $CR_9$;

X is selected from N and $CR_{14}$;

Y is selected from N and $CR_{15}$;

$R_1$ is selected from H, $CH_3$, and $CHF_2$;

$R_2$ is selected from $CH_3$ and Cl;

$R_3$, $R_4$, $R_5$, and $R_6$ are each independently selected from H, $C_{1-6}$ alkyl, OH, COOH, and $—C_{1-3}$ alkyl-COOH;

alternatively, $R_3$, $R_4$ together with the atom to which they are attached form azetidinyl, pyrrolidinyl, oxazolidinyl, or piperidyl, and the azetidinyl, pyrrolidinyl, oxazolidinyl, and piperidyl are each independently and optionally substituted by 1, 2, or 3 $R_{16}$;

alternatively, $R_5$, $R_6$ together with the atom to which they are attached form azetidinyl, pyrrolidinyl, oxazolidinyl, or piperidyl, and the azetidinyl, pyrrolidinyl, oxazolidinyl, and piperidyl are each independently and optionally substituted by 1, 2, or 3 $R_{16}$;

$R_7$ is selected from H, F, Cl, $CH_3$, and $CHF_2$;

$R_8$ is selected from $—OCH_3$, $—O—CH_2—F$, and $—O—CH_2—CN$;

$R_9$ is selected from H, F, and CN;

$R_{14}$ and $R_{15}$ are each independently selected from H and $C_{1-6}$ alkyl;

each $R_{16}$ is independently selected from H, $C_{1-6}$ alkyl, OH, =O, COOH, and $—C_{1-3}$ alkyl-COOH.

In some embodiments of the present disclosure, the compound or the pharmaceutically acceptable salt thereof, wherein the compound is selected from (II)

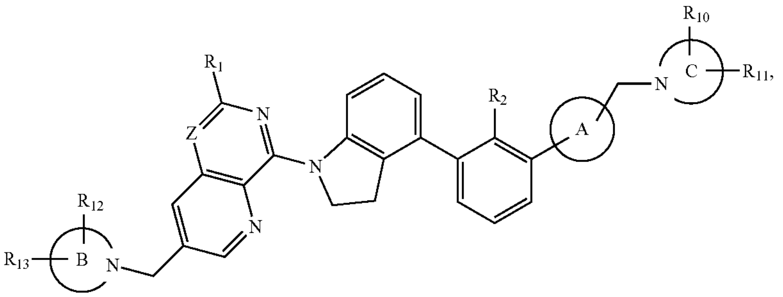

wherein ring B and ring C are each independently selected from azetidinyl, pyrrolidinyl, oxazolidinyl, and piperidyl;

$R_{10}$, $R_{11}$, $R_{12}$, and $R_{13}$ are each independently selected from H, $C_{1-4}$ alkyl, OH, =O, COOH, and $-C_{1-3}$ alkyl-COOH;

ring A, Z, $R_1$, and $R_2$ are as defined in the present disclosure.

In some embodiments of the present disclosure, the compound or the pharmaceutically acceptable salt thereof, wherein the compound is selected from (I-1)

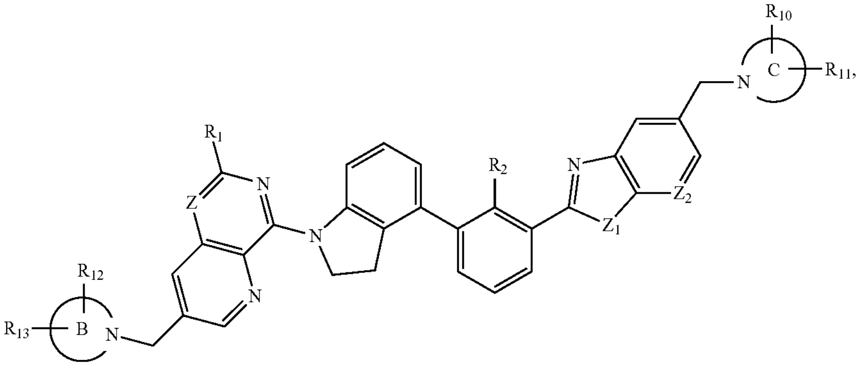

(I-2)

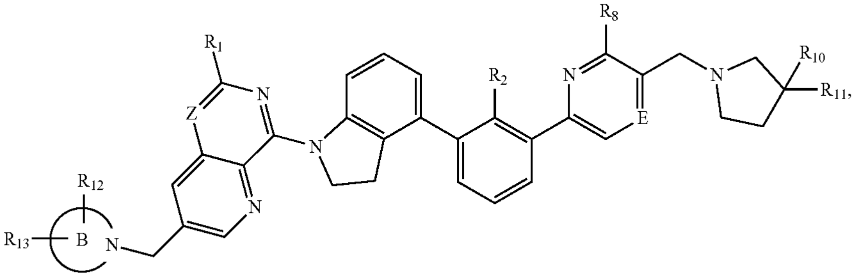

and

-continued (I-3)

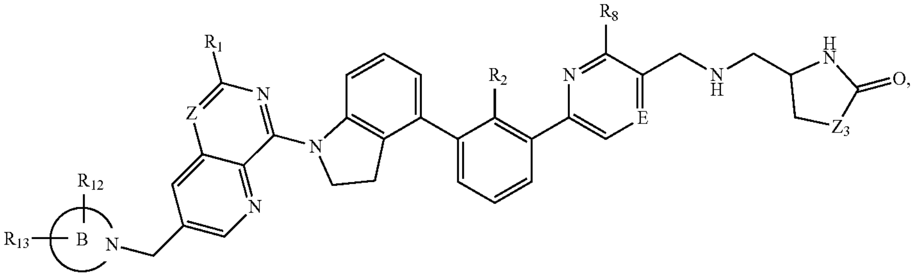

wherein ring B and ring C are each independently selected from azetidinyl, pyrrolidinyl, oxazolidinyl, and piperidyl;

$R_{10}$, $R_{11}$, $R_{12}$, and $R_{13}$ are each independently selected from H, $C_{1-4}$ alkyl, OH, =O, COOH, and $-C_{1-3}$ alkyl-COOH;

$Z_2$ is selected from $CH_2$ and O;

Z, $Z_1$, $Z_2$, E, $R_1$, $R_2$, and $R_8$ are as defined in the present disclosure.

In some embodiments of the present disclosure, the compound or the pharmaceutically acceptable salt thereof, wherein the compound is selected from (I-1-a)

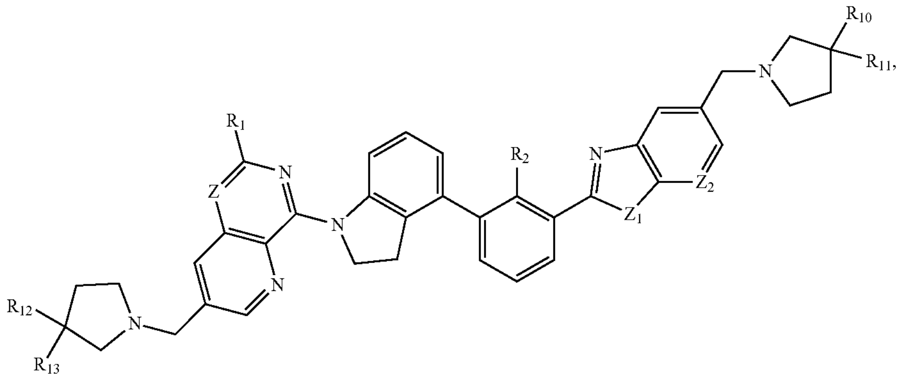

(I-2-a)

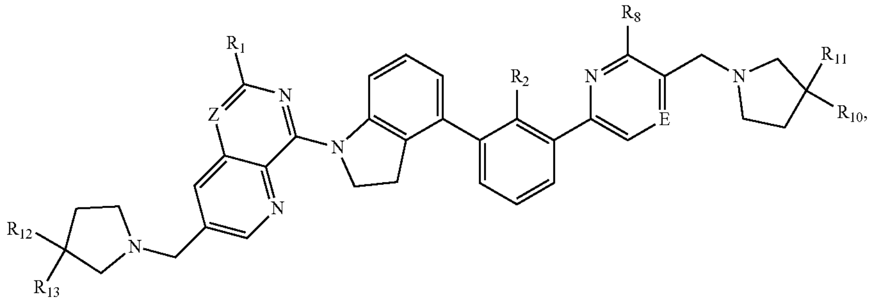

and (I-3-a)

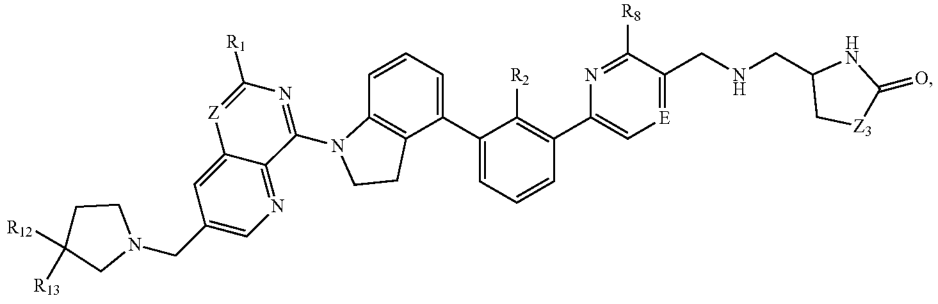

wherein $Z_3$ is selected from —$CH_2$— and —O—;

$R_{10}$, $R_{11}$, $R_{12}$, and $R_{13}$ are each independently selected from H, $C_{1-4}$ alkyl, OH, =O, COOH, and —$C_{1-3}$ alkyl-COOH, Z, $Z_1$, $Z_2$, E, $R_1$, $R_2$, and $R_8$ are as defined in the present disclosure.

In some embodiments of the present disclosure, the compound or the pharmaceutically acceptable salt thereof, wherein $Z_1$ is selected from O, $Z_2$ is selected from C(CN), and other variables are as defined in the present disclosure.

In some embodiments of the present disclosure, the compound or the pharmaceutically acceptable salt thereof, wherein X is selected from N, and other variables are as defined in the present disclosure.

In some embodiments of the present disclosure, the compound or the pharmaceutically acceptable salt thereof, wherein Y is selected from N, and other variables are as defined in the present disclosure.

In some embodiments of the present disclosure, the compound or the pharmaceutically acceptable salt thereof, wherein $R_1$ is selected from $CHF_2$, and other variables are as defined in the present disclosure.

In some embodiments of the present disclosure, the compound or the pharmaceutically acceptable salt thereof, wherein $R_3$, $R_4$, $R_5$, and $R_6$ are each independently selected from H, $CH_3$, isopropyl,

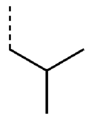,

COOH, and —$C_{1-3}$ alkyl-COOH, and other variables are as defined in the present disclosure.

In some embodiments of the present disclosure, the compound or the pharmaceutically acceptable salt thereof, wherein $R_7$ is selected from H, and other variables are as defined in the present disclosure.

In some embodiments of the present disclosure, the compound or the pharmaceutically acceptable salt thereof, wherein ring A is selected from

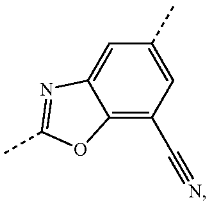 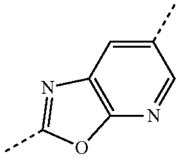,

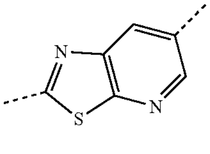, 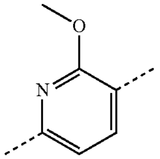,

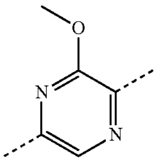, and 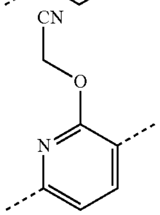, and other variables are as defined in the present disclosure.

In some embodiments of the present disclosure, the compound or the pharmaceutically acceptable salt thereof, wherein the structural moieties

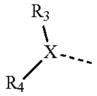 and 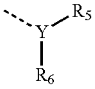

are each independently selected from

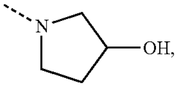 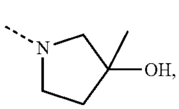

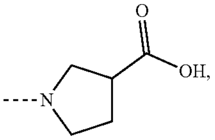 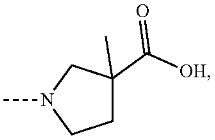

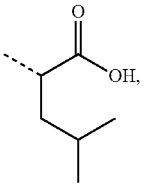 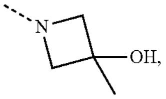 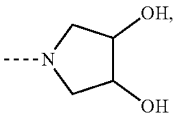

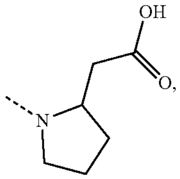 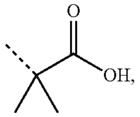 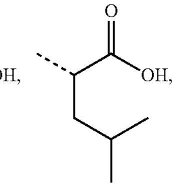

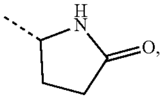 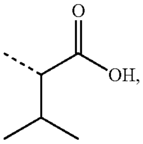 and 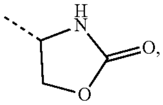

and other variables are as defined in the present disclosure.

In some embodiments of the present disclosure, the compound or the pharmaceutically acceptable salt thereof, wherein the structural moieties

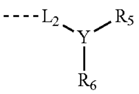 and 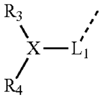

are each independently selected from

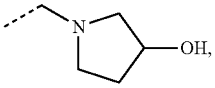 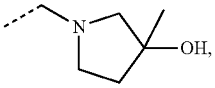

-continued

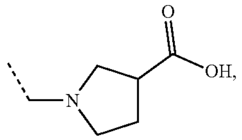
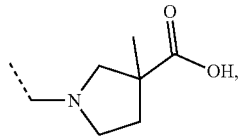
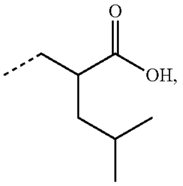
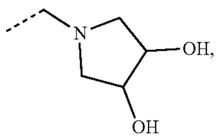
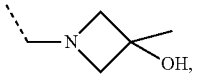
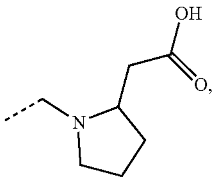
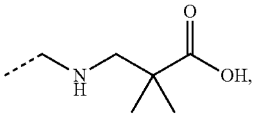
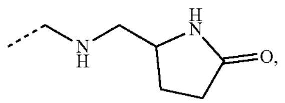
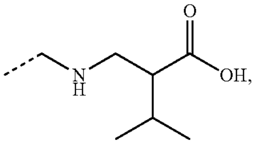
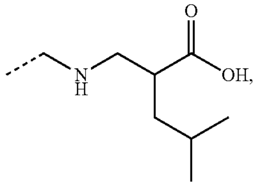 and
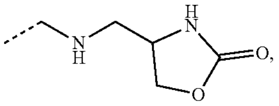

and other variables are as defined in the present disclosure.

In some embodiments of the present disclosure, the compound or the pharmaceutically acceptable salt thereof, the structural moieties

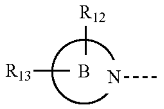 and 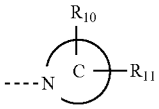

are each independently selected from

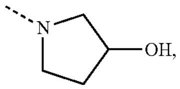
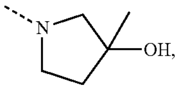
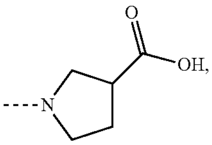
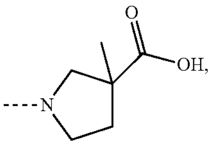
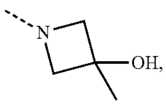
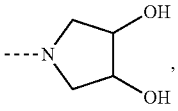, and
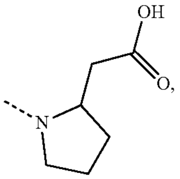

and other variables are as defined in the present disclosure.

The present disclosure also provides a compound of the following formula or a pharmaceutically acceptable salt thereof

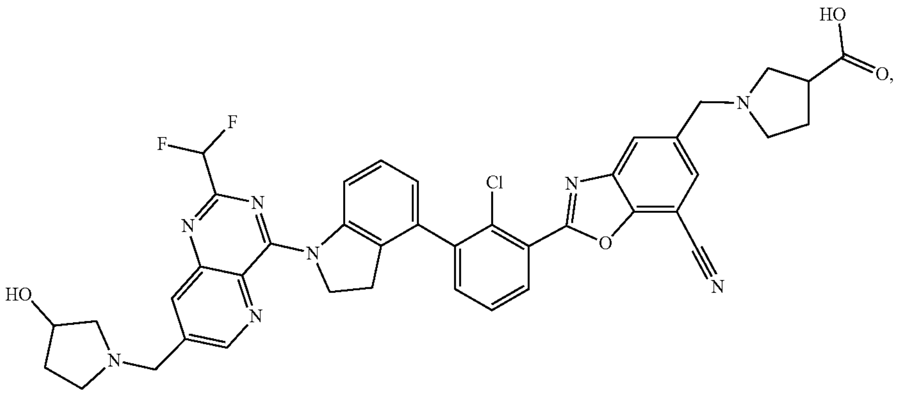

-continued
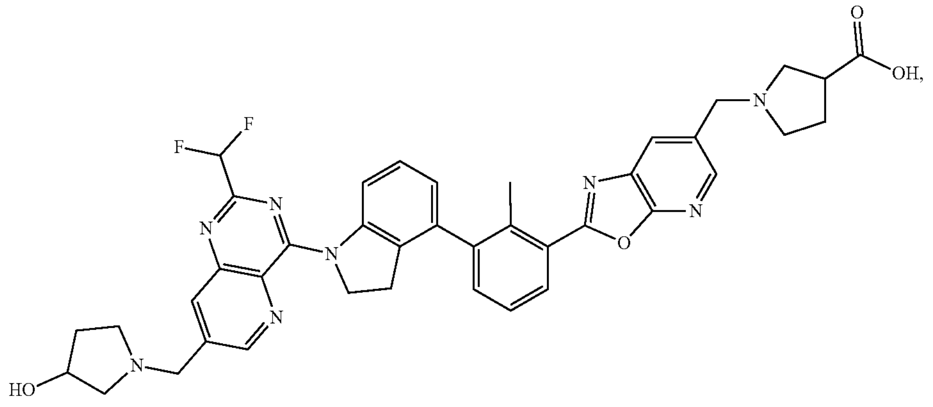
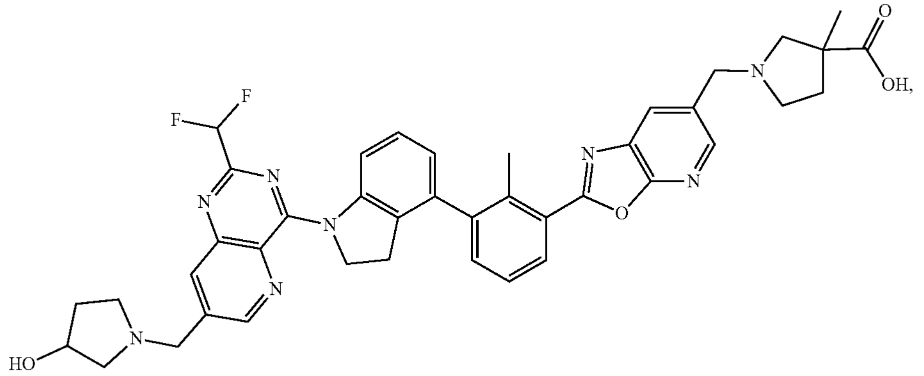
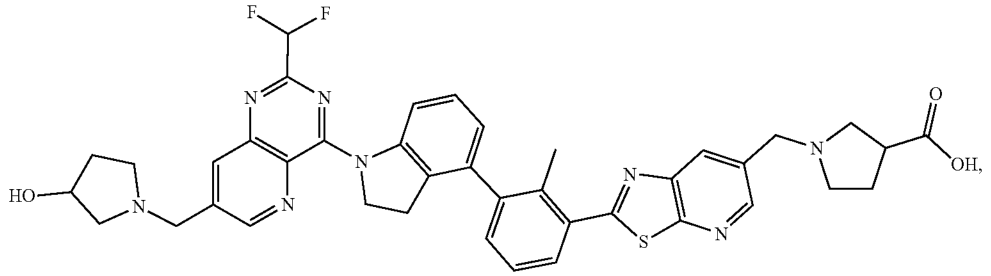
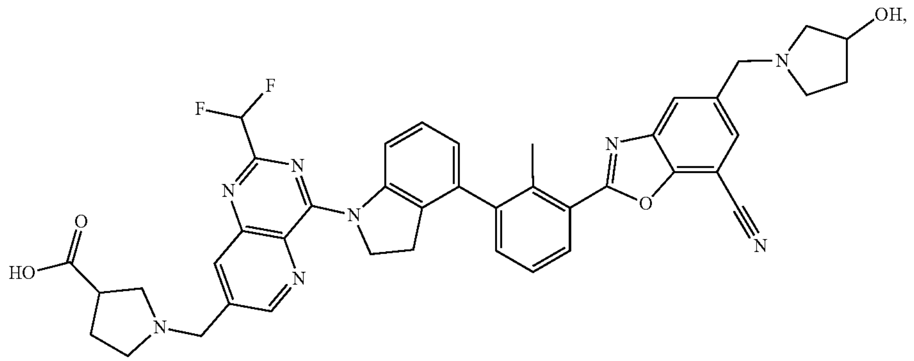
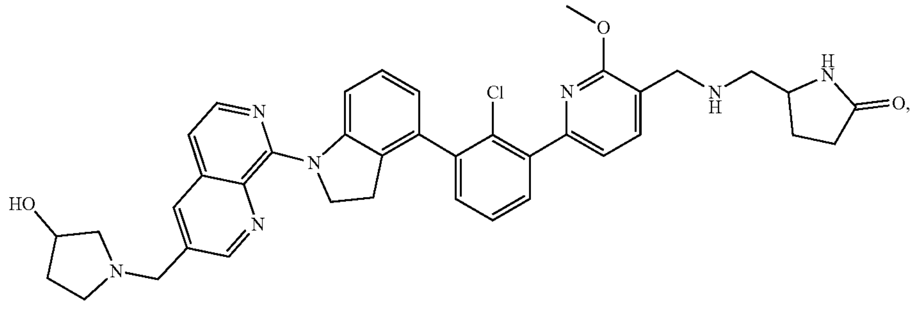

-continued
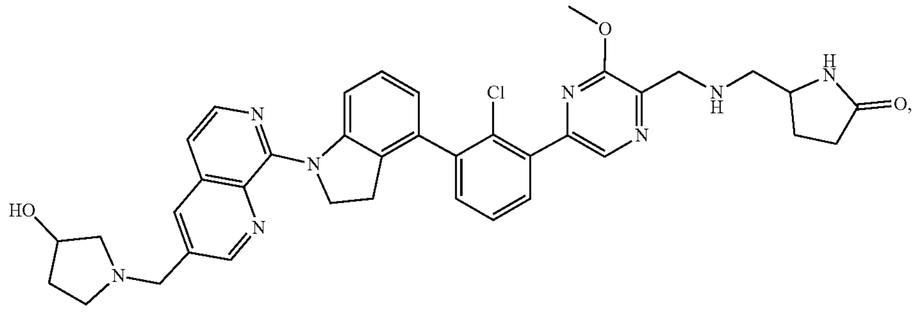
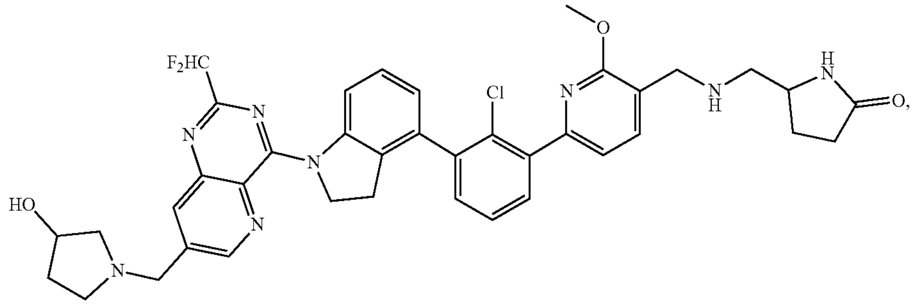
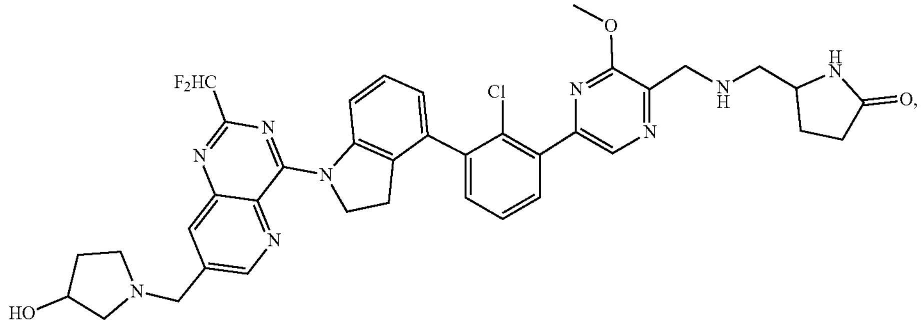
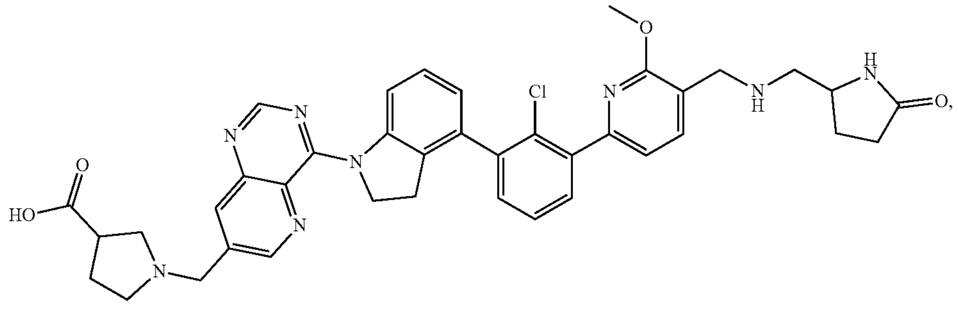
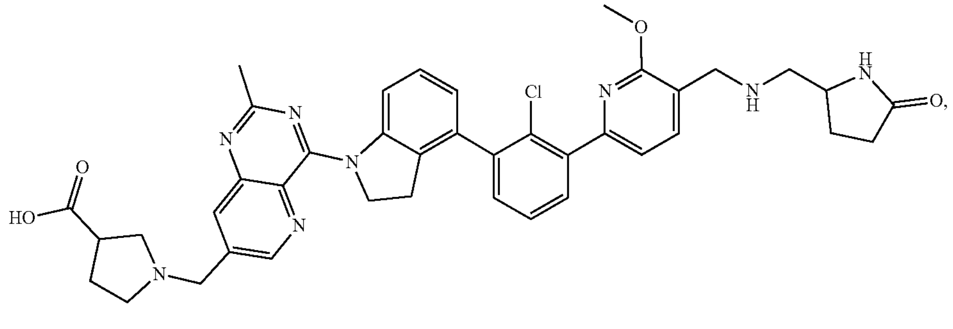

-continued
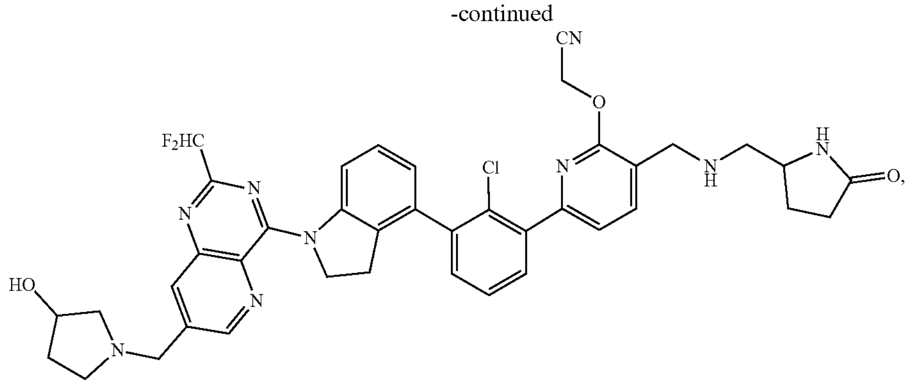
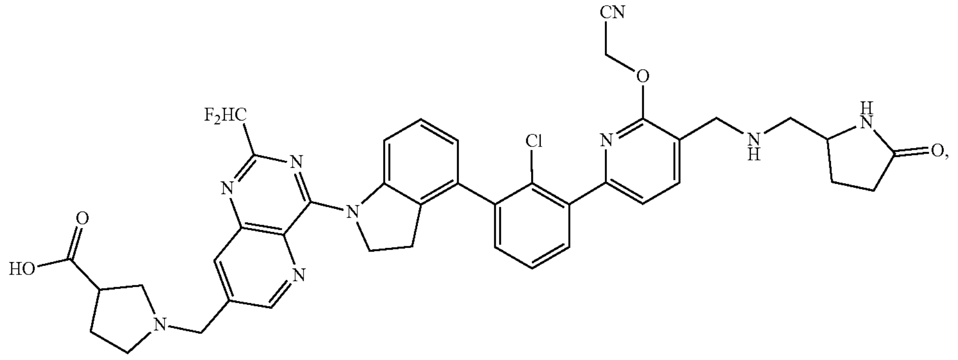
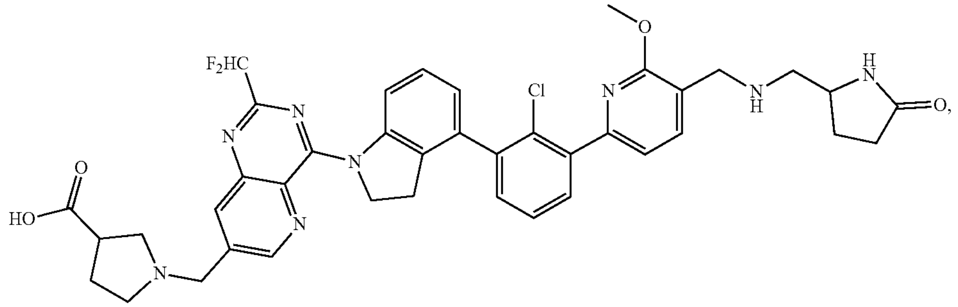
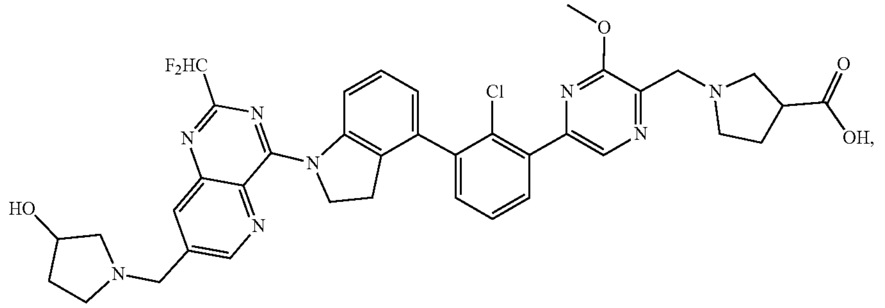
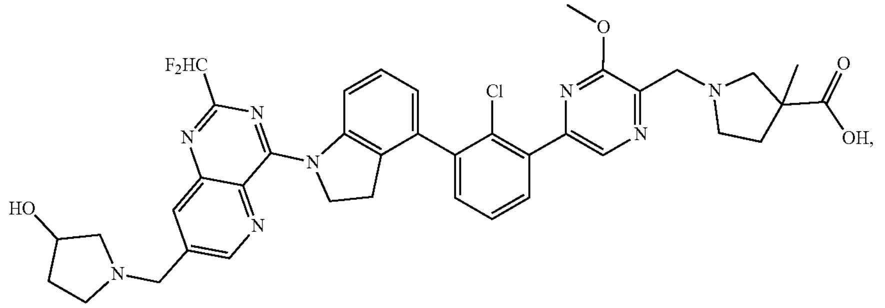

-continued
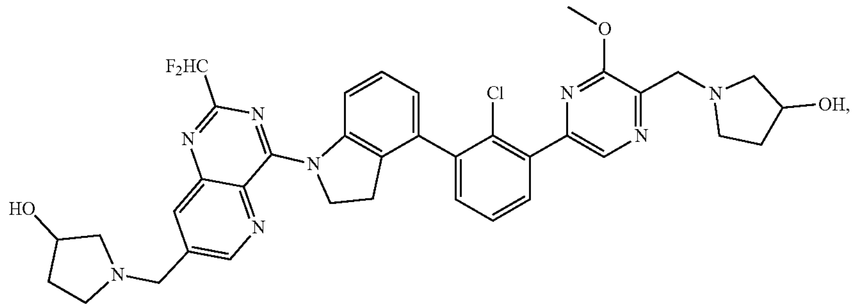
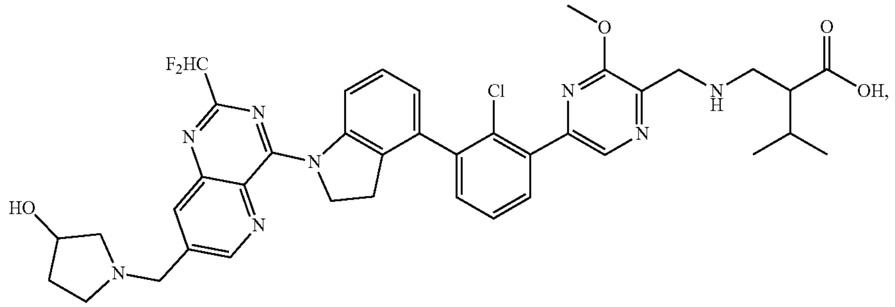
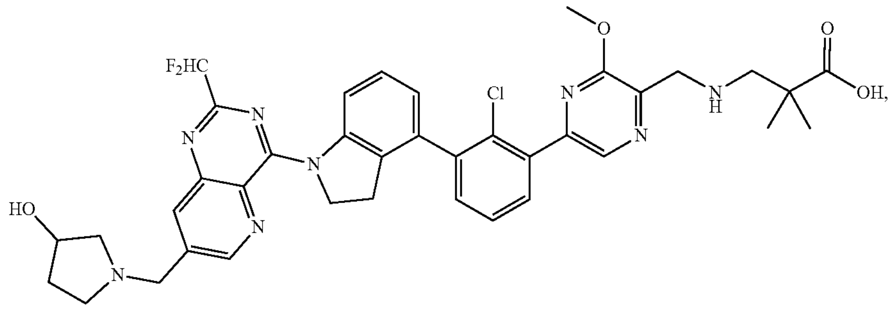
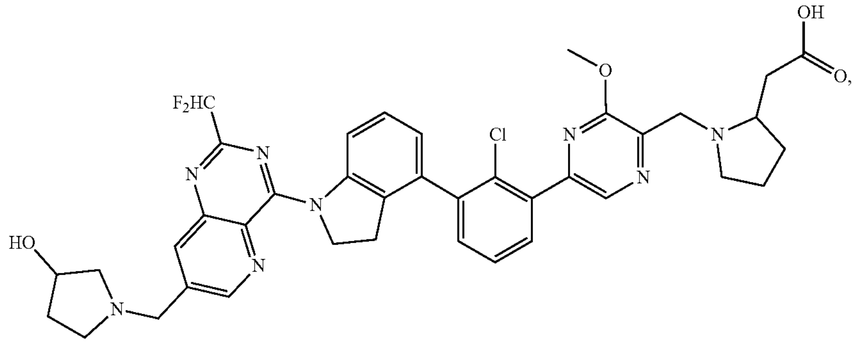
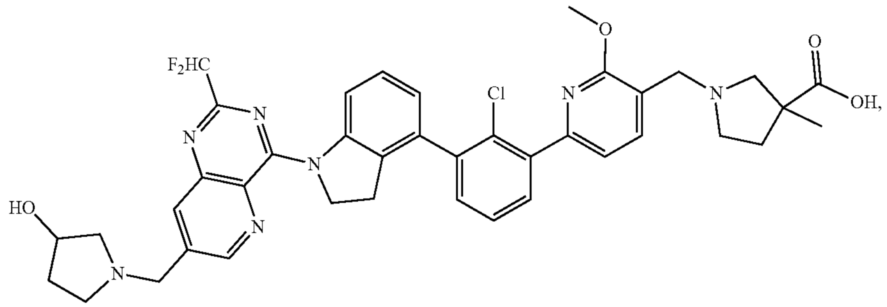

-continued
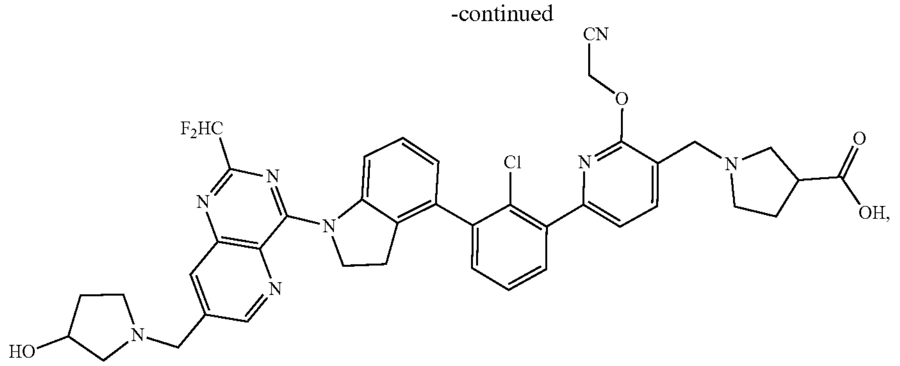
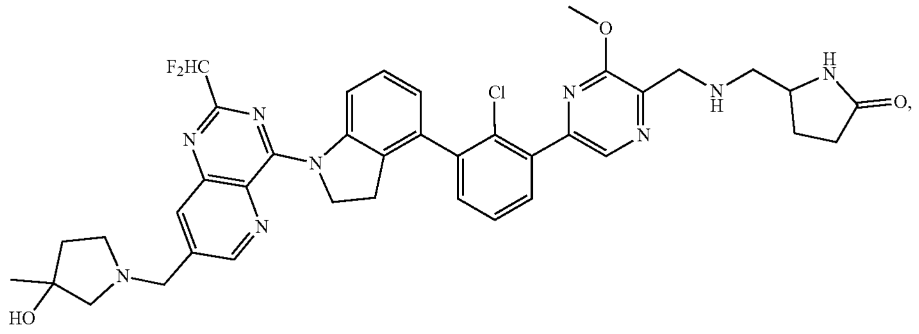
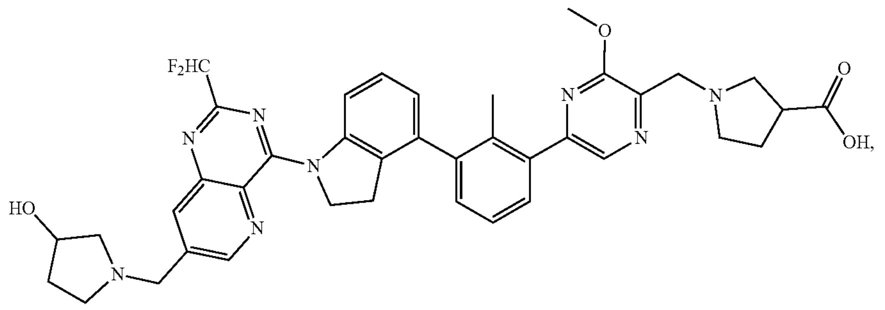
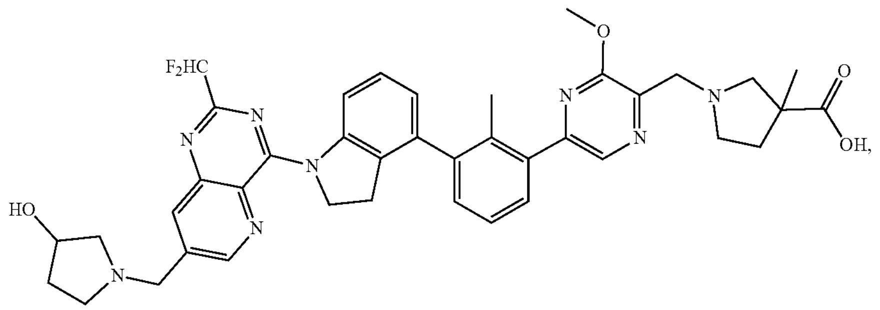
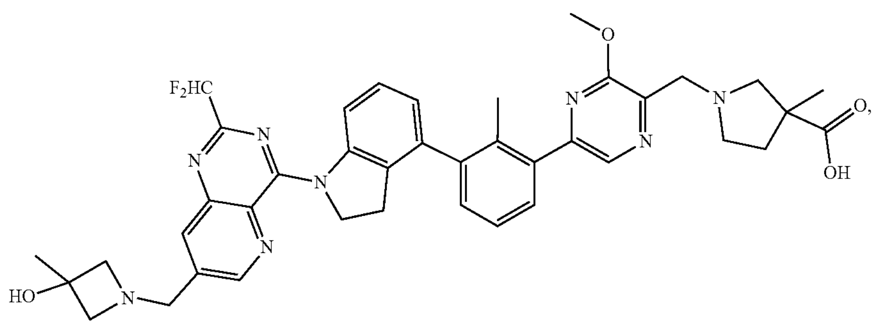

-continued
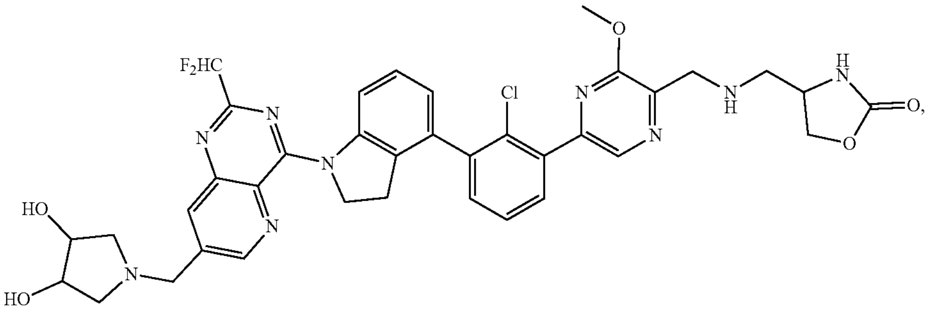
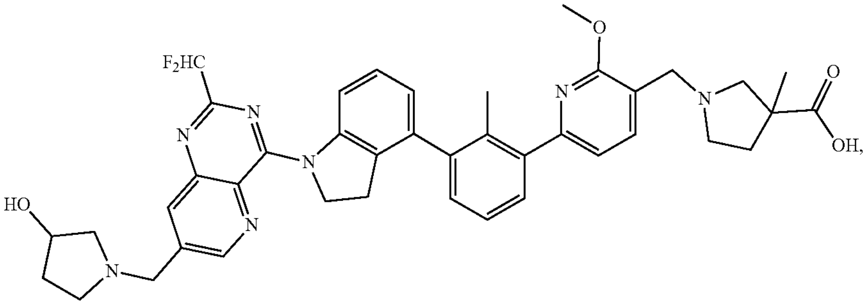
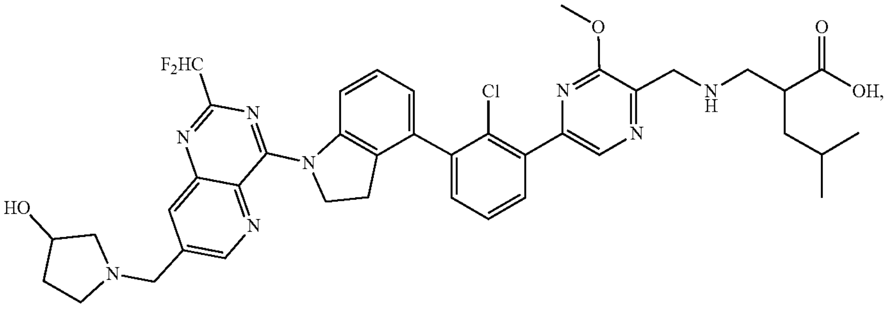
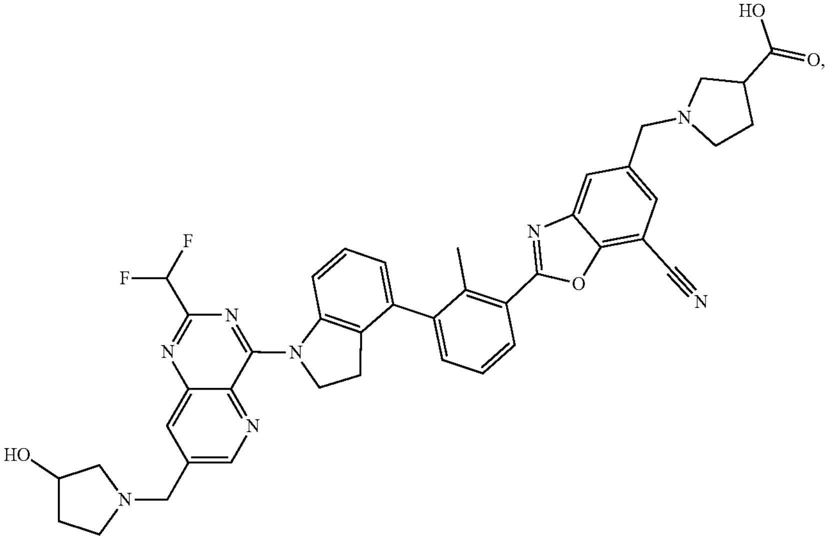
and

-continued
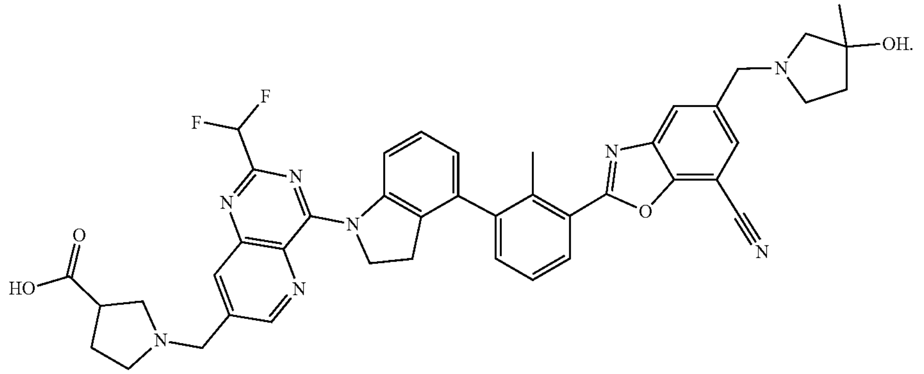 [SMILES: Cc1c(-c2nc3cc(CN4CCC(C)(O)C4)cc(C#N)c3o2)cccc1-c1cccc2c1CCN2c1nc(C(F)F)nc2cc(CN3CCC(C(=O)O)C3)cnc12]
In some embodiments of the present disclosure, the compound or the pharmaceutically acceptable salt thereof, wherein the compound is selected from
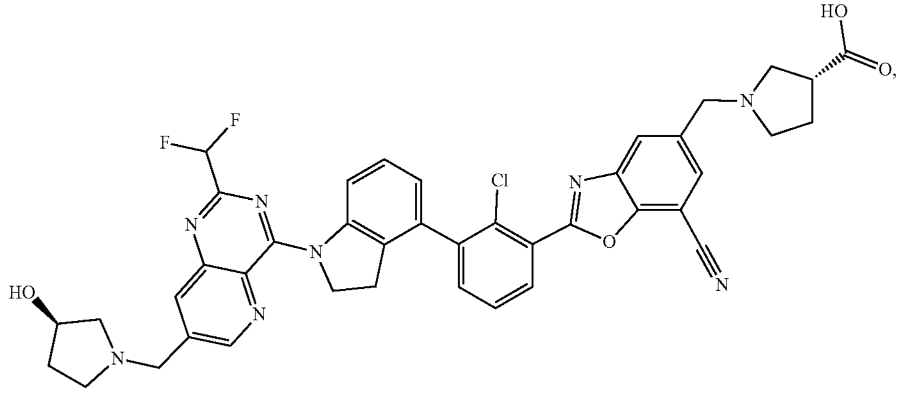
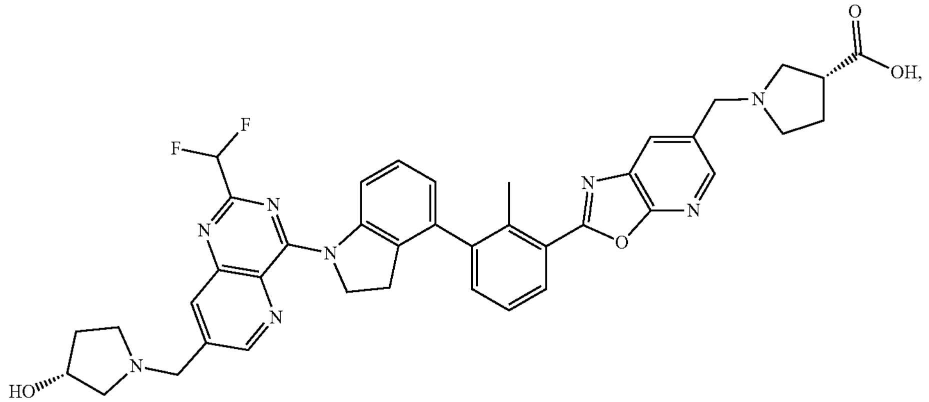
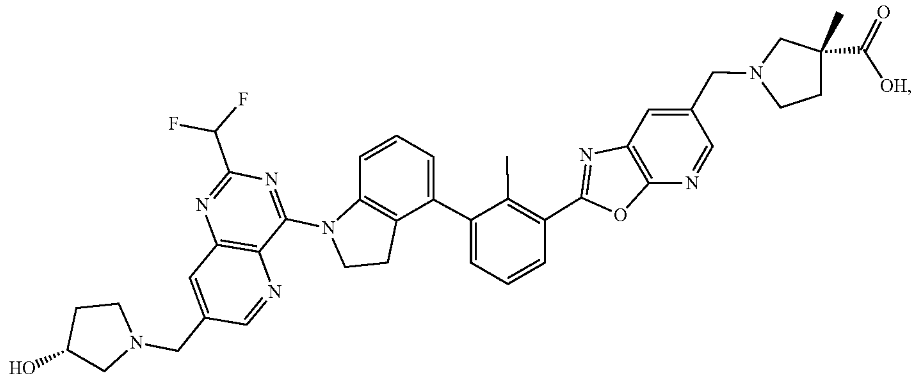

-continued
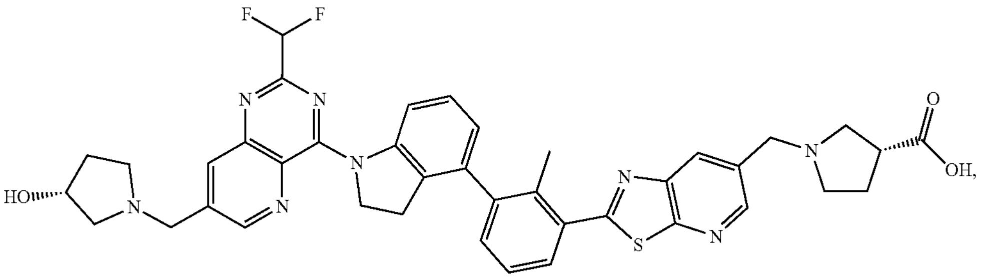
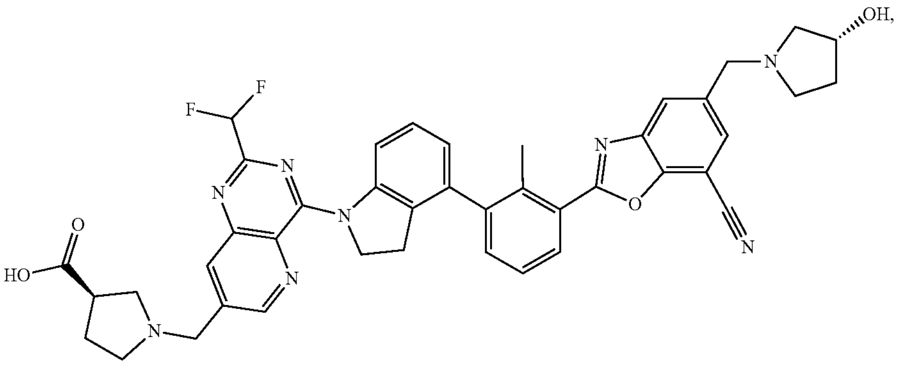
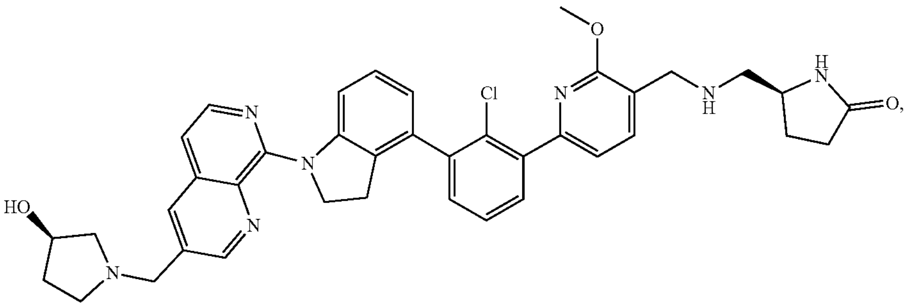
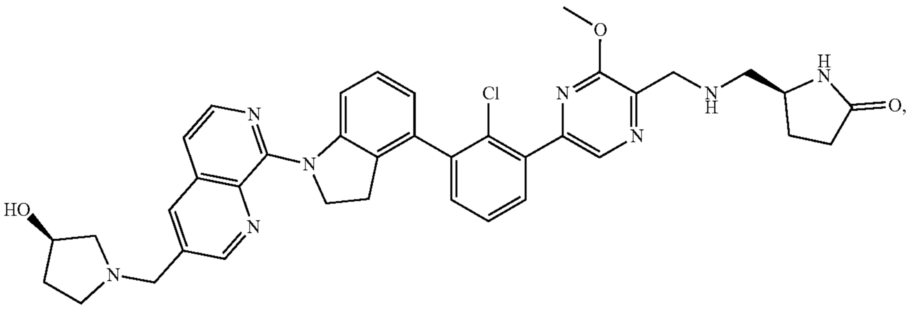
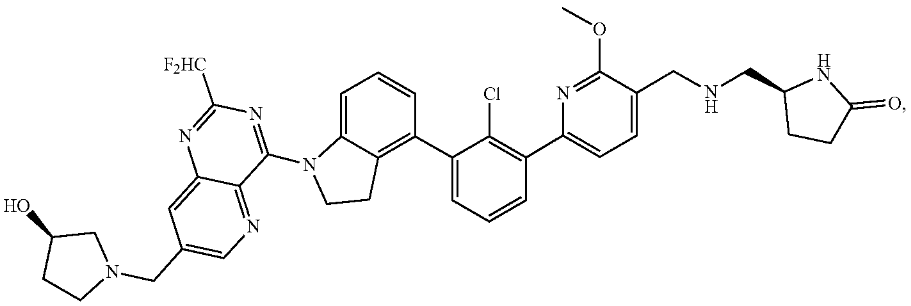

-continued
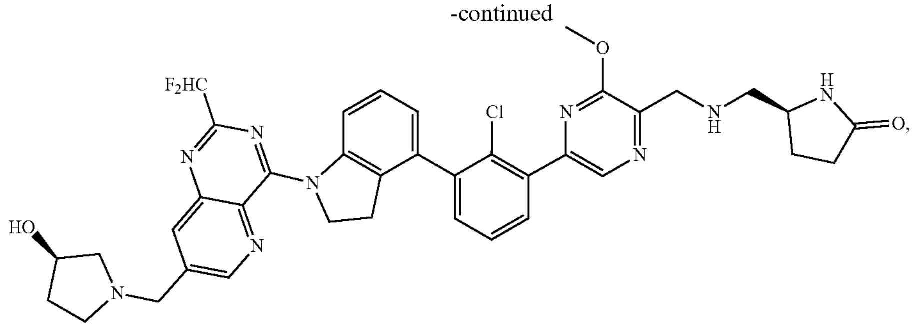
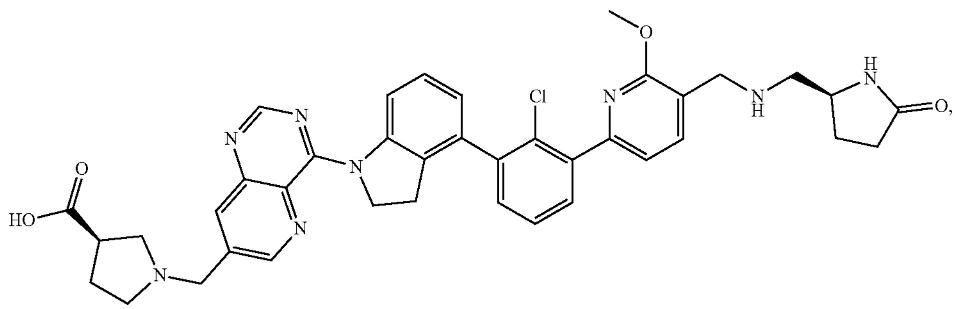
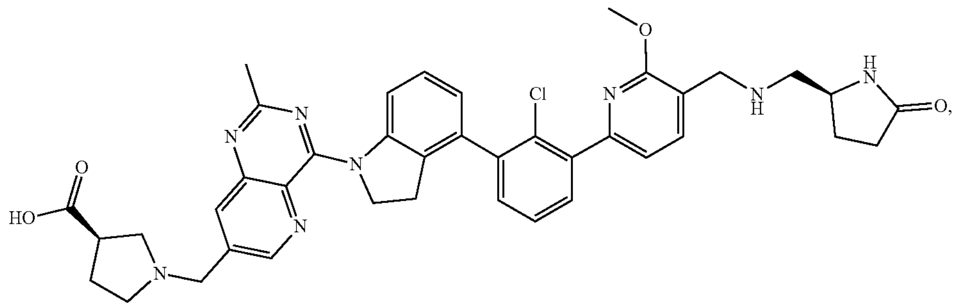
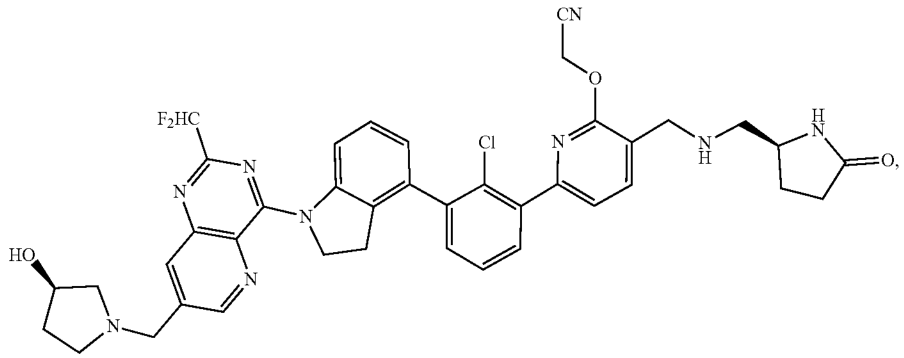
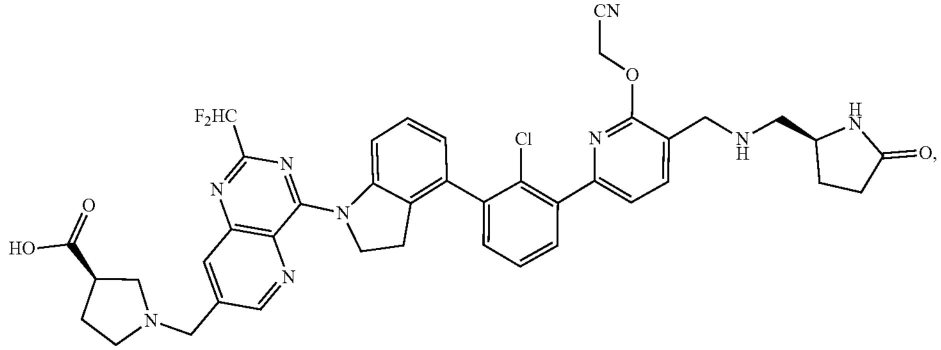

-continued
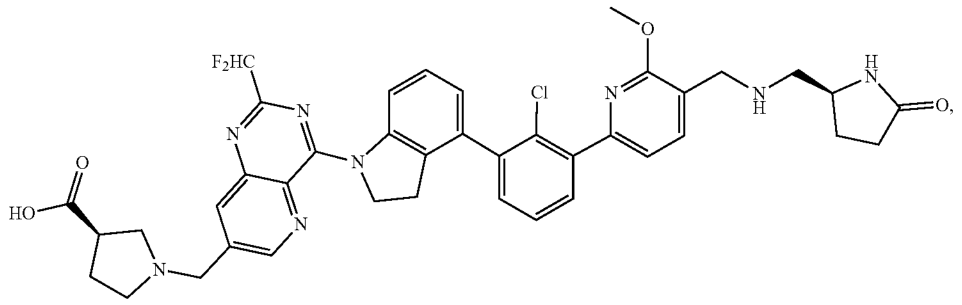
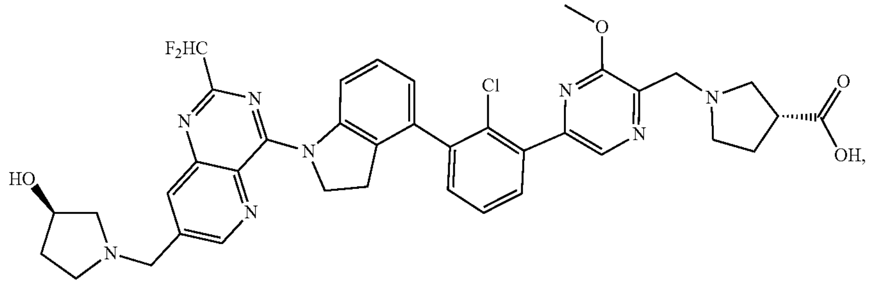
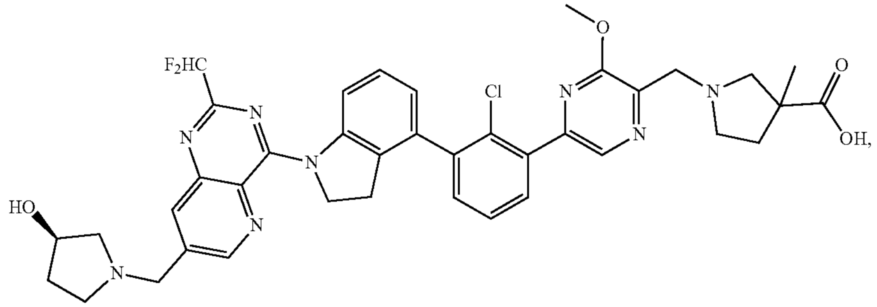
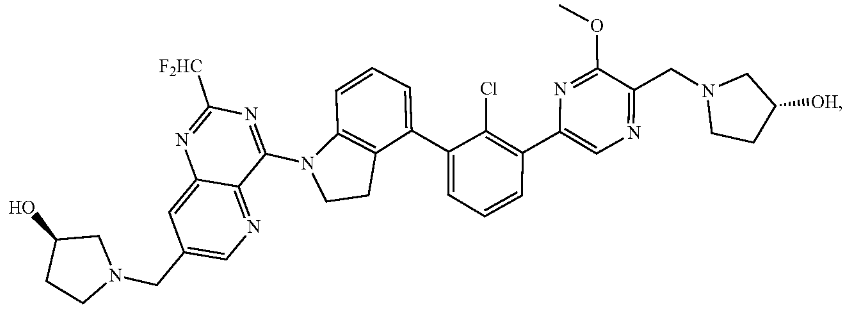
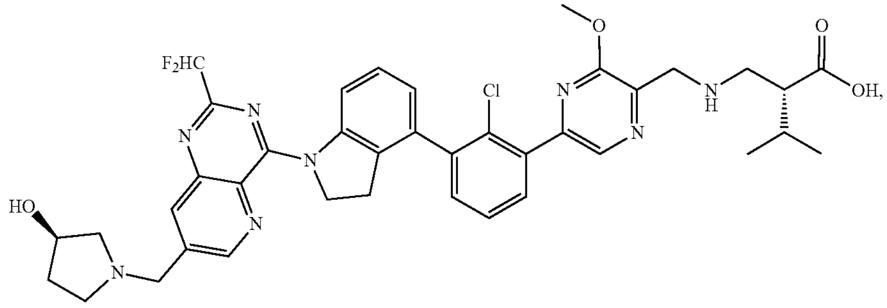

-continued
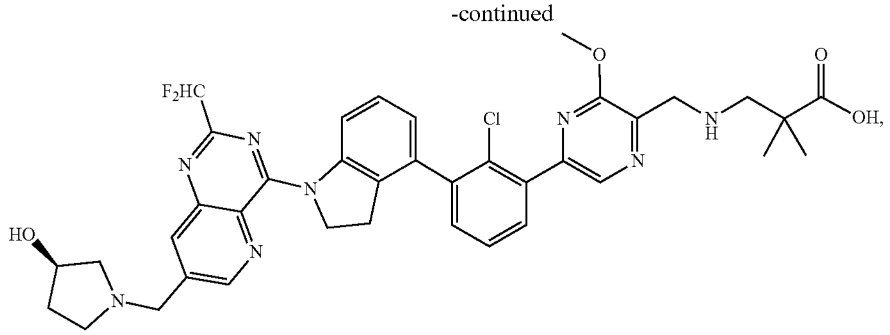
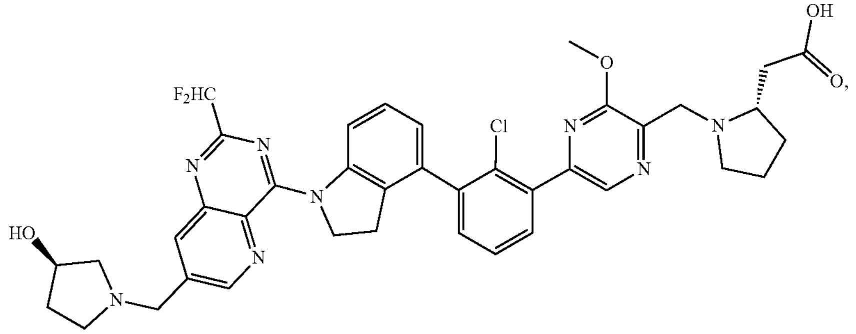
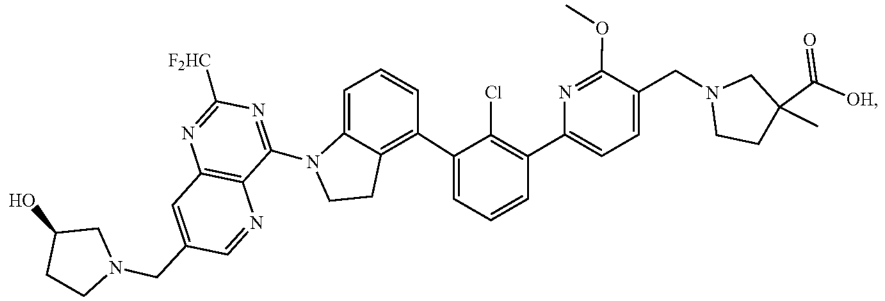
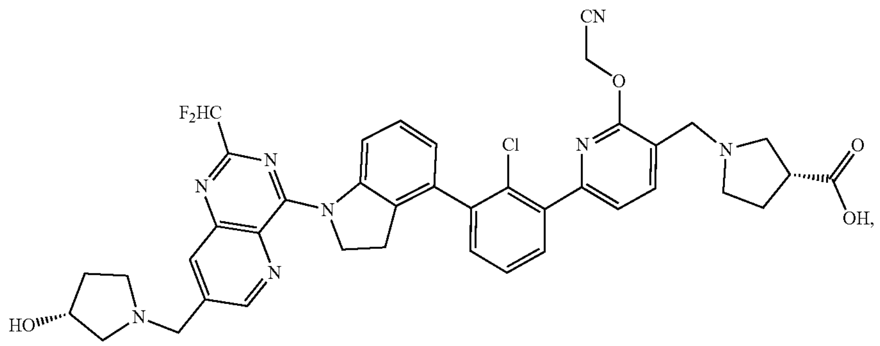
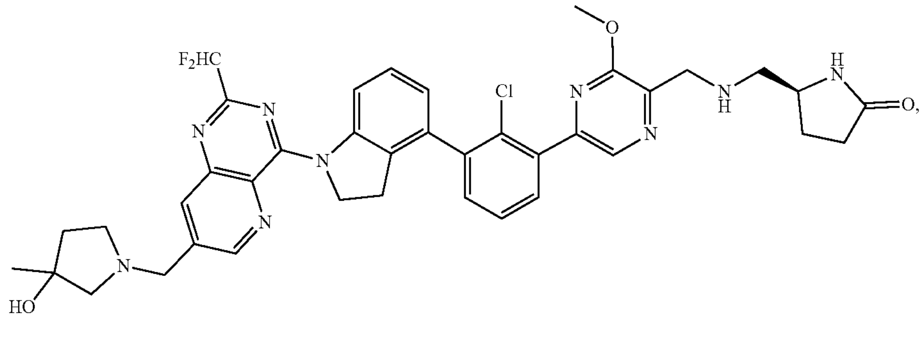

-continued
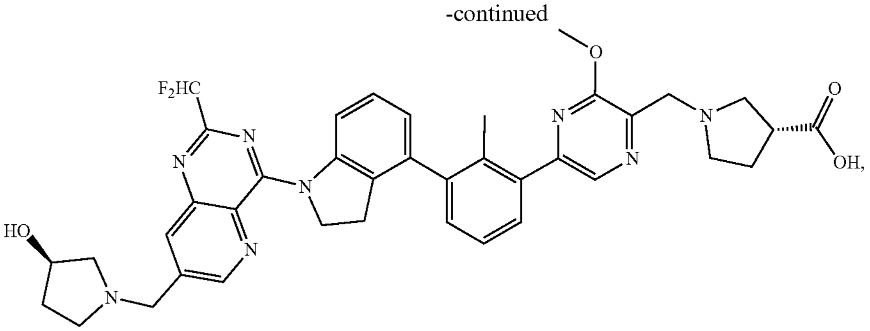
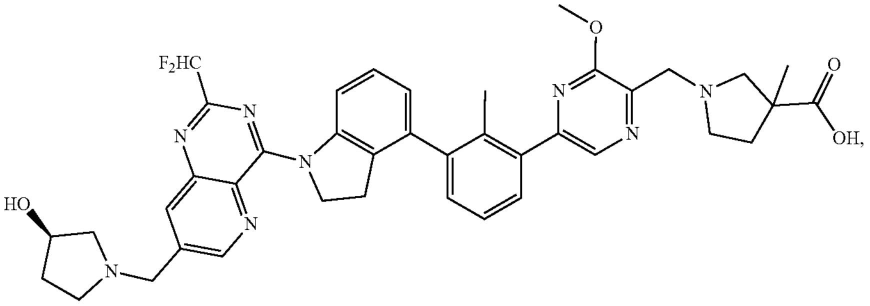
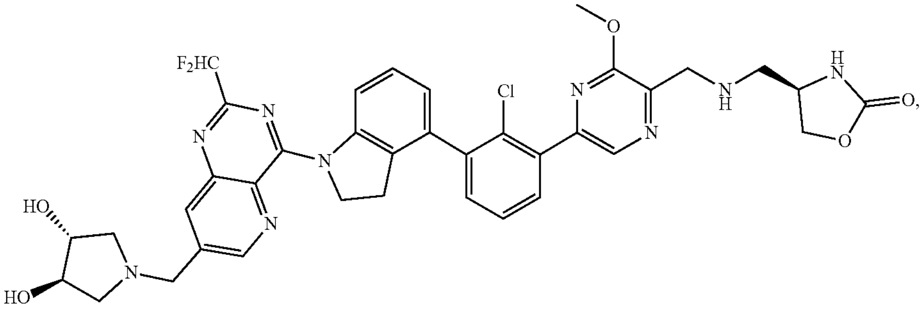
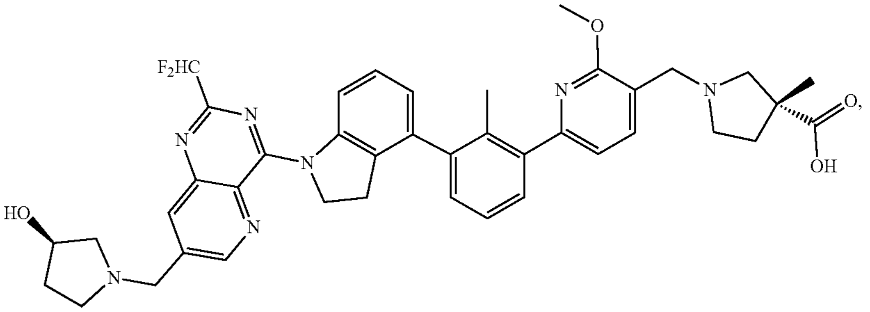
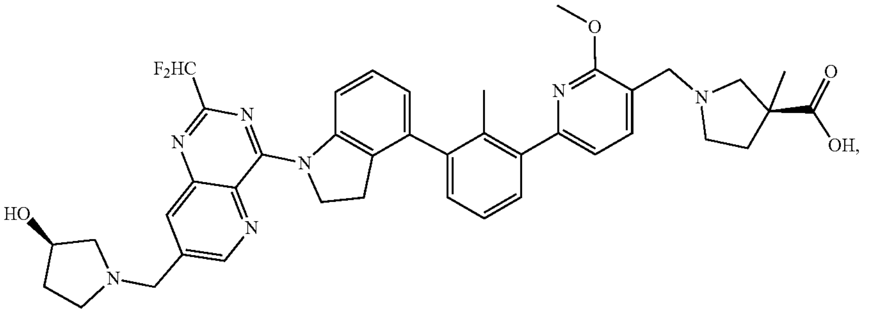

-continued
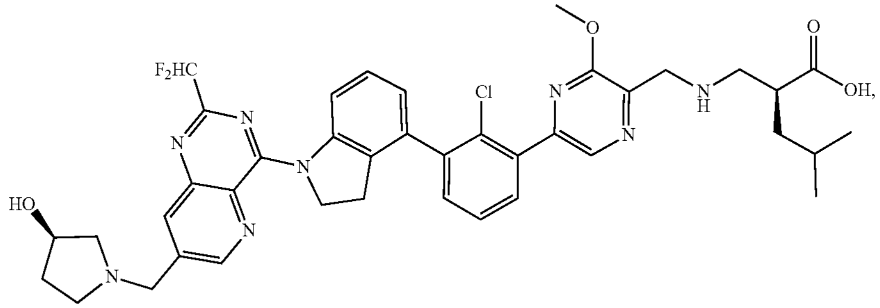
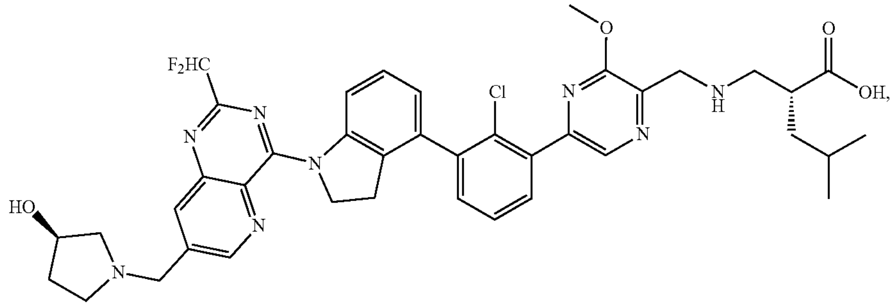
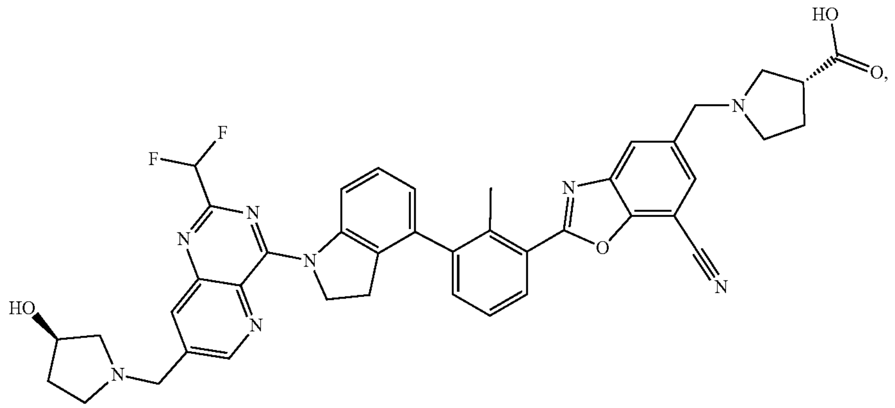
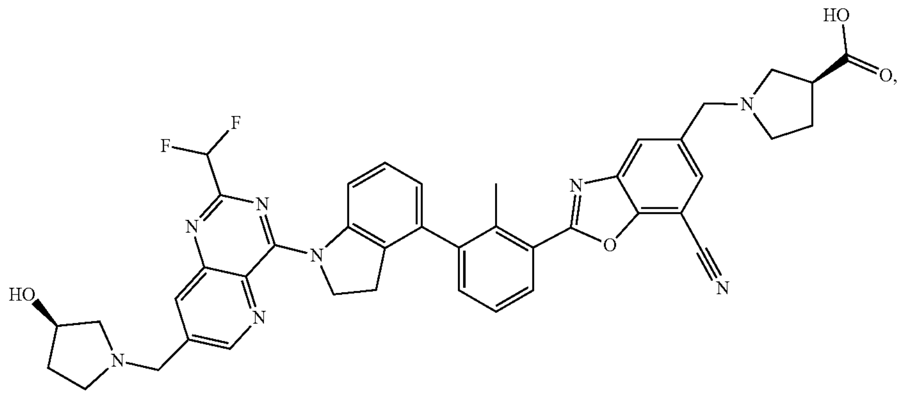

-continued
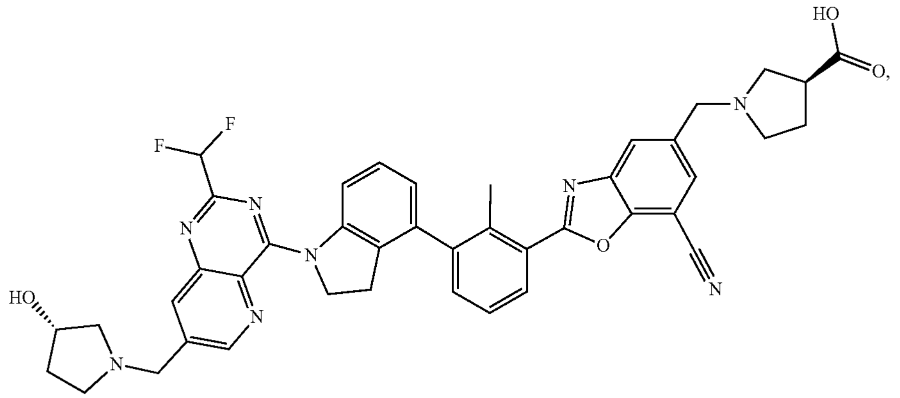
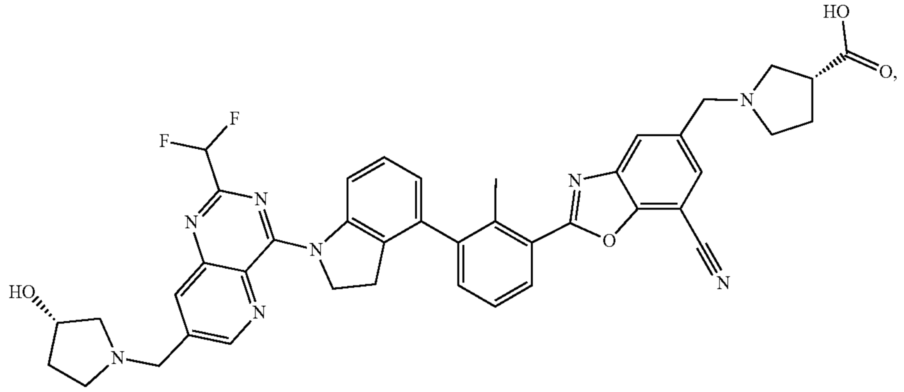
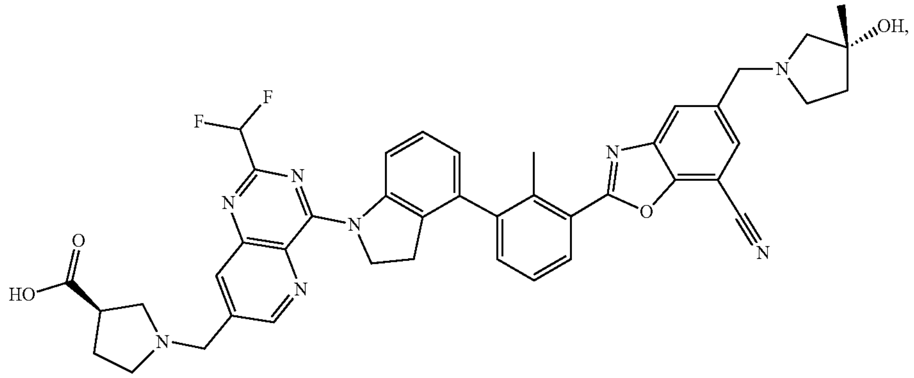
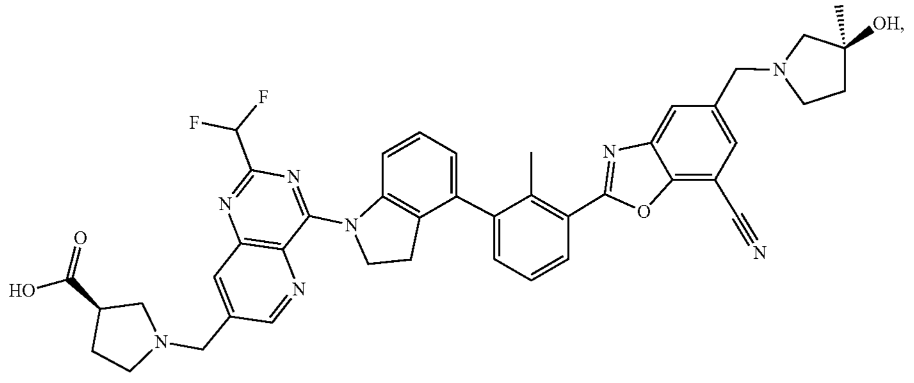

-continued

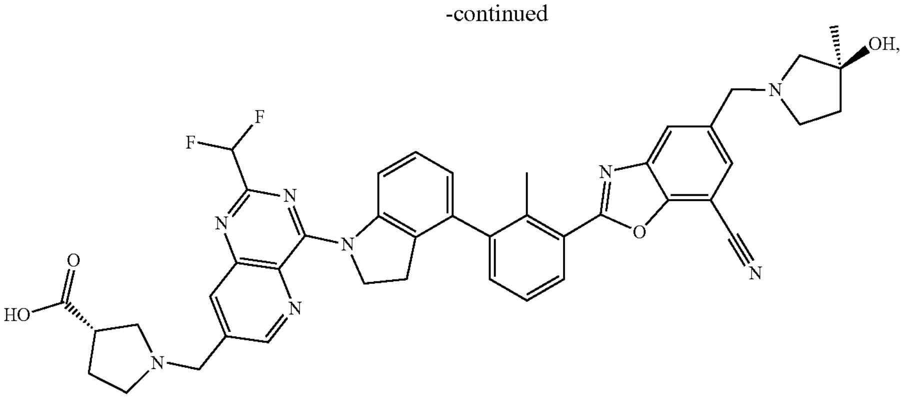

and

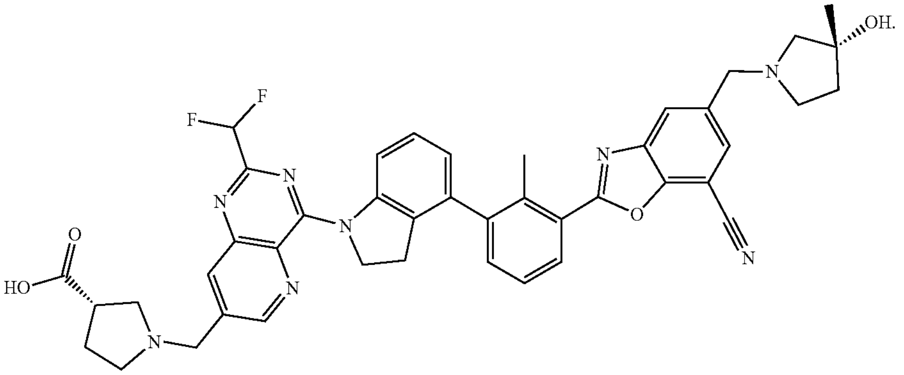

There are still some embodiments of the present disclosure which are obtained by any combination of the above variables.

In some embodiments of the present disclosure, a use of the compound or the pharmaceutically acceptable salt thereof in the manufacture of a medicament for treating diseases related to PD-L1 is provided.

In some embodiments of the present disclosure, a use of the compound or the pharmaceutically acceptable salt thereof in the manufacture of a medicament for treating tumors is provided.

In some embodiments of the present disclosure, the tumors are colon cancer, melanoma, non-small cell lung cancer, hepatocellular carcinoma, or renal cell carcinoma.

Technical Effect

The compound of the present disclosure is a small molecule inhibitor with good inhibitory activity against PD-L1, which differs from existing treatment solutions (PD-L1 monoclonal antibody medicaments). Small molecule inhibitors have lower costs in production than monoclonal antibody medicaments and are more suitable for large-scale production; at the same time, the pharmacokinetic properties of the small molecule medicaments significantly differ from those of macromolecular monoclonal antibody medicaments as small molecule medicaments possess faster half-life and broader tissue distribution. Therefore, compared with macromolecule medicaments, small molecule PD-L1 inhibitors can offer more flexible administration regimens and more manageable side effects in clinical applications. After multiple rounds of searching and evaluation, it was unexpectedly found that the compounds of the present disclosure possess excellent in vitro activity and pharmacokinetic properties, and demonstrate a high oral exposure in preclinical studies. Simultaneously, these compounds have shown remarkable potency in vivo, demonstrating good inhibitory activity against tumors (e.g. colon cancer, melanoma, non-small cell lung cancer, hepatocellular carcinoma, or renal cell carcinoma). These properties support that the series of compounds of the present disclosure are used for oral administration in the treatment of diseases caused by PD-L1 positivity, and have good prospects for drug-forming and clinical applications.

Definitions and Explanations

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commercial product or active ingredient thereof.

The term "pharmaceutically acceptable" is used herein in terms of those compounds, materials, compositions, and/or dosage forms, which are suitable for use in contact with human and animal tissues within the scope of reliable medical judgment, without excessive toxicity, irritation, anaphylactic reaction, or other problems, or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the compound with a sufficient amount of a base in a pure solution or a suitable inert solvent. The pharmaceutically acceptable base addition salt includes a salt of sodium, potassium, calcium, ammonium, organic amine, or magnesium, or similar salts.

When the compound of the present disclosure contains a relatively basic functional group, an acid addition salt can be obtained by contacting the compound with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of an amino acid (such as arginine), and a salt of an organic acid such as glucuronic acid. Certain specific compounds of the present disclosure contain both basic and acidic functional groups, and thus can be converted to any base or acid addition salt.

When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the bond of a substituent can be cross-linked to two or more atoms on a ring, this substituent can be bonded to any atom on this ring. For example, structural moieties

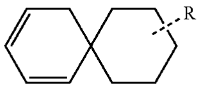 or 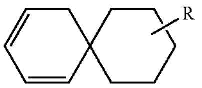

indicate that the substituent R can be substituted at any position on cyclohexyl or cyclohexadiene.

When the enumerative linking group does not indicate the direction for linking, the direction for linking is arbitrary, for example, the linking group L contained in

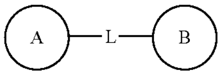

is -M-W—, then -M-W— can link ring A and ring B to form

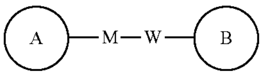

in the direction same as left-to-right reading order, and form

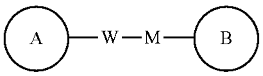

in the direction contrary to left-to-right reading order. A combination of the linking groups, substituents, and/or variables thereof is allowed only when such combination can result in a stable compound.

Unless otherwise specified, when a group has one or more than one linkable site, any one or more than one site of the group can be linked to other groups through chemical bonds. When the linking site of the chemical bond is not positioned, and there is an H atom at the linkable site, then the number of H atoms at the site will decrease correspondingly with the number of chemical bonds linking thereto so as to meet the corresponding valence. The chemical bond between the site and other groups can be represented by a straight solid bond (), a straight dashed bond () or a wavy line (). For example, the straight solid bond in —OCH3 means that it is linked to other groups through the oxygen atom in the group; the straight dashed bond in

means that it is linked to other groups through the two ends of the nitrogen atom in the group; the wave lines in

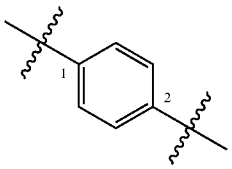 [SMILES: *c1ccc(*)cc1]

means that the phenyl group is linked to other groups through carbon atoms at position 1 and position 2;

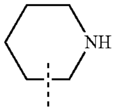

means that it can be linked to other groups through any linkable sites on the piperidinyl by one chemical bond, including at least four types of linkage, including

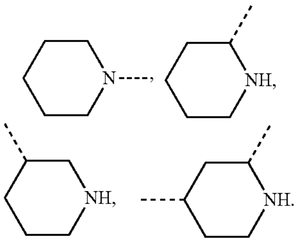

Even though the H atom is drawn on the —N—,

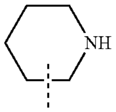

still includes the linkage of

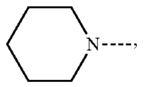

merely when one chemical bond was connected, the H of this site will be reduced by one to the corresponding monovalent piperidinyl.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc; it can be monovalent (such as methyl), divalent (such as methylene), or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, etc.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$, $C_{1-3}$, and $C_{2-3}$ alkyl, etc.; it can be monovalent (such as methyl), divalent (such as methylene), or multivalent (such as methine). Examples of $C_{1-4}$ alkyl include, but are not limited to, methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), etc.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art. Preferred embodiments include, but are not limited to, the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/scan, and after collecting the relevant data, the crystal structure can be further analyzed by direct method (Shelxs97).

The solvents used in the present disclosure are commercially available.

The present disclosure uses the following abbreviations: $Pd(PPh_3)_4$ stands for tetrakis(triphenylphosphine)palladium; $Pd(dppf)Cl_2{\cdot}CH_2Cl_2$ stands for 1,1'-bis(diphenylphosphino) ferrocene dichloropalladium(II) dichloromethane complex; $NaBH(OAc)_3$ stands for sodium triacetoxyborohydride; DIAD stands for diisopropyl azodicarboxylate; Boc2O stands for di-tert-butyl dicarbonate; t-BuXPhos-Pd-G3 stands for methanesulfonato(2-di-t-butylphosphino-2',4',6'-tri-i-propyl-1,1'-biphenyl)(2'-amino-1,1'-biphenyl-2-yl)palladium(II); DIBAL-H stands for diisobutylaluminium hydride; DMSO stands for dimethyl sulfoxide. The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
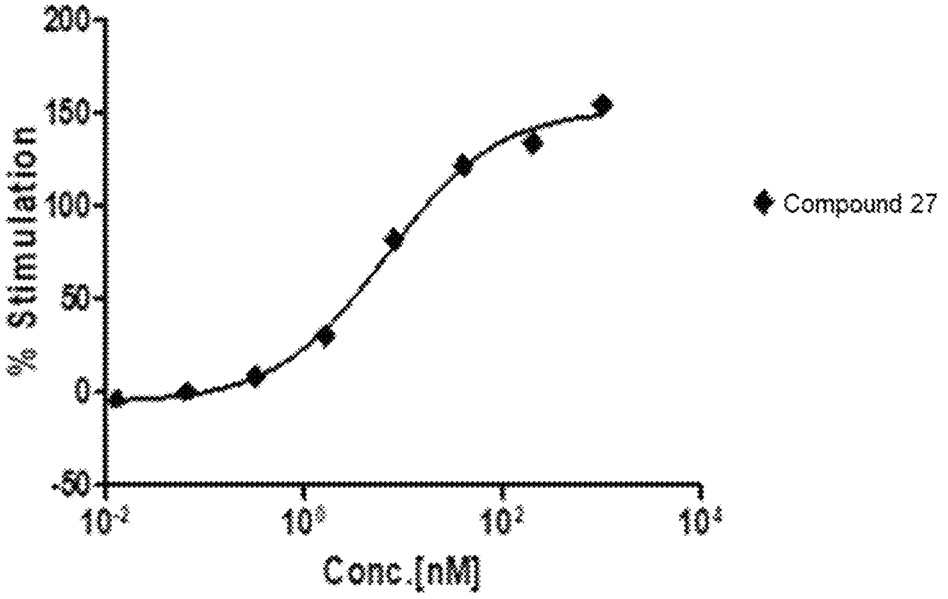
FIG. 1: Inhibitory activity of compounds of the present disclosure on PD-1/PD-L1 binding.

The present disclosure is described in detail by the examples below, but it does not mean that there are any adverse restrictions on the present disclosure. The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art. Preferred embodiments include, but are not limited to, the embodiments of the present disclosure. It is obvious for those skilled in the art to make various modifications and improvements to the embodiments of the present disclosure without departing from the spirit and scope of the present disclosure.

Example 1
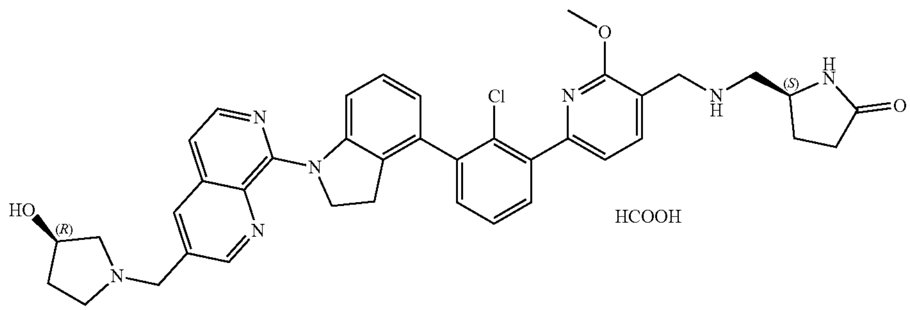
1
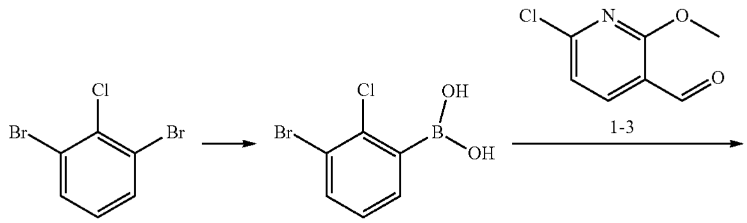
1-1 1-2 1-3
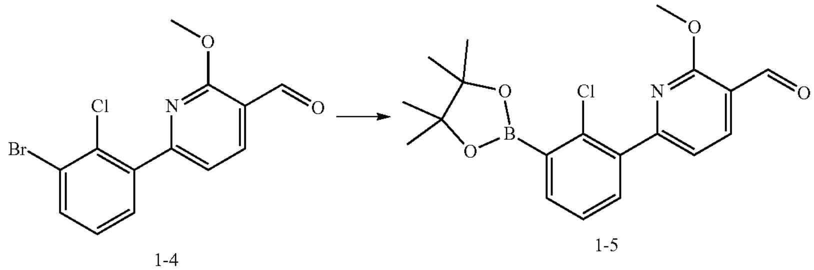
1-4 1-5
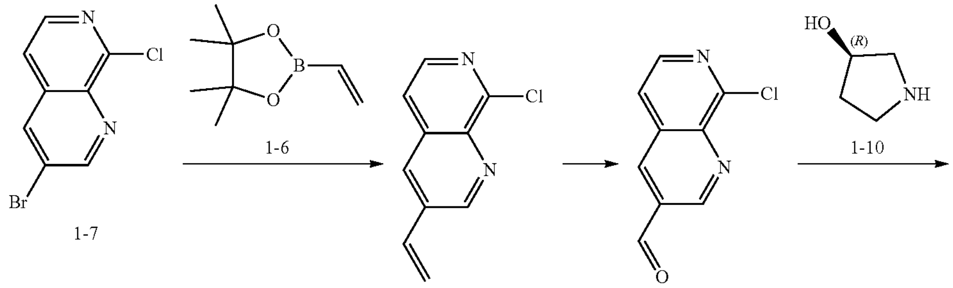
1-7 1-6 1-8 1-9 1-10
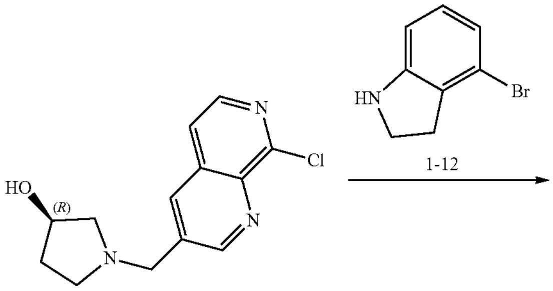
1-11 1-12

-continued

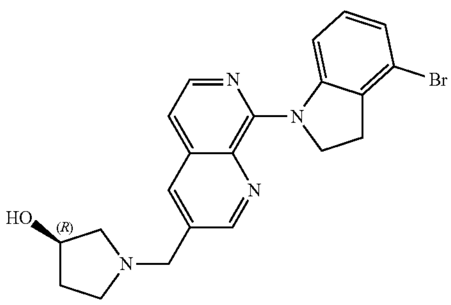

1-13

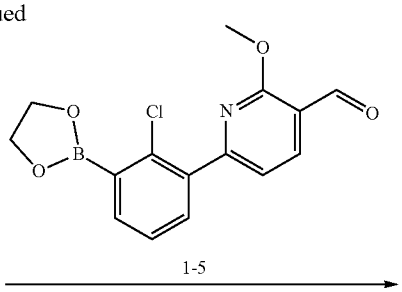

1-5

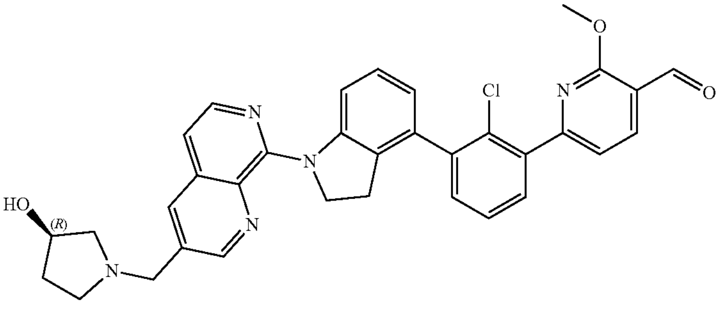

1-14

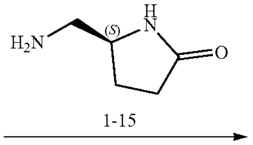

1-15

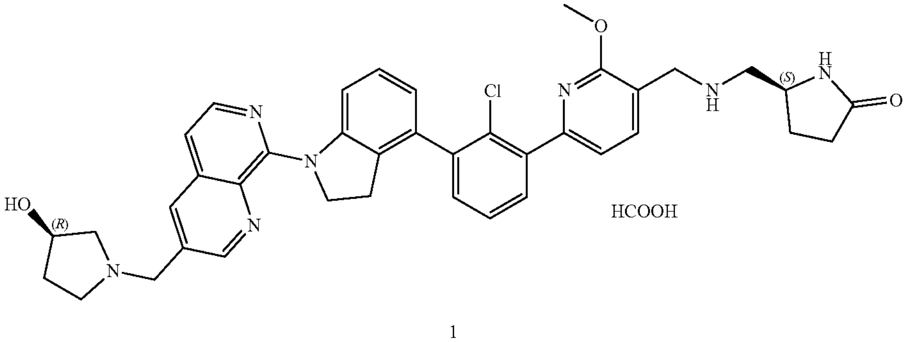

HCOOH

1

Step A: To a mixture of compound 1-1 (5 g, 18.49 mmol) and triisopropyl borate (4.17 g, 22.19 mmol) in 12.5 mL of 2-methyltetrahydrofuran and 50 mL of toluene was added dropwise a n-hexane solution (2.5 M, 8.88 mL) of n-butyllithium at −78° C. The reaction mixture was stirred at −78° C. for 1 hour, then slowly warmed to 25° C. and reacted for another 1 hour. Then 80 mL of hydrochloric acid (1 mol/L) was added thereto to quench the reaction, followed by the addition of 80 mL of water. Then the reaction mixture was extracted with ethyl acetate (80 mL×3). The organic phases were combined, washed with saturated brine (50 mL×2), dried over anhydrous sodium sulfate, and filtered. The filtrate was concentrated to obtain the crude product. To 40 mL of ethyl acetate was added the crude product, stirred at 25° C. for 0.5 hours, and filtered to obtain compound 1-2.

Step B: To a mixture of 30 mL of dioxane and 6 mL of water was added compound 1-2 (3 g, 12.75 mmol), compound 1-3 (2.19 g, 12.75 mmol), potassium carbonate (3.52 g, 25.50 mmol), and $Pd(PPh_3)_4$ (1.47 g, 1.28 mmol). The reaction system was replaced with nitrogen three times and reacted at 85° C. under nitrogen atmosphere for 12 hours. The reaction mixture was cooled to room temperature, then added with 20 mL of water, filtered through diatomite, and extracted with ethyl acetate (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=0:1 to 1:0, v/v) to obtain compound 1-4. MS (ESI) m/z: 328.2 $[M+H]^+$.

Step C: To 20 mL of dioxane solution was added compound 1-4 (1.29 g, 3.93 mmol), bis(pinacolato)diboron (2.00 g, 7.87 mmol), potassium acetate (772.34 mg, 7.87 mmol), and $Pd(dppf)Cl_2 \cdot CH_2Cl_2$ (321.33 mg, 393.48 μmol). The reaction system was replaced with nitrogen three times, and reacted at 85° C. under nitrogen atmosphere for 6 hours. The reaction mixture was cooled to room temperature, added with 15 mL of water, then filtered through diatomite, and extracted with ethyl acetate (40 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=0:1 to 1:0, v/v) to obtain compound 1-5. MS (ESI) m/z: 374.4 $[M+H]^+$.

Step D: A mixture of compound 1-7 (2 g, 8.21 mmol), compound 1-6 (1.52 g, 9.86 mmol, 1.67 mL), sodium carbonate (2.18 g, 20.53 mmol) and $Pd(PPh_3)_4$ (474.59 mg, 410.70 μmol) in tert-butanol (15 mL) and water (15 mL) was heated to 80° C. under nitrogen atmosphere and reacted for 2 hours. The reaction mixture was diluted with water, extracted with ethyl acetate (40 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=0:1 to 1:0, v/v) to obtain compound 1-8. MS (ESI) m/z: 191.1 $[M+H]^+$.

Step E: To a mixture of compound 1-8 (1 g, 5.25 mmol) in dioxane (20 mL) and water (20 mL) was added potassium osmate(VI) dihydrate (9.66 mg, 26.23 μmol). The mixture was stirred at 25° C. for 30 minutes, and then added with sodium periodate (2.63 g, 12.30 mmol) in batches. The reaction mixture was continued to be stirred for 3 hours, quenched with 50% sodium thiosulfate aqueous solution, and extracted with dichloromethane (60 mL×3). The organic phase was washed with saturated brine (30 mL×3), and dried over anhydrous sodium sulfate, and filtered. The filtrate was concentrated to obtain the crude compound 1-9, which was used directly in the next step. MS (ESI) m/z: 193.3 $[M+H]^+$.

Step F: A solution of compound 1-9 (0.64 g, 3.32 mmol) and compound 1-10 (578.99 mg, 6.65 mmol) in dichloromethane (20 mL) was stirred at 25° C. for 30 minutes, and $NaBH(OAc)_3$ (2.82 g, 13.29 mmol) was added thereto. The reaction mixture was stirred at 25° C. for 12 hours, diluted with water, and extracted with dichloromethane (50 mL×3). The organic phases were washed with saturated brine (20 mL), dried over anhydrous sodium sulfate, and filtered. The filtrate was concentrated to obtain the crude product. The crude product was purified by silica gel column chromatography (methanol:dichloromethane=0:1 to 1:0, v/v) to obtain compound 1-11. MS (ESI) m/z: 264.51 $[M+H]^+$.

Step G: Compound 1-11 (0.1 g, 379.19 μmol), compound 1-12 (78.86 mg, 398.15 μmol), and hydrogen chloride in dioxane (4 M, 94.80 μL) were dissolved in tert-butanol (4 mL), heated to 120° C. and stirred for 2 hours. The reaction mixture was cooled to room temperature, quenched with sodium bicarbonate aqueous solution, and extracted with dichloromethane (40 mL×3). The organic phase was washed with saturated brine (20 mL×3), dried over anhydrous sodium sulfate, and filtered. The filtrate was concentrated to obtain the crude product. The crude product was purified by preparative thin-layer chromatography silica gel plate (ethyl acetate) to obtain compound 1-13. MS (ESI) m/z: 427.3 $[M+H]^+$.

Step H: A mixture of compound 1-13 (106 mg, 249.22 μmol), compound 1-5 (93.12 mg, 249.22 μmol), sodium carbonate (66.04 mg, 623.06 μmol), and a solution of $Pd(PPh_3)_4$ (28.80 mg, 24.92 μmol) in dioxane (4 mL) and water (0.8 mL) was heated to 100° C. under nitrogen atmosphere and reacted for 1 hour. The reaction mixture was cooled to room temperature, added with 20 mL of water, then filtered through diatomite, and extracted with ethyl acetate (40 mL×3). The organic phases were combined, washed with saturated brine (20 mL×3), dried over anhydrous sodium sulfate, and filtered. The filtrate was concentrated to obtain the crude product. The crude product was purified by preparative thin-layer chromatography silica gel plate (ethyl acetate) to obtain compound 1-14. MS (ESI) m/z: 592.1 [M+H]+.

Step I: A solution of compound 1-14 (150 mg, 253.34 μmol) and compound 1-15 (57.84 mg, 506.68 μmol) in dichloromethane (8 mL) was stirred at 25° C. for 30 minutes, and $NaBH(OAc)_3$ (2.82 g, 13.29 mmol) was added thereto. The reaction mixture was stirred at 25° C. for 1 hour, diluted with water, and extracted with dichloromethane (20 mL×3). The organic phases were washed with saturated brine (20 mL), dried over anhydrous sodium sulfate, and filtered. The filtrate was concentrated to obtain the crude product. The crude product was purified by preparative HPLC (chromatographic column: Phenomenex luna C18 250*50 mm*15 m; mobile phase: [pure water (0.225% formic acid)–acetonitrile]; acetonitrile %: 12% to 42%, 10 minutes) to obtain compound 1. $^1H$ NMR (400 MHz, DMSO-$d_6$) δ=8.83 (d, J=2.0 Hz, 1H), 8.21-8.17 (m, 2H), 7.83 (d, J=7.6 Hz, 1H), 7.72 (s, 1H), 7.65-7.59 (m, 2H), 7.52 (t, J=7.6 Hz, 1H), 7.44 (dd, J=2.0, 7.6 Hz, 1H), 7.40 (d, J=5.6 Hz, 1H), 7.28 (d, J=7.2 Hz, 1H), 7.19 (t, J=8.0 Hz, 1H), 6.81 (d, J=6.8 Hz, 1H), 4.71-4.54 (m, 2H), 4.30-4.15 (m, 1H), 3.92 (s, 3H), 3.80 (d, J=7.6 Hz, 2H), 3.72 (d, J=2.0 Hz, 2H), 3.67-3.60 (m, 2H), 3.60 (bs, 4H), 2.98 (t, J=8.0 Hz, 2H), 2.77-2.73 (m, 1H), 2.69-2.63 (m, 1H), 2.56 (d, J=6.0 Hz, 2H), 2.30-2.37 (m, 1H), 2.17-1.97 (m, 4H), 1.78-1.50 (m, 2H), MS (ESI) m/z: 690.5 [M+H]+.

Example 2

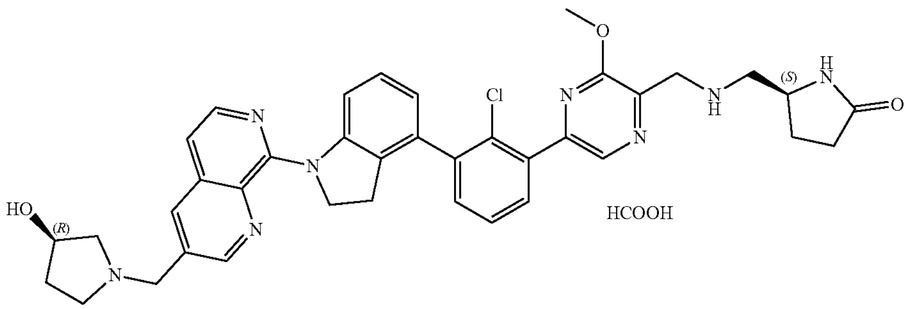

HCOOH

-continued
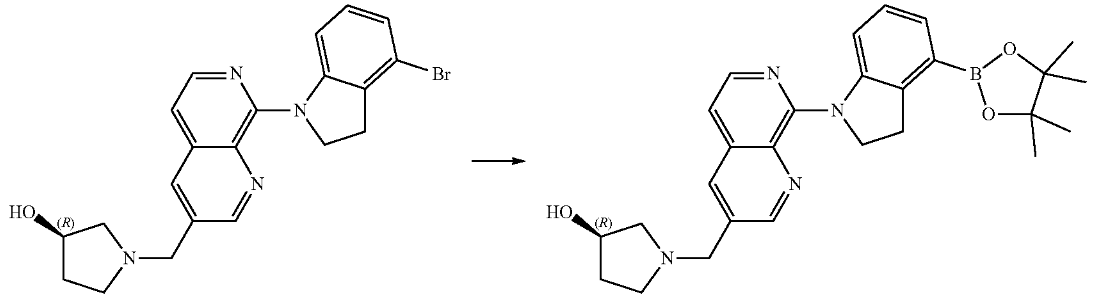
1-13
2-1
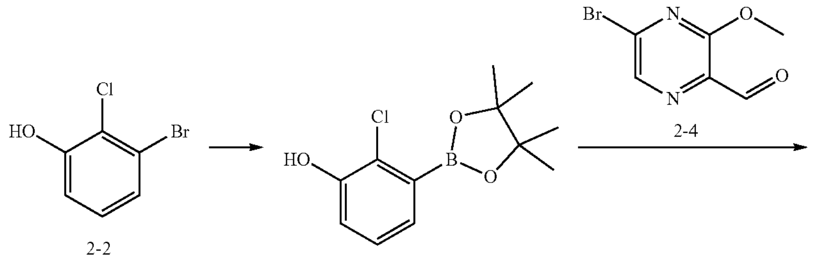
2-4
2-2
2-3
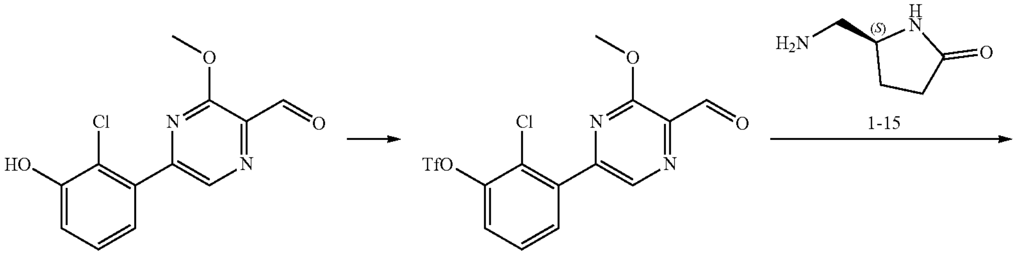
1-15
2-5
2-6
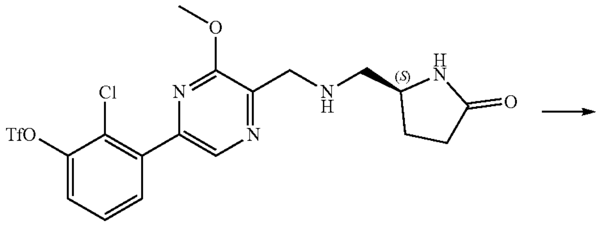
2-7
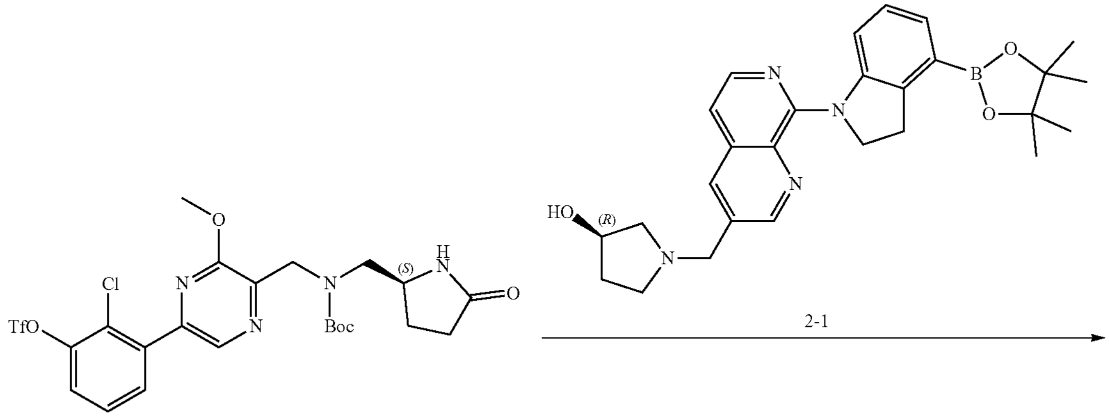
2-1
2-8

-continued

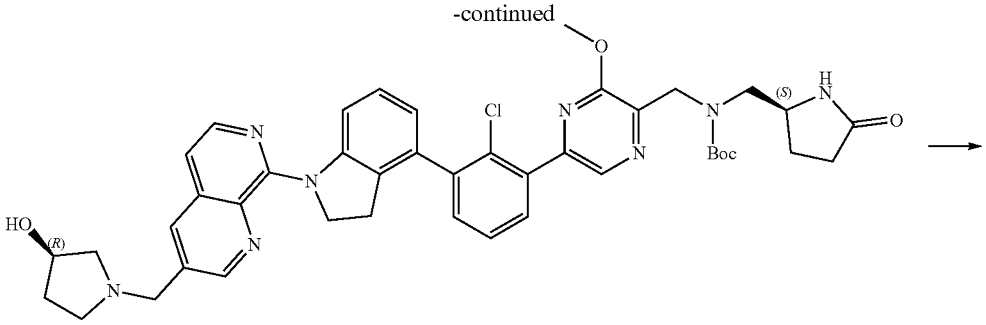

2-9

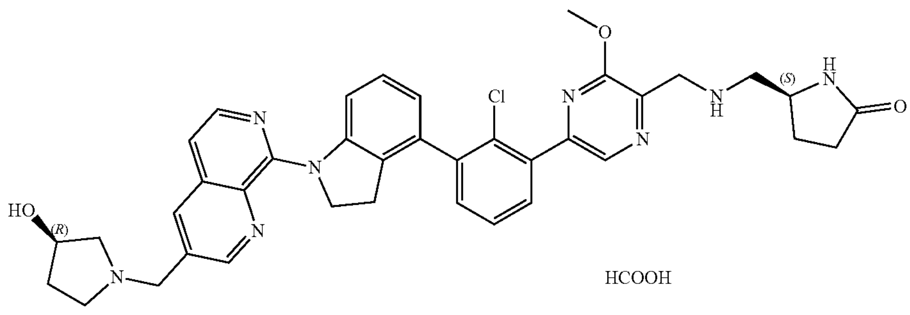

HCOOH

2

Step A: To 10 mL of dioxane solution was added compound 1-13 (0.5 g, 1.18 mmol), bis(pinacolato)diboron (597.052 mg, 2.35 mmol), potassium acetate (346.12 mg, 3.53 mmol), and Pd(dppf)$Cl_2$·$CH_2Cl_2$ (96 mg, 117.56 μmol). The reaction system was replaced with nitrogen three times, and reacted at 100° C. under nitrogen atmosphere for 3 hours. The reaction mixture was cooled to room temperature, added with 10 mL of water, then filtered through diatomite, and extracted with ethyl acetate (30 mL×3). The organic phases were combined, washed with saturated brine (20 mL×3), dried over anhydrous sodium sulfate, and filtered. The filtrate was concentrated to obtain the crude product. The crude product was purified by silica gel column chromatography (petroleum ether:ethyl acetate=2:1 to 0:1, v/v) to obtain compound 2-1. MS (ESI) m/z: 473.3 $[M+H]^+$.

Step B: To 40 mL of dioxane solution was added compound 2-2 (5 g, 24.10 mmol), bis(pinacolato)diboron (7.34 g, 28.92 mmol), potassium acetate (4.73 g, 48.20 mmol), and Pd(dppf)$Cl_2$·$CH_2Cl_2$ (1.97 g, 2.41 mmol). The reaction system was replaced with nitrogen three times, and reacted at 85° C. under nitrogen atmosphere for 12 hours. The reaction mixture was cooled to room temperature and filtered through diatomite. The filter cake was washed with 40 mL of dioxane solution. The filtrates were combined to obtain the crude compound 2-3.

Step C: To a mixture of compound 2-3 (6.13 g, 24.08 mmol) in 80 mL of dioxane solution and 16 mL of water was added compound 2-4 (5.23 g, 24.08 mmol), potassium carbonate (8.32 g, 60.21 mmol), and Pd(dppf)$Cl_2$·$CH_2Cl_2$ (1.97 g, 2.41 mmol). The reaction system was replaced with nitrogen three times and reacted at 85° C. under nitrogen atmosphere for 4 hours. The reaction mixture was cooled to room temperature, added with 20 mL of water, then filtered through diatomite, and extracted with ethyl acetate (80 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 2-5. MS (ESI) m/z: 265.1 $[M+H]^+$.

Step D: To a solution of compound 2-5 (3.15 g, 11.90 mmol) and N,N-diisopropylethylamine (9.23 g, 71.41 mmol) in 60 mL of dichloromethane was carefully and dropwise added trifluoromethanesulfonic anhydride (4.37 g, 15.47 mmol) at −78° C. The reaction mixture was stirred at −78° C. for 0.5 hours, quenched with 50 mL of saturated citric acid solution, then added with 20 mL of water, and extracted with dichloromethane (50 mL×3). The organic phases were combined, washed with saturated brine (20 mL×2), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 2-6.

Step E: To a solution of compound 2-6 (1.3 g, 3.28 mmol) and compound 1-15 (748.07 mg, 6.55 mmol) in dichloromethane (12 mL) was added with $NaBH(OAc)_3$ (3.47 g, 16.38 mmol). The reaction mixture was stirred at 25° C. for 2 hours, diluted with 100 mL of water, and extracted with ethyl acetate (100 mL×2). The organic phases were washed with saturated brine (100 mL), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 2-7. MS (ESI) m/z: 495.1 $[M+H]^+$.

Step F: To a solution of compound 2-7 (0.5 g, 1.01 mmol) and di-tert-butyl dicarbonate (441.02 mg, 2.02 mmol) in tetrahydrofuran (14 mL) was added triethylamine (306.72 mg, 3.03 mmol). The reaction mixture was stirred at 25° C. for 2 hours, added with 100 mL of water, and extracted with ethyl acetate (100 mL×2). The organic phases were washed with saturated brine (100 mL), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 2-8. MS (ESI) m/z: 595.1 $[M+H]^+$.

Step G: A mixture of compound 2-8 (100 mg, 211.69 μmol), compound 2-1 (125.95 mg, 211.69 μmol), sodium carbonate (56.09 mg, 529.23 μmol), and $Pd(PPh_3)_4$ (24.46 mg, 21.17 μmol) in dioxane (2 mL) and water (0.4 mL) was replaced with nitrogen three times, heated to 100° C. under nitrogen atmosphere, and stirred for 1 hour. The reaction mixture was cooled to room temperature, added with 10 mL of water, then filtered through diatomite, and extracted with ethyl acetate (30 mL×3). The organic phases were combined, washed with saturated brine (20 mL×3), dried over anhydrous sodium sulfate, and filtered. The filtrate was concentrated to obtain the crude product. The crude product was purified by preparative thin-layer chromatography silica gel plate (ethyl acetate) to obtain compound 2-9. MS (ESI) m/z: 791.5 [M+H]+.

Step H: To a solution of compound 2-9 (0.09 g, 113.73 μmol) in dichloromethane (1.8 mL) was added trifluoroacetic acid (924.00 mg, 8.10 mmol). The reaction mixture was stirred at 25° C. for 10 minutes and concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 10% to 40%, 10 minutes) to obtain compound 2. $^1H$ NMR (400 MHz, DMSO-$d_6$) δ=8.89 (d, J=2.0 Hz, 1H), 8.56 (s, 1H), 8.31 (s, 1H), 8.22 (d, J=5.6 Hz, 1H), 8.13 (s, 1H), 7.72-7.67 (m, 2H), 7.65 (d, J=8.0 Hz, 1H), 7.60 (t, J=7.6 Hz, 1H), 7.57-7.53 (m, 1H), 7.42 (d, J=5.6 Hz, 1H), 7.20 (t, J=8.0 Hz, 1H), 6.83 (d, J=7.2 Hz, 1H), 5.15-4.94 (m, 1H), 4.76-4.53 (m, 2H), 4.29 (s, 3H), 4.03 (s, 3H), 3.90-3.78 (m, 2H), 3.04-2.95 (m, 6H), 2.88-2.63 (m, 3H), 2.21-2.03 (m, 4H), 1.85-1.64 (m, 2H); MS (ESI) m/z: 691.2 $[M+H]^+$.

Example 3

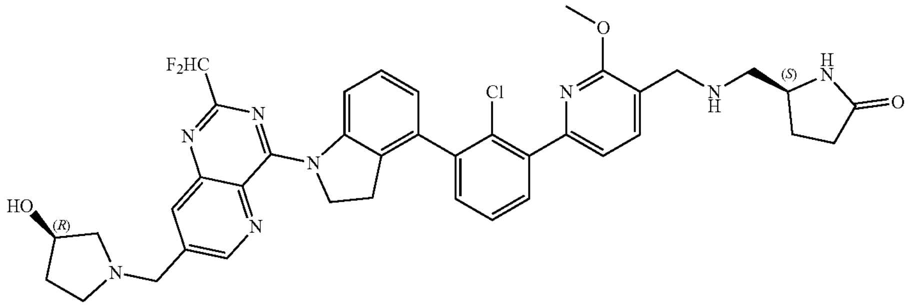

3

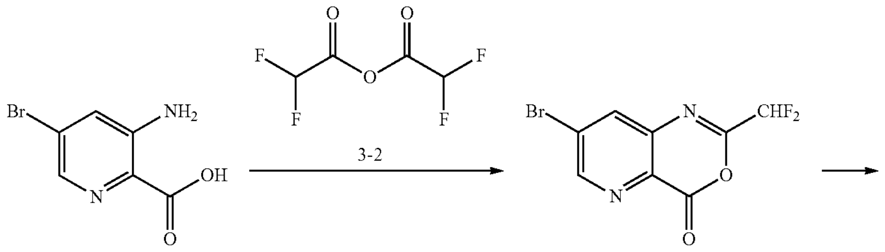

3-1 3-3

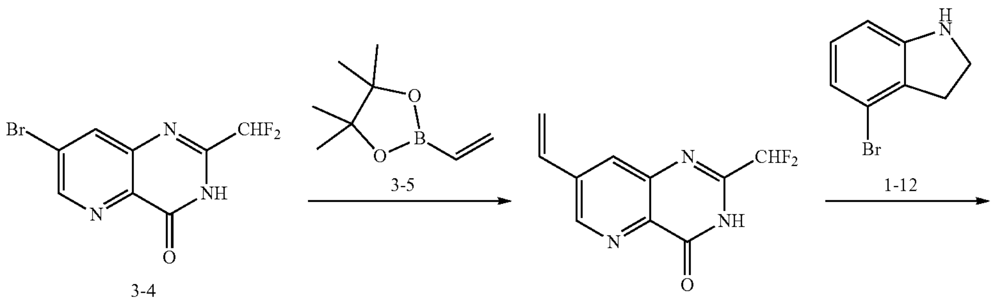

3-4 3-6

-continued

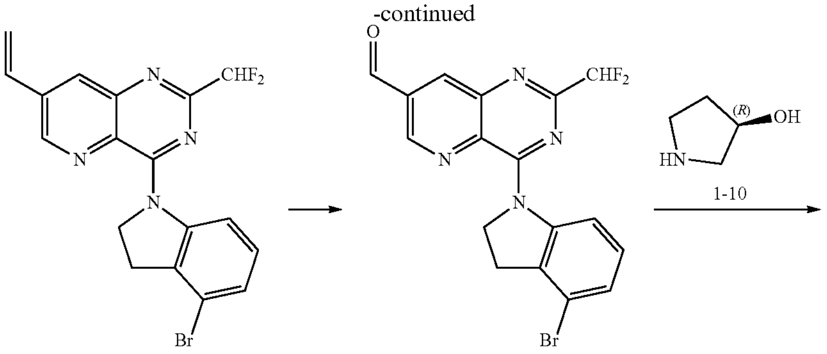

3-7 3-8

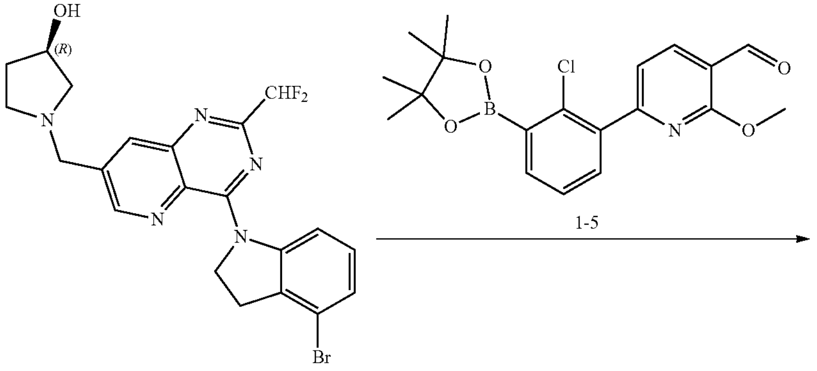

3-9

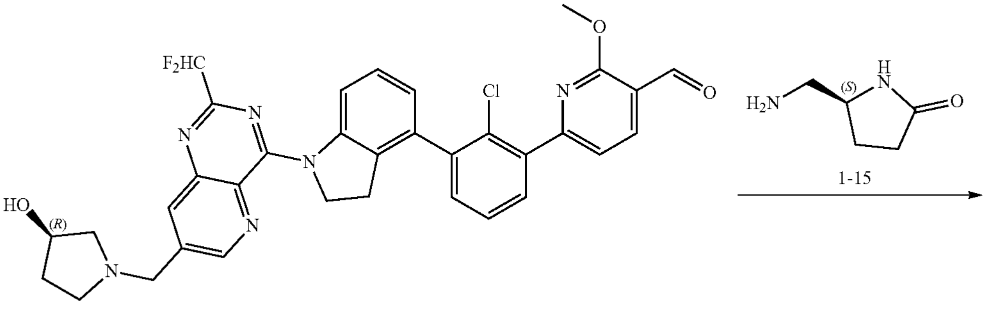

3-10

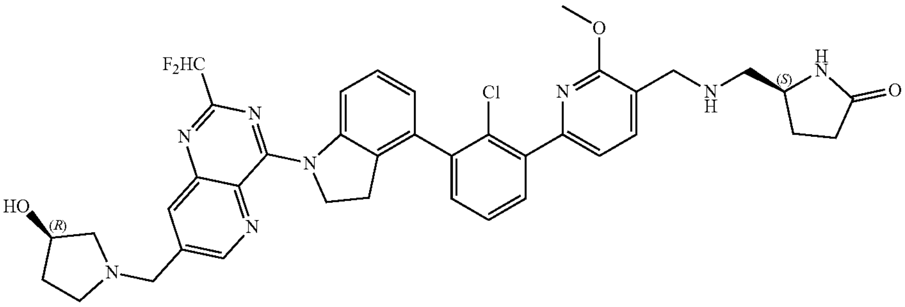

3

Step A: Compound 3-1 (10 g, 46.08 mmol) and compound 3-2 (64.16 g, 368.63 mmol) were stirred at 60° C. for 12 hours. The mixture was concentrated under reduced pressure to obtain compound 3-3. MS (ESI) m/z: 277.2 $[M+H]^+$ Step B: Compound 3-3 (6.38 g, 23.03 mmol) and ammonium water (28.83 g, 230.31 mmol, 31.68 mL, 28% amine) were stirred at 85° C. for 5 hours in a sealed container. The mixture was concentrated to obtain the crude product, to which 50 mL of solvent (dichloromethane/methanol=10/1) was added. The mixture was stirred at 25° C. for 1 hour, then filtered. The collected solids were concentrated to obtain compound 3-4. MS (ESI) m/z: 276.2 $[M+H]^+$ Step C: To a mixture of 20 mL of dioxane and 20 mL of water was added compound 3-4 (1.7 g, 6.16 mmol), compound 3-5 (1.9 g, 12.32 mmol), potassium phosphate (3.27 g, 15.40 mmol), and $Pd(PPh_3)_4$ (711.66 mg, 615.86 μmol). The reaction system was replaced with nitrogen three times and reacted at 100° C. under nitrogen atmosphere for 12 hours. The reaction mixture was concentrated to obtain the crude product. The crude product was purified by silica gel column chromatography (petroleum ether:ethyl acetate=0:1 to 1:0, v/v) to obtain compound 3-6. MS (ESI) m/z: 224.3 $[M+H]^+$.

Step D: To a solution of compound 3-6 (0.35 g, 1.57 mmol), N,N-dimethylaniline (285.06 mg, 2.35 mmol), and benzyltriethylammonium chloride (714.41 mg, 3.14 mmol) in 8 mL of acetonitrile was added phosphorus oxychloride (1.44 g, 9.41 mmol). The reaction system was reacted at 75° C. for 2 hours. The reaction mixture was concentrated after cooling to room temperature. Then the mixture and compound 1-12 (1.44 g, 9.41 mmol) were dissolved in 8 mL of isopropanol solution, and methanesulfonic acid (301.44 mg, 3.14 mmol) was added thereto. The reaction system was reacted at 80° C. for 2 hours before being concentrated, dissolved in a mixture of 30 mL of ethyl acetate and 20 mL of sodium bicarbonate solution, extracted with ethyl acetate (30 mL×2). The organic phases were combined, washed with saturated brine (20 mL×3), dried over anhydrous sodium sulfate, and filtered. The filtrate was concentrated to obtain the crude product. The crude product was purified by silica gel column chromatography (petroleum ether:ethyl acetate=0:1 to 1:0, v/v) to obtain compound 3-7. MS (ESI) m/z: 403.2 $[M+H]^+$.

Step E: To a mixture of compound 3-7 (0.1 g, 248.00 μmol) in tetrahydrofuran (4 mL) and water (1 mL) was added potassium osmate(VI) dihydrate (913.77 μg, 2.48 μmol) and sodium periodate (265.23 mg, 1.24 mmol). The reaction system was reacted at 25° C. for 3 hours, then quenched with 20 mL of 50% sodium thiosulfate solution. The mixture was then extracted with dichloromethane (30 mL×3), and the organic phases were combined, washed with saturated brine (30 mL×2), dried over anhydrous sodium sulfate, and filtered. The filtrate was concentrated to obtain the crude compound 3-8. MS (ESI) m/z: 405.2 $[M+H]^+$.

Step F: A solution of compound 3-8 (100 mg, 246.79 μmol) and compound 1-10 (43 mg, 493.59 μmol) in dichloromethane (6 mL) was stirred at 25° C. for 0.5 hours, and $NaBH(OAc)_3$ (209.22 mg, 987.18 μmol) was added thereto. The reaction mixture was stirred at 25° C. for 2 hours, added with 10 mL of water, and extracted with dichloromethane (20 mL×3). The organic phase was washed with saturated brine (20 mL×3), dried over anhydrous sodium sulfate, and filtered. The filtrate was concentrated to obtain the crude compound 3-9. MS (ESI) m/z: 478.3 $[M+H]^+$.

Step G: A mixture of compound 3-9 (90 mg, 188.95 μmol), compound 1-5 (70.60 mg, 188.95 μmol), sodium carbonate (50.07 mg, 472.38 μmol), and $Pd(PPh_3)_4$ (65.50 mg, 56.69 μmol) in dioxane (5 mL) and water (1 mL) was heated to 100° C. under nitrogen atmosphere, and stirred for 1 hour. The reaction mixture was added with 20 mL of water, filtered through diatomite, and extracted with ethyl acetate (30 mL×3). The organic phases were combined, washed with saturated brine (30 mL×3), dried over anhydrous sodium sulfate, and filtered. The filtrate was concentrated to obtain the crude product. The crude product was purified by preparative thin-layer chromatography silica gel plate (petroleum ether:ethyl acetate=1:1) to obtain compound 3-10. MS (ESI) m/z: 643.5 $[M+H]^+$.

Step H: A solution of compound 3-10 (40 mg, 62.20 μmol) and compound 1-15 (14.20 mg, 124.40 μmol) in dichloromethane (2 mL) was stirred at 25° C. for 0.5 hours, and $NaBH(OAc)_3$ (65.91 mg, 311.00 μmol) was added thereto. The reaction mixture was stirred at 25° C. for 0.5 hours, diluted with 10 mL of water, and extracted with dichloromethane (20 mL×5). The organic phase was washed with saturated brine (20 mL×2), dried over anhydrous sodium sulfate, and filtered. The filtrate was concentrated to obtain the crude product. The crude product was purified by preparative HPLC (chromatographic column: Phenomenex Synergi C18 150*25 mm*10 m; mobile phase: [pure water (0.225% formic acid)-acetonitrile]; acetonitrile %: 14% to 44%, 10 minutes) to obtain the formate of compound 3. $^1H$ NMR (400 MHz, $CD_3OD$) δ=8.98-8.86 (m, 1H), 8.74 (d, J=8.0 Hz, 1H), 8.50 (s, 1H), 8.14 (s, 1H), 7.76 (d, J=7.6 Hz, 1H), 7.61 (d, J=7.6 Hz, 1H), 7.53-7.45 (m, 1H), 7.42-7.32 (m, 2H), 7.26 (d, J=7.2 Hz, 1H), 7.14-6.98 (m, 1H), 6.87-6.51 (m, 1H), 5.08-5.02 (m, 2H), 4.41-4.38 (m, 1H), 4.03 (s, 3H), 3.98-3.80 (m, 5H), 3.20-2.98 (m, 2H), 2.95-2.84 (m, 2H), 2.83-2.72 (m, 2H), 2.72-2.58 (m, 2H), 2.44-2.11 (m, 4H), 1.92-1.68 (m, 2H); MS (ESI) m/z: 741.2 $[M+H]^+$.

Example 4: Compound 4

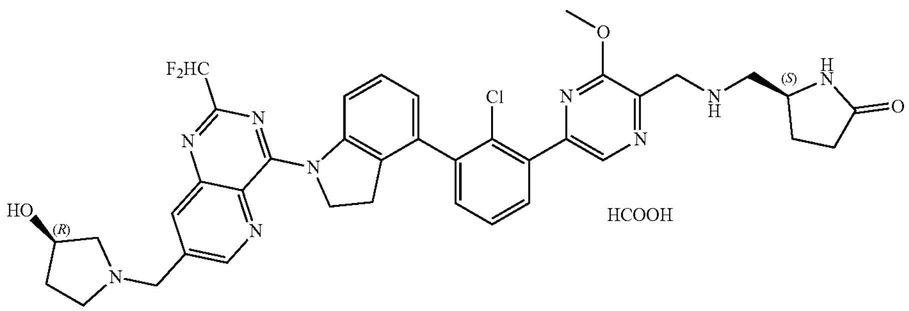

-continued
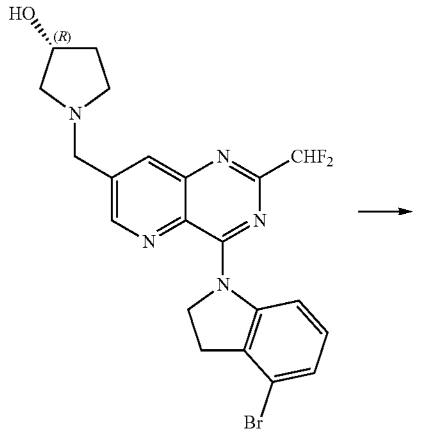
3-9
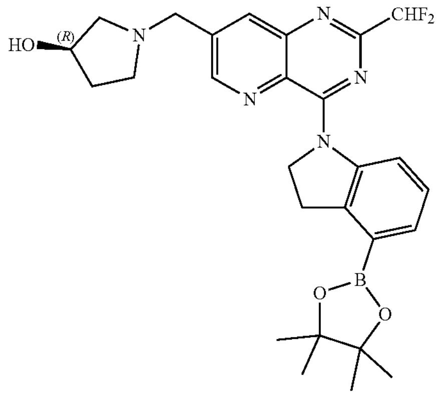
4-1
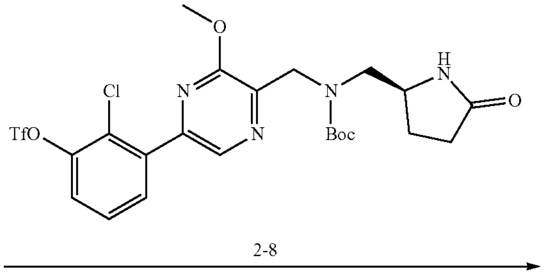
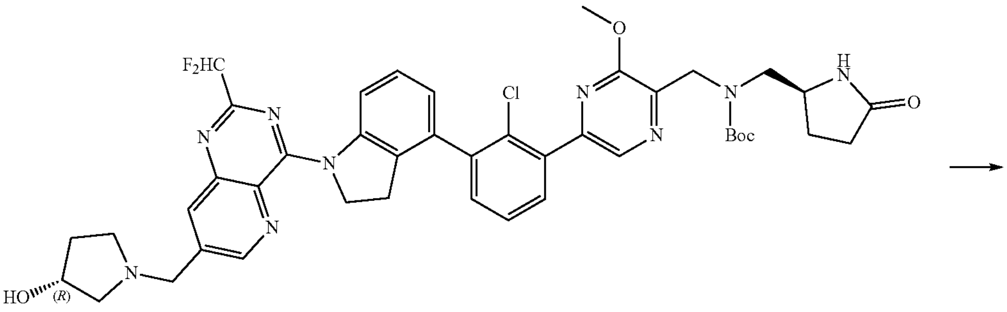
4-2
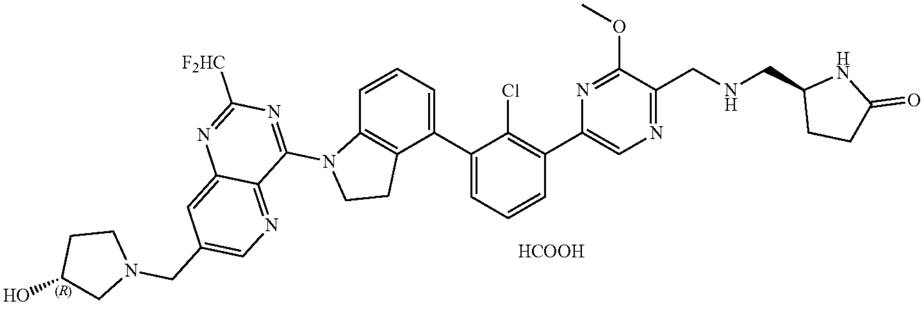
4

Step A: To 10 mL of dioxane solution was added compound 3-9 (0.2 g, 419.89 μmol), bis(pinacolato)diboron (213.25 mg, 839.78 μmol), potassium acetate (123.62 mg, 1.26 mmol), and $Pd(dppf)Cl_2{\cdot}CH_2Cl_2$ (34.29 mg, 41.99 μmol). The reaction system was replaced with nitrogen three times, and reacted at 95° C. under nitrogen atmosphere for 1 hour. The reaction mixture was cooled to room temperature, added with 100 mL of water, and extracted with ethyl acetate (100 mL×2). The organic phases were combined, washed with saturated brine (50 mL×2), dried over anhydrous sodium sulfate, and filtered. The filtrate was concentrated to obtain the crude product. The crude product was purified by thin-layer chromatography (dichloromethane: methanol=10:1) to obtain compound 4-1. MS (ESI) m/z: 524.2 $[M+H]^+$.

Step B: A mixture of compound 4-1 (90 mg, 171.96 μmol), compound 2-8 (112.54 mg, 189.15 μmol), sodium carbonate (36.45 mg, 343.92 μmol), and $Pd(PPh_3)_4$ (19.87 mg, 17.20 μmol) in dioxane (8 mL) and water (2 mL) was replaced with nitrogen three times, heated to 100° C. under nitrogen atmosphere, and stirred for 1 hour. The reaction mixture was cooled to room temperature, added with 50 mL of water, and extracted with ethyl acetate (25 mL×2). The organic phases were combined, washed with saturated brine (25 mL×2), dried over anhydrous sodium sulfate, and filtered. The filtrate was concentrated to obtain the crude product. The crude product was purified by preparative thin-layer chromatography (dichloromethane:methanol=10:1) to obtain compound 4-2. MS (ESI) m/z: 842.3 $[M+H]^+$.

Step C: To a solution of compound 4-2 (80 mg, 94.97 μmol) in dichloromethane (6 mL) was added trifluoroacetic acid (3.08 g, 27.01 mmol). The reaction mixture was stirred at 25° C. for 30 minutes, and then concentrated to obtain the crude product. The crude product was purified by preparative HPLC (chromatographic column: Phenomenex luna C18 150*25 mm*10 m; mobile phase: [pure water (0.225% formic acid)–acetonitrile]; acetonitrile %: 13% to 43%, 10 minutes) to obtain the formate of compound 4. $^1$H NMR (400 MHz, DMSO-$d_6$) δ=8.92 (d, J=1.6 Hz, 1H), 8.65 (d, J=8.0 Hz, 1H), 8.52 (s, 1H), 8.18 (d, J=1.6 Hz, 1H), 8.14 (s, 1H), 7.72 (dd, J=, 1H), 7.68 (s, 1H), 7.61 (t, 1H), 7.54 (dd, 1H), 7.42 (t, J=8.0 Hz, 1H), 7.13-6.75 (m, 2H), 5.00 (br t, J=8.0 Hz, 2H), 4.28-4.20 (m, 1H), 4.10 (s, 2H), 4.01 (s, 3H), 3.98-3.82 (m, 3H), 3.79-3.69 (m, 1H), 3.15-3.01 (m, 2H), 2.85-2.70 (m, 4H), 2.62-2.53 (m, 1H), 2.46 (br d, J=8.0 Hz, 2H), 2.20-1.97 (m, 4H), 1.80-1.68 (m, 1H), 1.66-1.54 (m, 1H); MS (ESI) m/z: 742.2 $[M+H]^+$.

Example 5: Compound 5

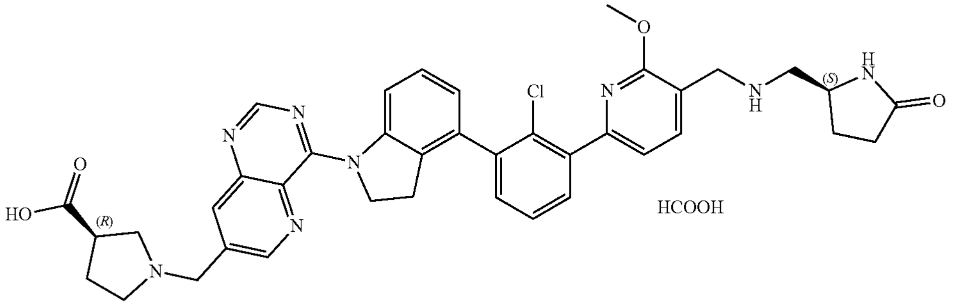

HCOOH

5

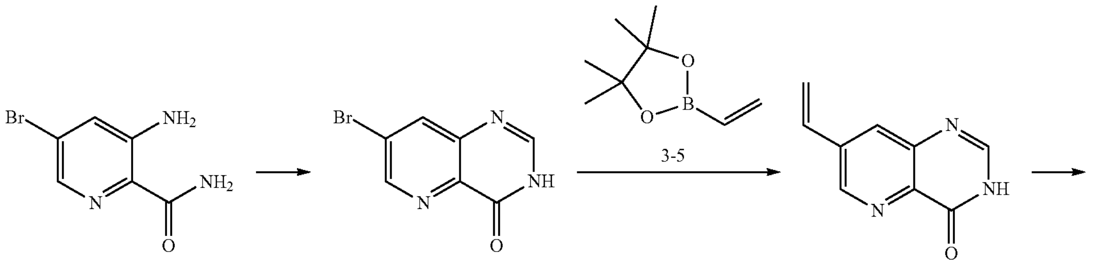

5-1 5-2 5-3

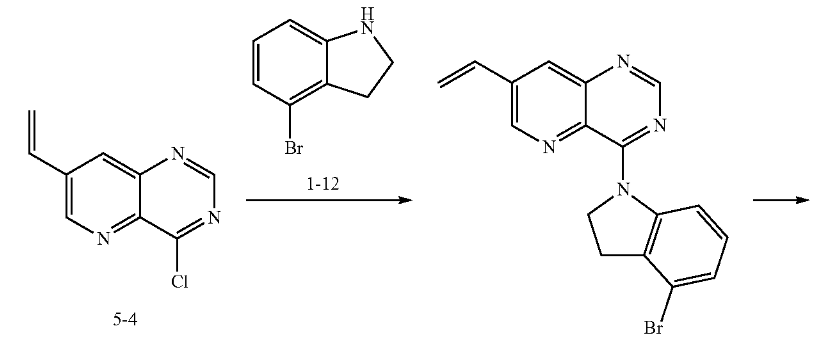

5-4 5-5

-continued

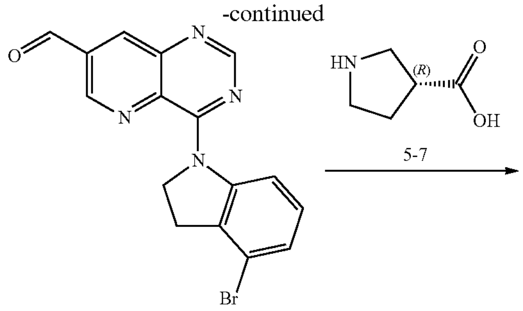

5-6

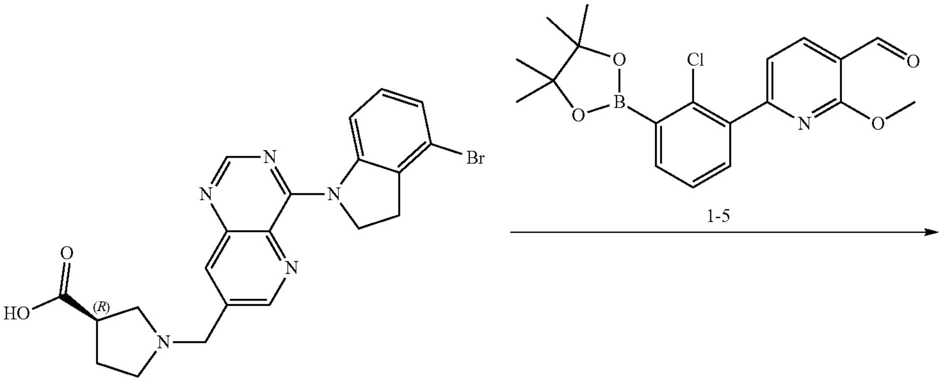

5-8

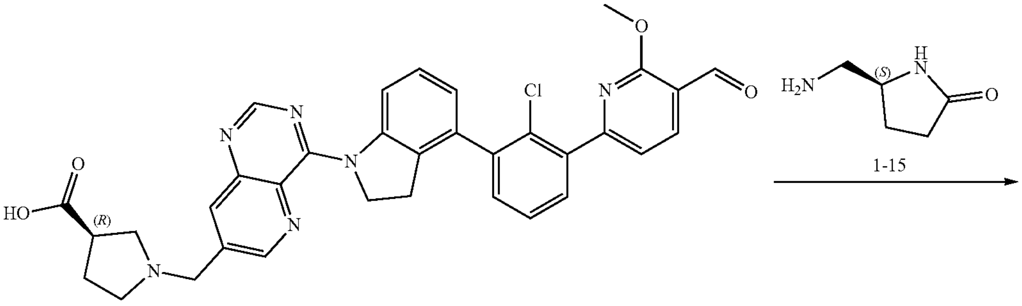

5-9

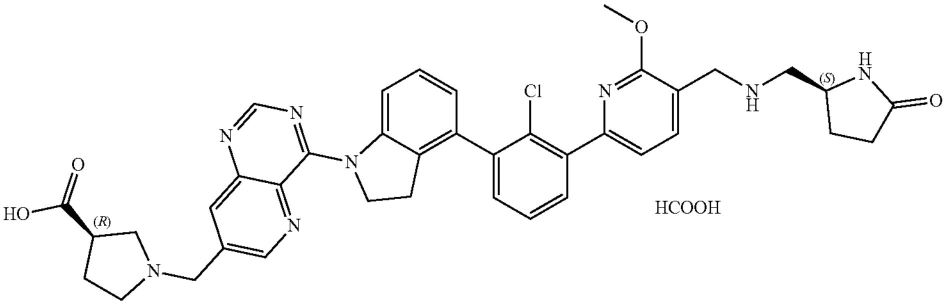

5

Step A: A mixture of compound 5-1 (500 mg, 2.31 mmol) and triethyl orthoformate (9.81 g, 66.21 mmol) was reacted at 110° C. for 5 hours. The reaction mixture was concentrated to obtain the crude compound 5-2.

Step B: To a mixture of 20 mL of dioxane and 4 mL of water was added compound 5-2 (550 mg, 2.43 mmol), compound 3-5 (749.53 mg, 4.87 mmol), potassium phosphate (1.29 g, 6.08 mmol), and $Pd(PPh_3)_4$ (281.18 mg, 243.33 μmol). The reaction system was replaced with nitrogen three times and reacted at 85° C. under nitrogen atmosphere for 12 hours. The reaction mixture was concentrated to obtain the crude compound 5-3. MS (ESI) m/z: 174.2 $[M+H]^+$.

Step C: To a solution of compound 5-3 (2.39 g, 13.80 mmol), N,N-dimethylaniline (2.51 g, 20.70 mmol), and benzyltriethylammonium chloride (6.29 g, 27.60 mmol) in 25 mL of acetonitrile was added phosphorus oxychloride (12.70 g, 82.81 mmol). The reaction system was reacted at 75° C. for 2 hours, and the reaction mixture was concentrated, added with ice and 30 mL of sodium bicarbonate solution, and then extracted with ethyl acetate (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 5-4. MS (ESI) m/z: 192.1 $[M+H]^+$.

Step D: To a solution of compound 5-4 (120 mg, 626.25 μmol) and compound 1-12 (124.03 mg, 626.25 μmol) in 5 mL of isopropanol was added methanesulfonic acid (120.38 mg, 1.25 mmol). The system was reacted at 80° C. for 2 hours, then added with 20 mL of sodium bicarbonate solution, and extracted with ethyl acetate (50 mL×3). The organic phases were combined, washed with saturated brine (30 mL×2), dried over anhydrous sodium sulfate, filtered, and then concentrated to obtain the crude compound 5-5. MS (ESI) m/z: 353.0 $[M+H]^+$.

Step E: To a mixture of compound 5-5 (227 mg, 6442.67 μmol) in tetrahydrofuran (25 mL) and water (5 mL) was added potassium osmate(VI) dihydrate (2.37 mg, 6.43 μmol) and sodium periodate (687.30 mg, 3.21 mmol). The reaction system was reacted at 25° C. for 12 hours, then quenched with 20 mL of 50% sodium thiosulfate solution. The mixture was then extracted with dichloromethane (60 mL×3), and the organic phases were combined, washed with saturated brine (30 mL×2), dried over anhydrous sodium sulfate, and filtered. The filtrate was concentrated to obtain the crude product. The crude product was purified by preparative thin-layer chromatography silica gel plate (petroleum ether: ethyl acetate=1:1) to obtain compound 5-6. MS (ESI) m/z: 355.3 $[M+H]^+$.

Step F: A solution of compound 5-6 (90 mg, 253.39 μmol) and compound 5-7 (58.34 mg, 506.77 μmol) in 6 mL of dichloromethane was stirred at 25° C. for 0.5 hours, and $NaBH(OAc)_3$ (161.11 mg, 760.16 μmol) was added thereto. The reaction system was stirred at 25° C. for 12 hours, then added with 10 mL of water, and extracted with dichloromethane (50 mL×5). The organic phase was washed with saturated brine (20 mL×1), dried over anhydrous sodium sulfate, and filtered. The filtrate was concentrated to obtain the crude compound 5-8. MS (ESI) m/z: 454.2 $[M+H]^+$.

Step G: A mixture of compound 5-8 (120 mg, 264.13 μmol), compound 1-5 (128.30 mg, 343.37 μmol), sodium carbonate (69.99 mg, 660.33 μmol), and $Pd(PPh_3)_4$ (30.52 mg, 26.41 μmol) in dioxane (10 mL) and water (2 mL) was replaced with nitrogen three times, heated to 100° C. under nitrogen atmosphere, and stirred for 1 hour. The reaction mixture was filtered through diatomite. The filter cake was washed with 100 mL of dichloromethane. The filtrates were combined, and concentrated to obtain the crude product. The crude product was purified by preparative thin-layer chromatography silica gel plate (dichloromethane:methanol=5:1) to obtain compound 5-9. MS (ESI) m/z: 621.1 $[M+H]^+$.

Step H: A solution of compound 5-9 (45 mg, 72.45 μmol) and compound 1-15 (16.54 mg, 144.91 μmol) in 2 mL of dichloromethane was stirred at 25° C. for 0.5 hours, and $NaBH(OAc)_3$ (76.78 mg, 362.27 μmol) was added thereto. The reaction system was stirred at 25° C. for 12 hours, diluted with 10 mL of water, and extracted with dichloromethane (20 mL×5). The organic phase was washed with saturated brine (20 mL×1), dried over anhydrous sodium sulfate, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 8% to 38%, 12 minutes) to obtain the formate of compound 5. $^1H$ NMR (400 MHz, DMSO-$d_6$) δ=8.84 (d, J=2.0 Hz, 1H), 8.74 (s, 1H), 8.52 (d, J=8.0 Hz, 1H), 8.23 (s, 1H), 8.07 (d, J=1.6 Hz, 1H), 7.83 (d, J=7.6 Hz, 1H), 7.71 (s, 1H), 7.65 (dd, J=1.6, 7.6 Hz, 1H), 7.54 (t, J=7.6 Hz, 1H), 7.46 (dd, J=2.0, 7.6 Hz, 1H), 7.38 (t, J=7.6 Hz, 1H), 7.29 (d, J=7.6 Hz, 1H), 7.03 (d, J=6.8 Hz, 1H), 4.99-4.88 (m, 2H), 3.93 (s, 3H), 3.85 (d, J=11.2 Hz, 2H), 3.73 (d, J=2.0 Hz, 2H), 3.10-2.92 (m, 4H), 2.79-2.69 (m, 2H), 2.62-2.55 (m, 4H), 2.17-1.94 (m, 5H), 1.78-1.60 (m, 1H); MS (ESI) m/z: 719.2 $[M+H]^+$.

Example 6: Compound 6

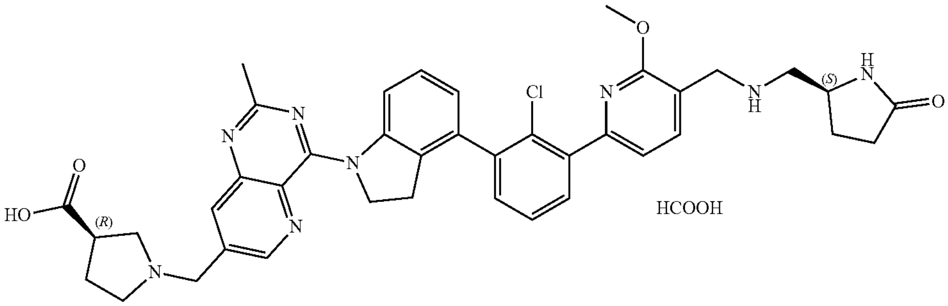

6

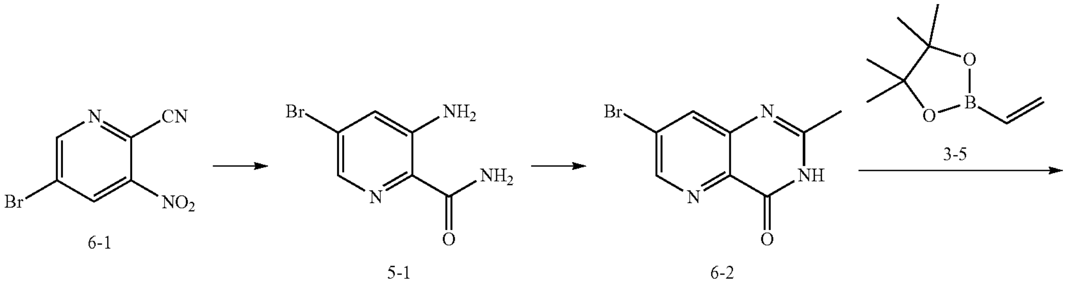

6-1

5-1

6-2

3-5

-continued
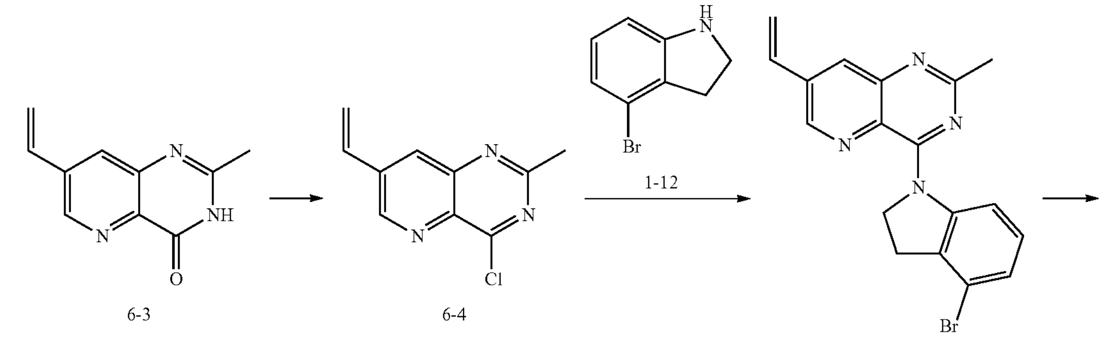
6-3
6-4
6-5
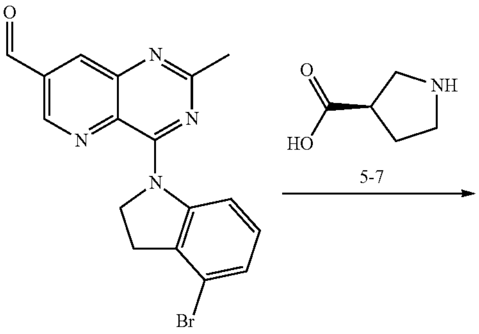
6-6
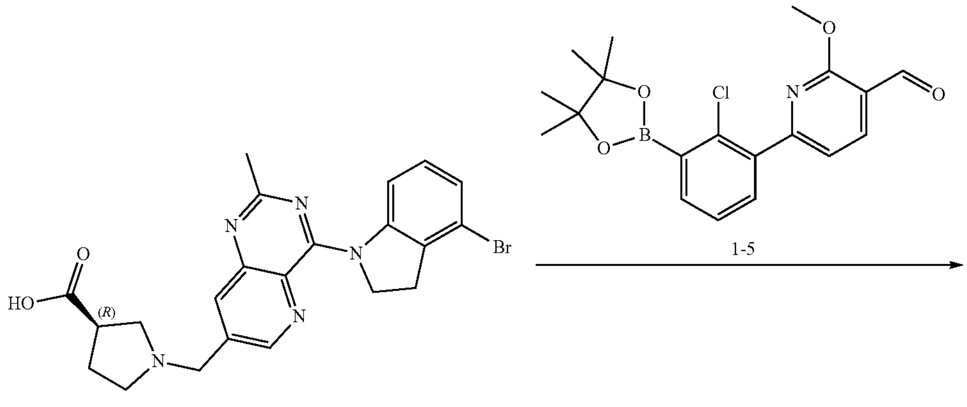
6-7
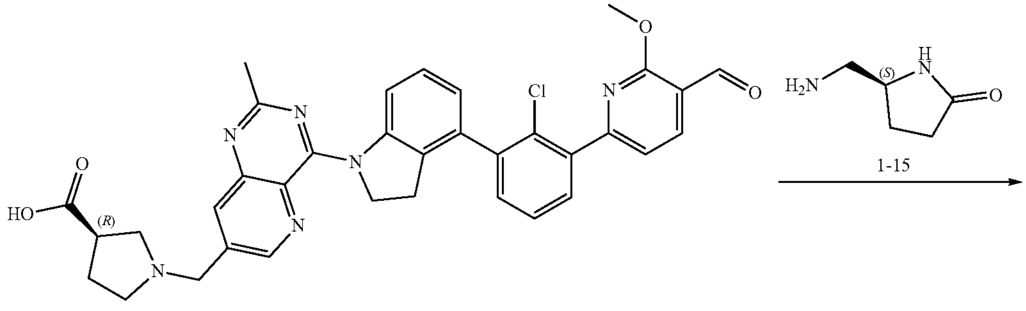
6-8

-continued

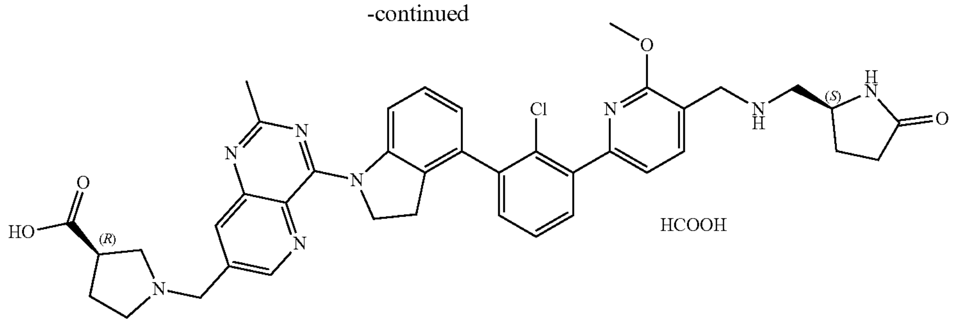

HCOOH

6

Step A: To 40 mL of dioxane was added compound 6-1 (8 g, 35.09 mmol), then added with 20 mL of water and ammonium water (18.01 g, 143.86 mmol, purity of 28%). The reaction system was stirred at 25° C. for 10 minutes, then sodium hydrosulfite (19.98 g, 114.74 mmol) was added thereto in batches, and the reaction was continued at 25° C. for 5 hours. The reaction mixture was filtered through diatomite, and the filter cake was washed with 100 mL of ethyl acetate. The filtrate was then diluted with 20 mL of water and extracted with ethyl acetate (40 mL×5). The organic phases were combined, washed with saturated brine (20 mL×1), dried over anhydrous sodium sulfate, and then filtered. The filtrate was concentrated to obtain the crude product. The crude product was purified by silica gel column chromatography (petroleum ether:ethyl acetate=1:0 to 0:1, v/v) to obtain compound 5-1.

Step B: A mixture of compound 5-1 (450 mg, 2.08 mmol) and triethyl orthoacetate (7.96 g, 49.10 mmol) was reacted at 120° C. for 5 hours. The reaction mixture was concentrated to obtain the crude compound 6-2. MS (ESI) m/z: 240.2 $[M+H]^+$.

Step C: To a mixture of 15 mL of dioxane and 3 mL of water was added compound 6-2 (690 mg, 2.87 mmol), compound 3-5 (885.37 mg, 5.75 mmol), potassium phosphate (1.53 g, 7.19 mmol), and $Pd(PPh_3)_4$ (332.15 mg, 287.43 μmol). The reaction system was replaced with nitrogen three times and reacted at 95° C. under nitrogen atmosphere for 12 hours. The reaction mixture was concentrated to obtain the crude compound 6-3. MS (ESI) m/z: 188.3 $[M+H]^+$.

Step D: To a solution of compound 6-3 (2.2 g, 11.75 mmol), N,N-dimethylaniline (2.14 g, 17.63 mmol), and benzyltriethylammonium chloride (5.35 g, 23.50 mmol) in 40 mL of acetonitrile was added phosphorus oxychloride (10.81 g, 70.51 mmol). The reaction system was reacted at 75° C. for 2 hours. The reaction mixture was concentrated, added with ice and 30 mL of sodium bicarbonate solution, extracted with ethyl acetate (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 6-4. MS (ESI) m/z: 206.0 $[M+H]^+$.

Step E: To a solution of compound 6-4 (230 mg, 1.12 mmol) and compound 1-12 (221.52 mg, 1.12 mmol) in 10 mL of isopropanol was added methanesulfonic acid (214.98 mg, 2.24 mmol). The mixture was reacted at 80° C. for 2 hours, then added with 30 mL of sodium bicarbonate solution, and extracted with ethyl acetate (50 mL×3). The organic phases were combined, washed with saturated brine (30 mL×2), dried over anhydrous sodium sulfate, filtered, and then concentrated to obtain the crude product. The crude product was purified by preparative thin-layer chromatography silica gel plate (petroleum ether:ethyl acetate=1:1) to obtain compound 6-5. MS (ESI) m/z: 367.3 $[M+H]^+$.

Step F: To a mixture of compound 6-5 (238 mg, 648.07 μmol) in tetrahydrofuran (25 mL) and water (5 mL) was added potassium osmate(VI) dihydrate (2.39 mg, 6.48 μmol) and sodium periodate (693.08 mg, 3.24 mmol). The reaction system was reacted at 25° C. for 5 hours, then quenched with 30 mL of 50% sodium thiosulfate solution. The mixture was then extracted with dichloromethane (80 mL×3), and the organic phases were combined, washed with saturated brine (30 mL×2), dried over anhydrous sodium sulfate, and filtered. The filtrate was concentrated to obtain the crude compound 6-6. MS (ESI) m/z: 369.3 $[M+H]^+$.

Step G: A solution of compound 6-6 (330 mg, 893.79 μmol) and compound 5-7 (205.80 mg, 1.79 mmol) in 15 mL of dichloromethane was stirred at 25° C. for 0.5 hours, and $NaBH(OAc)_3$ (568.29 mg, 2.68 mmol) was added thereto. The reaction system was stirred at 25° C. for 12 hours, added with 10 mL of water, and extracted with dichloromethane (50 mL×5). The organic phase was washed with saturated brine (20 mL×1), dried over anhydrous sodium sulfate, and filtered. The filtrate was concentrated to obtain the crude compound 6-7. MS (ESI) m/z: 468.2 $[M+H]^+$.

Step H: A mixture of compound 6-7 (657 mg, 1.40 mmol), compound 1-5 (681.39 mg, 1.82 mmol), sodium carbonate (371.71 mg, 3.51 mmol), and $Pd(PPh_3)_4$ (162.10 mg, 140.28 μmol) in dioxane (15 mL) and water (3 mL) was replaced with nitrogen three times, heated to 100° C. under nitrogen atmosphere, and stirred for 1 hour. The reaction mixture was filtered through diatomite. The filter cake was washed with 150 mL of dichloromethane. The filtrates were combined, and concentrated to obtain the crude product. The crude product was purified by silica gel column chromatography (petroleum ether:ethyl acetate=1:0 to 0:1, v/v) to obtain compound 6-8. MS (ESI) m/z: 635.0 $[M+H]^+$.

Step I: A solution of compound 6-8 (350 mg, 551.09 μmol) and compound 1-15 (125.81 mg, 1.10 mmol) in 10 mL of dichloromethane was stirred at 25° C. for 0.5 hours, and $NaBH(OAc)_3$ (583.99 mg, 2.76 mmol) was added thereto. The reaction system was stirred at 25° C. for 12 hours, diluted with 10 mL of water, and extracted with dichloromethane (20 mL×5). The organic phase was washed with saturated brine (20 mL×1), dried over anhydrous sodium sulfate, and filtered. The filtrate was concentrated to obtain the crude product. The crude product was purified by preparative HPLC (chromatographic column: Phenomenex luna C18 150*40 mm*15 m; mobile phase: [pure water (0.225% formic acid)-acetonitrile]; acetonitrile %: 70% to 37%, 10 minutes) to obtain the formate of compound 6. 1H NMR (400 MHz, DMSO-$d_6$) δ=8.73 (d, J=1.6 Hz, 1H), 8.53 (d, J=8.4 Hz, 1H), 8.20 (s, 1H), 7.95 (d, J=1.6 Hz, 1H), 7.85 (d, J=7.6 Hz, 1H), 7.72 (s, 1H), 7.64 (dd, J=1.6, 7.6 Hz, 1H), 7.53 (t, J=7.6 Hz, 1H), 7.44 (dd, J=1.6, 7.6 Hz, 1H), 7.36 (t, J=7.6 Hz, 1H), 7.30 (d, J=7.6 Hz, 1H), 7.00 (d, J=7.2 Hz, 1H), 4.89 (t, J=8.0 Hz, 2H), 3.94 (s, 3H), 3.87-3.63 (m, 5H), 3.09-2.90 (m, 3H), 2.81-2.67 (m, 2H), 2.66-2.55 (m, 7H), 2.19-1.89 (m, 5H), 1.78-1.62 (m, 1H); MS (ESI) m/z: 733.2 $[M+H]^+$.
Example 7: Compound 7
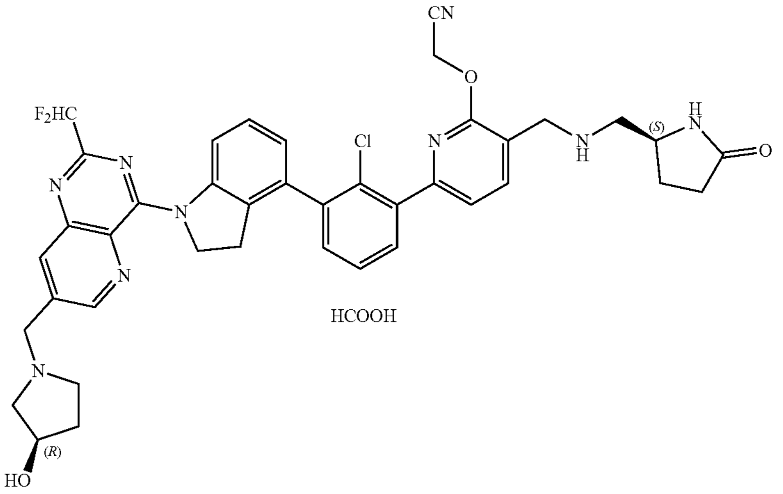
7
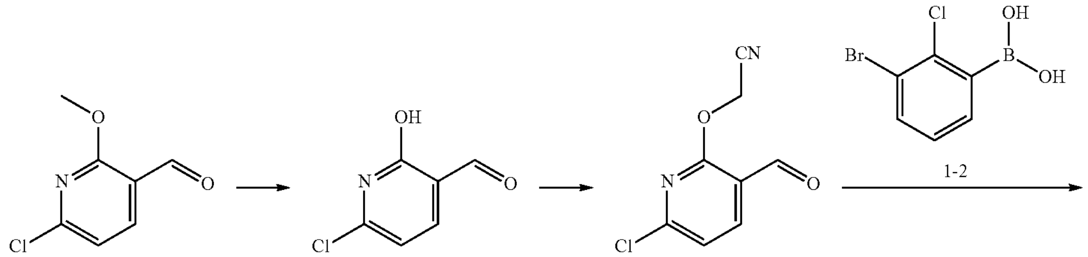
1-3 7-1 7-2 1-2
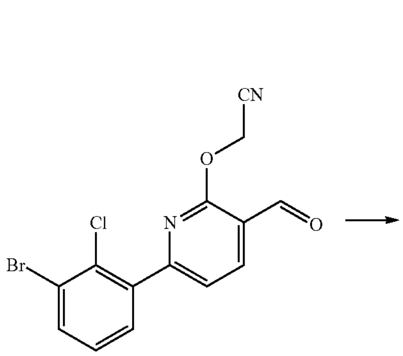
7-3

-continued

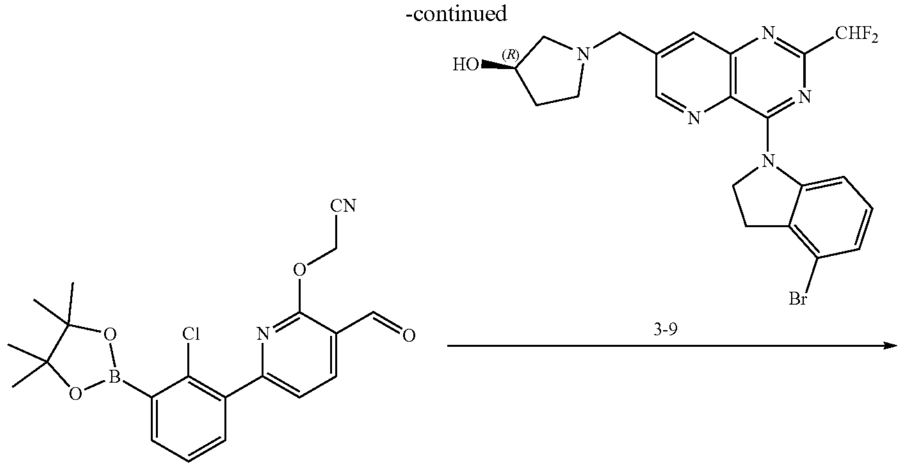

7-4

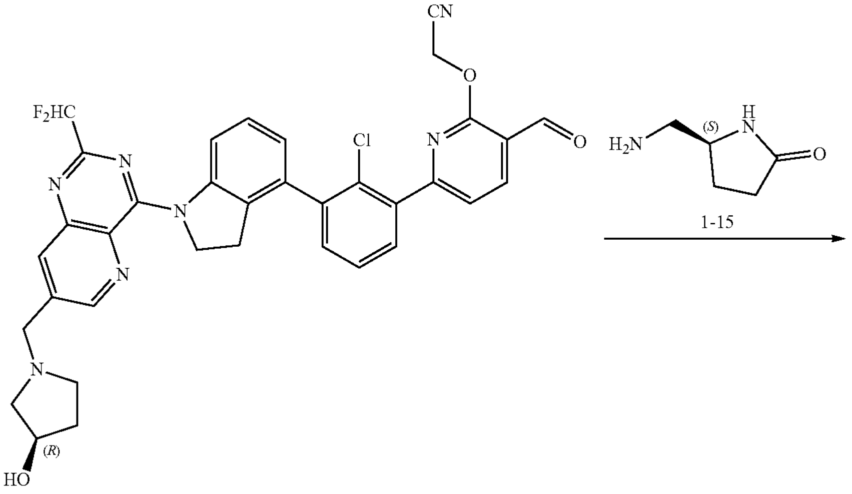

7-5

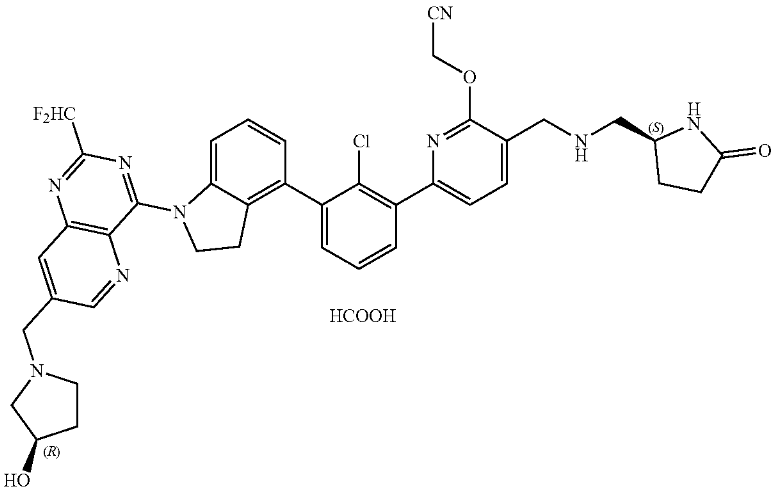

7

Step A: To a solution of compound 1-3 (5 g, 29.14 mmol) in 60 mL of dichloromethane was slowly and dropwise added boron tribromide (21.90 g, 87.42 mmol) at 0° C. The reaction mixture was reacted at 0° C. for 30 minutes, quenched with 80 mL of saturated sodium bicarbonate solution, diluted with 30 mL of water, and extracted with dichloromethane (40 mL×5). The organic phases were combined, washed with saturated brine (20 mL×1), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 7-1.

Step B: To a solution of compound 7-1 (3.2 g, 20.31 mmol) and bromoacetonitrile (4.87 g, 40.62 mmol) in 40 mL of acetonitrile was added silver carbonate (6.16 g, 22.34 mmol). The reaction system was stirred at 90° C. for 12 hours, and the reaction mixture was filtered through diatomite, and the filter cake was washed with 30 mL of ethyl acetate. The filtrate was diluted with 20 mL of water and extracted with ethyl acetate (30 mL×5). The organic phases were combined, washed with saturated brine (20 mL×1), dried over anhydrous sodium sulfate, and filtered. The filtrate was concentrated to obtain the crude product. The crude product was purified by silica gel column chromatography (petroleum ether:ethyl acetate=10:1 to 5:1, v/v) to obtain compound 7-2.

Step C: A mixture of compound 7-2 (0.496 g, 2.52 mmol), compound 1-2 (652.95 mg, 2.78 mmol), potassium carbonate (697.41 mg, 5.05 mmol), and $Pd(PPh_3)_4$ (291.55 mg, 252.30 μmol) in dioxane (10 mL) and water (2 mL) was replaced with nitrogen three times, heated to 85° C. under nitrogen atmosphere, and stirred for 5 hours. The reaction mixture was diluted with 20 mL of water, extracted with ethyl acetate (50 mL×3). The organic phases were combined, washed with saturated brine (30 mL×2), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 7-3. MS (ESI) m/z: 351.0 $[M+H]^+$.

Step D: A mixture of compound 7-3 (630 mg, 1.79 mmol), bis(pinacolato)diboron (910.07 mg, 3.58 mmol), potassium acetate (351.72 mg, 3.58 mmol), and $Pd(dppf)Cl_2 \cdot CH_2Cl_2$ (146.33 mg, 179.19 μmol) in 20 mL of dioxane was replaced with nitrogen three times, heated to 85° C. under nitrogen atmosphere, and stirred for 5 hours. The reaction mixture was filtered through diatomite. The filter cake was washed with 100 mL of ethyl acetate. The filtrates were combined, and concentrated to obtain the crude product. The crude product was purified by silica gel column chromatography (petroleum ether:ethyl acetate=1:0 to 0:1, v/v) to obtain compound 7-4. MS (ESI) m/z: 399.1 $[M+H]^+$.

Step E: A mixture of compound 7-4 (100.43 mg, 251.93 μmol), compound 3-9 (100 mg, 209.94 μmol), sodium carbonate (55.63 mg, 524.86 μmol), and $Pd(PPh_3)_4$ (24.26 mg, 20.99 mol) in dioxane (10 mL) and water (2 mL) was replaced with nitrogen three times, heated to 100° C. under nitrogen atmosphere, and stirred for 1 hour. The reaction mixture was filtered through diatomite, diluted with 20 mL of water, extracted with ethyl acetate (30 mL×3). The organic phases were combined, washed with saturated brine (30 mL×2), dried over anhydrous sodium sulfate, and filtered. The filtrate was concentrated to obtain the crude product. The crude product was purified by preparative thin-layer chromatography silica gel plate (dichloromethane:methanol=10:1) to obtain compound 7-5. MS (ESI) m/z: 668.4 $[M+H]^+$.

Step F: A solution of compound 7-5 (130 mg, 194.58 μmol) and compound 1-15 (44.42 mg, 389.17 μmol) in 6 mL of dichloromethane was stirred at 25° C. for 0.5 hours, and $NaBH(OAc)_3$ (206.20 mg, 972.92 μmol) was added thereto. The reaction system was stirred at 25° C. for 1 hour, diluted with 10 mL of water, and extracted with dichloromethane (20 mL×5). The organic phase was washed with saturated brine (20 mL×1), dried over anhydrous sodium sulfate, and filtered. The filtrate was concentrated to obtain the crude product. The crude product was purified by preparative HPLC (chromatographic column: Phenomenex Synergi C18 150*25 mm*10 m; mobile phase: [pure water (0.225% formic acid)-acetonitrile]; acetonitrile %: 9% to 39%, 10 minutes) to obtain the formate of compound 7. $^1H$ NMR (400 MHz, DMSO-$d_6$) δ=8.92 (d, J=2.0 Hz, 1H), 8.66 (d, J=8.0 Hz, 1H), 8.18 (s, 1H), 8.16 (d, J=1.6 Hz, 1H), 7.97 (d, J=7.6 Hz, 1H), 7.74 (dd, J=1.6, 7.6 Hz, 1H), 7.70 (s, 1H), 7.58 (t, J=7.6 Hz, 1H), 7.53-7.47 (m, 2H), 7.42 (t, J=8.0 Hz, 1H), 7.13-6.76 (m, 2H), 5.28 (s, 2H), 5.00 (t, J=8.0 Hz, 2H), 4.26-4.21 (m, 1H), 3.94-3.63 (m, 7H), 3.09 (t, J=8.0 Hz, 2H), 2.79-2.64 (m, 2H), 2.59 (d, J=6.0 Hz, 2H), 2.42 (dd, J=3.2, 9.6 Hz, 1H), 2.19-1.98 (m, 4H), 1.78-1.50 (m, 2H); MS (ESI) m/z: 766.5 $[M+H]^+$.

Example 8: Compound 8

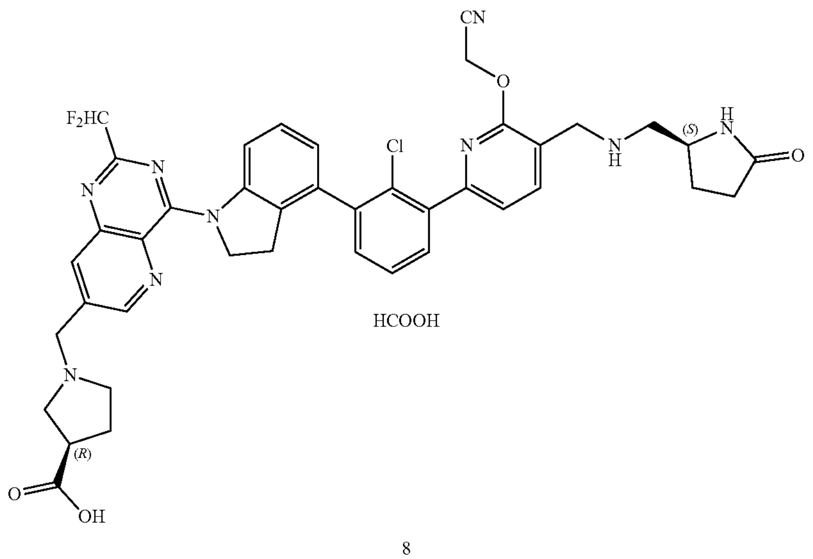

-continued
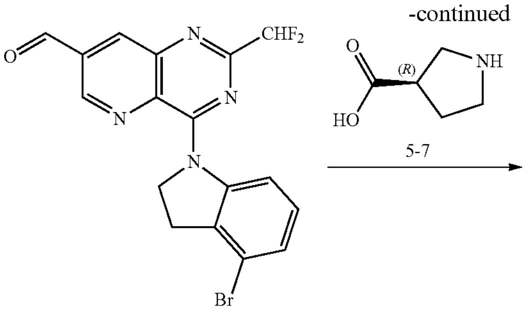
3-8
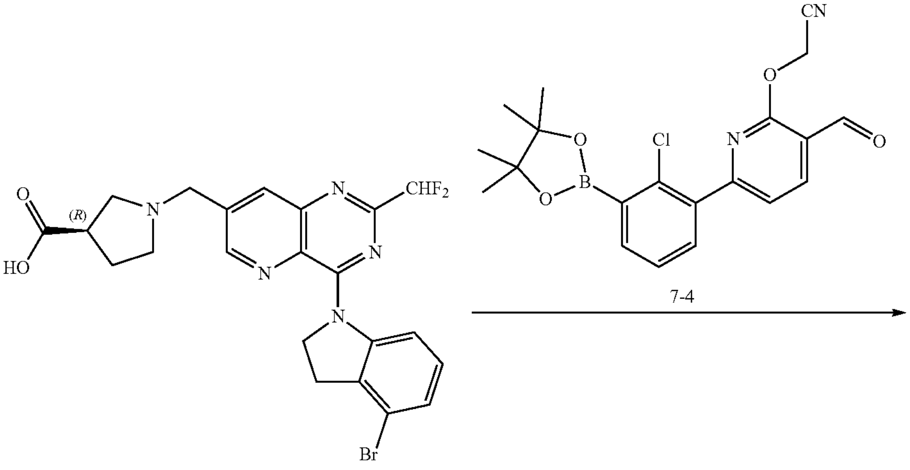
8-1
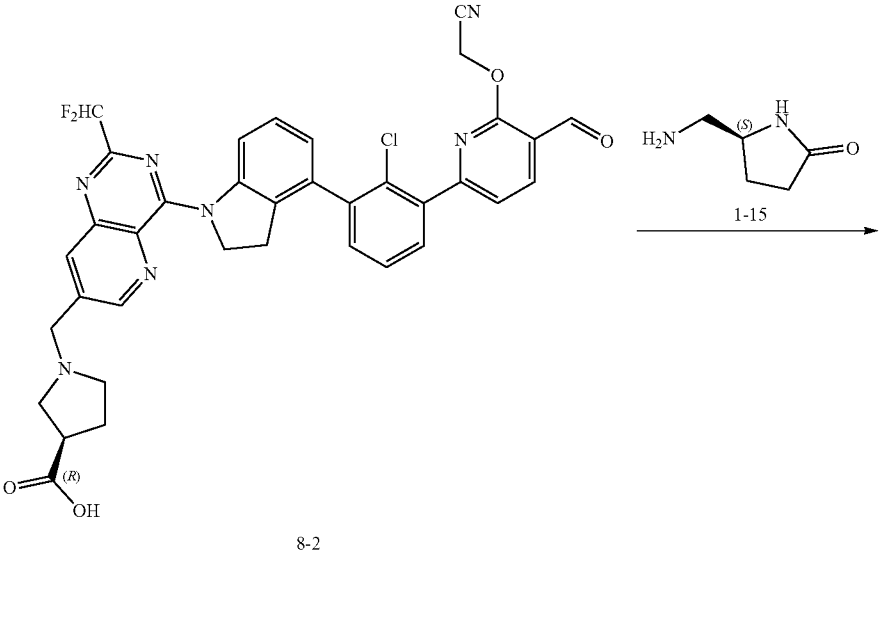
8-2

-continued

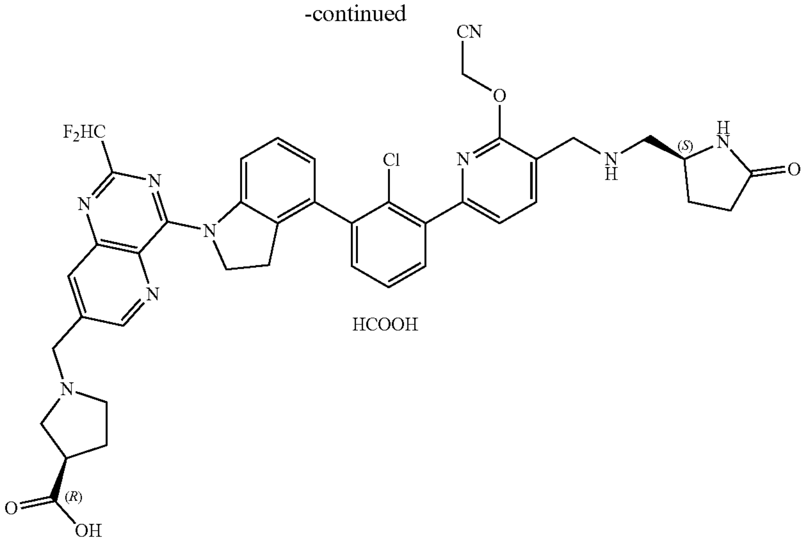

8

Step A: A solution of compound 3-8 (200 mg, 493.59 μmol) and compound 5-7 (113.65 mg, 987.18 μmol) in 15 mL of dichloromethane was stirred at 25° C. for 0.5 hours, and $NaBH(OAc)_3$ (313.83 mg, 1.48 mmol) was added thereto. The reaction system was stirred at 25° C. for 12 hours, diluted with 10 mL of water, and extracted with dichloromethane (40 mL×8). The organic phase was washed with saturated brine (20 mL×1), dried over anhydrous sodium sulfate, and filtered. The filtrate was concentrated to obtain the crude compound 8-1. MS (ESI) m/z: 504.3 $[M+H]^+$.

Step B: A mixture of compound 8-1 (150 mg, 297.43 μmol), compound 7-4 (118.57 mg, 297.43 μmol), sodium carbonate (78.81 mg, 743.57 μmol), and $Pd(PPh_3)_4$ (34.37 mg, 29.74 μmol) in dioxane (15 mL) and water (3 mL) was replaced with nitrogen three times, heated to 100° C. under nitrogen atmosphere, and stirred for 1 hour. The reaction mixture was filtered through diatomite. The filter cake was washed with 100 mL of ethyl acetate. The filtrates were combined, and concentrated to obtain the crude product. The crude product was purified by preparative thin-layer chromatography silica gel plate (dichloromethane:methanol=5:1) to obtain compound 8-2. MS (ESI) m/z: 696.4 $[M+H]^+$.

Step C: A solution of compound 8-2 (80 mg, 114.93 μmol) and compound 1-15 (26.24 mg, 229.85 μmol) in 10 mL of dichloromethane was stirred at 25° C. for 0.5 hours, and $NaBH(OAc)_3$ (121.79 mg, 574.63 μmol) was added thereto. The reaction system was stirred at 25° C. for 1 hour, diluted with 10 mL of water, and extracted with dichloromethane (20 mL×5). The organic phase was washed with saturated brine (20 mL×1), dried over anhydrous sodium sulfate, and filtered. The filtrate was concentrated to obtain the crude product. The crude product was purified by preparative HPLC (chromatographic column: Phenomenex Synergi C18 150*25 mm*10 m; mobile phase: [pure water (0.225% formic acid)-acetonitrile]; acetonitrile %: 9% to 39%, 10 minutes) to obtain the formate of compound 8. $^1H$ NMR (400 MHz, DMSO-$d_6$) δ=8.92 (d, J=2.0 Hz, 1H), 8.66 (d, J=8.0 Hz, 1H), 8.20 (s, 1H), 8.16 (d, J=1.6 Hz, 1H), 7.97 (d, J=7.6 Hz, 1H), 7.74 (dd, J=1.6, 7.6 Hz, 1H), 7.70 (s, 1H), 7.58 (t, J=7.6 Hz, 1H), 7.53-7.46 (m, 2H), 7.42 (t, J=7.6 Hz, 1H), 7.12-6.76 (m, 2H), 5.28 (s, 2H), 5.01 (t, J=8.0 Hz, 2H), 3.92-3.82 (m, 2H), 3.77 (s, 2H), 3.69-3.62 (m, 1H), 3.09 (t, J=8.0 Hz, 2H), 3.01-2.94 (m, 1H), 2.80-2.70 (m, 2H), 2.63-2.56 (m, 4H), 2.21-1.93 (m, 5H), 1.80-1.62 (m, 1H); MS (ESI) m/z: 794.1 $[M+H]^+$.

Example 9: Compound 9

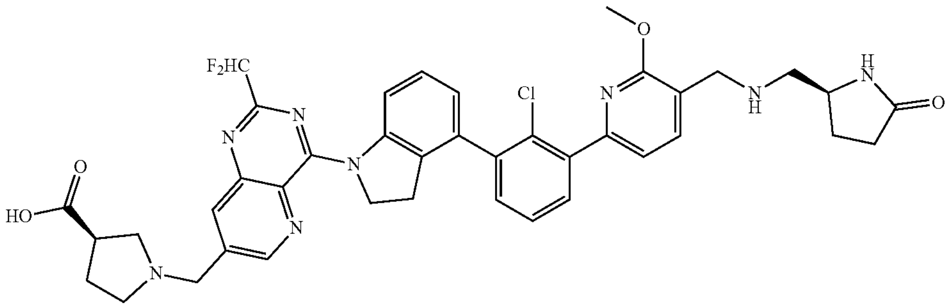

9

-continued
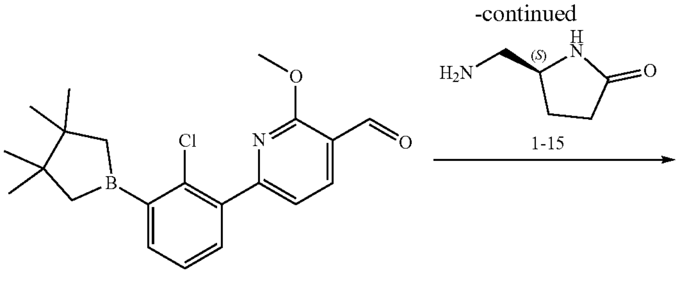
1-15
1-5
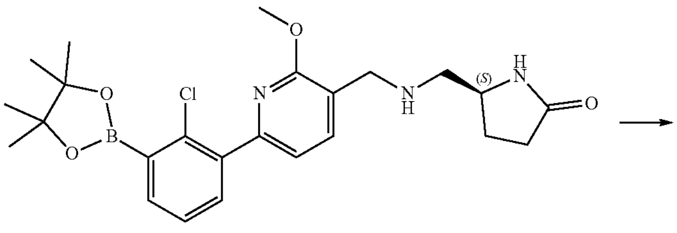
9-1
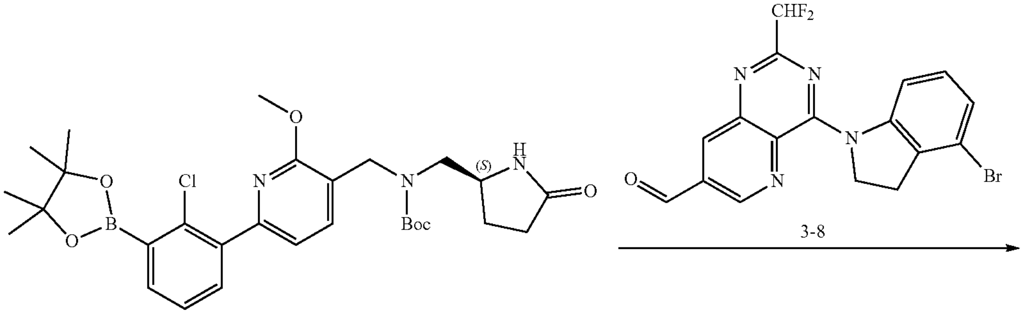
3-8
9-2
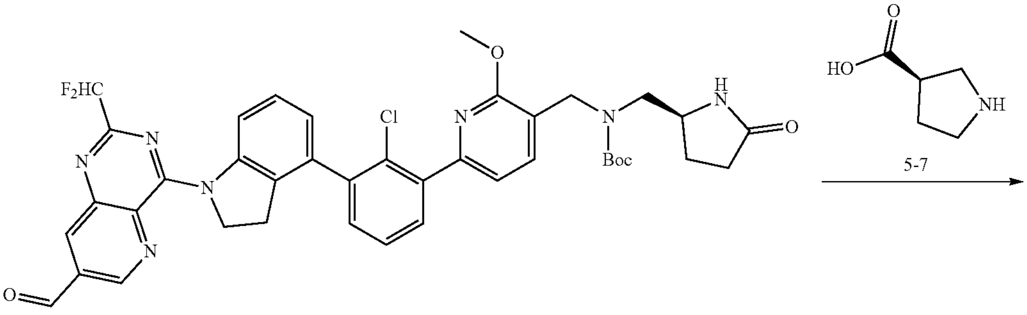
5-7
9-3
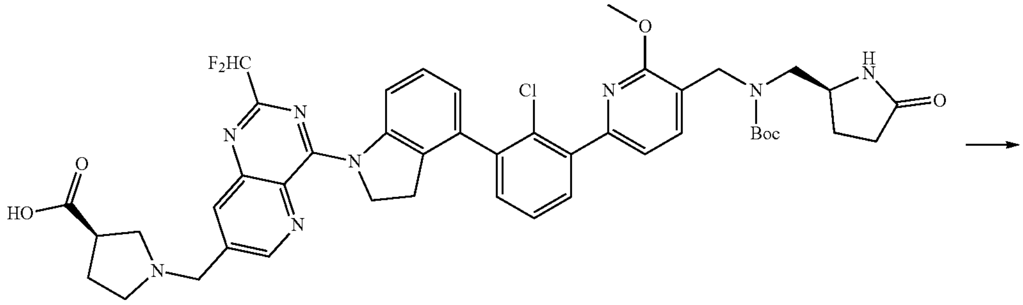
9-4

-continued

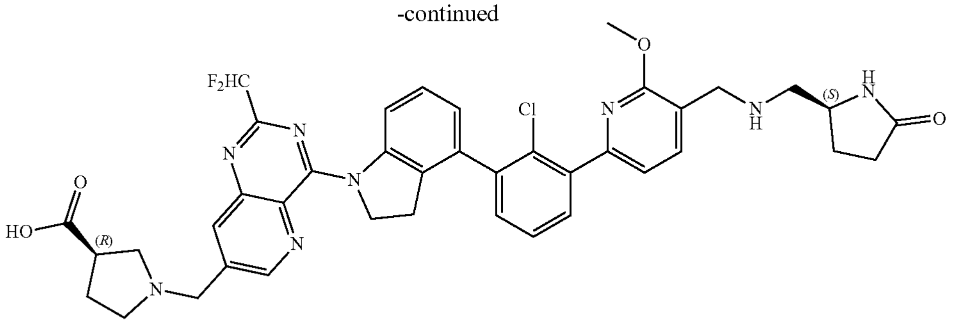

9

Step A: A solution of compound 1-5 (0.5 g, 1.34 mmol) and compound 1-15 (305.50 mg, 1.34 mmol) in 10 mL of dichloromethane was stirred at 25° C. for 0.5 hours, and $NaBH(OAc)_3$ (1.42 g, 6.69 mmol) was added thereto. The reaction system was stirred at 25° C. for 2 hours, diluted with 20 mL of water, and extracted with dichloromethane (30 mL×5). The organic phase was washed with saturated brine (20 mL×1), dried over anhydrous sodium sulfate, and filtered. The filtrate was concentrated to obtain the crude compound 9-1. MS (ESI) m/z: 472.4 $[M+H]^+$.

Step B: To a solution of compound 9-1 (200 mg, 423.92 μmol) in 5 mL of dichloromethane was added di-tert-butyl dicarbonate (138.78 mg, 635.89 μmol) and triethylamine (85.79 mg, 847.85 μmol). The reaction system was stirred at 25° C. for 2 hours, then diluted with 10 mL of water, and extracted with dichloromethane (20 mL×3). The organic phase was washed with saturated brine (20 mL×3), dried over anhydrous sodium sulfate, and filtered. The filtrate was concentrated to obtain the crude product. The crude product was purified by preparative thin-layer chromatography silica gel plate (ethyl acetate) to obtain compound 9-2. MS (ESI) m/z: 572.2 $[M+H]^+$.

Step C: A mixture of compound 9-2 (230 mg, 402.17 μmol), compound 3-8 (162.96 mg, 402.17 μmol), sodium carbonate (106.56 mg, 1.01 mmol), and $Pd(PPh_3)_4$ (46.47 mg, 40.22 mol) in dioxane (5 mL) and water (1 mL) was replaced with nitrogen three times, heated to 100° C. under nitrogen atmosphere, and stirred for 1 hour. The reaction mixture was diluted with 20 mL of water, filtered through diatomite, and extracted with ethyl acetate (40 mL×3). The organic phase was washed with saturated brine (20 mL×3), dried over anhydrous sodium sulfate, and filtered. The filtrate was concentrated to obtain the crude product. The crude product was purified by preparative thin-layer chromatography silica gel plate (ethyl acetate) to obtain compound 9-3. MS (ESI) m/z: 770.5 $[M+H]^+$.

Step D: To a solution of compound 9-3 (30 mg, 38.95 μmol) and compound 5-7 (8.97 mg, 77.90 μmol) in dichloromethane (2 mL) was added $NaBH(OAc)_3$ (41.28 mg, 194.75 μmol). The reaction mixture was stirred at 25° C. for 1 hour, diluted with 50 mL of water, and extracted with dichloromethane (50 mL×2). The organic phase was washed with saturated brine (100 mL), dried over anhydrous sodium sulfate, and filtered. The filtrate was concentrated to obtain the crude product 9-4, which was used directly in the next step. MS (ESI) m/z: 869.3 $[M+H]^+$.

Step E: To a solution of compound 9-4 (30 mg, 34.51 μmol) in dichloromethane (2 mL) was added trifluoroacetic acid (196.74 mg, 1.73 mmol). The reaction mixture was stirred at 25° C. for 1 hour, and then concentrated to obtain the crude product. The crude product was purified by preparative HPLC (chromatographic column: Phenomenex luna C18 150*25 mm*10 m; mobile phase: [pure water (0.225% formic acid)–acetonitrile]; acetonitrile %: 10% to 40%, 10 minutes) to obtain compound 9. $^1H$ NMR (400 MHz, DMSO-$d_6$) δ=8.92 (d, J=2.0 Hz, 1H), 8.65 (d, J=8.0 Hz, 1H), 8.17 (s, 1H), 7.88 (br s, 1H), 7.69-7.63 (m, 2H), 7.56 (t, J=7.6 Hz, 1H), 7.51-7.46 (m, 1H), 7.42 (t, J=8.0 Hz, 1H), 7.34 (br d, J=8.0 Hz, 1H), 7.11-6.79 (m, 2H), 5.01 (br t, J=8.0 Hz, 2H), 3.96 (s, 3H), 3.91-3.86 (m, 2H), 3.08 (br t, J=8.0 Hz, 2H), 3.03-2.90 (m, 2H), 2.81-2.73 (m, 2H), 2.64-2.56 (m, 2H), 2.24-2.07 (m, 4H), 2.06-1.92 (m, 4H), 1.24 (br s, 4H); MS (ESI) m/z: 769.2 $[M+H]^+$.

Example 10: Compound 10

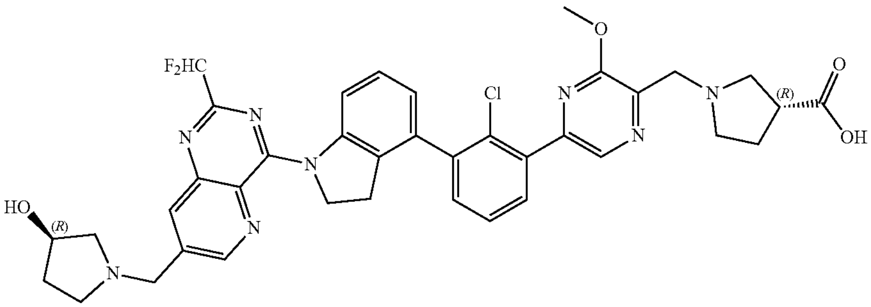

10

-continued

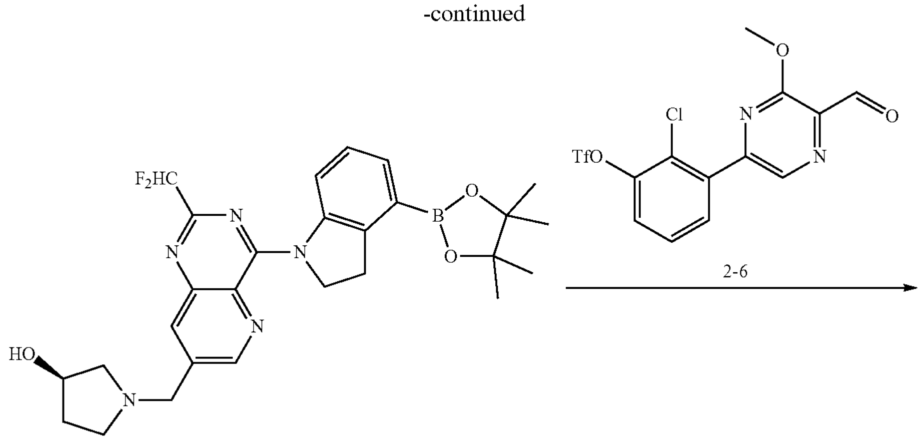

4-1

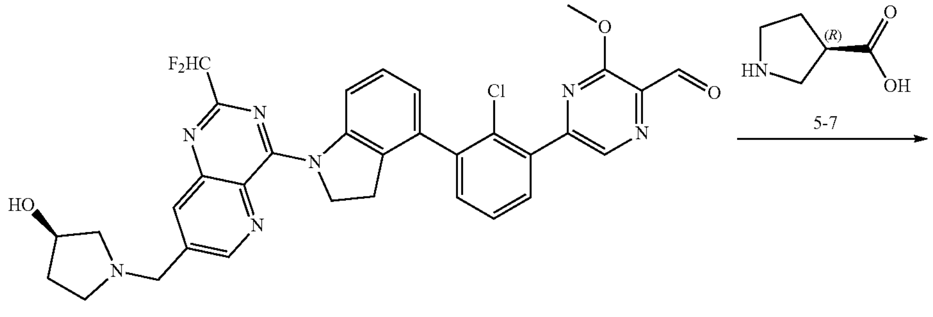

10-3

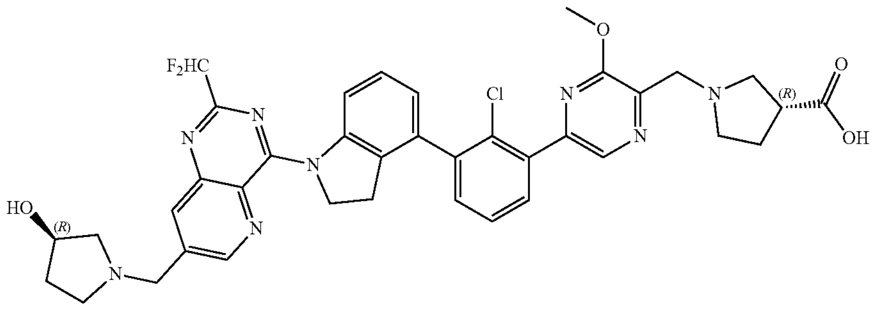

10

Step A: A mixture of compound 4-1 (1 g, 1.91 mmol), compound 2-6 (758.01 mg, 1.91 mmol), sodium carbonate (607.53 mg, 5.73 mmol), and Pd(dppf)$Cl_2$ (156.03 mg, 191.07 μmol) in tetrahydrofuran (32 mL) and water (8 mL) was replaced with nitrogen three times, heated to 50° C. under nitrogen atmosphere, and stirred for 12 hours. The reaction mixture was diluted with 20 mL of water, extracted with ethyl acetate (50 mL×3). The organic phase was washed with saturated brine (20 mL), dried over anhydrous sodium sulfate, and filtered. The filtrate was concentrated to obtain the crude product. The crude product was purified by silica gel column chromatography (methanol/dichloromethane=0% to 8%, v/v) to obtain compound 10-3. MS (ESI) m/z: 644.0 $[M+H]^+$.

Step B: A solution of compound 10-3 (40 mg, 62.11 μmol), compound 5-7 (21.45 mg, 186.33 μmol) and 4 Å molecule sieves (40 mg) in 5 mL of dichloromethane was stirred for 0.5 hours, and $NaBH(OAc)_3$ (65.81 mg, 310.55 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 10% to 40%, 10 minutes) to obtain the formate of compound 10. $^1H$ NMR (400 MHz, $CD_3OD$) δ=8.96 (d, J=2.0 Hz, 1H), 8.77 (d, J=8.0 Hz, 1H), 8.53 (s, 1H), 8.40 (br s, 1H), 8.24 (d, J=1.6 Hz, 1H), 7.70 (dd, J=1.6, 7.6 Hz, 1H), 7.56 (t, J=7.6 Hz, 1H), 7.51-7.46 (m, 1H), 7.40 (t, J=8.0 Hz, 1H), 7.08 (d, J=7.6 Hz, 1H), 6.86-6.53 (m, 1H), 5.06 (br t, J=8.4 Hz, 2H), 4.72-4.62 (m, 2H), 4.52-4.43 (m, 1H), 4.25-4.14 (m, 2H), 4.12 (s, 3H), 3.77 (dd, J=6.0, 11.2 Hz, 1H), 3.68-3.47 (m, 3H), 3.26-3.02 (m, 5H), 2.99-2.84 (m, 2H), 2.48-2.19 (m, 3H), 1.97-1.82 (m, 1H); MS (ESI) m/z: 743.3 $[M+H]^+$.

Example 11: Compound 11

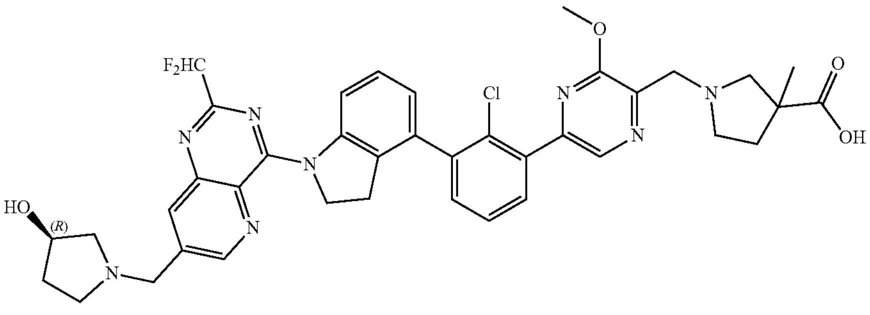

11

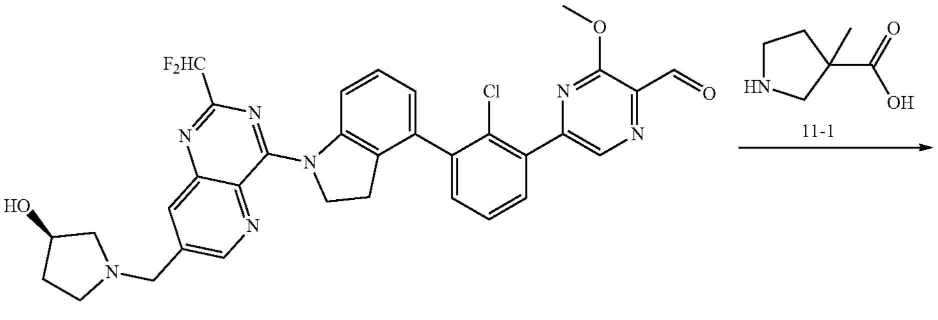

10-3

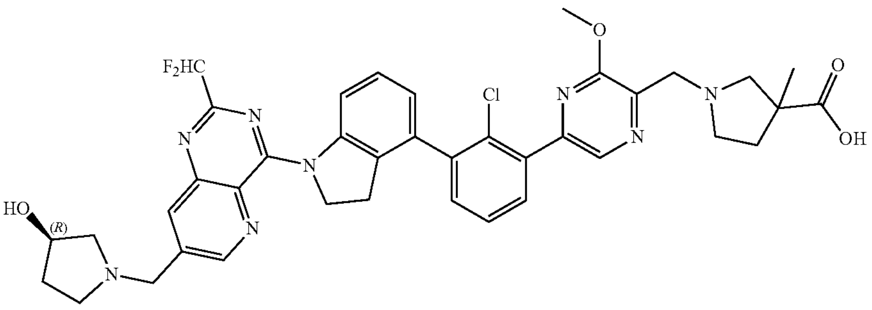

11

Step A: A solution of compound 10-3 (40 mg, 62.11 μmol), compound 11-1 (24.07 mg, 186.33 μmol), and 4 Å molecular sieves (40 mg) in 5 mL of dichloromethane was stirred for 0.5 hours, and $NaBH(OAc)_3$ (65.81 mg, 310.55 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 11% to 41%, 10 minutes) to obtain compound 11. $^1H$ NMR (400 MHz, $CD_3OD$) δ=8.97 (d, J=2.0 Hz, 1H), 8.78 (d, J=8.0 Hz, 1H), 8.52 (s, 1H), 8.24 (d, J=2.0 Hz, 1H), 7.70 (dd, J=1.6, 7.6 Hz, 1H), 7.57 (t, J=7.6 Hz, 1H), 7.52-7.46 (m, 1H), 7.41 (t, J=8.0 Hz, 1H), 7.08 (d, J=7.2 Hz, 1H), 6.89-6.51 (m, 1H), 5.08 (br t, J=8.4 Hz, 2H), 4.73-4.62 (m, 2H), 4.50-4.42 (m, 1H), 4.21-4.08 (m, 5H), 3.97 (d, J=11.2 Hz, 1H), 3.74-3.63 (m, 1H), 3.62-3.51 (m, 1H), 3.21 (br d, J=12.8 Hz, 1H), 3.16-3.02 (m, 4H), 2.92-2.80 (m, 2H), 2.56-2.44 (m, 1H), 2.25 (qd, J=7.2, 14.4 Hz, 1H), 2.02 (td, J=8.8, 13.1 Hz, 1H), 1.92-1.83 (m, 1H), 1.40 (s, 3H); MS (ESI) m/z: 757.2 $[M+H]^+$.

Example 12: Compound 12

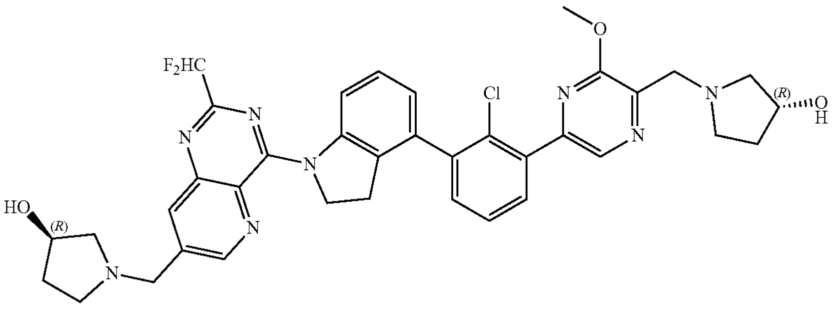

12

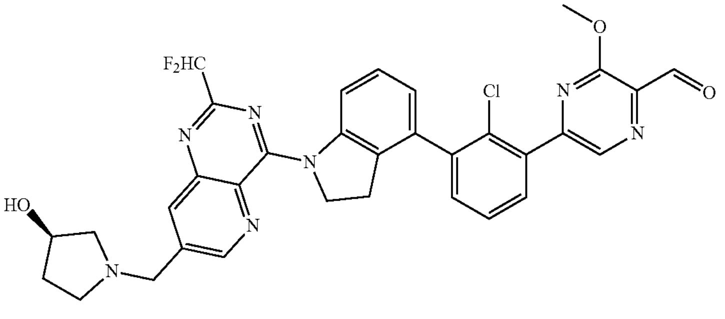

10-3

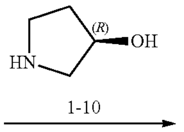

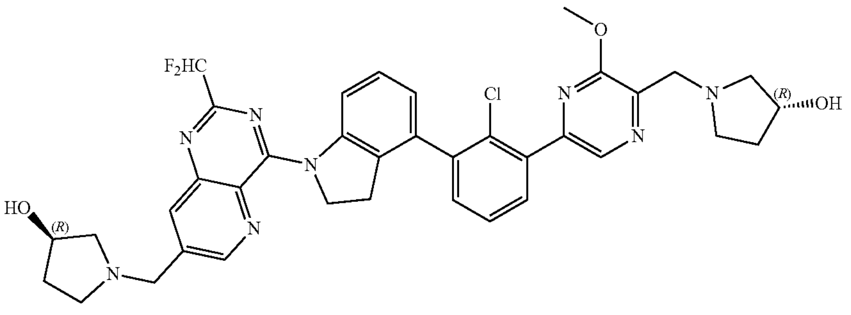

12

Step A: A solution of compound 10-3 (40 mg, 62.11 μmol), compound 1-10 (16.23 mg, 186.33 μmol), and 4 Å molecular sieves (40 mg) in 5 mL of dichloromethane was stirred for 0.5 hours, and $NaBH(OAc)_3$ (65.81 mg, 310.55 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 9% to 36%, 9 minutes) to obtain compound 12. $^1H$ NMR (400 MHz, $CD_3OD$) δ=8.97-8.88 (m, 1H), 8.77 (br dd, J=5.0, 8.1 Hz, 1H), 8.46 (d, J=2.4 Hz, 1H), 8.19-8.10 (m, 1H), 7.73-7.65 (m, 1H), 7.60-7.52 (m, 1H), 7.51-7.45 (m, 1H), 7.41 (dt, J=4.7, 7.9 Hz, 1H), 7.08 (dd, J=3.1, 7.6 Hz, 1H), 6.87-6.54 (m, 1H), 5.15-5.02 (m, 2H), 4.60 (br s, 1H), 4.41 (br dd, J=2.9, 6.6 Hz, 2H), 4.12-4.02 (m, 5H), 3.98-3.81 (m, 2H), 3.20-2.99 (m, 4H), 2.96-2.76 (m, 4H), 2.66-2.54 (m, 2H), 2.27-2.11 (m, 2H), 1.88-1.69 (m, 2H); MS (ESI) m/z: 715.1 $[M+H]^+$.

Example 13: Compound 13

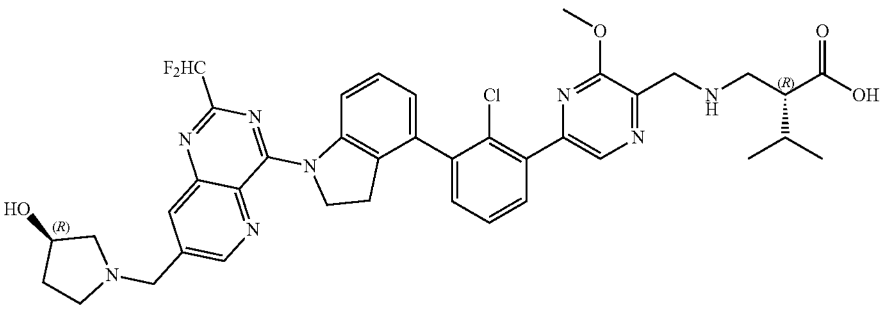

13

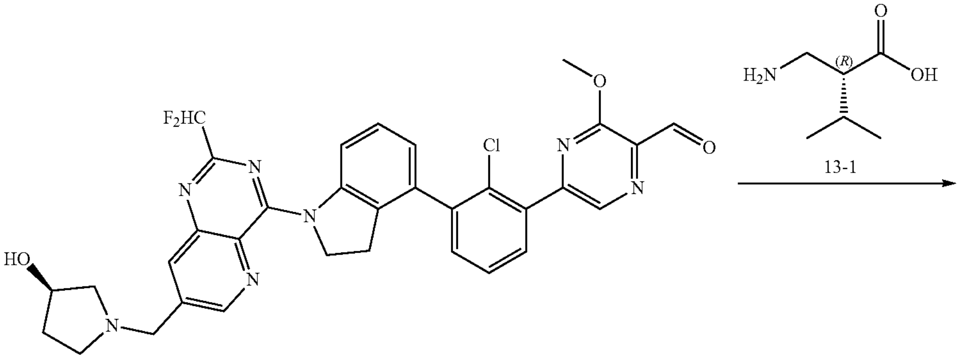

13-1

10-3

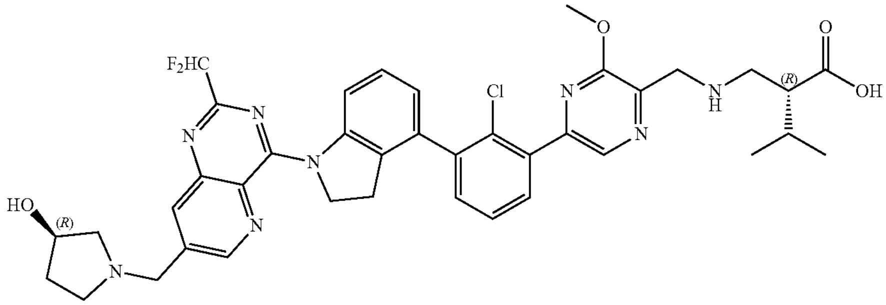

13

Step A: A solution of compound 10-3 (60 mg, 93.16 μmol), compound 13-1 (36.66 mg, 279.47 μmol), and 4 Å molecular sieves (60 mg) in 8 mL of dichloromethane was stirred for 0.5 hours, and $NaBH(OAc)_3$ (98.72 mg, 465.79 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: YMC Triart 30*150 mm*7 m; mobile phase: [pure water (hydrochloric acid)-acetonitrile]; acetonitrile %: 31% to 51%, 7 minutes) to obtain the hydrochloride of compound 13. $^1H$ NMR (400 MHz, DMSO-$d_6$) δ=12.16-11.44 (m, 1H), 9.54 (br d, J=4.4 Hz, 1H), 9.31-9.08 (m, 2H), 8.75-8.56 (m, 3H), 7.74 (br d, J=7.6 Hz, 1H), 7.68-7.54 (m, 2H), 7.44 (br t, J=7.6 Hz, 1H), 7.14-6.82 (m, 2H), 5.01 (br t, J=8.0 Hz, 2H), 4.71 (br d, J=14.8 Hz, 2H), 4.51-4.37 (m, 3H), 4.04 (s, 3H), 3.31-3.16 (m, 4H), 3.09 (br d, J=4.4 Hz, 3H), 2.86-2.74 (m, 1H), 2.39-2.26 (m, 1H), 2.15-1.82 (m, 3H), 0.93 (br dd, J=7.2, 9.6 Hz, 6H); MS (ESI) m/z: 759.1 $[M+H]^+$.

Example 14: Compound 14

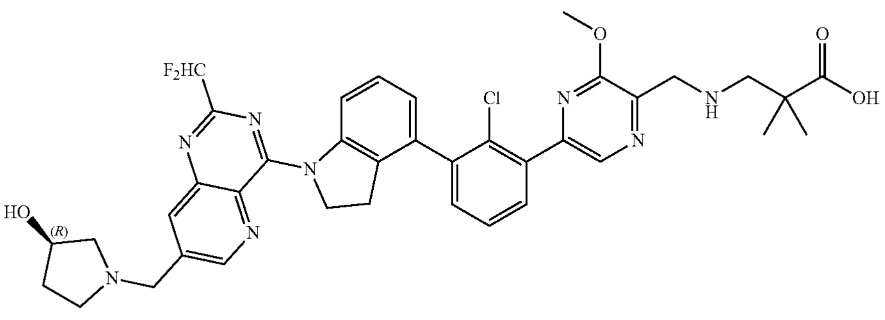

14

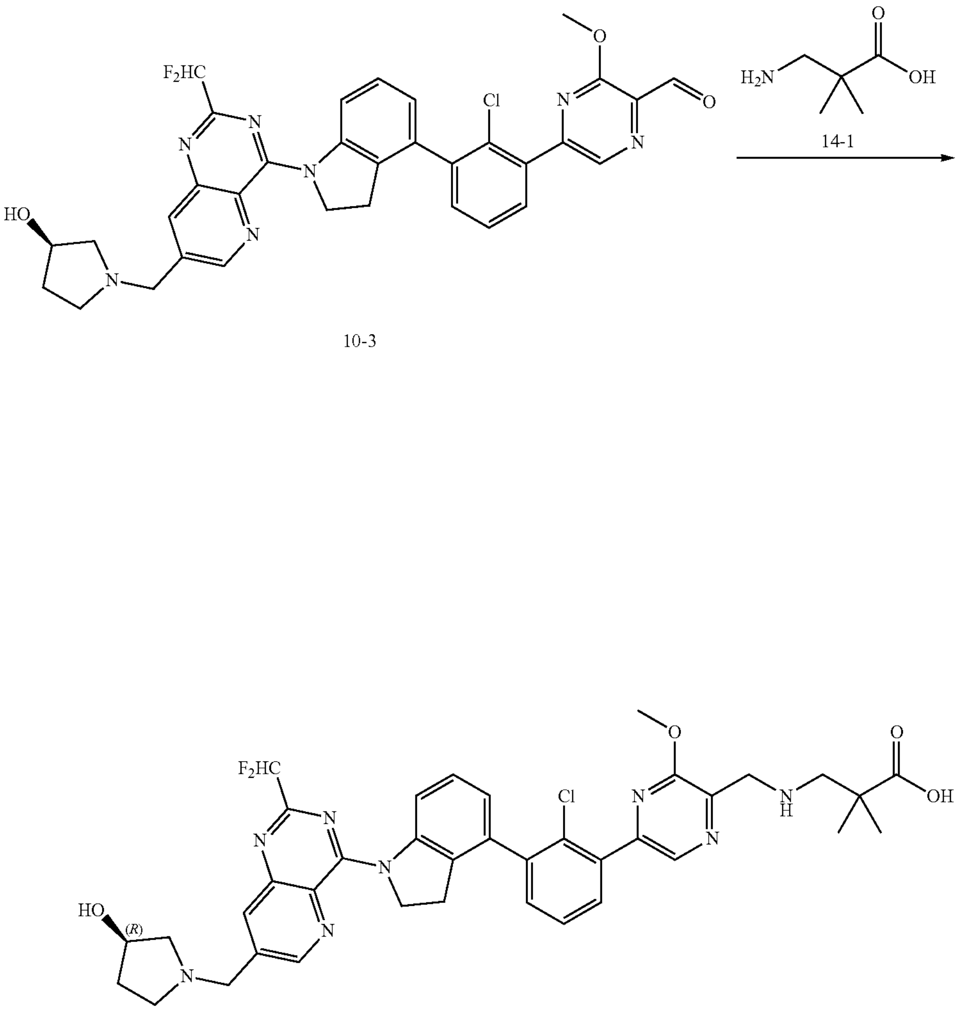

Step A: A solution of compound 10-3 (100 mg, 155.26 μmol), compound 14-1 (54.57 mg, 465.79 μmol), and 4 Å molecular sieves (100 mg) in 8 mL of dichloromethane was stirred for 0.5 hours, and $NaBH(OAc)_3$ (164.53 mg, 776.31 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 15% to 35%, 10 minutes) to obtain compound 14. $^{1}H$ NMR (400 MHz, $CD_3OD$) δ=8.90 (d, J=1.6 Hz, 1H), 8.70 (br d, J=8.4 Hz, 1H), 8.47-8.38 (m, 1H), 8.19 (d, J=1.2 Hz, 1H), 7.64 (dd, J=1.2, 7.6 Hz, 1H), 7.50 (t, J=7.6 Hz, 1H), 7.41 (dd, J=1.2, 7.6 Hz, 1H), 7.34 (br t, J=8.0 Hz, 1H), 7.02 (d, J=7.6 Hz, 1H), 6.80-6.49 (m, 1H), 4.51-4.39 (m, 3H), 4.24-4.12 (m, 2H), 4.08 (s, 3H), 3.22-3.10 (m, 4H), 3.05-2.86 (m, 4H), 2.31-2.17 (m, 1H), 1.90 (br dd, J=5.6, 7.6 Hz, 1H), 1.28 (s, 6H); MS (ESI) m/z: 745.1 $[M+H]^+$.

Example 15: Compound 15

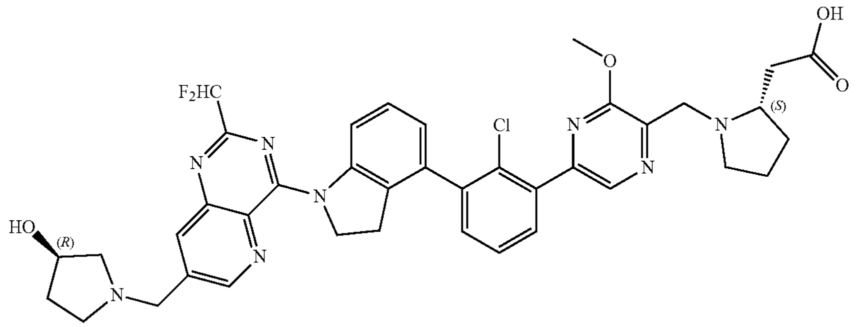

15

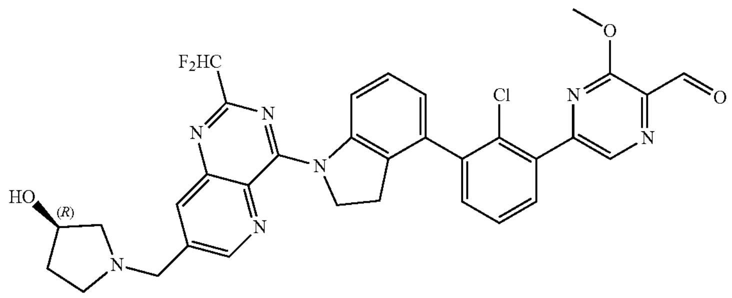

10-3

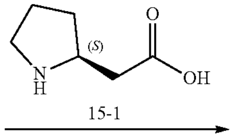

15-1

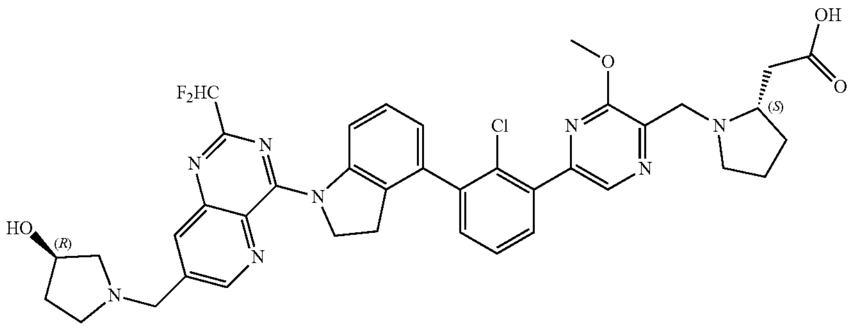

15

Step A: A solution of compound 10-3 (50.00 mg, 77.63 μmol), compound 15-1 (20.05 mg, 155.26 μmol), and molecular sieves (0.05 g) in dichloromethane (10 mL) was stirred at 25° C. for 0.5 hours, and $NaBH(OAc)_3$ (49.36 mg, 232.89 μmol) was added thereto. The reaction mixture was stirred at 25° C. for 1 hour, diluted with 20 mL of water, and extracted with dichloromethane (30 mL×3). The organic phase was washed with saturated brine (30 mL×3), dried over anhydrous sodium sulfate, and filtered. The filtrate was concentrated to obtain the crude product. The crude product was purified by preparative HPLC (chromatographic column: Phenomenex Synergi C18 150*25 mm*10 m; mobile phase: [pure water (formic acid)-acetonitrile]; acetonitrile %: 16% to 36%, 10 minutes) to obtain compound 15. $^{1}H$ NMR (400 MHz, $CD_3OD$) δ=8.96 (s, 1H), 8.77 (d, J=7.6 Hz, 1H), 8.50 (s, 1H), 8.23 (s, 1H), 7.70 (d, J=7.2 Hz, 1H), 7.56 (t, J=7.2 Hz, 1H), 7.52-7.45 (m, 1H), 7.41 (t, J=7.6 Hz, 1H), 7.08 (d, J=7.6 Hz, 1H), 6.90-6.52 (m, 1H), 5.05 (s, 3H), 4.59-4.42 (m, 2H), 4.15-4.10 (m, 4H), 3.94-3.77 (m, 2H), 3.27-3.19 (m, 1H), 3.17-3.03 (m, 4H), 2.95-2.77 (m, 3H), 2.67-2.55 (m, 1H), 2.46-2.34 (m, 1H), 2.31-2.08 (m, 3H), 2.02-1.83 (m, 2H), 1.41-1.28 (m, 1H); MS (ESI) m/z: 757.0 $[M+H]^{+}$.

Example 16: Compound 16

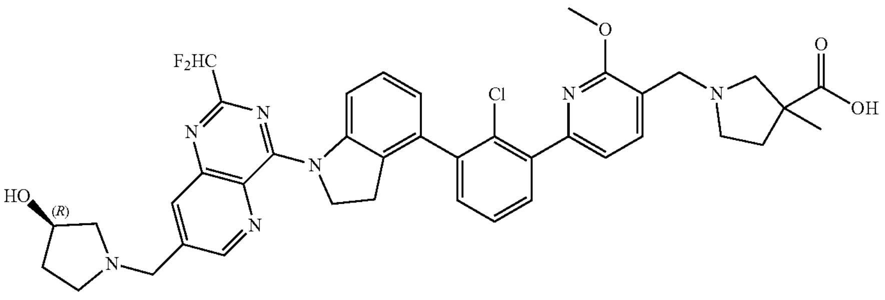

16

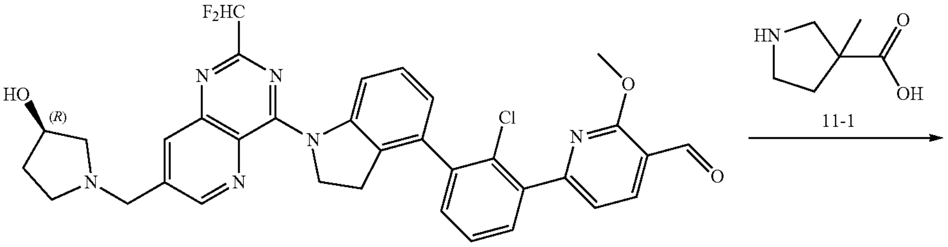

3-10

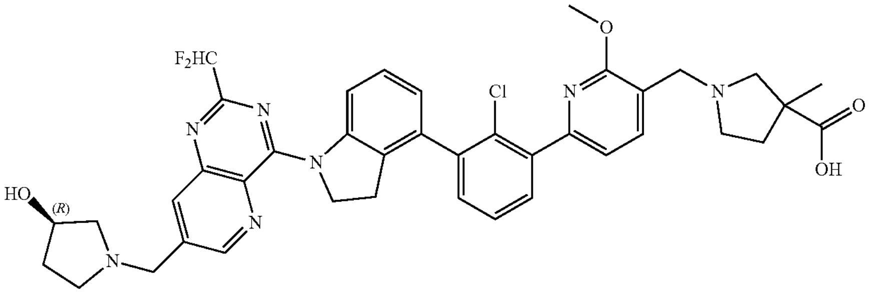

16

Step A: A solution of compound 3-10 (60 mg, 93.30 μmol) and compound 11-1 (24.10 mg, 186.60 μmol) in dichloromethane (5 mL) was stirred at 25° C. for 0.5 hours, and $NaBH(OAc)_3$ (98.87 mg, 466.50 μmol) was added thereto. The reaction mixture was stirred at 25° C. for 1 hour, diluted with 10 mL of water, and extracted with dichloromethane (20 mL×3). The organic phase was washed with saturated brine (20 mL×2), dried over anhydrous sodium sulfate, and filtered. The filtrate was concentrated to obtain the crude product. The crude product was purified by preparative HPLC (chromatographic column: Waters Xbridge 150*25 mm*5 m; mobile phase: [pure water (ammonium bicarbonate)-acetonitrile]; acetonitrile %: 35% to 65%, 9 minutes) to obtain compound 16. $^1H$ NMR (400 MHz, DMSO-$d_6$) δ=8.92 (d, J=2.0 Hz, 1H), 8.65 (d, J=8.0 Hz, 1H), 8.17 (d, J=1.6 Hz, 1H), 7.79 (d, J=7.6 Hz, 1H), 7.67 (dd, J=1.6, 7.6 Hz, 1H), 7.55 (t, J=7.6 Hz, 1H), 7.47 (d, J=1.6 Hz, 1H), 7.42 (t, J=8.0 Hz, 1H), 7.30 (d, J=7.6 Hz, 1H), 7.11-6.78 (m, 2H), 5.00 (br t, J=8.4 Hz, 2H), 4.28-4.17 (m, 1H), 3.99-3.79 (m, 6H), 3.63 (br d, J=4.0 Hz, 2H), 3.12-2.97 (m, 4H), 2.80-2.62 (m, 4H), 2.46-2.24 (m, 4H), 2.04 (dd, J=6.8, 13.2 Hz, 1H), 1.65-1.53 (m, 2H), 1.28 (s, 3H); MS (ESI) m/z: 756.2 $[M+H]^+$.

Example 17: Compound 17

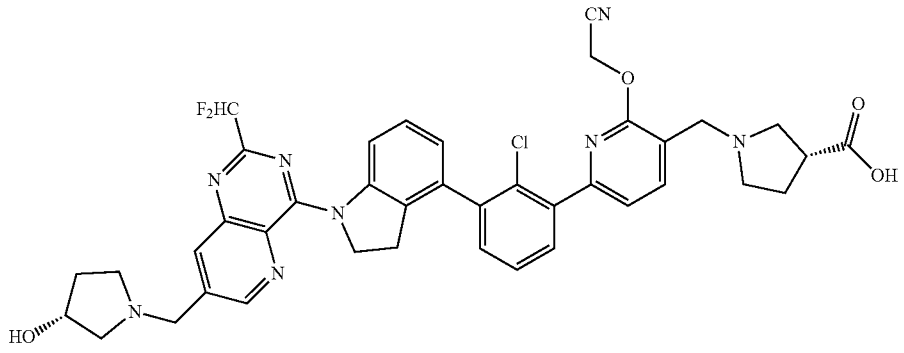

17

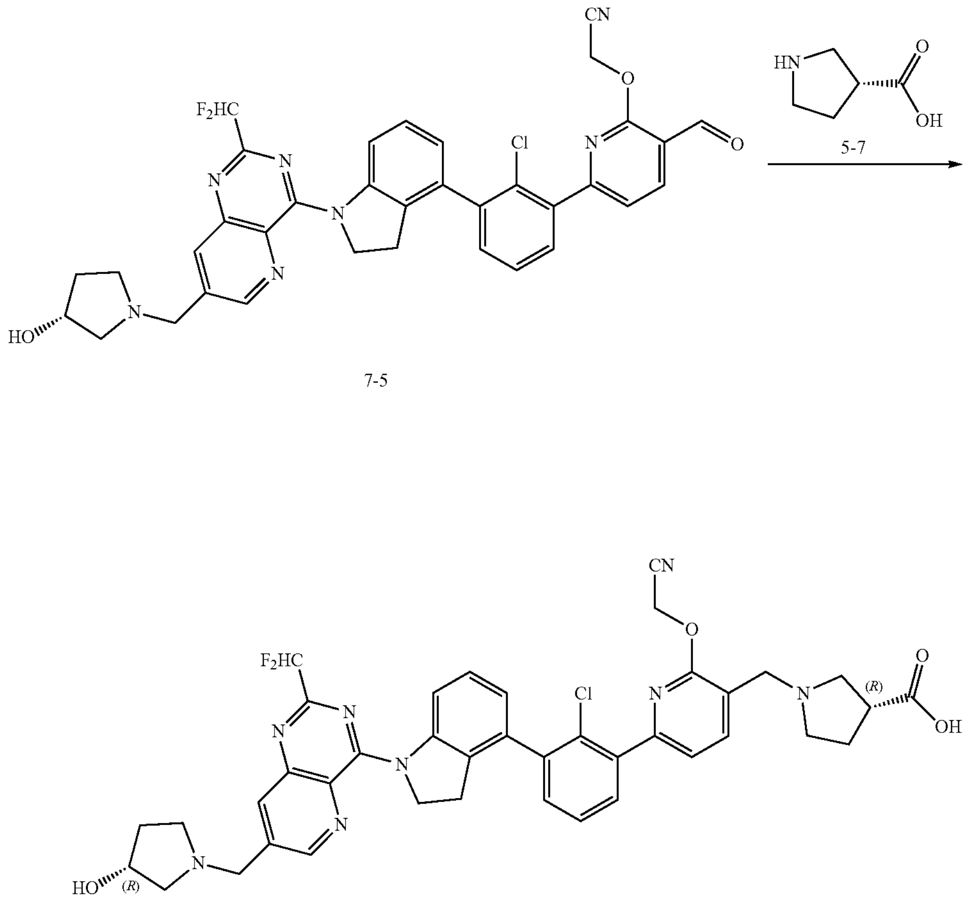

7-5

5-7

17

Step A: A solution of compound 7-5 (0.1 g, 149.68 μmol) and compound 5-7 (34.47 mg, 299.36 μmol) in 10 mL of dichloromethane was stirred at 25° C. for 0.5 hours, and $NaBH(OAc)_3$ (158.62 mg, 748.40 μmol) was added thereto. The reaction system was stirred at 25° C. for 12 hours, diluted with 10 mL of water, and extracted with dichloromethane (20 mL×5). The organic phase was washed with saturated brine (20 mL×1), dried over anhydrous sodium sulfate, and filtered. The filtrate was concentrated to obtain the crude product. The crude product was purified by preparative HPLC (chromatographic column: Phenomenex Synergi C18 150*25 mm*10 m; mobile phase: [pure water (0.225% formic acid)-acetonitrile]; acetonitrile %: 10% to 40%, 10 minutes) to obtain the formate of compound 17. $^1H$ NMR (400 MHz, DMSO-$d_6$) δ=8.92 (d, J=1.6 Hz, 1H), 8.66 (d, J=8.4 Hz, 1H), 8.28-8.19 (m, 1H), 8.16 (d, J=1.6 Hz, 1H), 7.91 (d, J=7.6 Hz, 1H), 7.75 (dd, J=1.6, 7.6 Hz, 1H), 7.58 (t, J=7.6 Hz, 1H), 7.53-7.46 (m, 2H), 7.42 (t, J=8.0 Hz, 1H), 7.12-6.78 (m, 2H), 5.28 (s, 2H), 5.01 (t, J=8.0 Hz, 2H), 4.26-4.21 (m, 1H), 3.96-3.78 (m, 3H), 3.70-3.60 (m, 3H), 3.09 (t, J=8.0 Hz, 2H), 2.99-2.90 (m, 1H), 2.81-2.56 (m, 6H), 2.10-1.93 (m, 3H), 1.68-1.51 (m, 1H); MS (ESI) m/z: 767.1 $[M+H]^+$.

Example 18: Compound 18
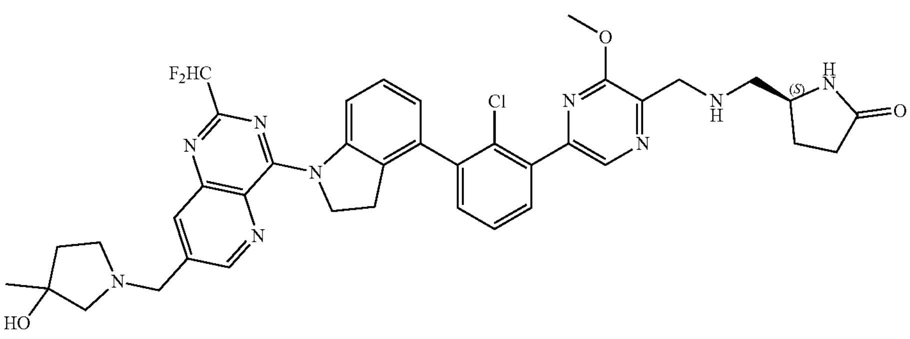
18
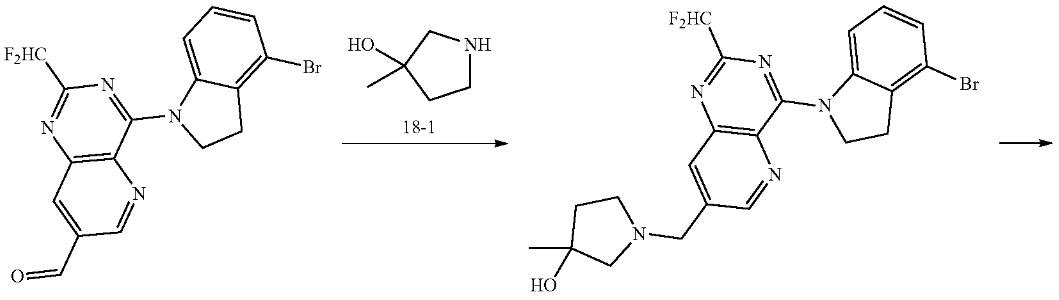
3-8
18-2
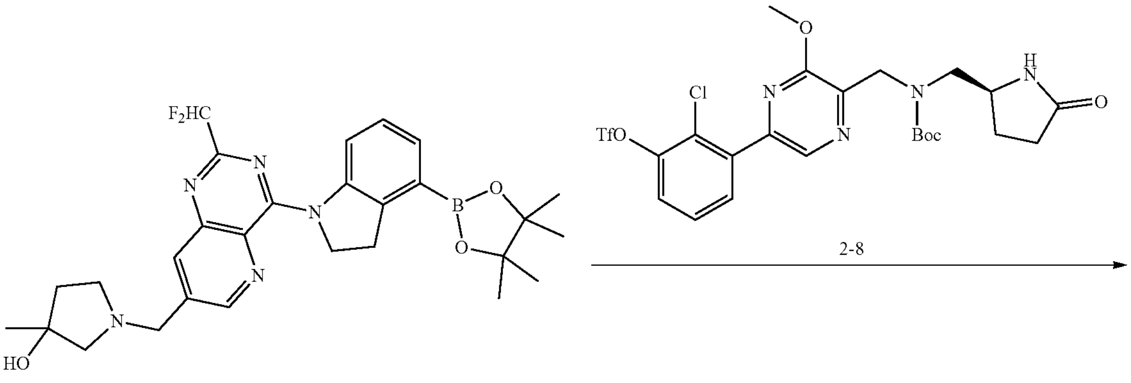
18-3
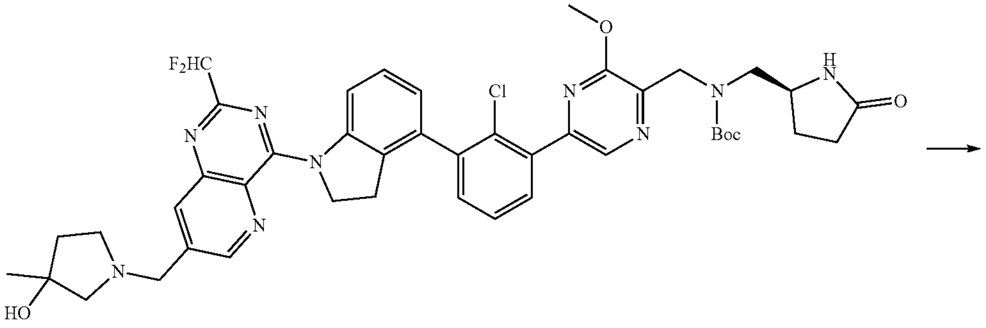
18-4

-continued

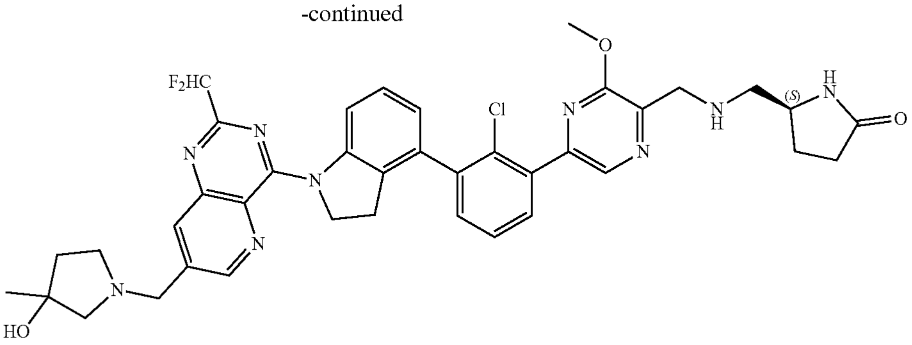

18

Step A: To a solution of compound 3-8 (150 mg, 370.19 μmol) and compound 18-1 (74.89 mg, 740.38 μmol) in dichloromethane (20 mL) was added 4 Å molecule sieves (150 mg), stirred at 25° C. for 30 minutes, and then $NaBH(OAc)_3$ (235.38 mg, 1.11 mmol) was added thereto. The reaction mixture was stirred at 25° C. for 1 hour, and filtered through diatomite, added with 20 mL water, and extracted with dichloromethane (40 mL×3). The organic phases were combined, washed with saturated brine (30 mL×3), dried over anhydrous sodium sulfate, and filtered. The filtrate was concentrated to obtain compound 18-2. MS (ESI) m/z: 491.9 $[M+H]^+$.

Step B: To 10 mL of dioxane solution was added compound 18-2 (0.17 g, 346.70 μmol), bis(pinacolato)diboron (132.06 mg, 520.04 μmol), potassium acetate (85.06 mg, 866.74 μmol), and $Pd(dppf)Cl_2 \cdot CH_2Cl_2$ (28.31 mg, 34.67 μmol). The reaction system was replaced with nitrogen three times, and reacted at 100° C. under nitrogen atmosphere for 1 hour. The reaction mixture was cooled to room temperature, and then filtered through diatomite. The filter cake was rinsed with dichloromethane (100 mL), and the organic phases were combined, then concentrated to obtain the crude product. The crude product was purified by silica gel column chromatography (methanol:dichloromethane=0 to 10%, v/v) to obtain compound 18-3. MS (ESI) m/z: 538.2 $[M+H]^+$.

Step C: To a mixture of 5 mL of dioxane and 1 mL of water was added compound 18-3 (65 mg, 120.95 μmol), compound 2-8 (75.56 mg, 127.00 μmol), sodium carbonate (32.05 mg, 302.38 μmol), and $Pd(PPh_3)_4$ (13.98 mg, 12.10 μmol). The reaction system was replaced with nitrogen three times and reacted at 100° C. under nitrogen atmosphere for 1 hour. The reaction mixture was cooled to room temperature, added with 20 mL of water, and extracted with ethyl acetate (30 mL×3). The organic phases were combined, washed with saturated brine (30 mL×3), dried over anhydrous sodium sulfate, and filtered. The filtrate was concentrated to obtain the crude product. The crude product was purified by silica gel plate (dichloromethane:methanol=10:1) to obtain compound 18-4. MS (ESI) m/z: 856.2 $[M+H]^+$.

Step D: To a solution of compound 18-4 (0.1 g, 116.77 μmol) in dichloromethane (3 mL) was added trifluoroacetic acid (1.54 g, 13.51 mmol). The reaction mixture was stirred at 25° C. for 12 hours. The reaction mixture was concentrated to obtain the crude product. The crude product was purified by preparative HPLC (chromatographic column: Phenomenex Synergi C18 150*25 mm*10 m; mobile phase: [pure water (0.225% formic acid)–acetonitrile]; acetonitrile %: 8% to 38%, 10 minutes) to obtain compound 18. $^1H$ NMR (400 MHz, DMSO-$d_6$) δ=8.94 (d, J=2.0 Hz, 1H), 8.66 (d, J=8.0 Hz, 1H), 8.53 (s, 1H), 8.21 (s, 1H), 8.14 (s, 1H), 7.75-7.67 (m, 2H), 7.61 (t, J=7.6 Hz, 1H), 7.57-7.52 (m, 1H), 7.42 (t, J=8.0 Hz, 1H), 7.14-6.79 (m, 2H), 5.00 (t, J=8.0 Hz, 2H), 4.80-4.52 (m, 1H), 4.13 (s, 2H), 4.01 (s, 3H), 3.97-3.92 (m, 2H), 3.79-3.71 (m, 2H), 3.10-3.05 (m, 2H), 2.85 (d, J=5.6 Hz, 2H), 2.73-2.66 (m, 1H), 2.64-2.57 (m, 2H), 2.19-2.07 (m, 3H), 1.85-1.69 (m, 3H), 1.26 (s, 3H); MS (ESI) m/z: 756.2 $[M+H]^+$.

Example 19: Compound 19

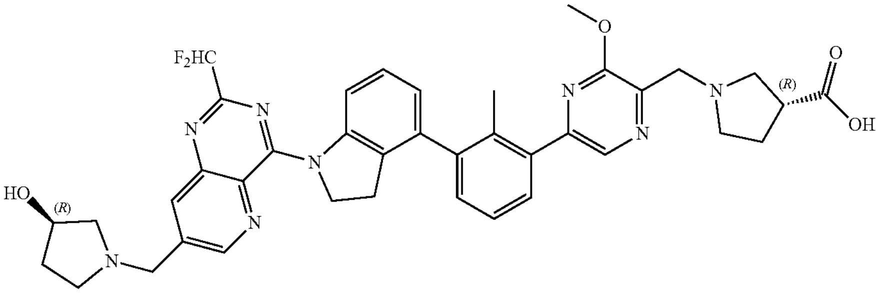

19

-continued
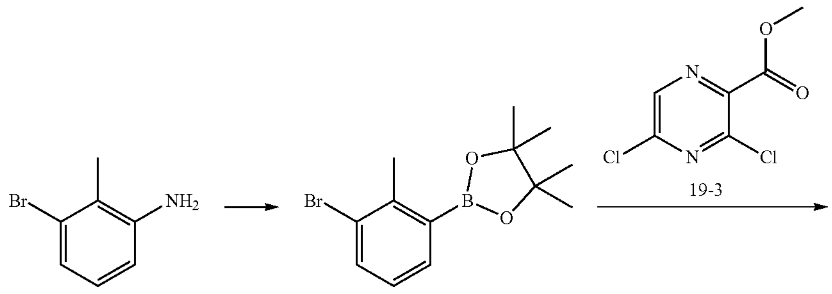
19-3
19-1 19-2
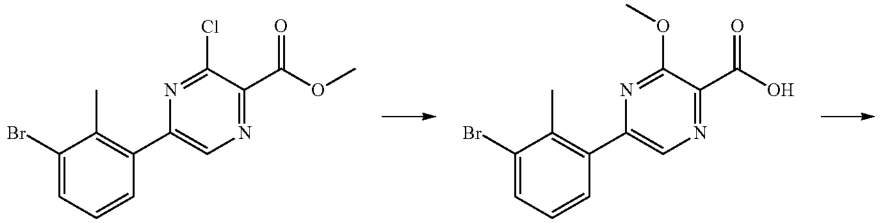
19-4 19-5
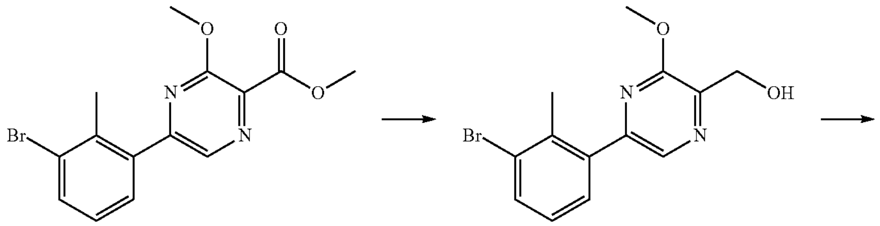
19-6 19-7
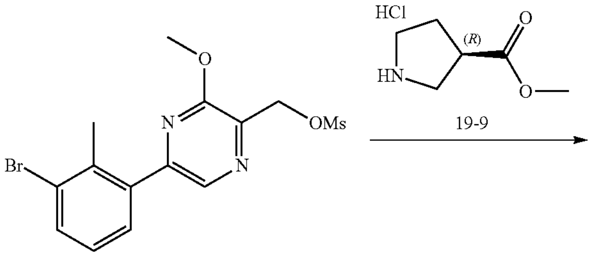
19-9
19-8
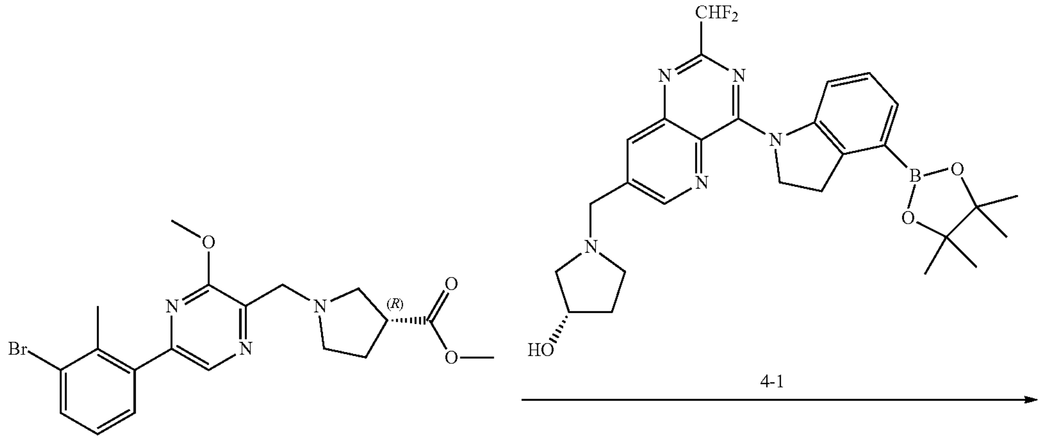
4-1
19-10

-continued

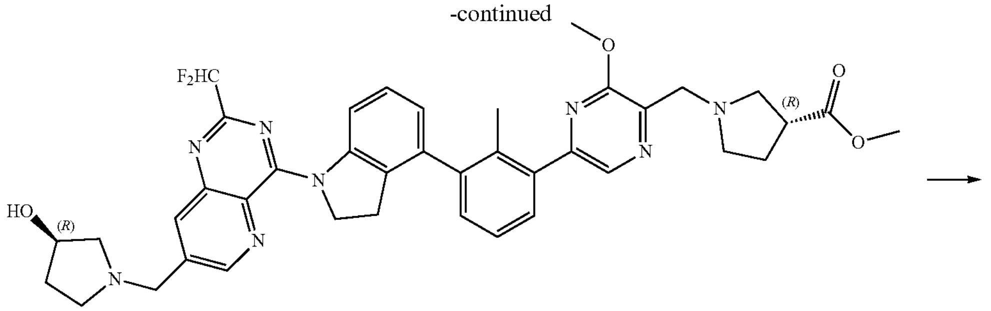

19-11

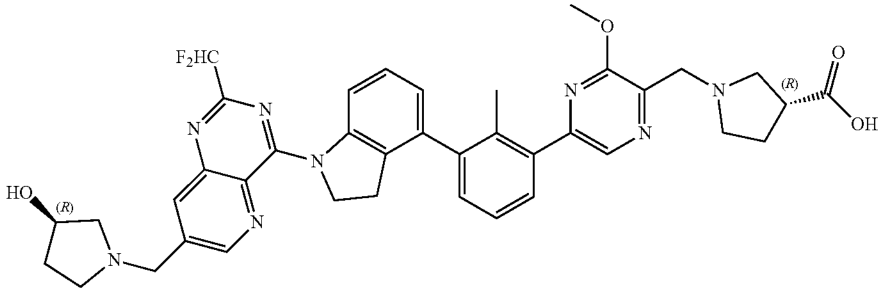

19

Step A: Compound 19-1 (5 g, 26.87 mmol) was dissolved in methanol (30 mL), and hydrochloric acid (12 M, 6.72 mL) and water (15 mL) were added thereto. The mixture was cooled, and at 0° C., sodium nitrite (2.23 g, 32.25 mmol) was dissolved in water (15 mL) and added dropwise to the reaction system. The mixture was stirred at 0° C. for 0.5 hours, then added with bis(pinacolato)diboron (20.47 g, 80.62 mmol) dissolved in methanol (30 mL). The mixture was stirred at 25° C. for 1 hour. The reaction mixture was quenched with 50 mL of water, and extracted with ethyl acetate (100 mL×3). The organic phases were combined, washed with saturated brine (50 mL×3), dried over anhydrous sodium sulfate, and filtered. The filtrate was concentrated to obtain the crude product. The crude product was purified by silica gel column chromatography (petroleum ether:ethyl acetate=1:0 to 0:1) to obtain compound 19-2.

Step B: To a mixture of 50 mL of dioxane and 10 mL of water was added compound 19-2 (5.79 g, 19.50 mmol), compound 19-3 (3.84 g, 18.57 mmol), potassium carbonate (3.94 g, 37.13 mmol), and $Pd(dppf)Cl_2 \cdot CH_2Cl_2$ (1.52 g, 1.86 mmol). The reaction system was replaced with nitrogen three times and reacted at 50° C. under nitrogen atmosphere for 12 hours. The reaction mixture was cooled to room temperature, added with 30 mL of water, then filtered through diatomite, and extracted with ethyl acetate (80 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 19-4. MS (ESI) m/z: 342.9 $[M+H]^+$.

Step C: To 40 mL of methanol was added compound 19-4 (3.99 g, 11.69 mmol) and sodium methoxide (4.21 g, 23.38 mmol, 4.68 mL, purity of 30%). The mixture was stirred at 50° C. for 12 hours. Then 8 mL of water was added thereto, and the mixture was stirred at 50° C. for another 2 hours. After the reaction mixture was cooled to room temperature, 30 mL of water was added thereto, and the pH was adjusted to 5 with 12M HCl. The mixture was filtered, and the filter cake was evaporated to dryness by rotary evaporation to obtain compound 19-5. MS (ESI) m/z: 322.7 $[M+H]^+$.

Step D: To 20 mL of methanol was added compound 19-5 (2 g, 6.19 mmol) and concentrated sulfuric acid (60.70 mg, 618.92 μmol). The mixture was stirred at 80° C. for 12 hours. The reaction mixture was evaporated to dryness by rotary evaporation to obtain the crude product, which was purified by silica gel column chromatography (petroleum ether:ethyl acetate=1:0 to 0:1, v/v) to obtain compound 19-6. MS (ESI) m/z: 338.9 $[M+H]^+$.

Step E: To 25 mL of tetrahydrofuran was added compound 19-6 (1.39 g, 4.12 mmol), and diisobutylaluminium hydride (1 M, 10.31 mL) was added dropwise thereto at −78° C. The mixture was stirred at 0° C. for 1 hour. The reaction mixture was warmed to room temperature, added with 50 mL of water, and extracted with ethyl acetate (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 19-7.

Step F: To 25 mL of dichloromethane was added compound 19-7 (1.33 g, 4.30 mmol) and triethylamine (870.64 mg, 8.60 mmol, 1.20 mL). The mixture was cooled, and methanesulfonyl chloride (1.59 g, 13.88 mmol, 1.07 mL) was added thereto at 0° C. The mixture was stirred at 0° C. for 1 hour. The reaction mixture was warmed to room temperature, added with 40 mL of water, and extracted with ethyl acetate (40 mL×3). The organic phases were combined, washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 19-8. MS (ESI) m/z: 388.8 $[M+H]^+$.

Step G: To 25 mL of N,N-dimethylformamide was added compound 19-8 (0.2 g, 516.46 μmol), compound 19-9 (89.81 mg, 542.29 μmol), and triethylamine (209.04 mg, 2.07 mmol). The mixture was stirred at 25° C. for 12 hours. The reaction mixture was added with 20 mL of water, then extracted with ethyl acetate (30 mL×3). The organic phases were combined, washed with saturated brine (30 mL×3), dried over anhydrous sodium sulfate, and filtered. The filtrate was concentrated to obtain the crude product. The crude product was purified by preparative thin-layer chromatography silica gel plate (petroleum ether:ethyl acetate=1:1) to obtain compound 19-10. MS (ESI) m/z: 422.0 $[M+H]^+$.

Step H: A mixture of compound 19-10 (52.20 mg, 124.19 μmol), compound 4-1 (65 mg, 124.19 μmol), sodium carbonate (32.91 mg, 310.48 μmol), and $Pd(PPh_3)_4$ (14.35 mg, 12.42 μmol) in dioxane (5 mL) and water (1 mL) was heated to 100° C. under nitrogen atmosphere, and stirred for 1 hour. The reaction mixture was diluted with 20 mL of water, filtered through diatomite, and extracted with dichloromethane (20 mL×3). The organic phases were combined, washed with saturated brine (30 mL×3), dried over anhydrous sodium sulfate, and filtered. The filtrate was concentrated to obtain the crude product. The crude product was purified by preparative thin-layer chromatography silica gel plate (dichloromethane:methanol=10:1) to obtain compound 19-11. MS (ESI) m/z: 643.5 $[M+H]^+$. MS (ESI) m/z: 737.1 $[M+H]^+$.

Step I: To a solution of compound 19-11 (0.05 g, 67.86 μmol) in methanol (5 mL) and water (1 mL) was added lithium hydroxide monohydrate (5.70 mg, 135.72 μmol). The reaction mixture was stirred at 50° C. for 1 hour. The reaction mixture was concentrated after cooling to room temperature. Then the mixture was dissolved in 10 mL of water, the pH of which was adjusted to 5 with concentrated hydrochloric acid. The mixture was further concentrated to obtain the crude product. The crude product was purified by preparative HPLC (chromatographic column: Phenomenex Synergi C18 150*25 mm*10 m; mobile phase: [water (formic acid)–acetonitrile]; acetonitrile %: 11% to 41%, 10 minutes) to obtain compound 19. $^1H$ NMR (400 MHz, DMSO-$d_6$) δ=8.92 (d, J=2.0 Hz, 1H), 8.65 (d, J=8.0 Hz, 1H), 8.36 (s, 1H), 8.16 (d, J=2.0 Hz, 1H), 7.53 (dd, J=1.2, 7.6 Hz, 1H), 7.42 (q, J=7.6 Hz, 2H), 7.33 (dd, J=1.2, 7.6 Hz, 1H), 7.09-6.78 (m, 2H), 5.00 (t, J=8.4 Hz, 2H), 4.30-4.15 (m, 1H), 3.96 (s, 3H), 3.91-3.76 (m, 4H), 3.12-3.03 (m, 2H), 2.97-2.86 (m, 3H), 2.77-2.57 (m, 6H), 2.41 (dd, J=3.2, 9.6 Hz, 1H), 2.16 (s, 3H), 2.10-1.98 (m, 2H), 1.63-1.55 (m, 1H); MS (ESI) m/z: 723.1 $[M+H]^+$.

Example 20: Compound 20

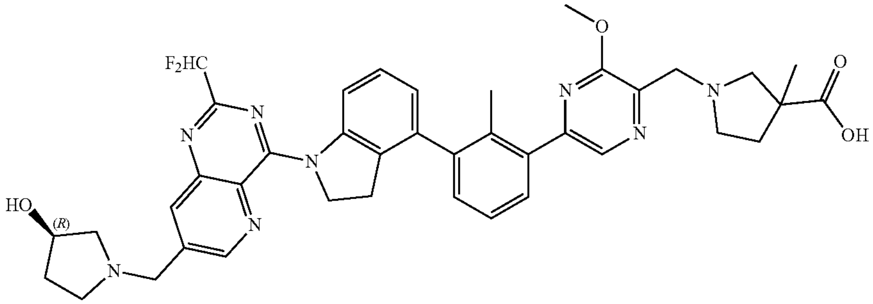

20

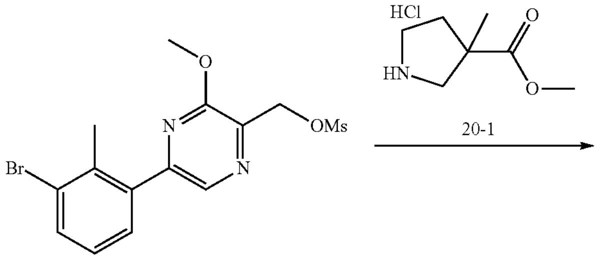

19-8

20-1

-continued

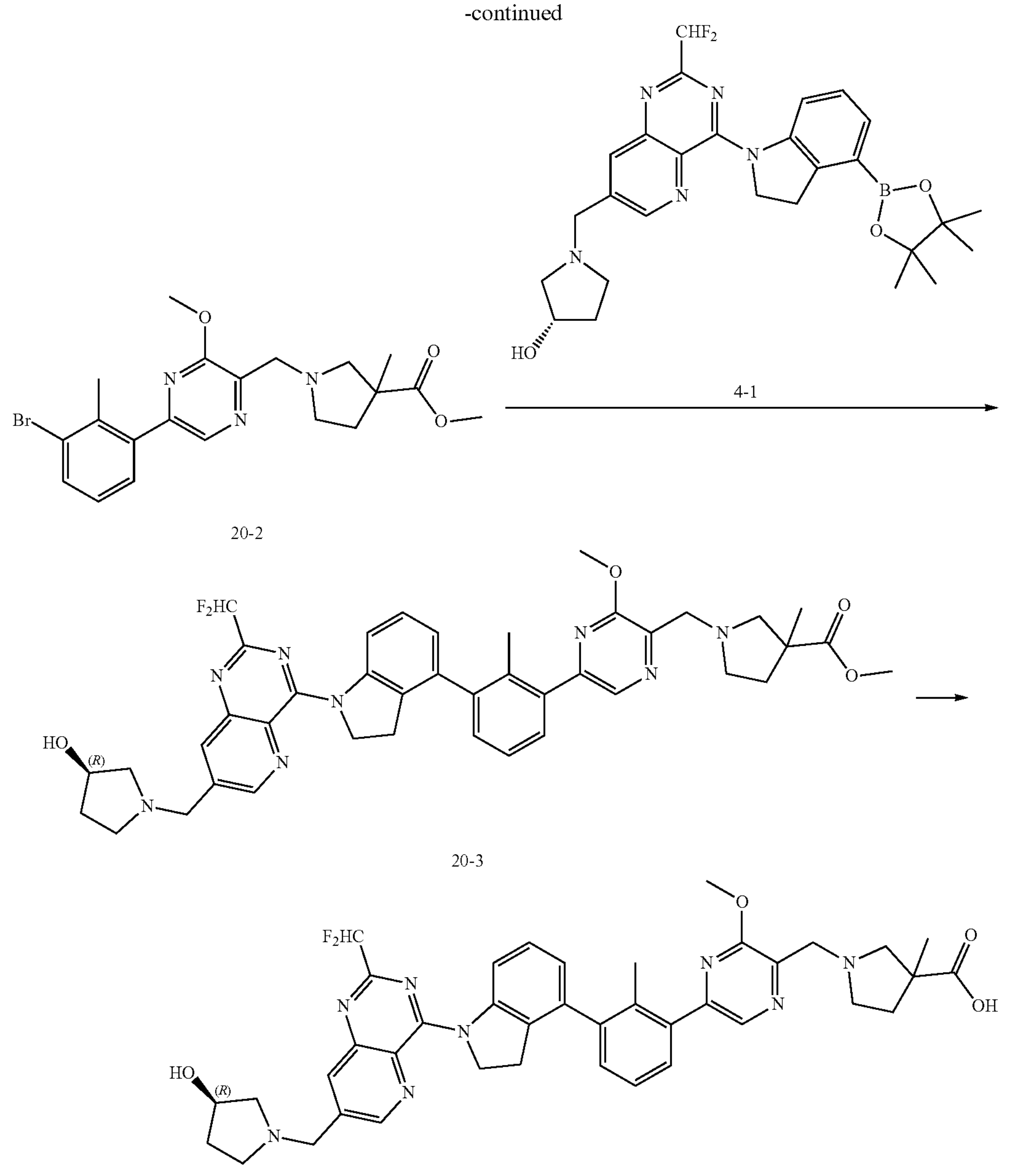

20-2

20-3

20

Step A: To 2 mL of N,N-dimethylformamide solution was added compound 19-8 (135 mg, 348.61 μmol), compound 20-1 (65.76 mg, 366.04 μmol), and triethylamine (141.10 mg, 1.39 mmol). The mixture was reacted at 25° C. for 4 hours. The reaction mixture was cooled to room temperature, added with 20 mL of water, and extracted with ethyl acetate (20 mL×3). The organic phases were combined, washed with saturated brine (20 mL×3), dried over anhydrous sodium sulfate, and filtered. The filtrate was concentrated to obtain the crude product. The crude product was purified by thin-layer chromatography (petroleum ether: ethyl acetate=1:1) to obtain compound 20-2. MS (ESI) m/z: 435.9 $[M+H]^+$.

Step B: A mixture of compound 20-2 (9.79 mg, 114.64 μmol), compound 4-1 (60 mg, 114.64 μmol), sodium carbonate (30.38 mg, 286.60 μmol), and $Pd(PPh_3)_4$ (13.25 mg, 11.46 μmol) in dioxane (5 mL) and water (1 mL) was replaced with nitrogen three times, heated to 100° C. under nitrogen atmosphere, and stirred for 1 hour. The reaction mixture was cooled to room temperature, added with 20 mL of water, and extracted with ethyl acetate (20 mL×3). The organic phases were combined, washed with saturated brine (20 mL×3), dried over anhydrous sodium sulfate, and filtered. The filtrate was concentrated to obtain the crude product. The crude product was purified by preparative thin-layer chromatography (dichloromethane:methanol=10:1) to obtain compound 20-3. MS (ESI) m/z: 751.2 $[M+H]^+$.

Step C: To a solution of compound 20-3 (0.07 g, 93.23 μmol) in methanol (2 mL) and water (0.4 mL) was added lithium hydroxide monohydrate (7.82 mg, 186.46 μmol). The reaction mixture was stirred at 50° C. for 1 hour. The reaction mixture was concentrated after cooling to room temperature. Then the mixture was dissolved in 10 mL of water, the pH of which was adjusted to 5 with 12M HCL.

The mixture was further concentrated to obtain the crude product. The crude product was purified by preparative HPLC (chromatographic column: Phenomenex luna C18 150*25 mm*10 m; mobile phase: [water (formic acid)–acetonitrile]; acetonitrile %: 13% to 43%, 10 minutes) to obtain compound 20. $^{1}$H NMR (400 MHz, DMSO-$d_6$) δ=8.91 (d, J=1.6 Hz, 1H), 8.65 (d, J=8.4 Hz, 1H), 8.37 (s, 1H), 8.16 (s, 1H), 7.54 (d, J=7.6 Hz, 1H), 7.41 (q, J=7.6 Hz, 2H), 7.33 (d, J=7.6 Hz, 1H), 7.10-6.76 (m, 2H), 5.00 (t, J=7.6 Hz, 2H), 4.30-4.16 (m, 1H), 3.96 (s, 3H), 3.92-3.78 (m, 4H), 3.09-2.92 (m, 3H), 2.77-2.65 (m, 4H), 2.41 (dd, J=3.2, 9.6 Hz, 1H), 2.28-2.20 (m, 1H), 2.16 (s, 3H), 2.09-1.96 (m, 2H), 1.64-1.46 (m, 2H), 1.24 (s, 4H); MS (ESI) m/z: 737.1 [M+H]$^+$.

Example 21: Compound 21

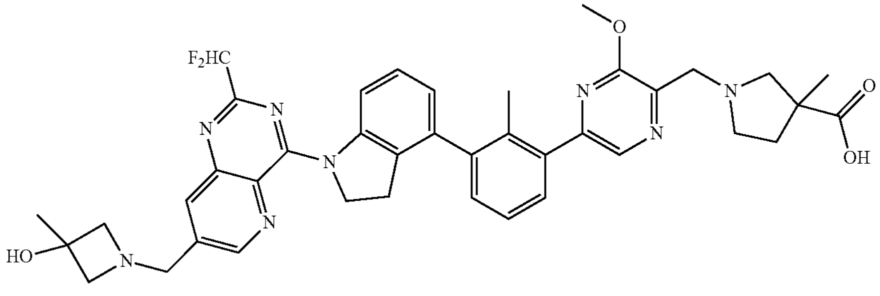

21

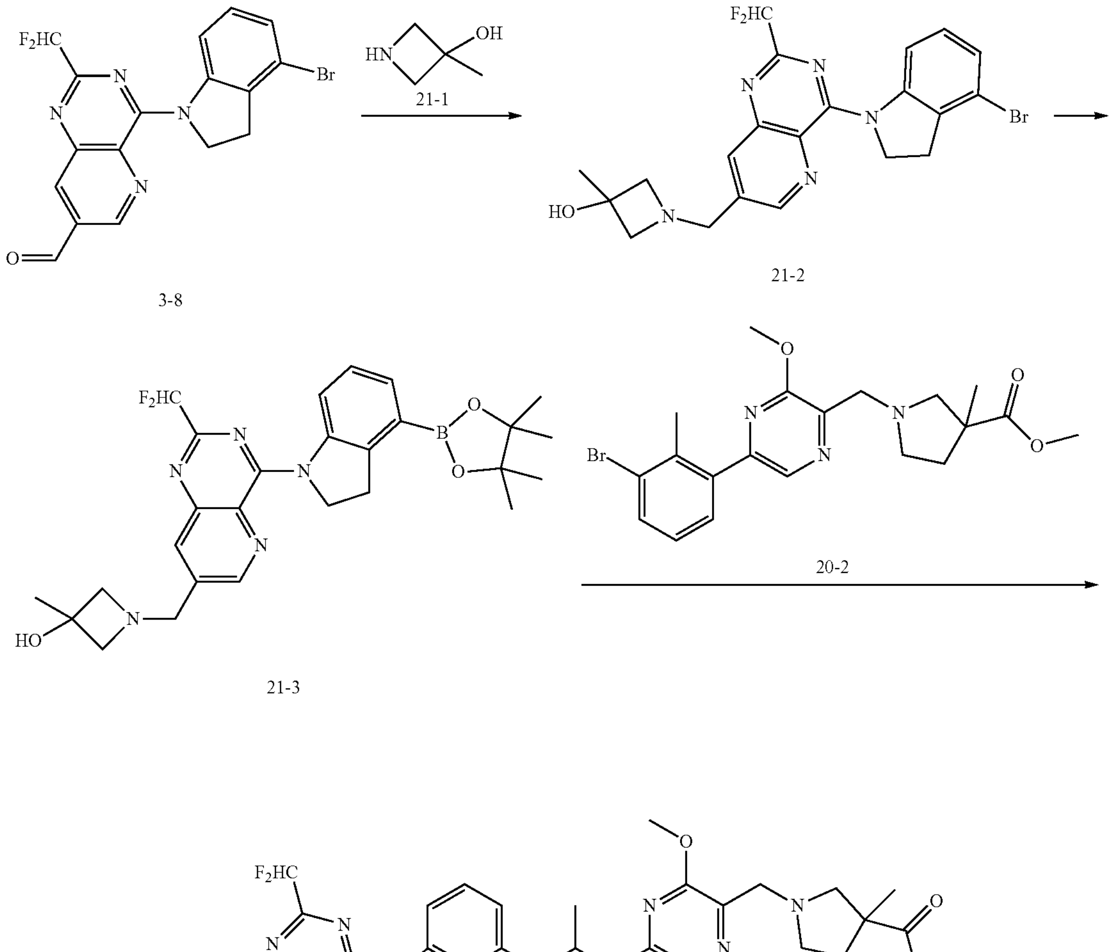

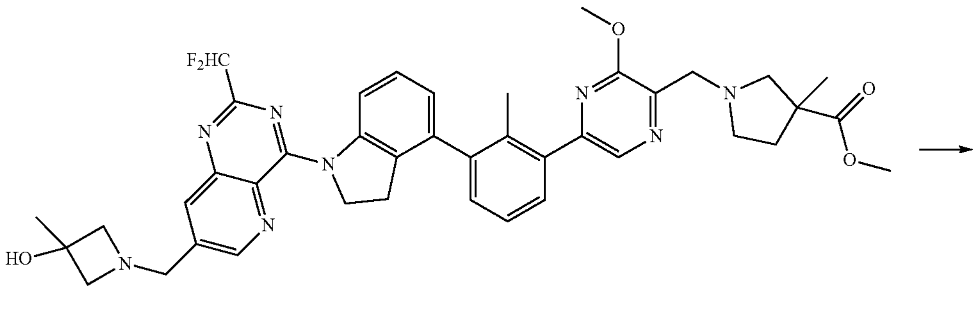

21-4

-continued

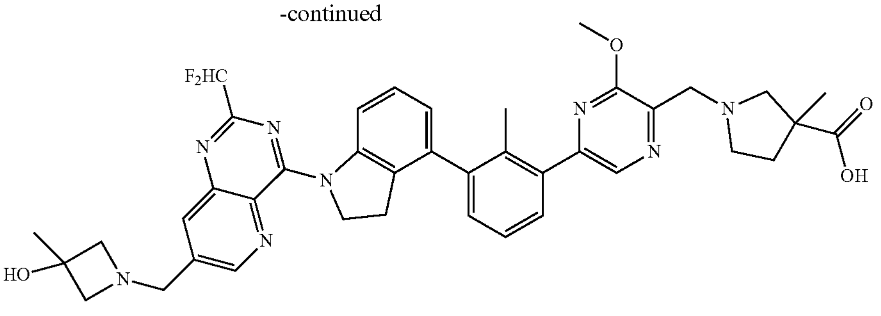

21

Step A: A mixture of compound 3-8 (0.6 g, 1.48 mmol), compound 21-1 (365.99 mg, 2.96 mmol), acetic acid (444.61 mg, 7.40 mmol), and 4 Å molecule sieves (0.6 g) in 15 mL of dichloromethane was stirred at 25° C. for 0.5 hours, and $NaBH(OAc)_3$ (941.50 mg, 4.44 mmol) was added thereto. The reaction system was stirred at 25° C. for 12 hours and filtered through diatomite. The filtrate was diluted with 20 mL of water, and extracted with dichloromethane (30 mL×3). The organic phase was washed with saturated brine (30 mL×3), dried over anhydrous sodium sulfate, and filtered. The filtrate was concentrated to obtain the crude product. The crude product was purified by silica gel column chromatography (dichloromethane:methanol=1:0 to 4:1, v/v) to obtain compound 21-2. MS (ESI) m/z: 477.9 $[M+H]^+$.

Step B: A solution of compound 21-2 (559.78 mg, 2.20 mmol), bis(pinacolato)diboron (0.7 g, 1.47 mmol), potassium acetate (360.57 mg, 3.67 mmol), and Pd(dppf)$Cl_2 \cdot CH_2Cl_2$ (120.01 mg, 149.96 μmol) in 15 mL of dioxane was replaced with nitrogen three times, heated to 100° C. under nitrogen atmosphere, and stirred for 1 hour. The reaction mixture was filtered through diatomite. The filter cake was washed with 100 mL of dichloromethane. The filtrate was concentrated to obtain the crude product. The crude product was purified by silica gel column chromatography (dichloromethane:methanol=1:0 to 4:1, v/v) to obtain compound 21-3. MS (ESI) m/z: 524.3 $[M+H]^+$.

Step C: A mixture of compound 21-3 (200 mg, 382.13 μmol), compound 20-2 (165.97 mg, 382.13 μmol), sodium carbonate (101.26 mg, 955.33 μmol), and $Pd(PPh_3)_4$ (44.16 mg, 38.21 μmol) in dioxane (5 mL) and water (1 mL) was replaced with nitrogen three times, heated to 100° C. under nitrogen atmosphere, and stirred for 1 hour. The reaction mixture was diluted with 20 mL of water, and extracted with ethyl acetate (40 mL×3). The organic phases were combined, washed with saturated brine (20 mL×3), dried over anhydrous sodium sulfate, and filtered. The filtrate was concentrated to obtain the crude product. The crude product was purified by preparative thin-layer chromatography silica gel plate (dichloromethane:methanol=10:1) to obtain compound 21-4. MS (ESI) m/z: 751.0 $[M+H]^+$.

Step D: To a mixture of compound 21-4 (120 mg, 159.82 μmol) in methanol (5 mL) and water (1 mL) was added lithium hydroxide monohydrate (13.41 mg, 319.64 μmol). The reaction system was stirred at 50° C. for 0.5 hours, then concentrated, diluted with 10 mL of water, and the pH was adjusted to 5 with concentrated hydrochloric acid. The mixture was concentrated to obtain the crude product. The crude product was purified by preparative HPLC (chromatographic column: Phenomenex luna C18 150*40 mm*15 m; mobile phase: [pure water (0.225% formic acid)-acetonitrile]; acetonitrile %: 13% to 43%, 10 minutes) to obtain the formate of compound 21. $^1H$ NMR (400 MHz, $CD_3OD$) δ=8.90 (s, 1H), 8.75 (d, J=8.4 Hz, 1H), 8.38 (d, J=1.6 Hz, 2H), 8.18 (d, J=1.2 Hz, 1H), 7.51 (d, J=7.6 Hz, 1H), 7.41 (q, J=7.6 Hz, 2H), 7.34 (d, J=7.2 Hz, 1H), 7.04 (d, J=7.6 Hz, 1H), 6.88-6.53 (m, 1H), 5.13-5.02 (m, 2H), 4.67 (d, J=1.6 Hz, 2H), 4.14 (s, 2H), 4.10 (s, 3H), 3.98 (d, J=11.2 Hz, 1H), 3.76-3.53 (m, 4H), 3.45 (d, J=8.0 Hz, 2H), 3.23 (d, J=11.2 Hz, 1H), 3.18-3.04 (m, 1H), 3.03-2.85 (m, 1H), 2.57-2.42 (m, 1H), 2.21 (s, 3H), 2.06-1.99 (m, 1H), 1.53 (s, 3H), 1.41 (s, 3H); MS (ESI) m/z: 737.0 $[M+H]^+$.

Example 22: Compound 22

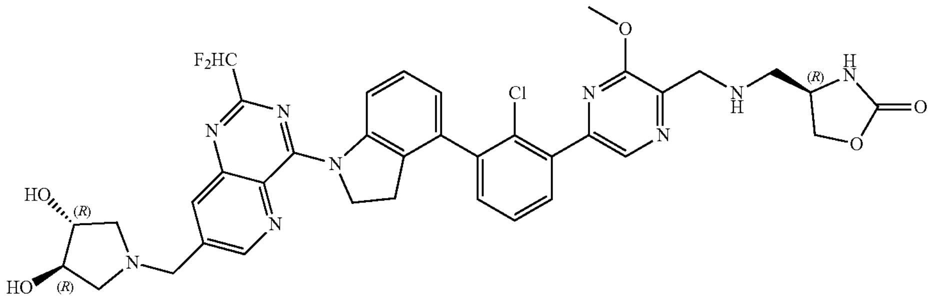

22

-continued
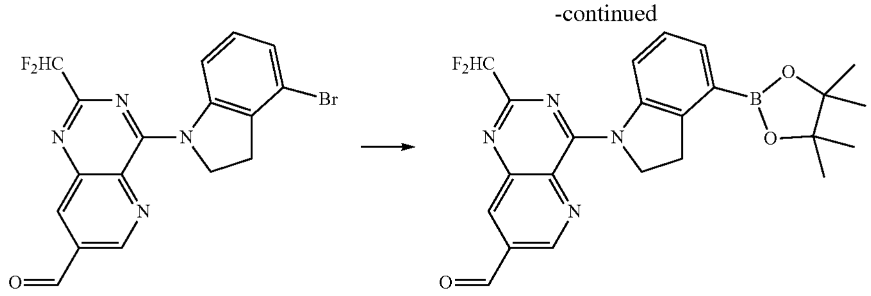
3-8 22-1
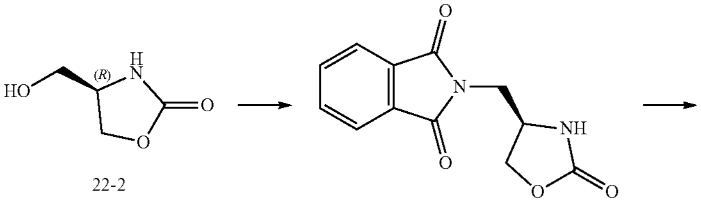
22-2
22-3
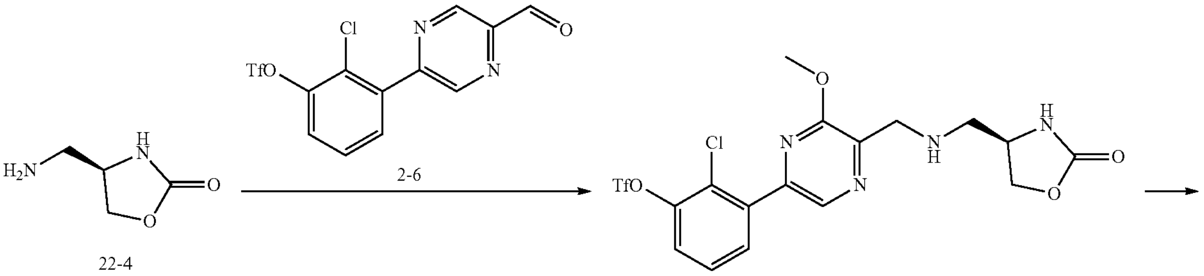
22-4
22-5
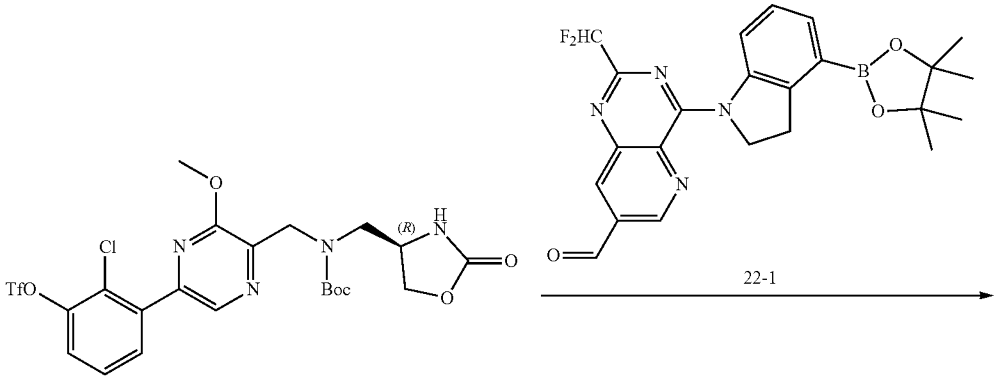
22-6
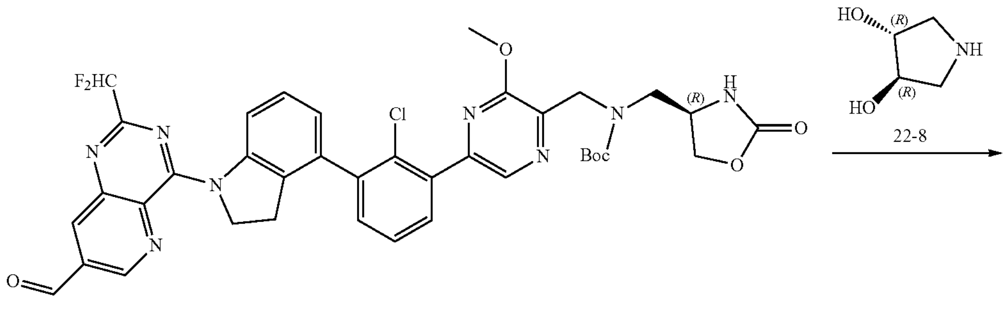
22-7

-continued

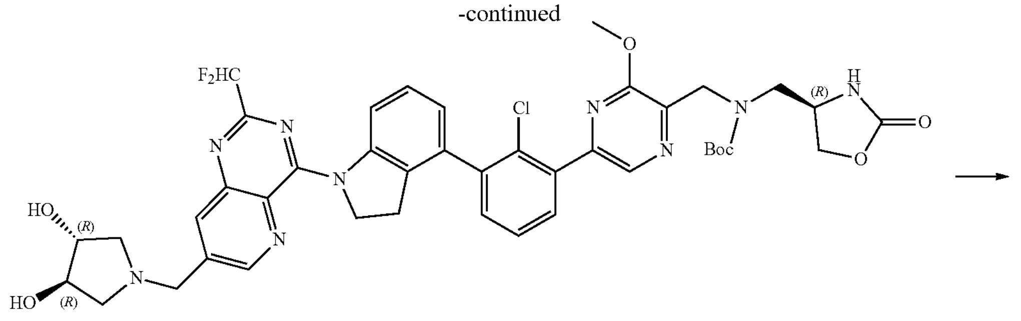

22-9

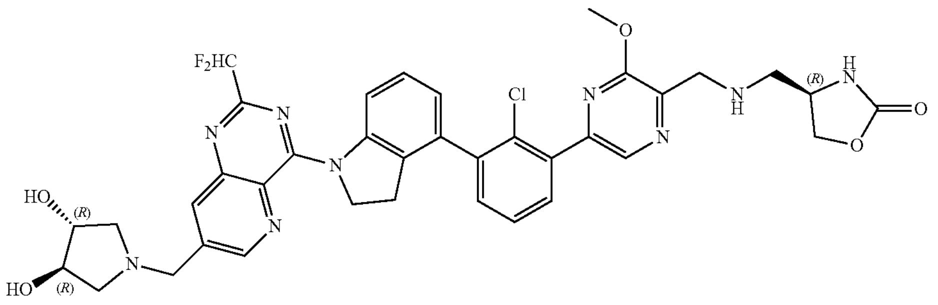

22

Step A: To 10 mL of dioxane solution was added compound 3-8 (0.5 g, 1.23 mmol), bis(pinacolato)diboron (470.03 mg, 1.85 mmol), potassium acetate (363.31 mg, 3.70 mmol), and Pd(dppf)$Cl_2$·$CH_2Cl_2$ (100.77 mg, 123.40 μmol). The reaction system was replaced with nitrogen three times, and reacted at 100° C. under nitrogen atmosphere for 2 hours. The reaction mixture was cooled to room temperature, added with 50 mL of water, and extracted with ethyl acetate (50 mL×2). The organic phases were combined, washed with saturated brine (50 mL), dried over anhydrous sodium sulfate, and filtered. The filtrate was concentrated to obtain the crude product. The crude product was purified by silica gel column chromatography (petroleum ether:ethyl acetate=0 to 20%, v/v) to obtain compound 22-1. MS (ESI) m/z: 453.1 $[M+H]^+$.

Step B: Compound 22-2 (2 g, 17.08 mmol) was dissolved in tetrahydrofuran (20 mL), and triphenylphosphine (4.93 g, 18.79 mmol) and DIAD (3.80 g, 18.79 mmol) were added thereto. The mixture was stirred at 25° C. for 6 hours. Petroleum ether (100 mL) was added thereto, then the mixture was filtered. The collected filter cake was dried under reduced pressure and purified by preparative HPLC (chromatographic column: Phenomenex luna C18 (250*70 mm*10 m); mobile phase: [pure water (0.1% trifluoroacetic acid)-acetonitrile)]; acetonitrile %: 10% to 40%, 20 minutes) to obtain compound 22-3. MS (ESI) m/z: 247.1 $[M+H]^+$.

Step C: To a solution of compound 22-3 (2.8 g, 10.94 mmol) in ethanol (30 mL) was added hydrazine hydrate (2.54 g, 49.72 mmol). The mixture was stirred at 50° C. for 0.5 hours, then heated to 75° C. and continued to be stirred for 2 hours. A white solid precipitated out, which was filtered out. The filtrate was then concentrated and ethanol (50 mL) was added thereto, leading to the precipitation of a white solid, which was also filtered out. The resulting filtrate was concentrated to obtain compound 22-4.

Step D: To a solution of compound 2-6 (256.24 mg, 645.89 μmol) in methanol (10 mL) was added $NaBH(OAc)_3$ (405.89 mg, 6.46 mmol) and compound 22-4 (150 mg, 1.29 mmol). The mixture was stirred at 25° C. for 5 hours. At 0° C., the reaction was quenched by the addition of water (10 mL), then extracted with dichloromethane (15 mL×3). The organic phases were combined, washed with saturated brine (15 mL×2), dried over anhydrous sodium sulfate, and filtered. The filtrate was then concentrated to obtain compound 22-5.

Step E: To a solution of compound 22-5 (400 mg, 805.08 μmol) in dichloromethane (10 mL) was added $Boc_2O$ (263.56 mg, 1.21 mmol) and triethylamine (244.40 mg, 2.42 mmol). The reaction mixture was stirred at 25° C. for 3 hours. The mixture was added with saturated sodium bicarbonate (10 mL) and extracted with dichloromethane (20 mL×2). The organic phases were combined, washed with saturated brine (20 mL×2), dried over anhydrous sodium sulfate, and filtered. The filtrate was concentrated to obtain the crude product. The crude product was purified by silica gel column chromatography (petroleum ether:ethyl acetate=50:1 to 0:1, v/v) to obtain compound 22-6.

Step F: To a mixture of 8 mL of tetrahydrofuran and 2 mL of water was added compound 22-1 (318.19 mg, 703.56 μmol), compound 22-6 (350 mg, 586.30 μmol), sodium carbonate (155.36 mg, 1.47 mmol), and Pd(dppf) $Cl_2$·$CH_2Cl_2$ (47.88 mg, 58.63 μmol). The reaction system was replaced with nitrogen three times and reacted at 50° C. under nitrogen atmosphere for 12 hours. The reaction mixture was cooled to room temperature, added with 20 mL of water, then filtered through diatomite, and extracted with ethyl acetate (20 mL×2). The organic phases were combined, washed with saturated brine (20 mL), dried over anhydrous sodium sulfate, and filtered. The filtrate was concentrated to obtain the crude product. The crude product was purified by silica gel plate (petroleum ether:ethyl acetate=2:3, v/v) to obtain compound 22-7. MS (ESI) m/z: 773.0 $[M+H]^+$.

Step G: To a solution of compound 22-7 (70 mg, 90.53 μmol) and compound 22-8 (37.34 mg, 362.14 μmol) in dichloromethane (20 mL) was added 4 Å molecule sieves (100 mg) and acetic acid (543.68 g, 9.05 μmol). The mixture was stirred at 25° C. for 30 minutes, then added with $NaBH(OAc)_3$ (76.75 mg, 362.14 μmol). The reaction mixture was stirred at 25° C. for 2 hours, and filtered through diatomite. The filtrate was concentrated to obtain the crude product. The crude product was purified by silica gel plate (methanol/dichloromethane=1:10, v/v) to obtain compound 22-9. MS (ESI) m/z: 860.2 $[M+H]^+$.

Step H: To a solution of compound 22-9 (11 mg, 12.79 μmol) in dichloromethane (3 mL) was added trifluoroacetic acid (1.13 g, 9.90 mmol). The reaction mixture was stirred at 25° C. for 20 minutes, and concentrated to obtain the crude product. The crude product was purified by preparative HPLC (chromatographic column: Phenomenex luna C18 150*50 mm*10 m; mobile phase: [pure water (0.225% formic acid)-acetonitrile]; acetonitrile %: 10% to 40%, 10 minutes) to obtain the formate of compound 22. $^1H$ NMR (400 MHz, $CD_3OD$) δ=8.85 (d, J=2.0 Hz, 1H), 8.67 (d, J=8.0 Hz, 1H), 8.33 (s, 1H), 8.09 (d, J=2.0 Hz, 1H), 7.57 (dd, J=2.0, 7.6 Hz, 1H), 7.45 (t, J=7.6 Hz, 1H), 7.37 (dd, J=2.0, 7.6 Hz, 1H), 7.31 (t, J=8.0 Hz, 1H), 6.97 (dd, J=0.8, 7.6 Hz, 1H), 6.76-6.45 (m, 2H), 5.00 (s, 2H), 4.42 (s, 1H), 4.12 (dd, J=5.6, 8.8 Hz, 1H), 4.01 (br dd, J=3.2, 4.0 Hz, 2H), 3.99-3.97 (m, 3H), 3.96 (s, 2H), 3.94-3.86 (m, 1H), 3.42 (s, 1H), 3.12-2.88 (m, 6H), 2.80-2.75 (m, 2H), 2.62-2.57 (m, 2H); MS (ESI) m/z: 760.1 $[M+H]^+$.

Example 23: Compound 23

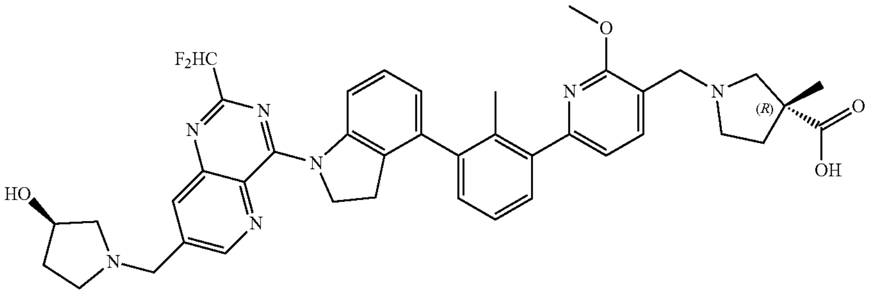

23

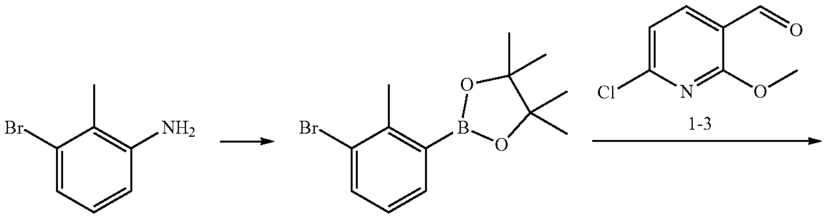

1-3

23-1 23-2

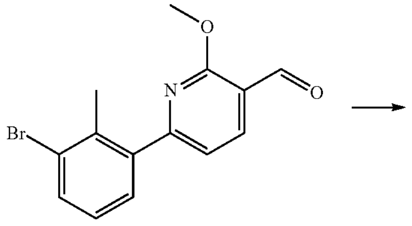

23-3

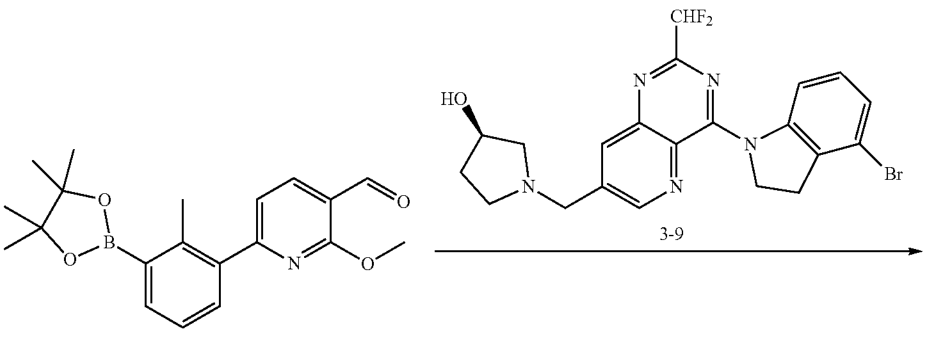

3-9

23-4

-continued

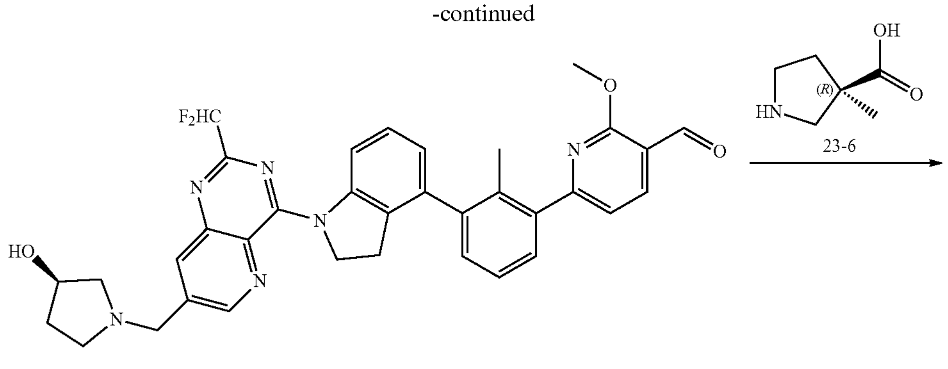

23-6

23-5

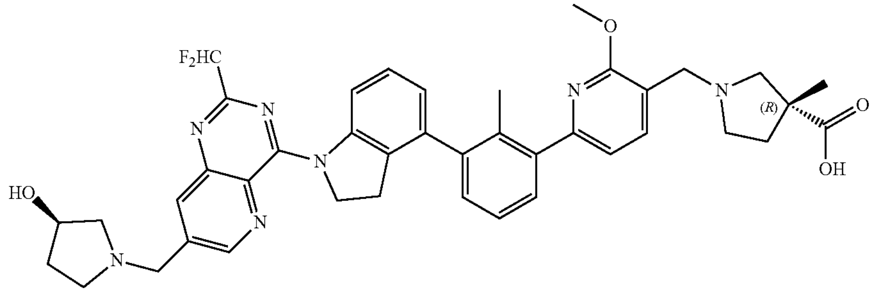

23

Step A: Compound 23-1 (3.5 g, 18.81 mmol) was dissolved in methanol (40 mL), and an aqueous solution (20 mL) of HCl (12M, 4.70 mL) was added thereto. The mixture was stirred at 0° C. and added with an aqueous solution (10 mL) of sodium nitrite (1.56 g, 22.57 mmol). The reaction was stirred at 0° C. for 30 minutes, then a methanol solution (40 mL) of bis(pinacolato)diboron (14.33 g, 56.44 mmol) was slowly added to the reaction. The reaction mixture was stirred at 20° C. for 1 hour, diluted with 100 mL of water, and extracted with ethyl acetate (100 mL×3). The organic phase was washed with saturated brine, dried over anhydrous sodium sulfate, and filtered. The filtrate was concentrated to obtain the crude product. The crude product was purified by silica gel column chromatography (petroleum ether:ethyl acetate=1:0 to 100:1) to obtain compound 23-2.

Step B: A mixture of compound 23-2 (1.5 g, 8.74 mmol), compound 1-3 (2.86 g, 9.62 mmol), $Pd(PPh_3)_4$ (1.01 g, 874.22 μmol), and potassium carbonate (2.42 g, 17.48 mmol) in dioxane (30 mL) and water (6 mL) was replaced with nitrogen, heated to 90° C. under nitrogen atmosphere, and stirred for 10 hours. The reaction mixture was diluted with dichloromethane (50 mL), filtered through diatomite, and the filtrate is evaporated to dryness by rotary evaporation to obtain the crude product. The crude product was purified by silica gel column chromatography (petroleum ether:ethyl acetate=20:1 to 5:1, v/v) to obtain compound 23-3. MS (ESI) m/z: 308.0 $[M+H]^+$.

Step C: A solution of compound 23-3 (1.4 g, 4.57 mmol), bis(pinacolato)diboron (2.32 g, 9.15 mmol), dichloromethane, bis(triphenylphosphine)palladium(II) chloride (373.44 mg, 457 μmol), and potassium acetate (897 mg, 9.15 mmol) in dioxane was replaced with nitrogen and then heated to 85° C. under nitrogen atmosphere, and stirred for 5 hours. The reaction mixture was diluted with dichloromethane (50 mL), filtered through diatomite, and the filtrate is evaporated to dryness by rotary evaporation to obtain the crude product. The crude product was purified by silica gel column chromatography (petroleum ether:ethyl acetate=100:1 to 10:1, v/v) to obtain compound 23-4. MS (ESI) m/z: 354.3 $[M+H]^+$.

Step D: To a mixture of 32 mL of dioxane and 8 mL of water was added compound 3-9 (750 mg, 1.57 mmol), compound 23-4 (556.17 mg, 1.57 mmol), sodium carbonate (417.22 mg, 3.94 mmol), and $Pd(dppf)Cl_2 \cdot CH_2Cl_2$ (128.59 mg, 157.46 μmol). The reaction system was replaced with nitrogen three times and reacted at 100° C. under nitrogen atmosphere for 2 hours. The reaction mixture was cooled to room temperature, concentrated in vacuum, then added with 30 mL of water, and extracted with dichloromethane (30 mL×2). The organic phases were combined and concentrated to obtain a crude product. The crude product was purified by silica gel column chromatography (methanol: dichloromethane=0 to 6%, v/v) to obtain compound 23-5. MS (ESI) m/z: 623.1 $[M+H]^+$.

Step E: To a solution of compound 23-5 (100 mg, 160.60 μmol) and compound 23-6 (82.97 mg, 642.40 μmol) in dichloromethane (10 mL) was added 4 Å molecule sieves (20 mg). The reaction mixture was stirred at 25° C. for 30 minutes, then added with $NaBH(OAc)_3$ (136.15 mg, 642.40 μmol). The reaction mixture was stirred at 25° C. for 12 hours, and filtered through diatomite. The filtrate was concentrated to obtain the crude product. The crude product was purified by preparative HPLC (chromatographic column: Waters Xbridge 150*25 mm*5 m; mobile phase: [pure water (sodium bicarbonate)-acetonitrile]; acetonitrile %: 40% to 70%, 7 minutes) to obtain compound 23. $^1H$ NMR (400 MHz, $CD_3OD$) δ=9.03 (d, J=2.0 Hz, 1H), 8.78 (d, J=8.0 Hz, 1H), 8.36 (d, J=2.0 Hz, 1H), 7.93 (d, J=7.6 Hz, 1H), 7.49-7.35 (m, 3H), 7.33-7.20 (m, 2H), 7.06 (d, J=7.6 Hz, 1H), 6.91-6.58 (m, 1H), 5.10 (br t, J=8.4 Hz, 2H), 4.62-4.53 (m, 3H), 4.48 (s, 2H), 4.10 (s, 3H), 3.85 (br d, J=10.8 Hz, 1H), 3.58-3.46 (m, 3H), 3.41-3.35 (m, 2H), 3.23 (br d, J=12.0 Hz, 1H), 3.18-3.08 (m, 2H), 3.05-2.93 (m, 1H), 2.56-2.44 (m, 1H), 2.40-2.27 (m, 1H), 2.19 (s, 3H), 2.11-1.99 (m, 2H), 1.42 (s, 3H); MS (ESI) m/z: 736.2 $[M+H]^+$.

Example 24: Compound 24

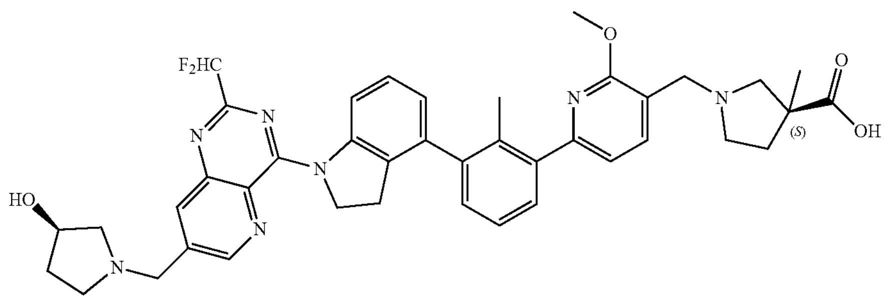

24

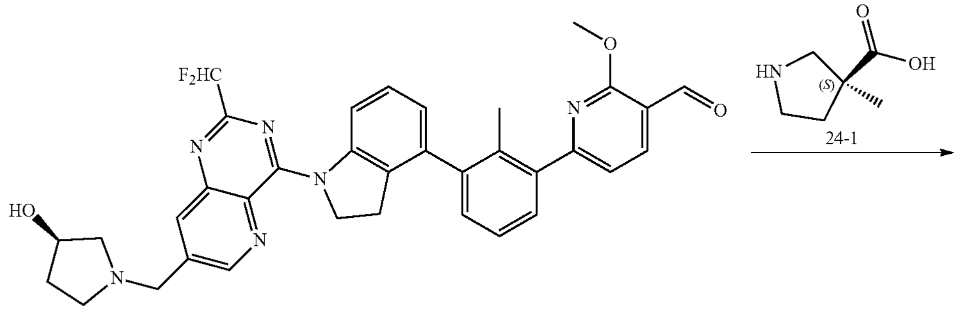

23-5

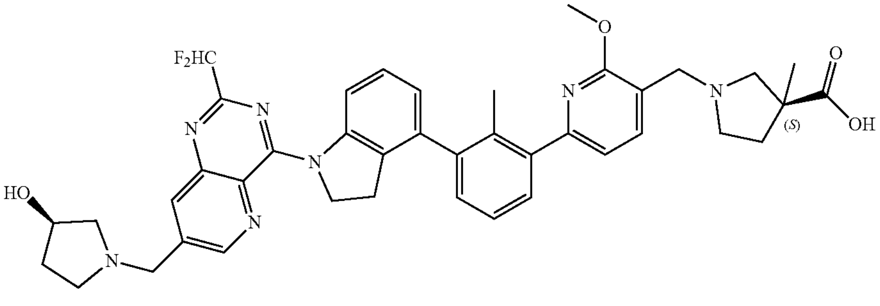

24

To a solution of compound 23-5 (100 mg, 160.60 μmol) and compound 24-1 (82.97 mg, 642.40 μmol) in dichloromethane (10 mL) was added 4 Å molecule sieves (20 mg). The reaction mixture was stirred at 25° C. for 30 minutes, then added with $NaBH(OAc)_3$ (136.15 mg, 642.40 μmol). The reaction mixture was stirred at 25° C. for 12 hours, and filtered through diatomite. The filtrate was concentrated to obtain the crude product. The crude product was purified by preparative HPLC (chromatographic column: Waters Xbridge 150*25 mm*5 m; mobile phase: [pure water (sodium bicarbonate)-acetonitrile]; acetonitrile %: 40% to 70%, 7 minutes) to obtain compound 24. $^1H$ NMR (400 MHz, $CD_3OD$) δ=8.95 (d, J=2.0 Hz, 1H), 8.75 (d, J=8.0 Hz, 1H), 8.17 (d, J=2.0 Hz, 1H), 7.91 (d, J=7.6 Hz, 1H), 7.51-7.44 (m, 1H), 7.39 (q, J=7.6 Hz, 2H), 7.32-7.27 (m, 1H), 7.22 (d, J=7.6 Hz, 1H), 7.04 (d, J=7.2 Hz, 1H), 6.90-6.52 (m, 1H), 5.10 (br t, J=8.0 Hz, 2H), 4.70-4.50 (m, 3H), 4.46-4.35 (m, 3H), 4.10 (s, 3H), 3.80-3.67 (m, 1H), 3.59-3.46 (m, 1H), 3.19-3.06 (m, 1H), 3.04-2.93 (m, 2H), 2.93-2.82 (m, 2H), 2.68-2.58 (m, 2H), 2.42 (br dd, J=4.4, 7.6 Hz, 1H), 2.25-2.14 (m, 4H), 2.05 (s, 3H), 2.02-1.92 (m, 1H), 1.85-1.71 (m, 1H); MS (ESI) m/z: 736.3 $[M+H]^+$.

Example 25: Compound 25

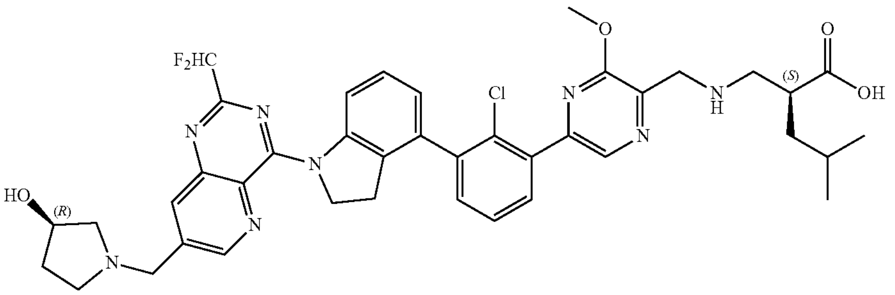

25

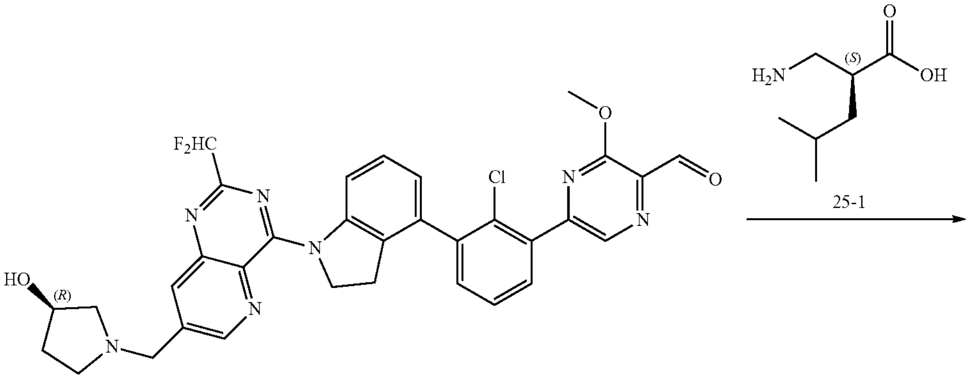

10-3

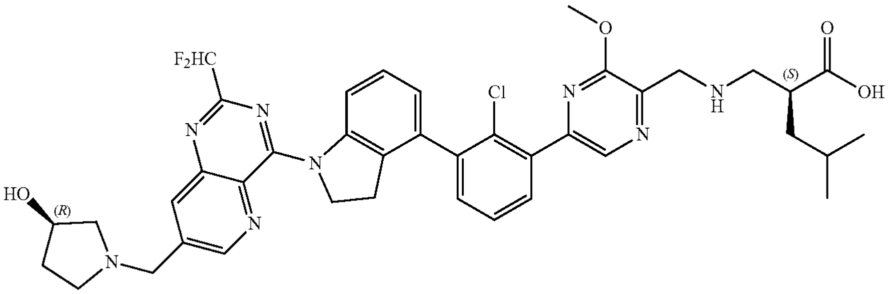

25

Step A: A solution of compound 10-3 (40 mg, 62.11 μmol), compound 25-1 (27.05 mg, 186.33 μmol), and 4 Å molecular sieves (40 mg) in 5 mL of dichloromethane was stirred for 0.5 hours, and $NaBH(OAc)_3$ (65.81 mg, 310.55 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 14% to 44%, 10 minutes) to obtain compound 25. $^1H$ NMR (400 MHz, $CD_3OD$) δ=9.00 (d, J=2.0 Hz, 1H), 8.84-8.74 (m, 1H), 8.55-8.46 (m, 1H), 8.30 (d, J=2.0 Hz, 1H), 7.74-7.66 (m, 1H), 7.62-7.54 (m, 1H), 7.53-7.47 (m, 1H), 7.47-7.38 (m, 1H), 7.13-7.04 (m, 1H), 6.89-6.57 (m, 1H), 5.15-5.06 (m, 2H), 4.54-4.44 (m, 3H), 4.38-4.25 (m, 2H), 4.16-4.08 (m, 3H), 3.29 (br d, J=6.8 Hz, 3H), 3.22-2.96 (m, 5H), 2.77-2.67 (m, 1H), 2.34-2.23 (m, 1H), 2.00-1.89 (m, 1H), 1.80-1.69 (m, 2H), 1.43-1.34 (m, 1H), 0.99 (t, J=6.4 Hz, 6H); MS (ESI) m/z: 773.1 $[M+H]^+$.

Example 26: Compound 26

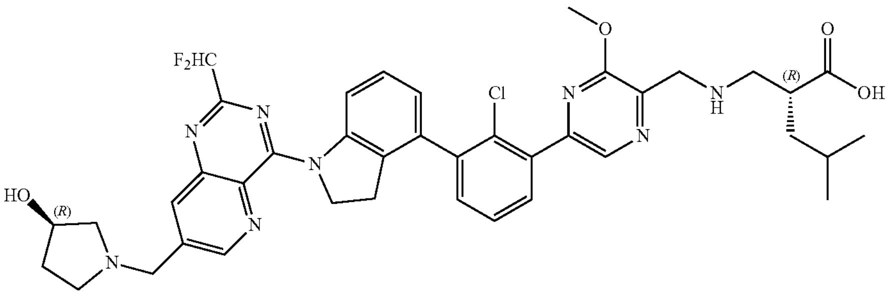

26

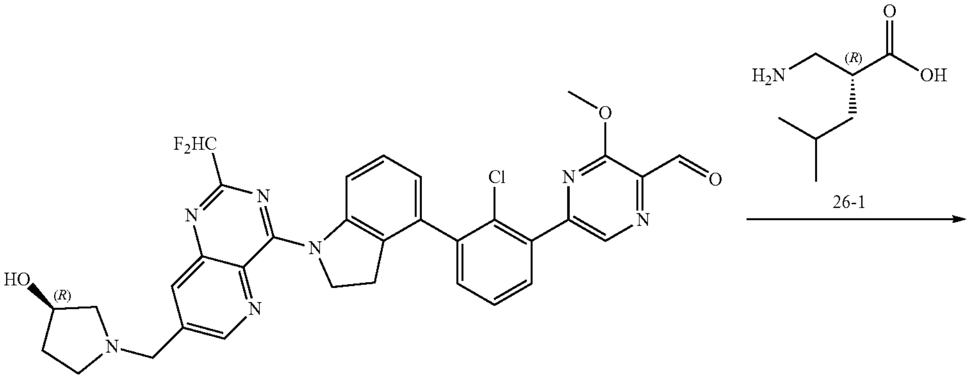

10-3

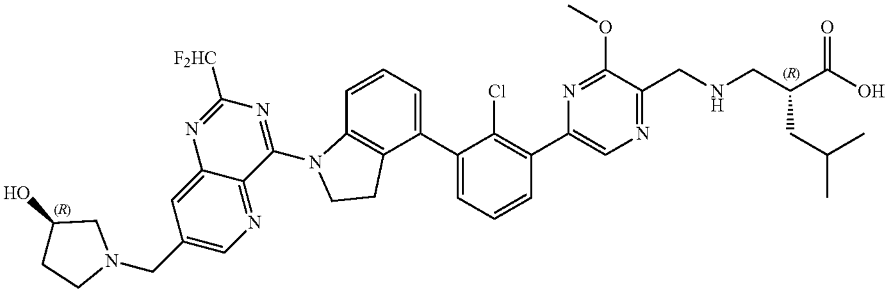

26

Step A: A solution of compound 10-3 (40 mg, 62.11 μmol), compound 26-1 (27.05 mg, 186.33 μmol), and 4 Å molecular sieves (40 mg) in 5 mL of dichloromethane was stirred for 0.5 hours, and $NaBH(OAc)_3$ (65.81 mg, 310.55 μmol) was added thereto. The reaction system was stirred at 15° C. for 1.5 hours, then added with 2 mL of water, and filtered. The filtrate was concentrated to obtain the crude product. The crude product was purified by preparative HPLC (chromatographic column: Phenomenex luna C18 150*25 mm*10 m; mobile phase: [pure water (0.225% formic acid)-acetonitrile]; acetonitrile %: 14% to 44%, 10 minutes) to obtain compound 26. $^1H$ NMR (400 MHz, $CD_3OD$) δ=8.94 (d, J=2.0 Hz, 1H), 8.77 (d, J=8.0 Hz, 1H), 8.50 (s, 1H), 8.19 (d, J=1.6 Hz, 1H), 7.69 (dd, J=1.6, 7.6 Hz, 1H), 7.56 (t, J=7.6 Hz, 1H), 7.51-7.46 (m, 1H), 7.40 (t, J=8.0 Hz, 1H), 7.07 (d, J=7.6 Hz, 1H), 6.87-6.53 (m, 1H), 5.06 (br t, J=8.0 Hz, 2H), 4.48-4.41 (m, 3H), 4.12 (s, 3H), 4.09-3.97 (m, 2H), 3.30-3.20 (m, 2H), 3.17-3.04 (m, 2H), 3.04-2.92 (m, 2H), 2.82-2.64 (m, 3H), 2.23 (qd, J=7.2, 14.1 Hz, 1H), 1.88-1.68 (m, 3H), 1.43-1.26 (m, 1H), 0.98 (t, J=6.4 Hz, 6H); MS (ESI) m/z: 773.1 $[M+H]^+$.

Example 27: Compound 27
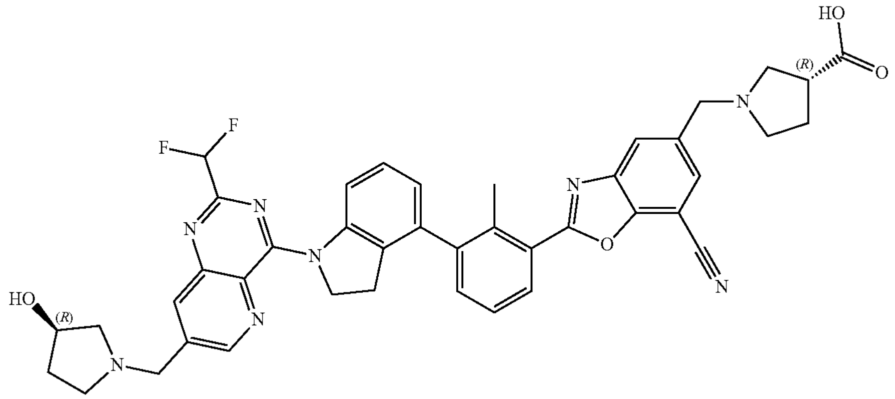
27
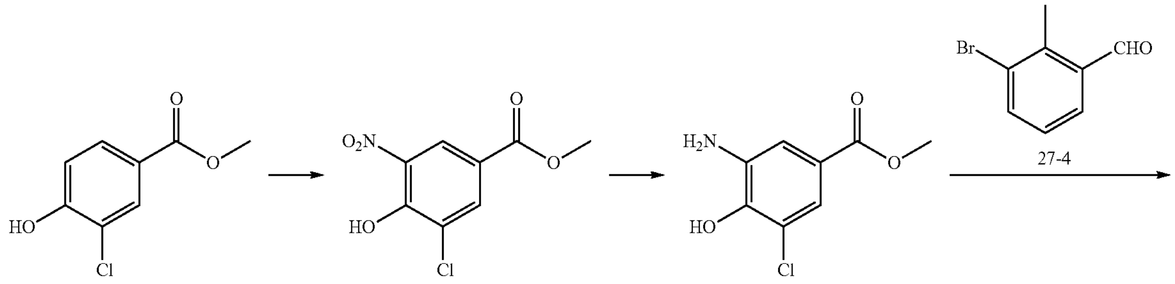
27-1 27-2 27-3
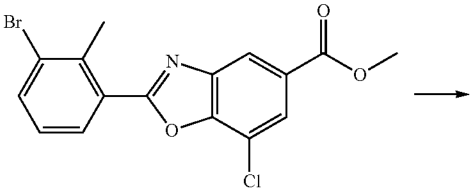
27-5
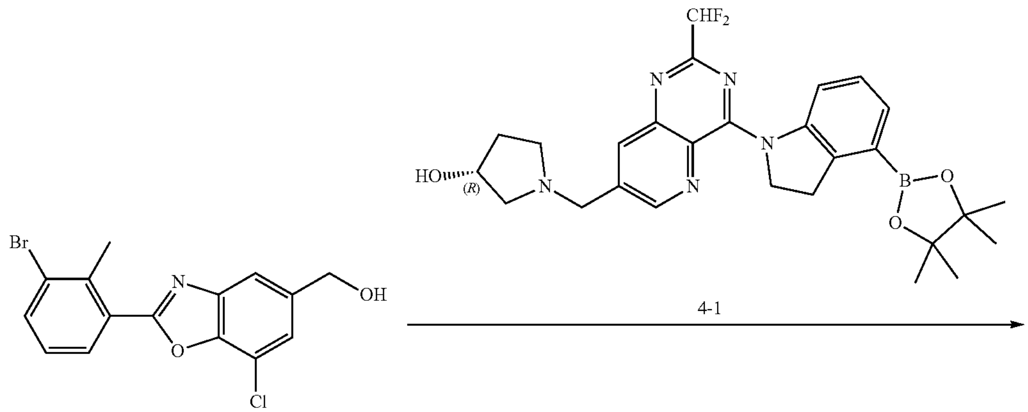
27-6

-continued

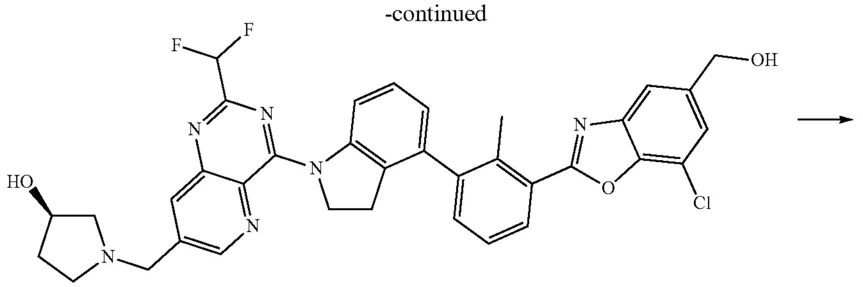

27-7

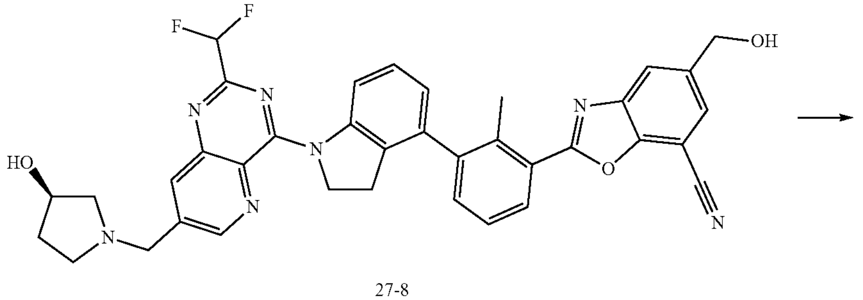

27-8

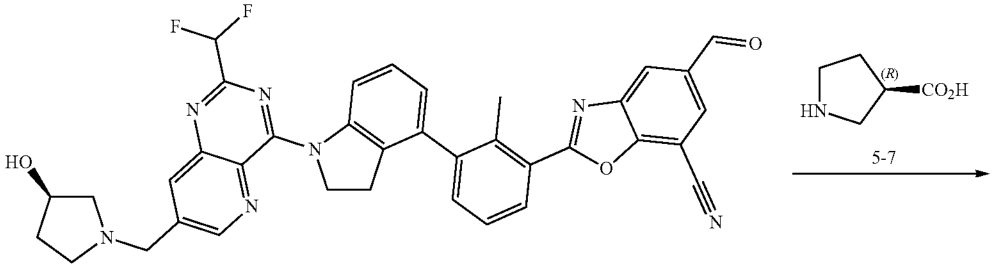

27-9

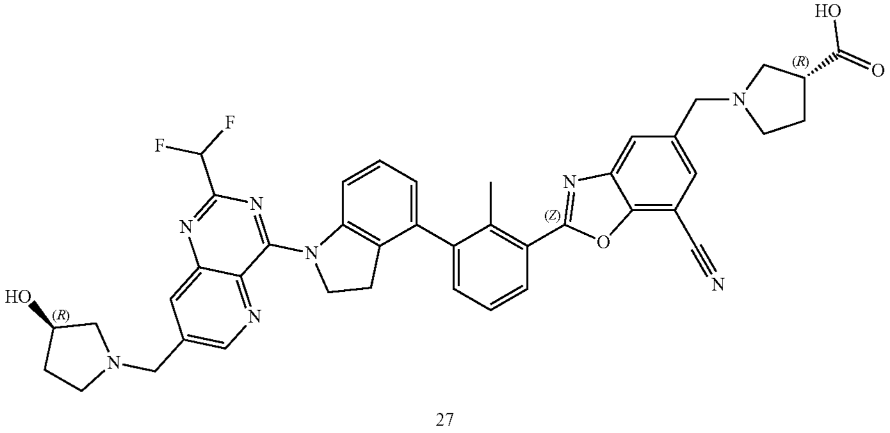

27

Step H: At 0° C., to a solution of compound 27-1 (10 g, 53.59 mmol) in 20 mL of acetic acid was added a solution of nitric acid (9.16 g, 145.30 mmol) in 20 mL of acetic acid. The reaction system was stirred at 25° C. for 2 hours, then diluted with 50 mL of water, filtered. The filter cake was washed with 50 mL of water, then dried to obtain the crude compound 27-2.

Step I: To a mixture of compound 27-2 (3 g, 12.95) in 30 mL of methanol and 6 mL of water was added sodium hydrosulfite (13.53 g, 77.72 mmol). The reaction mixture was stirred at 70° C. for 12 hours, and filtered. The filter cake was washed with 100 mL of methanol. The filtrate was concentrated to obtain the crude product. The crude product was purified by silica gel column chromatography (dichloromethane:methanol=1:0 to 4:1, v/v) to obtain compound 27-3. MS (ESI) m/z: 202.1 $[M+H]^+$.

Step J: A solution of compound 27-3 (4.2 g, 20.83 mmol) and compound 27-4 (3.94 g, 19.79 mmol) in 100 mL of ethanol was stirred at 25° C. for 1 hour, then concentrated, and dissolved in 100 mL of dichloromethane solution, and added with 2,3-dicyano-5,6-dichlorobenzoquinone (4.49 g, 19.79 mmol). The reaction system was stirred at 25° C. for 12 hours, then quenched with 100 mL of saturated sodium sulfite solution, extracted with dichloromethane (80 mL×3). The organic phases were combined, washed with saturated brine (50 mL×3), dried over anhydrous sodium sulfate, and filtered. The filtrate was concentrated to obtain the crude product. The crude product was purified by silica gel column chromatography (petroleum ether:dichloromethane=1:0 to 0:1, v/v) to obtain compound 27-5. MS (ESI) m/z: 381.7 $[M+H]^+$.

Step K: At −78° C., to a solution of compound 27-5 (7.62 g, 20.02 mmol) in 120 mL of dichloromethane was dropwise added a solution of DIBAL-H in toluene (1 mol/L, 40.04 mL). The reaction system was stirred at 25° C. for 2 hours, then quenched with 200 mL of saturated potassium sodium tartrate solution, and then extracted with dichloromethane (100 mL×3). The organic phases were combined and washed with saturated brine (50 mL×3), dried over anhydrous sodium sulfate, and filtered. The filtrate was concentrated to obtain the crude product. The crude product was purified by silica gel column chromatography (dichloromethane:methanol=1:0 to 4:1, v/v) to obtain compound 27-6. MS (ESI) m/z: 354.0 $[M+H]^+$.

Step L: A mixture of compound 4-1 (2.5 g, 4.78 mmol), compound 27-6 (1.68 g, 4.78 mmol), sodium carbonate (1.27 g, 11.94 mmol), and $Pd(PPh_3)_4$ (551.97 mg, 477.66 μmol) in dioxane (15 mL) and water (3 mL) was replaced with nitrogen three times, heated to 100° C. under nitrogen atmosphere, and stirred for 12 hours. The reaction mixture was diluted with 30 mL of water and then filtered through diatomite, and the filtrate was extracted with dichloromethane (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (dichloromethane:methanol=1:0 to 3:1, v/v) to obtain compound 27-7. MS (ESI) m/z: 669.3 $[M+H]^+$.

Step M: A mixture of compound 27-7 (2.7 g, 4.04 mmol), potassium ferrocyanide (1.70 g, 4.04 mmol), potassium acetate (79.20 mg, 807.03 μmol), and t-BuXPhos-Pd-G3 (320.54 mg, 403.52 μmol) in dioxane (30 mL) and water (30 mL) was replaced with nitrogen three times, heated to 100° C. under nitrogen atmosphere, and stirred for 3 hours. The reaction mixture was diluted with 20 mL of water, filtered through diatomite, and the filtrate was extracted with dichloromethane (50 mL×3). The organic phases were combined, washed with saturated brine (30 mL×3), dried over anhydrous sodium sulfate, and filtered. The filtrate was concentrated to obtain the crude product. The crude product was purified by silica gel column chromatography (dichloromethane:methanol=1:0 to 3:1, v/v) to obtain compound 27-8. MS (ESI) m/z: 660.0 $[M+H]^+$.

Step N: To a solution of compound 27-8 (2.4 g, 3.64 mmol) in 40 mL of dichloromethane was added manganese dioxide (6.33 g, 72.76 mmol). The reaction mixture was stirred at 50° C. for 12 hours, then filtered through diatomite, and the filter cake was washed with 500 mL of dichloromethane. The filtrate was concentrated to obtain the crude compound 27-9. MS (ESI) m/z: 658.3 $[M+H]^+$.

Step O: A solution of compound 27-9 (2.33 g, 3.54 mmol), compound 5-7 (815.77 mg, 7.09 mmol), and triethylamine (717.00 mg, 7.09 mmol) in 30 mL of dichloromethane was stirred at 45° C. for 1 hour, cooled to room temperature, then added with $NaBH(OAc)_3$ (1.5 g, 7.09 mmol) and acetic acid (319.12 mg, 5.31 mmol). The mixture was stirred at 25° C. for another 2 hours, then concentrated to obtain the crude product. The crude product was first purified by silica gel column chromatography (dichloromethane:methanol=1:0 to 3:1, v/v), and further purified by preparative HPLC (chromatographic column: Phenomenex Synergi Max-RP 250*50 mm*10 m; mobile phase: [pure water (0.225% formic acid)-acetonitrile]; acetonitrile %: 15% to 45%, 20 minutes) to obtain compound 27. $^1H$ NMR (400 MHz, DMSO-$d_6$) δ=8.90 (s, 1H), 8.66 (d, J=8.4 Hz, 1H), 8.19-8.07 (m, 3H), 7.87 (s, 1H), 7.59-7.53 (m, 1H), 7.53-7.49 (m, 1H), 7.42 (t, J=7.6 Hz, 1H), 7.10-6.74 (m, 2H), 4.97 (t, J=8.4 Hz, 2H), 4.23 (s, 1H), 3.94-3.73 (m, 7H), 3.09-2.82 (m, 4H), 2.81-2.63 (m, 4H), 2.52 (s, 3H), 2.12-1.86 (m, 3H), 1.61-1.58 (m, 1H); MS (ESI) m/z: 757.3 $[M+H]^+$.

Example 28: Compound 28

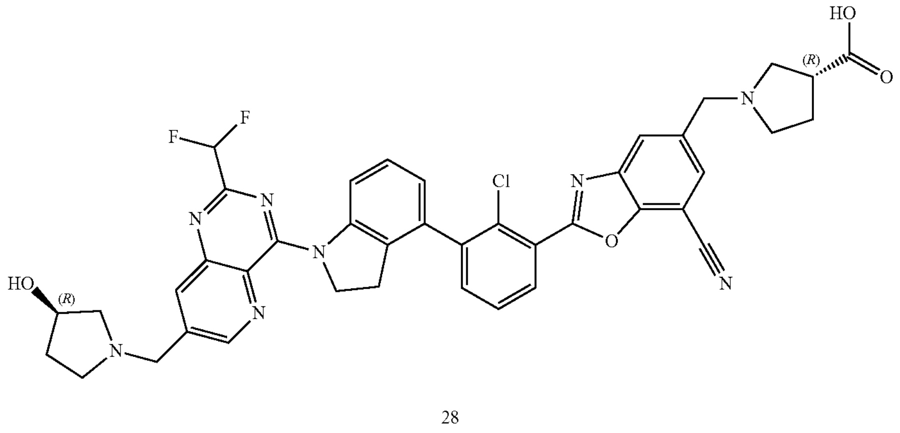

-continued
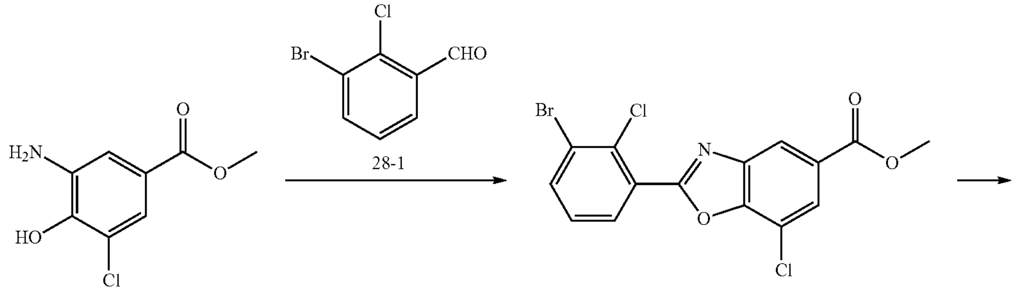
27-3 28-1 28-2
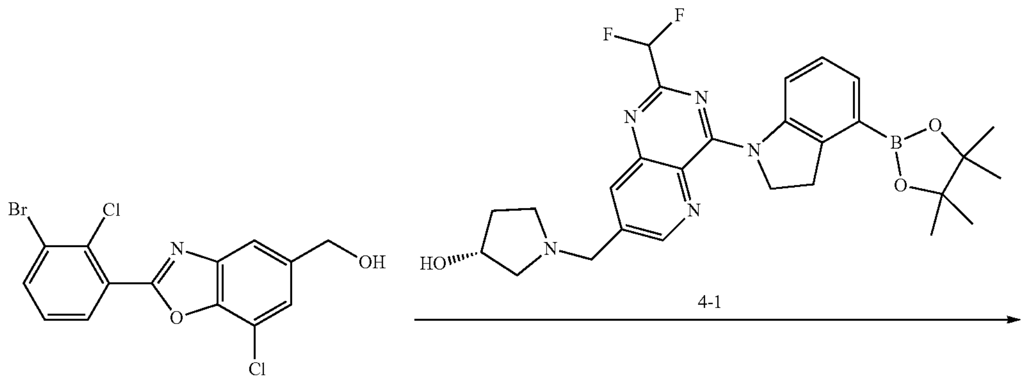
28-3 4-1
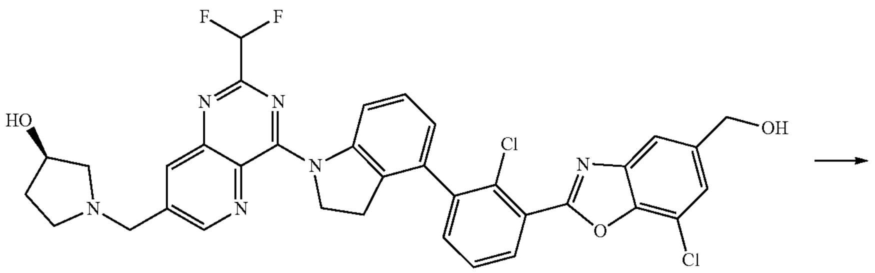
28-4
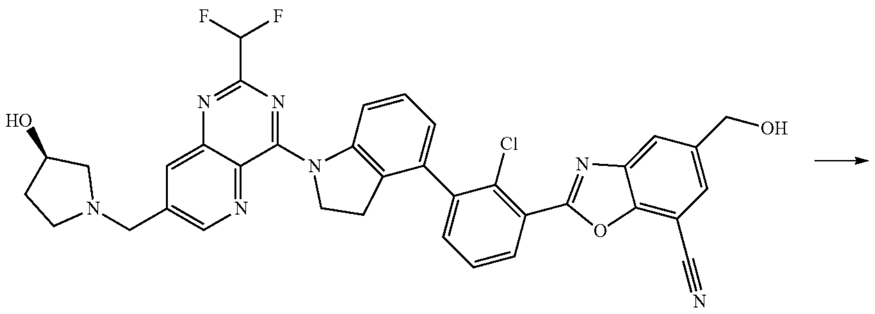
28-5

-continued

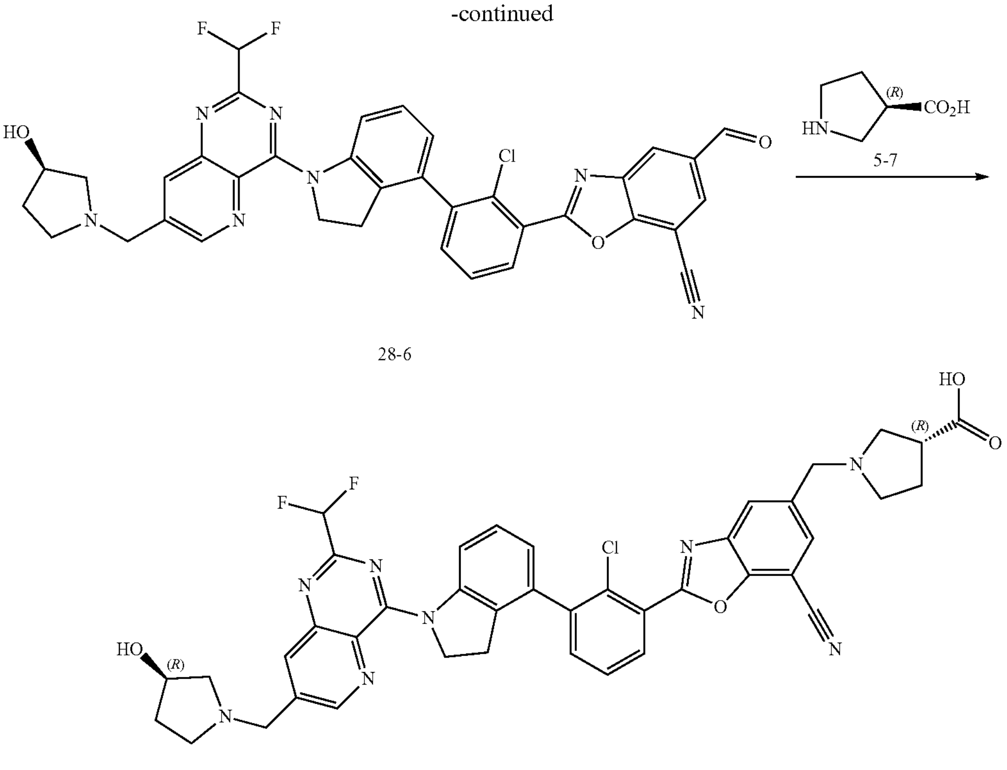

28-6

28

Step A. A solution of compound 27-3 (3.0 g, 14.88 mmol) and compound 28-1 (3.10 g, 14.14 mmol) in 60 mL of ethanol was stirred at 25° C. for 1 hour, then concentrated, dissolved in 60 mL of dichloromethane solution, and added with 2,3-dicyano-5,6-dichlorobenzoquinone (3.21 g, 14.14 mmol). The reaction system was stirred at 25° C. for 12 hours, then quenched with 30 mL of saturated sodium sulfite solution, extracted with dichloromethane (40 mL×3). The organic phases were combined, washed with saturated brine (20 mL×3), dried over anhydrous sodium sulfate, and filtered. The filtrate was concentrated to obtain the crude product. The crude product was purified by silica gel column chromatography (petroleum ether:dichloromethane=1:0 to 0:1, v/v) to obtain compound 28-2. MS (ESI) m/z: 401.7 $[M+H]^+$.

Step B: At −78° C., to a solution of compound 28-2 (1.4 g, 3.49 mmol) in 30 mL of dichloromethane was dropwise added a solution of DIBAL-H in toluene (1 mol/L, 7.68 mL). The reaction system was stirred at 25° C. for 2 hours, then quenched with 50 mL of saturated potassium sodium tartrate solution, and then extracted with dichloromethane (40 mL×3). The organic phases were combined and washed with saturated brine (30 mL×3), dried over anhydrous sodium sulfate, and filtered. The filtrate was concentrated to obtain the crude product. The crude product was purified by silica gel column chromatography (petroleum ether:ethyl acetate=1:0 to 0:1, v/v) to obtain compound 28-3. MS (ESI) m/z: 373.7 $[M+H]^+$.

Step C: A mixture of compound 28-3 (570.18 mg, 1.53 mmol), compound 4-1 (0.8 g, 1.53 mmol), sodium carbonate (405.02 mg, 3.82 mmol), and $Pd(PPh_3)_4$ (176.63 mg, 152.85 μmol) in dioxane (15 mL) and water (3 mL) was replaced with nitrogen three times, heated to 100° C. under nitrogen atmosphere, and stirred for 12 hours. The reaction mixture was diluted with 20 mL of water, filtered through diatomite, and the filtrate was extracted with dichloromethane (40 mL×3). The organic phases were combined, washed with saturated brine (30 mL×3), dried over anhydrous sodium sulfate, and filtered. The filtrate was concentrated to obtain the crude product. The crude product was purified by silica gel column chromatography (dichloromethane:methanol=1:0 to 3:1, v/v) to obtain compound 28-4. MS (ESI) m/z: 688.9 $[M+H]^+$.

Step D: A mixture of compound 28-4 (0.78 g, 1.13 mmol), potassium ferrocyanide (477.80 mg, 1.13 mmol), potassium acetate (22.20 mg, 226.24 μmol), and t-BuXPhos-Pd-G3 (89.86 mg, 113.12 μmol) in dioxane (10 mL) and water (10 mL) was replaced with nitrogen three times, heated to 100° C. under nitrogen atmosphere, and stirred for 3 hours. The reaction mixture was diluted with 20 mL of water, filtered through diatomite, and the filtrate was extracted with dichloromethane (40 mL×3). The organic phases were combined, washed with saturated brine (30 mL×3), dried over anhydrous sodium sulfate, and filtered. The filtrate was concentrated to obtain the crude product. The crude product was purified by silica gel column chromatography (dichloromethane:methanol=1:0 to 3:1, v/v) to obtain compound 28-5. MS (ESI) m/z: 679.9 $[M+H]^+$.

Step E: To a solution of compound 28-5 (0.72 g, 1.06 mmol) in 30 mL of dichloromethane was added manganese dioxide (1.84 g, 21.17 mmol). The reaction mixture was stirred at 50° C. for 12 hours, then filtered through diatomite, and the filter cake was washed with 400 mL of dichloromethane. The filtrate was concentrated to obtain the crude compound 28-6. MS (ESI) m/z: 677.9 $[M+H]^+$.

Step F: A solution of compound 28-6 (0.2 g, 294.95 μmol), compound 5-7 (67.91 mg, 589.90 mmol), and triethylamine (59.69 mg, 589.90 μmol) in 15 mL of dichloromethane was stirred at 45° C. for 1 hour. The mixture was cooled to room temperature, then added with $NaBH(OAc)_3$ (125.02 mg, 589.90 μmol) and acetic acid (26.57 mg, 442.42 μmol). The mixture was stirred at 25° C. for another 12 hours, then concentrated to obtain the crude product. The crude product was first purified by preparative thin-layer chromatography silica gel plate (dichloromethane:methanol=10:1), and further purified by preparative HPLC (chromatographic column: Phenomenex Synergi C18 150*25 mm*10 m; mobile phase: [pure water (0.225% formic acid)-acetonitrile]; acetonitrile %: 16%-36%, 10 minutes) to obtain the compound 28. $^1$H NMR (400 MHz, DMSO-$d_6$) δ=8.90 (d, J=1.6 Hz, 1H), 8.66 (d, J=8.4 Hz, 1H), 8.19 (t, J=4.8 Hz, 1H), 8.16-8.12 (m, 2H), 7.92 (s, 1H), 7.71 (d, J=4.8 Hz, 2H), 7.43 (t, J=8.0 Hz, 1H), 7.12-6.77 (m, 2H), 4.98 (t, J=8.8 Hz, 2H), 4.27-4.16 (m, 1H), 3.90-3.71 (m, 6H), 3.05 (t, J=8.0 Hz, 2H), 2.99-2.87 (m, 1H), 2.76-2.63 (m, 4H), 2.41 (dd, J=3.6, 9.6 Hz, 2H), 2.09-1.93 (m, 3H), 1.64-1.51 (m, 1H); MS (ESI) m/z: 777.3 $[M+H]^+$.

Example 29: Compound 29

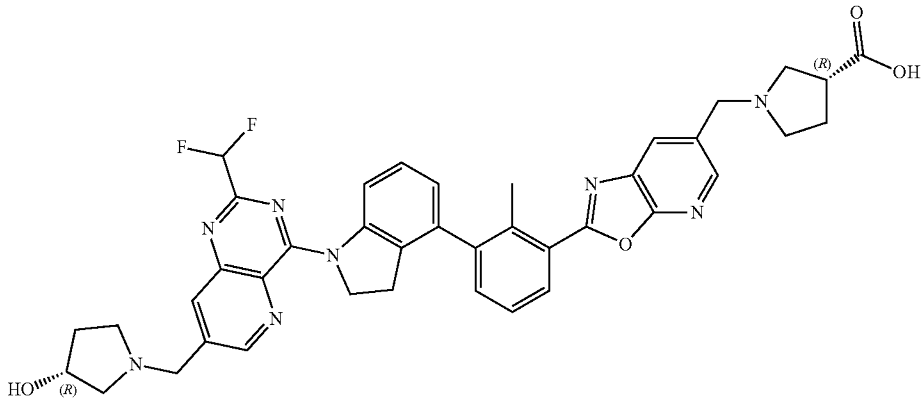

29

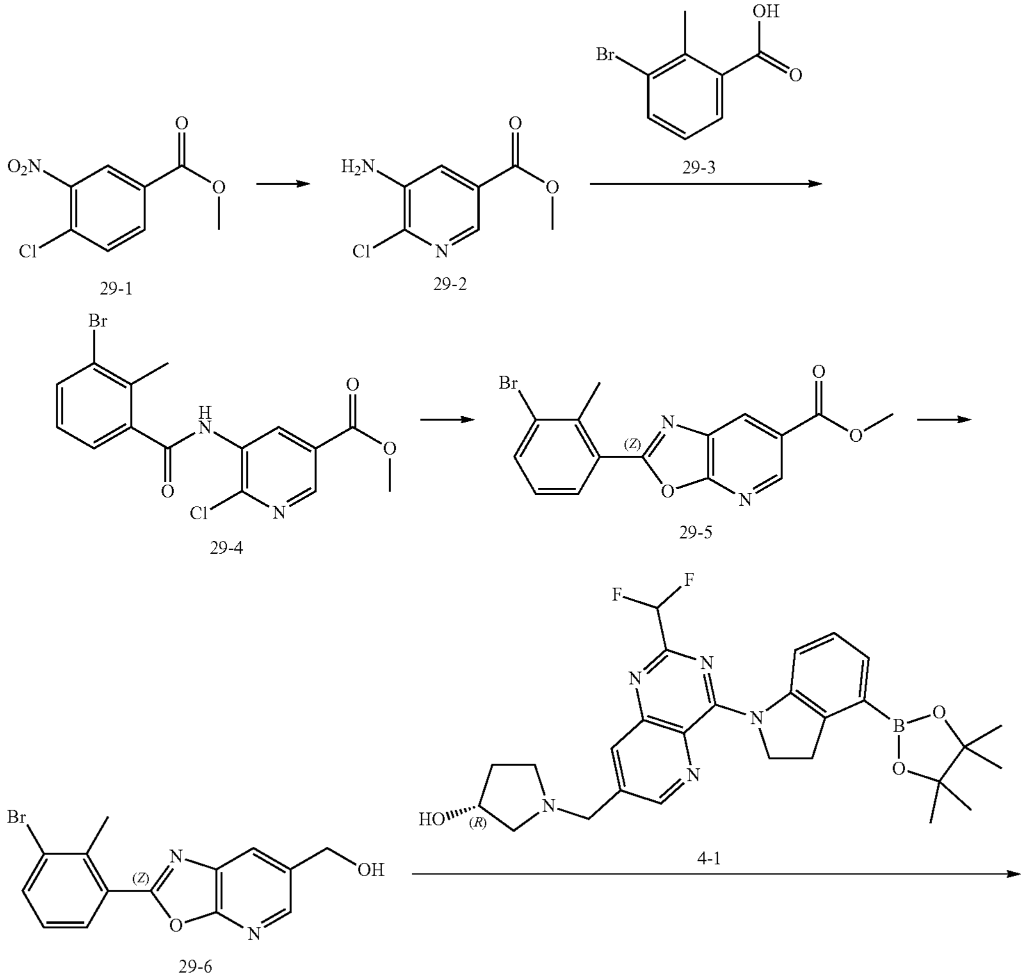

29-1 29-2 29-3 29-4 29-5 29-6 4-1

-continued

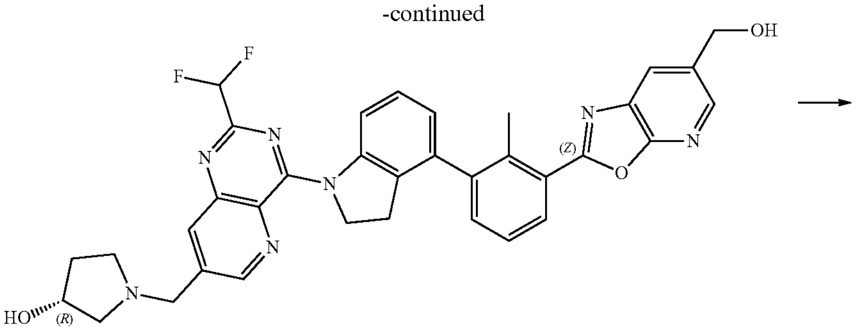

29-7

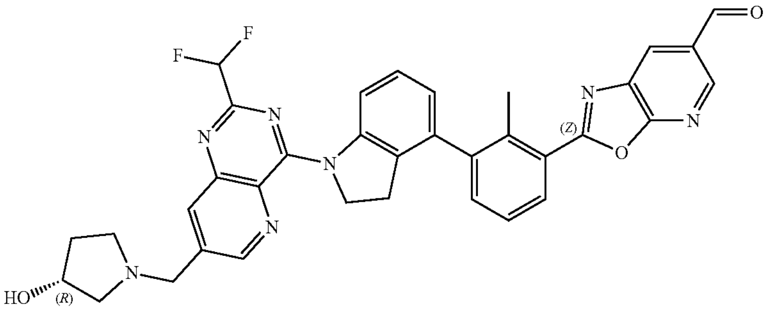

29-8

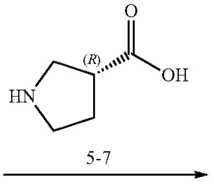

5-7

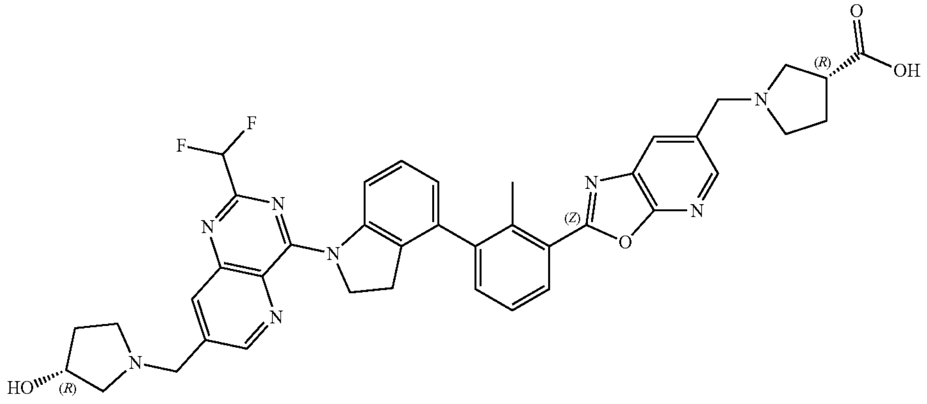

29

Step A: To a 100 mL methanol solution was added compound 29-1 (5 g, 23.09 mmol), iron powder (12.89 g, 230.82 mmol), and a saturated solution of ammonium chloride (5 mL). The reaction is conducted at 75° C. for 2 hours. The reaction mixture was cooled to room temperature, then filtered through diatomite. The filtrate was concentrated, then diluted with 20 mL of water, and extracted with ethyl acetate (20 mL×2). The organic phases were combined, washed with saturated brine (20 mL), dried over anhydrous sodium sulfate, and filtered. The filtrate was concentrated to obtain the crude product, compound 29-2. MS (ESI) m/z: 186.9 $[M+H]^+$.

Step B: To compound 29-3 (16.83 g, 78.24 mmol) was added 100 mL of dichloromethane solution, then oxalyl chloride (24.83 g, 195.61 mmol) was added thereto at 0° C., and N,N-dimethylformamide (285.96 mg, 3.91 mmol) was added thereto at 25° C. The mixture was reacted under nitrogen atmosphere at 25° C. for 0.5 hours. Then the reaction mixture was concentrated under vacuum and added with 100 mL of dichloromethane solution. Afterwards, a dichloromethane solution (100 mL) of compound 29-2 (7.3 g, 39.12 mmol) and pyridine (15.47 g, 195.61 mmol) were added at 0° C. The mixture is reacted under nitrogen atmosphere at 25° C. for 0.5 hours. To the reaction mixture was added 200 mL of water, and the mixture was extracted with dichloromethane (200 mL×2). The organic phases were combined, concentrated under vacuum to obtain the crude product, added with 200 mL of petroleum ether and 50 mL of ethyl acetate. The mixture was stirred at room temperature for 0.5 hours, filtered, and the resulting filter cake was dried under vacuum to obtain compound 29-4. MS (ESI) m/z: 384.7 $[M+H]^+$.

Step D: To a solution of compound 29-4 (2.3 g, 6.00 mmol) in N,N-dimethylformamide (40 mL) was added sodium carbonate (635.45 mg, 6.00 mmol). The reaction mixture was stirred at 140° C. for 12 hours. After cooling, the reaction mixture was added with 300 mL of ethyl acetate. The mixture was washed with water (200 mL×2) and brine (100 mL), dried over anhydrous sodium sulfate, and filtered. The filtrate was then concentrated to obtain the crude product. The crude product was purified by silica gel column chromatography (petroleum ether:ethyl acetate=10:1, v/v) to obtain compound 29-5. MS (ESI) m/z: 348.7 $[M+H]^+$.

Step D: Under nitrogen atmosphere and at −78° C., to a solution of compound 29-5 (0.8 g, 2.30 mmol) in dichloromethane (30 mL) was slowly added a solution of DIBAL-H in toluene (1 mol/L, 4.61 mL). The reaction mixture was stirred at −78° C. for 1 hour. To the reaction mixture was slowly added 20 mL of saturated sodium sulfate solution. After returning to room temperature, the mixture was stirred for 0.5 hours and then filtered through diatomite. The filtrate was extracted with dichloromethane (50 mL×2), and the organic phases were combined, washed with saturated brine (50 mL), dried over anhydrous sodium sulfate, and filtered. The filtrate was concentrated to obtain a crude product. The crude product was purified by silica gel column chromatography (dichloromethane/methanol=10/1, v/v) to obtain compound 29-6. MS (ESI) m/z: 319.0 $[M+H]^+$.

Step E: To a solution of compound 29-6 (0.4 g, 1.25 mmol) in dioxane (20 mL) and water (4 mL) was added compound 4-1 (655.96 mg, 1.25 mmol), $Pd(PPh_3)_4$ (144.83 mg, 125.33 μmol) and sodium carbonate (332.09 mg, 3.13 mmol). The mixture was stirred at 100° C. under nitrogen atmosphere for 4 hours. After cooling, the reaction mixture was directly concentrated to obtain a crude product. The crude product was purified by silica gel column chromatography (dichloromethane:methanol=10:1, v/v) to obtain compound 29-7. MS (ESI) m/z: 636.3 $[M+H]^+$.

Step F: To a solution of compound 29-7 (0.6 g, 943.90 μmol) in dichloromethane (20 mL) was added manganese dioxide (1.64 g, 18.88 mmol). The reaction mixture was stirred at 45° C. for 48 hours. The reaction mixture was cooled and filtered through diatomite. The filtrate was concentrated to obtain compound 29-8. MS (ESI) m/z: 634.0 $[M+H]^+$.

Step G: To a solution of compound 29-8 (0.2 g, 315.23 μmol) in dichloromethane (10 mL) was added compound 5-7 (72.68 mg, 631.27 μmol) and triethylamine (70.27 mg, 694.39 μmol). The reaction mixture was stirred under nitrogen atmosphere at 45° C. for 1 hour. After the reaction mixture was cooled to room temperature, the reaction mixture was added with $NaBH(OAc)_3$ (147.17 mg, 694.39 μmol) and acetic acid (30.33 mg, 505.01 μmol). The reaction mixture was stirred at 25° C. under nitrogen atmosphere for 12 hours. The reaction mixture was concentrated under vacuum to obtain the crude product. The crude compound was purified by silica gel plate (dichloromethane/methanol=10/1, v/v), and then purified by preparative HPLC (chromatographic column: Waters Xbridge 150*25 mm*5 m; mobile phase: [pure water (ammonium water)-acetonitrile]; acetonitrile %: 31% to 61%, 9 minutes) to obtain compound 29. $^1H$ NMR (400 MHz, DMSO-$d_6$) δ=12.07-11.56 (m, 1H), 11.53-11.13 (m, 1H), 9.19 (br s, 1H), 8.70 (d, J=8.4 Hz, 1H), 8.66-8.58 (m, 3H), 8.21 (dd, J=1.6, 7.7 Hz, 1H), 7.63-7.51 (m, 2H), 7.45 (t, J=8.0 Hz, 1H), 7.15-6.81 (m, 2H), 5.68-5.38 (m, 1H), 5.00 (br t, J=8.8 Hz, 2H), 4.78-4.64 (m, 2H), 4.60 (br s, 2H), 4.45 (br s, 1H), 3.66-3.47 (m, 4H), 3.17 (br s, 4H), 3.10-3.02 (m, 1H), 2.99-2.87 (m, 1H), 2.55 (s, 3H), 2.37-1.80 (m, 4H); MS (ESI) m/z: 733.2 $[M+H]^+$.

Example 30: Compound 30

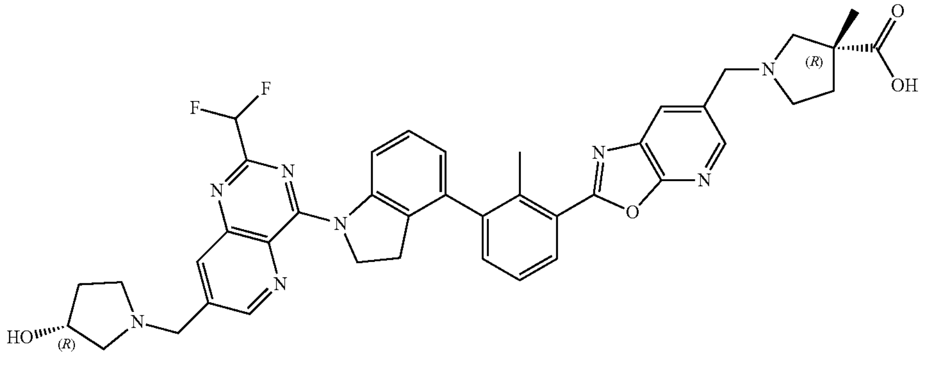

30

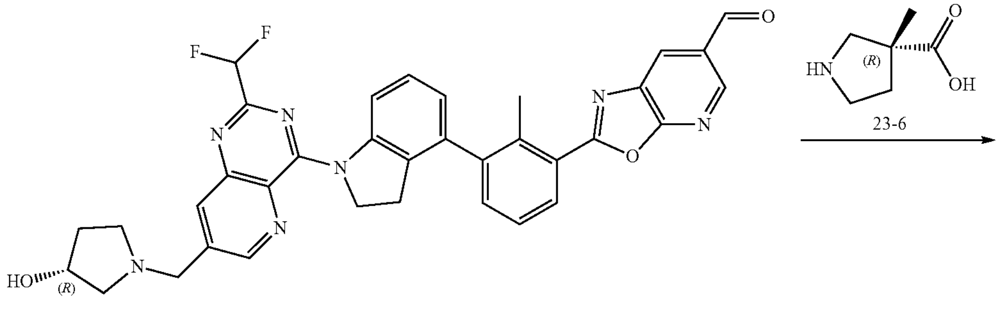

29-8

-continued

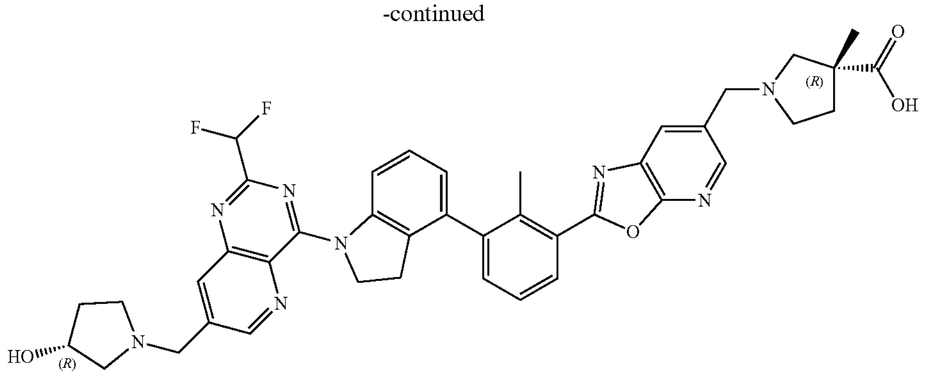

30

Step A: To a solution of compound 29-8 (60 mg, 94.69 μmol) in dichloromethane (10 mL) was added compound 23-6 (24.46 mg, 189.38 μmol) and 4 Å molecular sieves (20 mg). The mixture was stirred at 25° C. for 0.5 hours, then added with sodium triacetoxyborohydride (60.21 mg, 284.07 mol), and continued to stir at 25° C. for 1 hour. The reaction mixture was filtered through diatomite and the filtrate was concentrated to obtain the crude product. The crude product was purified by silica gel plate (dichloromethane:methanol=10:1, v/v) to obtain the crude product. The crude product was purified by preparative HPLC (chromatographic column: Waters Xbridge 150*25 mm*5 m; mobile phase: [pure water (ammonium bicarbonate)–acetonitrile]; acetonitrile %: 33% to 63%, 8 minutes) to obtain compound 30. $^1H$ NMR (400 MHz, DMSO-$d_6$) δ=8.91 (d, J=2.0 Hz, 1H), 8.67 (d, J=8.4 Hz, 1H), 8.34 (d, J=2.0 Hz, 1H), 8.24-8.13 (m, 3H), 7.59-7.48 (m, 2H), 7.43 (t, J=8.0 Hz, 1H), 7.09-6.77 (m, 2H), 4.99 (br t, J=8.8 Hz, 2H), 4.27-4.17 (m, 1H), 3.92-3.82 (m, 2H), 3.81-3.71 (m, 2H), 3.10-2.96 (m, 1H), 2.96-2.90 (m, 2H), 2.74 (dd, J=6.0, 9.6 Hz, 1H), 2.69 (br d, J=7.2 Hz, 1H), 2.65-2.57 (m, 2H), 2.54 (s, 3H), 2.49-2.46 (m, 1H), 2.42 (dd, J=3.6, 9.6 Hz, 1H), 2.35-2.32 (m, 1H), 2.32-2.25 (m, 1H), 2.07-1.97 (m, 1H), 1.63-1.54 (m, 2H), 1.26 (s, 3H); MS (ESI) m/z: 747.4 $[M+H]^+$.

Example 31: Compound 31

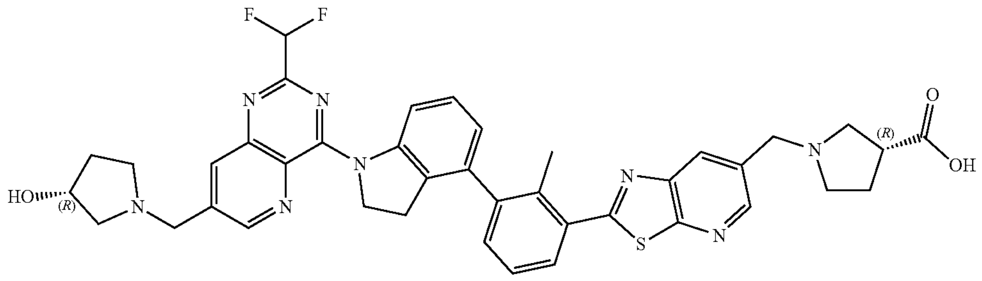

31

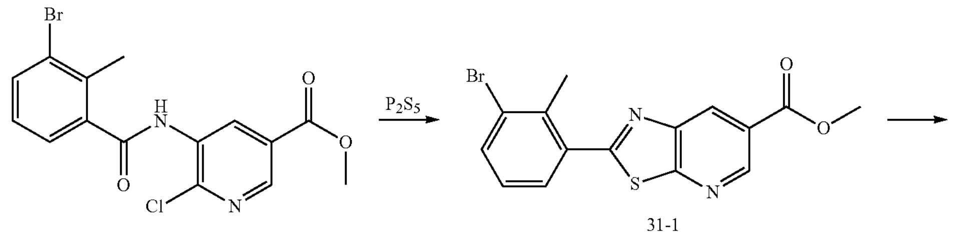

29-4 31-1

-continued

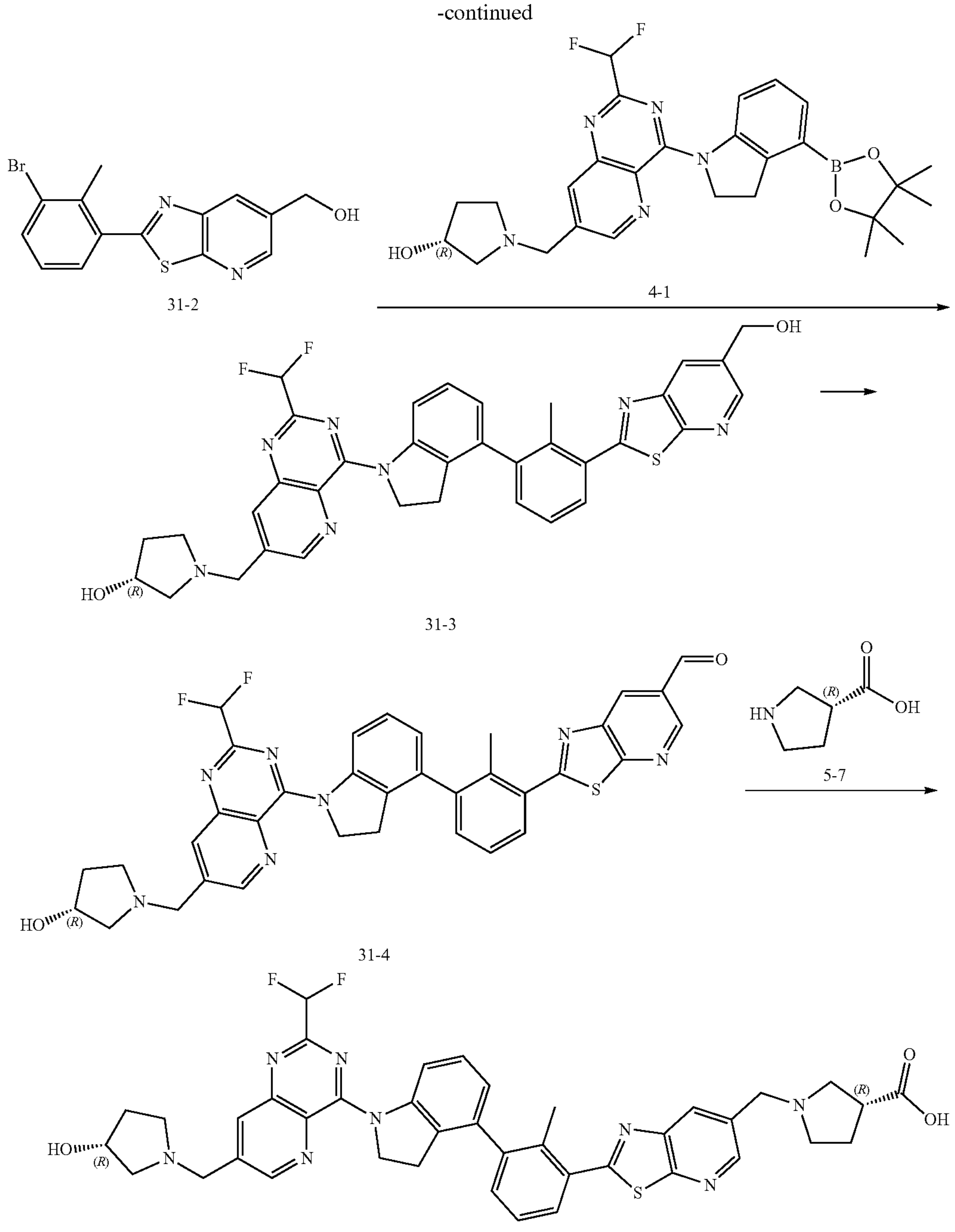

31-2

31-3

31-4

31

Step A: To a round-bottom flask was added compound 29-4 (1 g, 2.61 mmol), phosphorus pentasulfide (1.16 g, 5.21 mmol), pyridine (20 mL), and xylene (80 mL). The mixture was reacted at 140° C. for 12 hours. The solvent was concentrated under reduced pressure and purified by silica gel column chromatography (ethyl acetate/petroleum ether=0 to 20%, v/v) to obtain compound 31-1.

Step B: To a round-bottom flask was added compound 31-1 (189 mg, 520.33 μmol) and dichloromethane (10 mL). The mixture was cooled to −78° C., then a solution of DIBAL-H in toluene (1 mol/L, 1.04 mL) was added dropwise thereto, keeping the temperature did not exceed −65° C. After the addition, the mixture was stirred at −78° C. for 3 hours. While stirring, saturated sodium sulfate solution (10 mL) was carefully added thereto. The mixture was filtered and the filtrate was concentrated to obtain compound 31-2, which was used directly in the next step.

Step C: A mixture of compound 31-2 (80 mg, 238.65 μmol, 1 eq), compound 4-1 (124.91 mg, 238.65 μmol), sodium carbonate (63.24 mg, 596.63 μmol) and $Pd(PPh_3)_4$ (27.58 mg, 23.87 μmol) in dioxane (10 mL) and water (2 mL) was heated to 100° C. under nitrogen atmosphere and stirred for 12 hours. The reaction mixture was filtered and concentrated to obtain the crude product. The crude product was purified by preparative thin-layer chromatography plate (methanol/dichloromethane=0% to 10%, v/v) to obtain compound 31-3.

Step D: To a solution of compound 31-3 (110 mg, 168.78 μmol) in dichloromethane (10 mL) was added active manganese dioxide (293.48 mg, 3.38 mmol). The reaction mixture was stirred at 45° C. for 48 hours. The reaction mixture was filtered. The filtrate was concentrated to obtain compound 31-4, which was used directly in the next step.

Step E: To a mixture of compound 31-4 (80 mg, 123.13 μmol), compound 1-22 (28.35 mg, 246.26 μmol), and dichloromethane (10 mL) was added triethylamine (37.38 mg, 369.39 μmol). The mixture was stirred at 45° C. for 1 hour, and added with $NaBH(OAc)_3$ (78.29 mg, 369.39 μmol) and acetic acid (14.79 mg, 246.26 μmol) at 25° C., and continued to stir for 12 hours. The crude product was concentrated under reduced pressure, preliminarily purified by preparative silica gel thin-layer chromatography (methanol/dichloromethane=1/8), and further purified by preparative HPLC (chromatographic column: Phenomenex Synergi C18 150*25 mm*10 m; mobile phase: [pure water (formic acid)-acetonitrile]; acetonitrile %: 13% to 43%, 10 minutes) to obtain the compound 31. $^1H$ NMR (400 MHz, DMSO-$d_6$) δ=11.89-11.52 (m, 1H), 11.43-11.13 (m, 1H), 9.19 (br d, J=16.0 Hz, 1H), 8.92-8.76 (m, 2H), 8.75-8.55 (m, 2H), 7.85 (d, J=7.2 Hz, 1H), 7.61-7.36 (m, 3H), 7.16-6.79 (m, 2H), 5.78-5.29 (m, 1H), 5.00 (br t, J=8.0 Hz, 2H), 4.78-4.56 (m, 4H), 4.52-4.39 (m, 1H), 3.69-3.56 (m, 4H), 3.28-3.17 (m, 4H), 3.13-3.03 (m, 1H), 3.01-2.90 (m, 1H), 2.39 (s, 3H), 2.35-2.16 (m, 2H), 2.11-1.83 (m, 2H); MS (ESI) m/z: 749.3 $[M+H]^+$.

Example 32: Compound 32

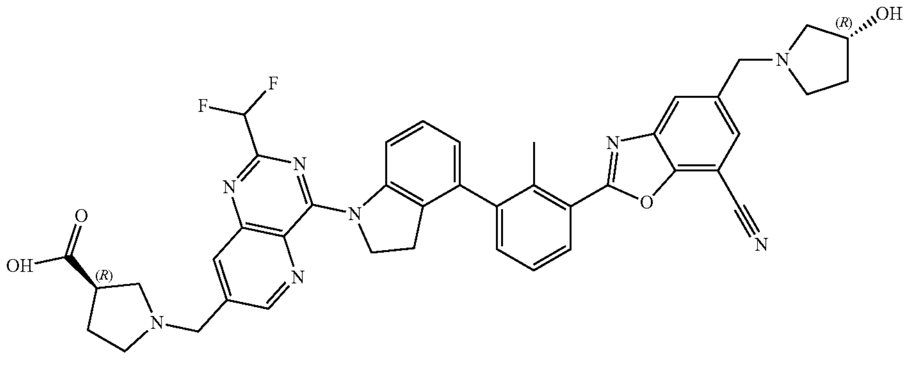

32

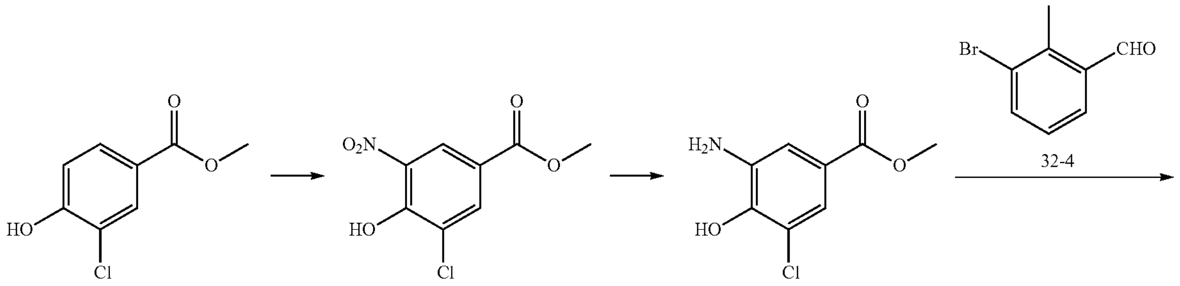

32-4

32-1 32-2 32-3

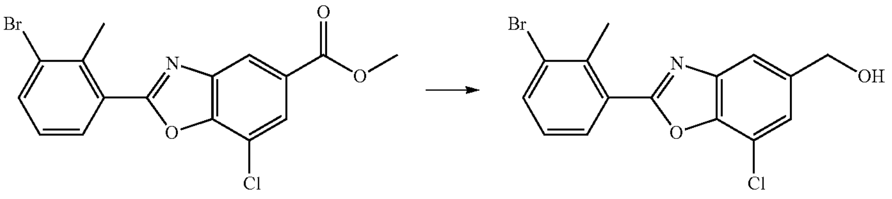

32-5 32-6

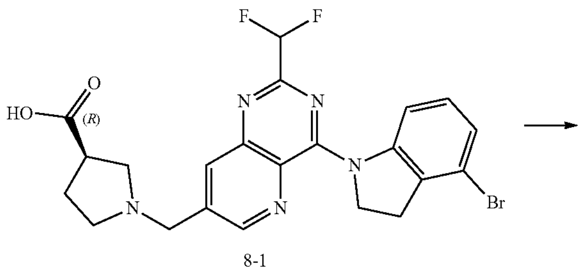

8-1

-continued
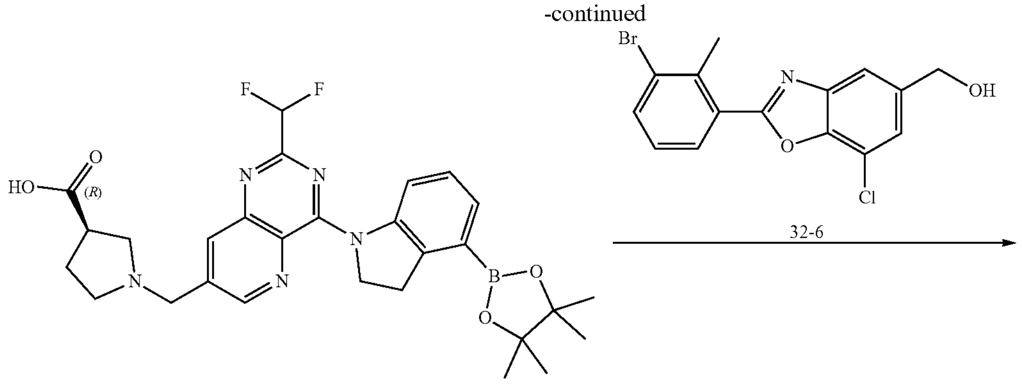
32-7
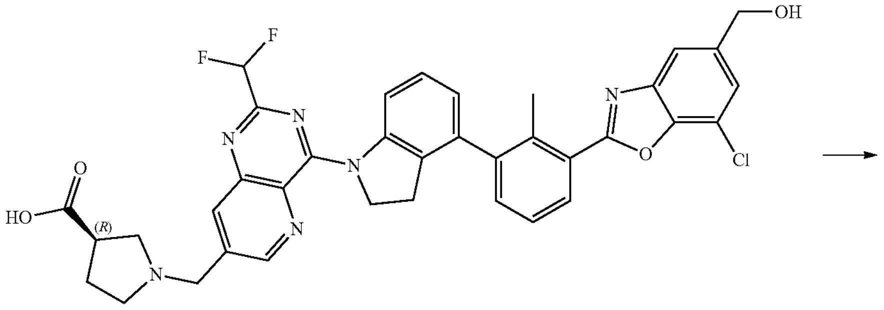
32-8
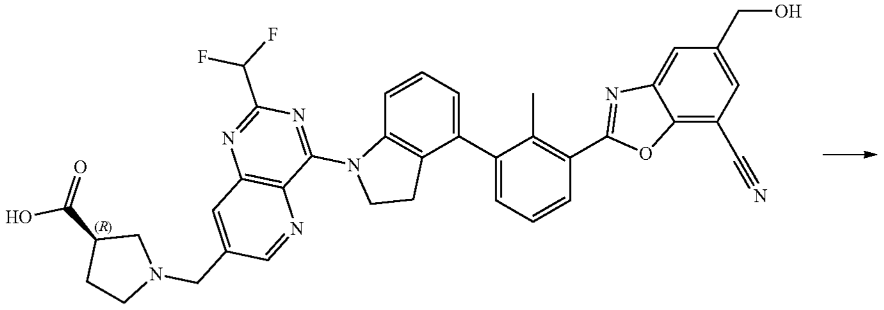
32-9
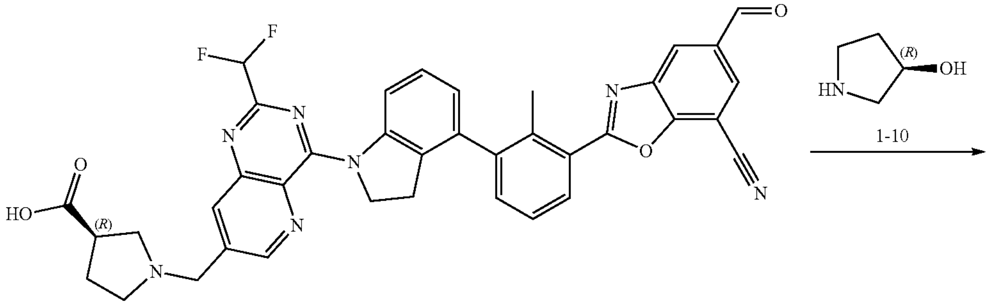
32-10

-continued

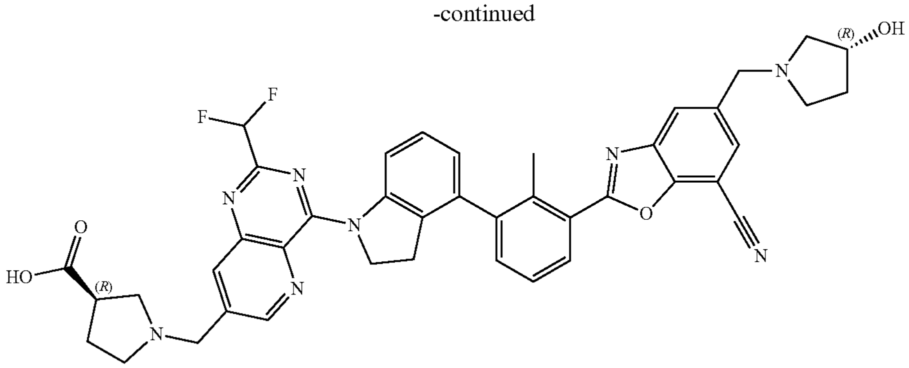

32

Step A: At 0° C., to a solution of compound 32-1 (10 g, 53.59 mmol) in 20 mL of acetic acid was added a solution of nitric acid (9.16 g, 145.30 mmol) in 20 mL of acetic acid. The reaction system was stirred at 25° C. for 2 hours, then diluted with 50 mL of water, filtered. The filter cake was washed with 50 mL of water, then concentrated to obtain the crude compound 32-2.

Step B: To a mixture of compound 32-2 (3 g, 12.95 mmol) in 30 mL of methanol and 6 mL of water was added sodium hydrosulfite (13.53 g, 77.72 mmol). The reaction system was stirred at 70° C. for 12 hours, and filtered. The filter cake was washed with 100 mL of methanol. The filtrate was concentrated to obtain the crude product. The crude product was purified by silica gel column chromatography (dichloromethane:methanol=1:0 to 4:1, v/v) to obtain compound 32-3. MS (ESI) m/z: 202.1 $[M+H]^+$.

Step C: A solution of compound 32-3 (4.2 g, 20.83 mmol) and compound 32-4 (3.94 g, 19.79 mmol) in 100 mL of ethanol was stirred at 25° C. for 1 hour, then concentrated, and dissolved in 100 mL of dichloromethane solution, and added with 2,3-dicyano-5,6-dichlorobenzoquinone (4.49 g, 19.79 mmol). The reaction system was stirred at 25° C. for 12 hours, then quenched with 100 mL of saturated sodium sulfite solution, extracted with dichloromethane (80 mL×3). The organic phases were combined, washed with saturated brine (50 mL×3), dried over anhydrous sodium sulfate, and filtered. The filtrate was concentrated to obtain the crude product. The crude product was purified by silica gel column chromatography (petroleum ether:dichloromethane=1:0 to 0:1, v/v) to obtain compound 32-5. MS (ESI) m/z: 381.7 $[M+H]^+$.

Step D: At −78° C., to a solution of compound 32-5 (7.62 g, 20.02 mmol) in 120 mL of dichloromethane was dropwise added a solution of DIBAL-H in toluene (1 mol/L, 40.04 mL). The reaction system was stirred at 25° C. for 2 hours, then quenched with 200 mL of saturated potassium sodium tartrate solution and extracted with dichloromethane (100 mL×3). The organic phases were combined and washed with saturated brine (50 mL×3), dried over anhydrous sodium sulfate, and filtered. The filtrate was concentrated to obtain the crude product. The crude product was purified by silica gel column chromatography (dichloromethane:methanol=1:0 to 4:1, v/v) to obtain compound 32-6. MS (ESI) m/z: 354.0 $[M+H]^+$.

Step E: Under nitrogen atmosphere, to a solution of compound 8-1 (1.11 g, 2.20 mmol) and bis(pinacolato) diboron (1.12 g, 4.40 mmol) in 30 mL dioxane was added $Pd(dppf)Cl_2 \cdot CH_2Cl_2$ (179.74 mg, 220.10 μmol) and potassium acetate (648.01 mg, 6.60 mmol). The reaction system was stirred at 100° C. for 1 hour. After cooling, the reaction mixture was filtered through diatomite. The filter cake was washed with 200 mL of dichloromethane. The filtrate was concentrated to obtain the crude product. The crude product was purified by silica gel column (dichloromethane:methanol=1:0 to 5:1, v/v) to obtain compound 32-7. MS (ESI) m/z: 552.2 $[M+H]^+$.

Step F: Under nitrogen atmosphere, to a mixture of compound 32-7 (0.4 g, 725.44 μmol), compound 32-6 (255.80 mg, 725.44 μmol) in dioxane (10 mL) and water (2 mL) was added sodium carbonate (192.22 mg, 1.81 mmol) and $Pd(PPh_3)_4$ (83.83 mg, 72.54 μmol). The system was replaced with nitrogen three times and then heated to 100° C. under nitrogen atmosphere, and stirred for 1 hour. The reaction mixture was concentrated to obtain the crude product. The crude product was purified by silica gel column (dichloromethane:methanol=1:0 to 3:1, v/v) to obtain compound 32-8. MS (ESI) m/z: 697.0 $[M+H]^+$.

Step G: A mixture of compound 32-8 (0.515 g, 738.74 μmol), potassium ferrocyanide (468.06 mg, 1.11 mmol), potassium acetate (14.50 mg, 147.75 μmol), and t-BuXPhos-Pd-G3 (58.68 mg, 73.87 μmol) in dioxane (15 mL) and water (5 mL) was replaced with nitrogen three times, heated to 100° C. under nitrogen atmosphere, and stirred for 3 hours. The reaction mixture was concentrated to obtain the crude product. The crude product was purified by silica gel column (dichloromethane:methanol=1:0 to 3:1, v/v) to obtain compound 32-9. MS (ESI) m/z: 688.0 $[M+H]^+$.

Step H: To a solution of compound 32-9 (0.435 g, 632.55 μmol) in 15 mL of dimethyl sulfoxide was added IBX (354.25 g, 1.27 mmol). The reaction system was stirred at 25° C. for 12 hours. 20 mL of saturated sodium thiosulfate solution was slowly added to the reaction mixture, and the mixture was extracted with dichloromethane (30 mL×5). The organic phases were combined, washed with saturated brine (30 mL×3), dried over anhydrous sodium sulfate, and filtered. The filtrate was concentrated to obtain a crude product. The crude product was purified by silica gel column chromatography (dichloromethane:methanol=1:0 to 3:1, v/v) to obtain compound 32-10. MS (ESI) m/z: 686.1 $[M+H]^+$.

Step I: A solution of compound 32-10 (0.15 g, 218.76 μmol) and compound 1-10 (38.12 mg, 437.52 μmol) in 5 mL of dichloromethane was stirred at 25° C. for 0.5 hours, and $NaBH(OAc)_3$ (139.09 mg, 656.29 μmol) was added thereto. The reaction system was stirred at 25° C. for 12 hours. The reaction mixture was concentrated to obtain the crude product, which was first purified by silica gel column chromatography (dichloromethane:methanol=1:0 to 2:1, v/v), and further purified by preparative HPLC (chromatographic column: Phenomenex Synergi C18 150*25 mm*10 m; mobile phase: [pure water (formic acid)–acetonitrile]; acetonitrile %: 11% to 41%, 10 minutes) to obtain compound 32. $^1$H NMR (400 MHz, DMSO-$d_6$) δ=8.91 (d, J=2.0 Hz, 1H), 8.68 (d, J=8.0 Hz, 1H), 8.21-8.12 (m, 3H), 7.90 (d, J=1.2 Hz, 1H), 7.61-7.55 (m, 1H), 7.55-7.51 (m, 1H), 7.44 (t, J=8.0 Hz, 1H), 7.09-6.78 (m, 2H), 5.00 (br t, J=8.4 Hz, 2H), 4.22 (tt, J=3.2, 6.6 Hz, 1H), 3.90-3.81 (m, 3H), 3.77 (br d, J=12.0 Hz, 2H), 3.03-2.92 (m, 3H), 2.80-2.70 (m, 3H), 2.69-2.65 (m, 1H), 2.60 (br t, J=6.8 Hz, 2H), 2.54 (br s, 3H), 2.40 (br dd, J=3.2, 9.6 Hz, 1H), 2.07-1.95 (m, 3H), 1.67-1.49 (m, 1H); MS(ESI) m/z: 757.0 [M+H]$^+$.
Example 33: Compound 33
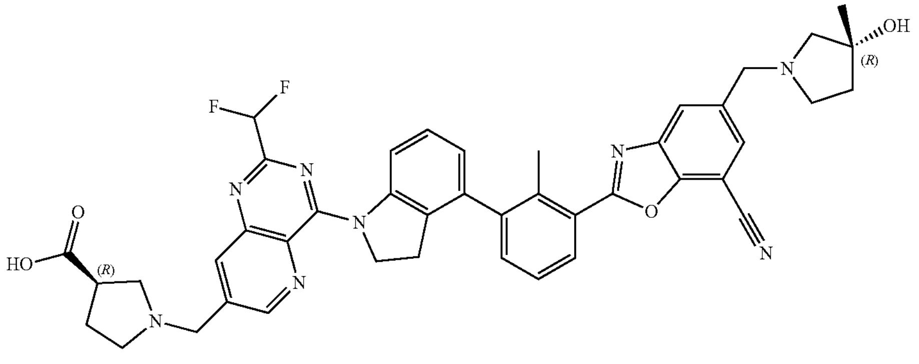
33
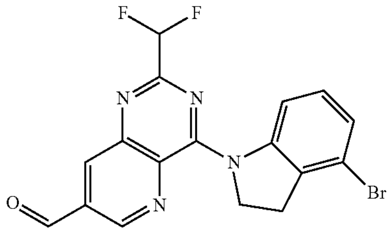
3-8
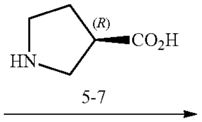
5-7
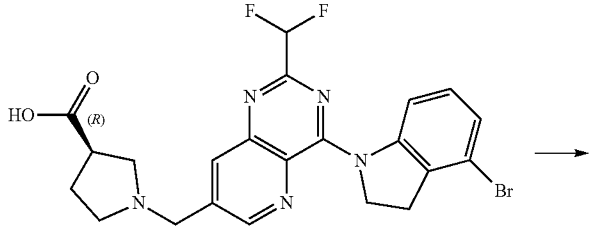
33-1
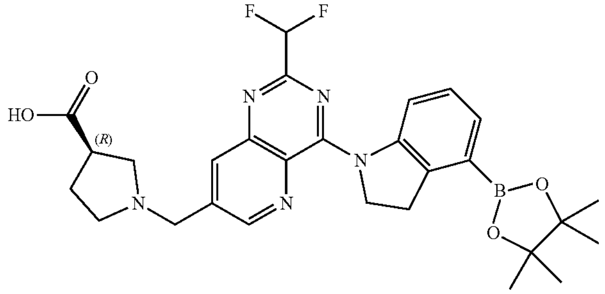
33-2
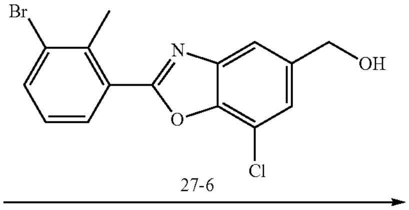
27-6
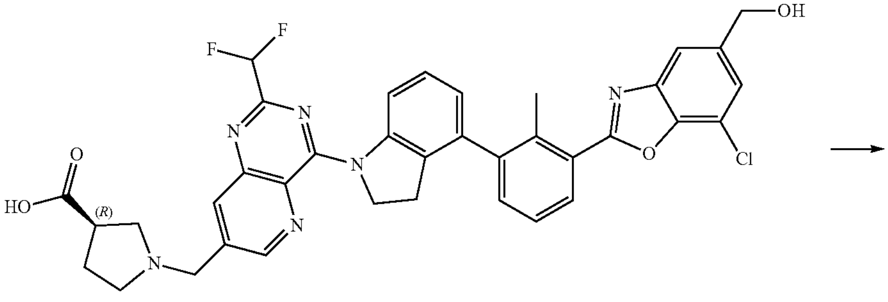
33-3

-continued

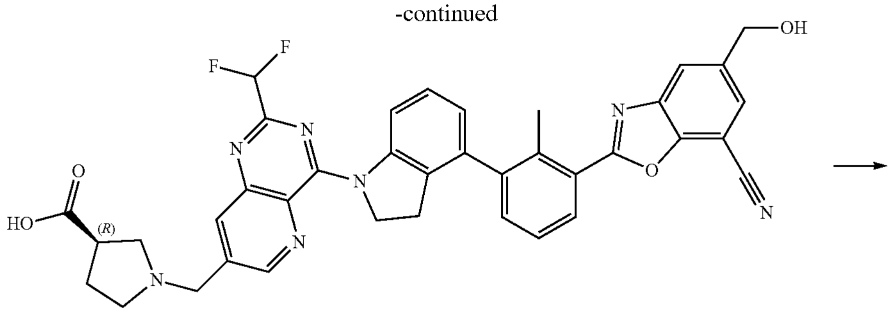

33-4

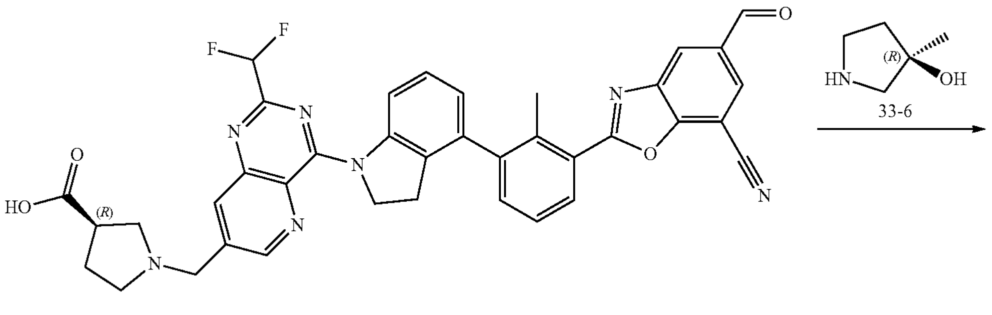

33-5

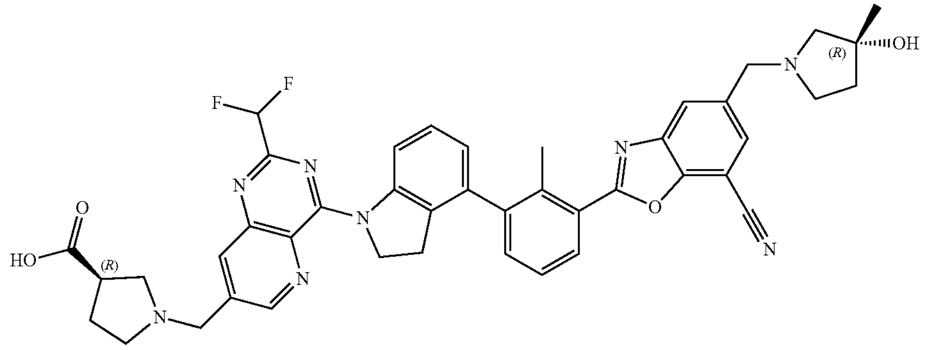

33

Step A: A solution of compound 3-8 (1.0 g, 2.47 mmol) and compound 5-7 (568.27 mg, 4.94 mmol) in 20 mL of dichloromethane was stirred at 25° C. for 0.5 hours, and $NaBH(OAc)_3$ (1.57 g, 7.40 mmol) was added thereto. The reaction system was stirred at 25° C. for 1 hour. The reaction mixture was diluted with 30 mL of water, extracted with dichloromethane (40 mL×3). The organic phases were combined, washed with saturated brine (30 mL×3), dried over anhydrous sodium sulfate, and filtered. The filtrate was concentrated to obtain the crude product. The crude product was purified by silica gel column (dichloromethane:methanol=1:0 to 10:1, v/v) to obtain compound 33-1. MS (ESI) m/z: 504.2 $[M+H]^+$.

Step B: Under nitrogen atmosphere, to a solution of compound 33-1 (1.11 g, 2.20 mmol) and bis(pinacolato) diboron (1.12 g, 4.40 mmol) in 30 mL of dioxane was added $Pd(dppf)Cl_2 \cdot CH_2Cl_2$ (179.74 mg, 220.10 μmol) and potassium acetate (648.01 mg, 6.60 mmol). The reaction system was stirred at 100° C. for 1 hour. After cooling, the reaction mixture was filtered through diatomite. The filter cake was washed with 200 mL of dichloromethane. The filtrate was concentrated to obtain the crude product. The crude product was purified by silica gel column (dichloromethane:methanol=1:0 to 5:1, v/v) to obtain compound 33-2. MS (ESI) m/z: 552.2 $[M+H]^+$.

Step C: Under nitrogen atmosphere, to a mixture of compound 33-2 (0.4 g, 725.44 μmol), compound 27-6 (255.80 mg, 725.44 μmol) in dioxane (10 mL) and water (2 mL) was added sodium carbonate (192.22 mg, 1.81 mmol) and $Pd(PPh_3)_4$ (83.83 mg, 72.54 μmol). The system was replaced three times with nitrogen and then heated to 100° C. under nitrogen atmosphere, and stirred for 1 hour. The reaction mixture was concentrated to obtain the crude product. The crude product was purified by silica gel column (dichloromethane:methanol=1:0 to 3:1, v/v) to obtain compound 33-3. MS (ESI) m/z: 697.0 $[M+H]^+$.

Step D: A mixture of compound 33-3 (0.515 g, 738.74 μmol), potassium ferrocyanide (468.06 mg, 1.11 mmol), potassium acetate (14.50 mg, 147.75 μmol), and t-BuXPhos-Pd-G3 (58.68 mg, 73.87 μmol) in dioxane (15 mL) and water (5 mL) was replaced with nitrogen three times, heated to 100° C. under nitrogen atmosphere, and stirred for 3 hours. The reaction mixture was concentrated to obtain the crude product. The crude product was purified by silica gel column (dichloromethane:methanol=1:0 to 3:1, v/v) to obtain compound 33-4. MS (ESI) m/z: 688.0 $[M+H]^+$.

Step E: To a solution of compound 33-4 (0.435 g, 632.55 μmol) in 15 mL of dimethyl sulfoxide was added IBX (354.25 g, 1.27 mmol). The reaction system was stirred at 25° C. for 12 hours. 20 mL of saturated sodium thiosulfate solution was slowly added to the reaction mixture, and the mixture was extracted with dichloromethane (30 mL×5). The organic phases were combined, washed with saturated brine (30 mL×3), dried over anhydrous sodium sulfate, and filtered. The filtrate was concentrated to obtain a crude product. The crude product was purified by silica gel column chromatography (dichloromethane:methanol=1:0 to 3:1, v/v) to obtain compound 33-5. MS (ESI) m/z: 686.1 $[M+H]^+$.

Step F: A solution of compound 33-5 (0.15 g, 218.76 μmol) and compound 33-6 (44.25 mg, 437.52 μmol) in 5 mL of dichloromethane was stirred at 25° C. for 0.5 hours, and $NaBH(OAc)_3$ (139.09 mg, 656.29 μmol) was added thereto. The reaction system was stirred at 25° C. for 12 hours. The reaction mixture was concentrated to obtain the crude product, which was first purified by silica gel column chromatography (dichloromethane:methanol=1:0 to 2:1, v/v), and further purified by preparative HPLC (chromatographic column: Phenomenex Synergi C18 150*25 mm*10 m; mobile phase: [pure water (formic acid)–acetonitrile]; acetonitrile %: 11% to 41%, 10 minutes) to obtain compound 33. $^1H$ NMR (400 MHz, DMSO-$d_6$) δ=8.91 (d, J=2.0 Hz, 1H), 8.68 (d, J=8.0 Hz, 1H), 8.23-8.12 (m, 3H), 7.93 (d, J=1.2 Hz, 1H), 7.64-7.50 (m, 2H), 7.44 (t, J=8.0 Hz, 1H), 7.12-6.68 (m, 2H), 5.00 (br t, J=8.8 Hz, 2H), 3.93-3.80 (m, 5H), 3.03-2.94 (m, 3H), 2.81-2.77 (m, 1H), 2.76-2.69 (m, 2H), 2.60 (br t, J=6.8 Hz, 3H), 2.54 (br s, 3H), 2.06-1.95 (m, 2H), 1.88-1.65 (m, 2H), 1.32-1.19 (m, 4H); MS (ESI) m/z: 771.0 $[M+H]^+$.

Experimental Example 1: PD-L1 Binding Assay

Experimental Materials:

PD1:PD-L1 TR-FRET assay kit, purchased from BPS Biosciences. Nivo multimode microplate reader (PerkinElmer)

Experimental Method:

PD1-Eu, dye-labeled acceptor, PD-L1-biotin, and compound to be tested were all diluted using the buffer in the kit.

The compound to be tested was diluted 5-fold to the 8th concentration, i.e., from 4 μM to 0.05 nM, and the DMSO concentration was 4%. The experiment was set up in duplicate wells. 5 μL of each concentration gradient of the compound to be tested was added to a microtiter plate, wherein 5 μL of a buffer containing 4% DMSO and 5 μL of PD-L1-biotin (60 nM) was added to the Max signal well, and only 5 μL of buffer was added to the Min signal well. The plate was incubated at 25° C. for 20 minutes. After the incubation, 5 μL of diluted PD1-Eu (10 nM) and 5 μL of diluted dye-labeled acceptor were added to each well. The system was reacted at 25° C. for 90 minutes. After the reaction, the multimode microplate reader was used to read the time-resolved fluorescence analysis signal.

Data Analysis:

Raw data was converted into inhibition rate using the equation: (sample−Min)/(Max−Min)*100%. The $IC_{50}$ value could then be derived by performing a curve fit using a four-parameter logistic model (obtained using the "log(inhibitor) vs. response—Variable slope" mode in GraphPad Prism). Inhibitory activity of the compounds of the present disclosure on PD1/PD-L1 binding is provided in Table 1.

TABLE 1

| Test Compound | PD1/PD-L1 binding $IC_{50}$ (nM) |
|---|---|
| 1 | 1.95 |

Experimental conclusion: The compounds of the present disclosure demonstrate good inhibitory activity on the PD1/PD-L1 binding at the enzymatic level.

Experimental Example 2: NFAT Binding Assay

Experimental Materials:

PD1:PD-L1 TR-FRET assay kit, purchased from BPS Biosciences. Bright-Glo reagents purchased from Promega. Nivo multimode microplate reader (PerkinElmer)

Experimental Method:

TCR Activitor/PD-L1 CHO cells with a growth confluence of 80% were seeded at 35,000 cells per well in a plate and then incubated overnight in a 37° C. cell culture incubator. The compound to be tested was 5-fold diluted with a pipette to the 8th concentration, i.e., from 100 μmol to 1.28 nmol, with a DMSO concentration of 100%. Experiments were set up in duplicate wells. 147 μL of culture medium was added to an intermediate plate, and then 3 μL of gradient diluted compound per well was transferred to the intermediate plate according to the corresponding position, resulting in compound concentrations ranging from 2 μmol to 0.0256 nmol with a DMSO concentration of 2%. The T cell receptor/PD-L1 CHO cell supernatant was discarded, and 50 μL of compound working solution was added to each well, followed by incubation at 37° C. for 30 minutes. After incubation, 50 μL of a PD-1/NFAT Reporter-Jurkat cell suspension at a density of $4\times10^5$/mL was added to each well, and the plate was incubated at 37° C. for 5 hours. After the incubation, 100 μL of Bright-Glo was added to each well. After mixing, chemiluminescence signals were read using a Nivo the multimode microplate reader.

Data Analysis:

Raw data was converted into inhibition rate using the equation: (Sample−Min)/(Max−Min)*100%. The $IC_{50}$ value could then be derived by performing a curve fit using a four-parameter logistic model (obtained using the "log(inhibitor) vs. response—Variable slope" mode in GraphPad Prism). The degree of inhibition of the compound on PD-1/PD-L1 was calculated using the equation (Max−Min)/Min. The higher the multiple, the stronger the inhibition of the PD-1/PD-L1 pathway.

Experimental results: Inhibitory activity of the compounds of the present disclosure on PD-1/PD-L1 binding is provided in FIG. 1 and Table 2.

TABLE 2

| Test Compound | $IC_{50}$ (nM) in NFAT cells | Relative DMSO activation fold |
|---|---|---|
| 1 | 35 | 7.81 |
| 2 | 16 | 5.63 |
| 3 | 4.7 | 6.74 |
| 4 | 4.5 | 5.18 |
| 7 | 3.0 | 5.5 |
| 8 | 3.9 | 4.69 |
| 9 | 4.4 | 4.63 |
| 11 | 24.6 | 4.42 |
| 12 | 10.9 | 3.54 |
| 13 | 19.0 | 4.54 |
| 14 | 10.7 | 3.71 |

TABLE 2-continued

| Test Compound | $IC_{50}$ (nM) in NFAT cells | Relative DMSO activation fold |
|---|---|---|
| 15 | 35.1 | 4.36 |
| 16 | 9.2 | 4.53 |
| 17 | 7.5 | 4.72 |
| 18 | 3.5 | 4.23 |
| 19 | 30.7 | 4.28 |
| 20 | 42.7 | 4.39 |
| 22 | 22.6 | 3.62 |
| 23 | 32.6 | 4.82 |
| 24 | 32.6 | 4.79 |
| 27 | 6.71 | 5.12 |
| 28 | 4.67 | 4.43 |
| 29 | 6.03 | 4.03 |
| 30 | 14.54 | 4.13 |
| 32 | 8.98 | 4.05 |
| 33 | 13.62 | 3.84 |

Experimental conclusion: The compounds of the present disclosure can effectively block the PD-1/PD-L1 signaling pathway at the cellular level and restore T cell activity.

Experimental Example 3: In Vivo Pharmacokinetics Study in Mice

Male C57BL/6 mice were used as test animals, and the drug concentration in plasma at different times after intragastric administration of the test compound was determined by LC/MS/MS method. The pharmacokinetic behavior of the test compounds in mice in vivo was studied to evaluate their pharmacokinetic characteristics.

Test animals: Healthy male C57BL/6 mice. Drug preparation: For the IV group, the vehicle was 5% DMSO+95% (20% hydroxypropyl-β-cyclodextrin); for the PO group, the vehicle was 5% DMSO+95% (20% HP-β-CD). Administration: The dosage of the test compound was 1 mg/kg for the IV group, and 10 mg/kg or 30 mg/kg for the PO group (note: the PO group was fasted overnight before administration).

Experimental operations: After administration, whole blood was collected for a certain period of time and prepared into plasma. The drug concentration was analyzed by the LC-MS/MS method, and the pharmacokinetic parameters were calculated using Phoenix WinNonlin software (Pharsight, USA)

Experimental results: As shown in Table 3 and Table 4.

TABLE 3

[]Evaluation results of PK properties in vivo (1)

| Administration | Parameters | Compound 1 | Compound 2 |
|---|---|---|---|
| p.o. (30 mg/kg) | $C_{max}$ (nM) | 1455 | 1965 |
| | $T_{1/2}$ (h) | 12 | 6.9 |
| | $AUC_{0\text{-}last}$ (nM · h) | 13680 | 20645 |
| | $AUC_{0\text{-}inf}$ (nM · h) | 18763 | 22984 |

TABLE 4

[]Evaluation results of PK properties in vivo (2)

| Administration | Parameters | Compound 27 |
|---|---|---|
| i.v. (1 mg/kg) | $T_{1/2}$ (h) | 12.50 |
| | $Vd_{ss}$ (L/kg) | 8.97 |
| | Cl (mL/min/kg) | 10.55 |
| | $AUC_{0\text{-}last}$ (nM · h) | 1645 |
| | $AUC_{0\text{-}inf}$ (nM · h) | 2103 |
| p.o. (10 mg/kg) | $C_{max}$ (nM) | 680.5 |
| | $T_{max}$ (h) | 3.33 |
| | $T_{1/2}$ (h) | 6.23 |
| | $AUC_{0\text{-}last}$ (nM · h) | 8908 |
| | $AUC_{0\text{-}inf}$ (nM · h) | 9726 |
| | F % | 46.3% |

Experimental conclusion: The compounds of the present disclosure demonstrate excellent pharmacokinetic properties, with a longer half-life, higher plasma exposure, and bioavailability in vivo, indicating promising drugability.

Experimental Example 4: PD-L1 Antibody Drug Efficacy Experiment Based on MC38-hPD-L1 Colon Cancer Animal Model of B-hPD-L1 Humanized Mice Experimental Method:

1. Cell Culture

Mouse colon cancer MC38 cells were purchased from Shunran Shanghai Biotech Co., Ltd. Biocytogen (Beijing) Co. Ltd genetically modified the MC38 cells to express human PD-L1, and named it MC38-hPD-L1. These cells were adherent cells, cultured in a 37° C., 5% $CO_2$ incubator. The culture medium composition was Dulbecco's Modified Eagle's Medium (DMEM) containing 10% inactivated fetal bovine serum.

2. Inoculation and Grouping of Tumor Cells

MC38-hPD-L1 cells resuspended in PBS were inoculated subcutaneously into the right flank of B-hPD-L1 mice at a volume of $5\times10^5$ cells/0.1 mL per mouse. When the average tumor volume reached 150±50 $mm^3$, suitable mice were selected based on tumor volume and body weight, and were evenly distributed into each group, with 8 mice per group. Drug administration started on the day of grouping. The administration vehicle of the oral administration group was 5% DMSO+95% (20% HP-β-CD in water), while the administration vehicle of the intraperitoneal injection group was 0.9% sodium chloride injection. The specific administration scheme is shown in Table 5:

TABLE 5

Administration scheme for MC38-hPD-L1 experiment

| Group | Test samples | Number of test animals | Dosage (mg/kg)[a] | Route of administration[c] | Frequency of administration[d] | Cycle of administration |
|---|---|---|---|---|---|---|
| G1 | Vehicle in PO group | 8 | — | p.o. | BID | 21 days |
| G2 | Atezolizumab | 8 | 5 | i.p. | TIW | 10 times |

TABLE 5-continued

Administration scheme for MC38-hPD-L1 experiment

| Group | Test samples | Number of test animals | Dosage (mg/kg)[a] | Route of administration[c] | Frequency of administration[d] | Cycle of administration |
|---|---|---|---|---|---|---|
| G4 | Compound 4 | 8 | 20 to 50[b] | p.o. | BID | 21 days |
| G5 | Compound 27 | 8 | 20 to 50[b] | p.o. | BID | 21 days |

Note:
[a]The administration volume was calculated based on the weight of the experimental animals at 10 μL/g;
[b]The dose was 20 mg/kg within 5 days after grouping, and the dose was adjusted to 50 mg/kg starting from the $6^{th}$ day;
[c]"p.o." refers to oral administration, "i.p." refers to intraperitoneal;
[d]"TIW" refers to three times a week, "BID" refers to twice a day.

3. Medicament Evaluation Indicator

Tumor growth inhibition ($TGI_{TV}$): $TGI_{TV}$ (%)=[1−(Ti−T0)/(Vi−V0)]λ100% (Ti: mean tumor volume of the treatment group on day i of administration, T0: mean tumor volume of the treatment group on day 0 of administration, Vi: mean tumor volume of the vehicle control group on day i of administration, V0: mean tumor volume of the vehicle control group on day 0 of administration).

Figure 2:
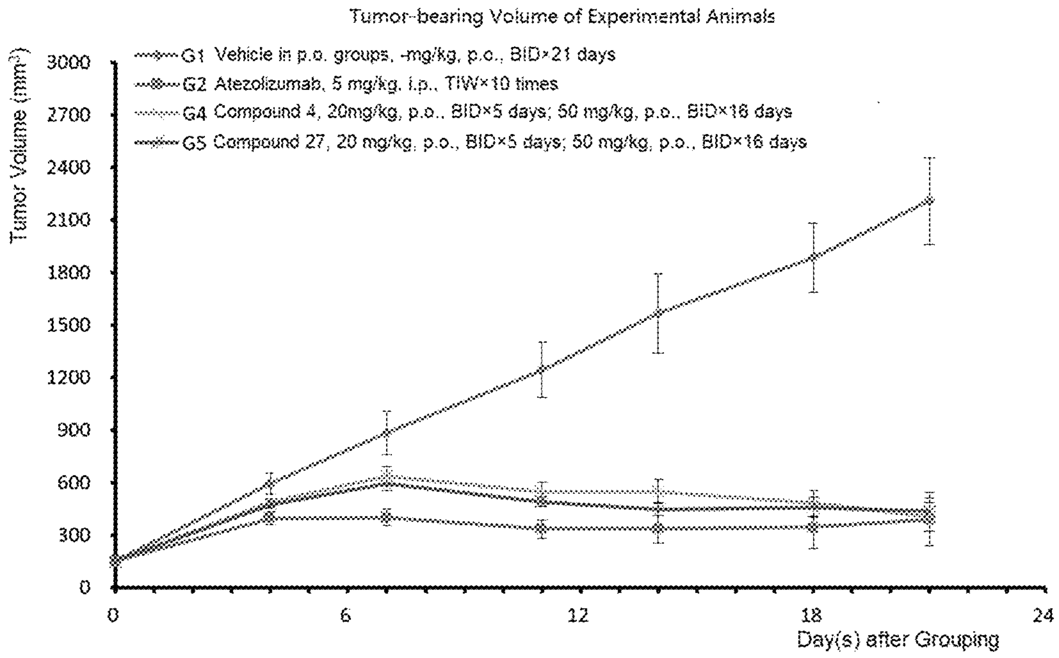
FIG. 2: Tumor-bearing volume of experimental animals.
Figure 3:
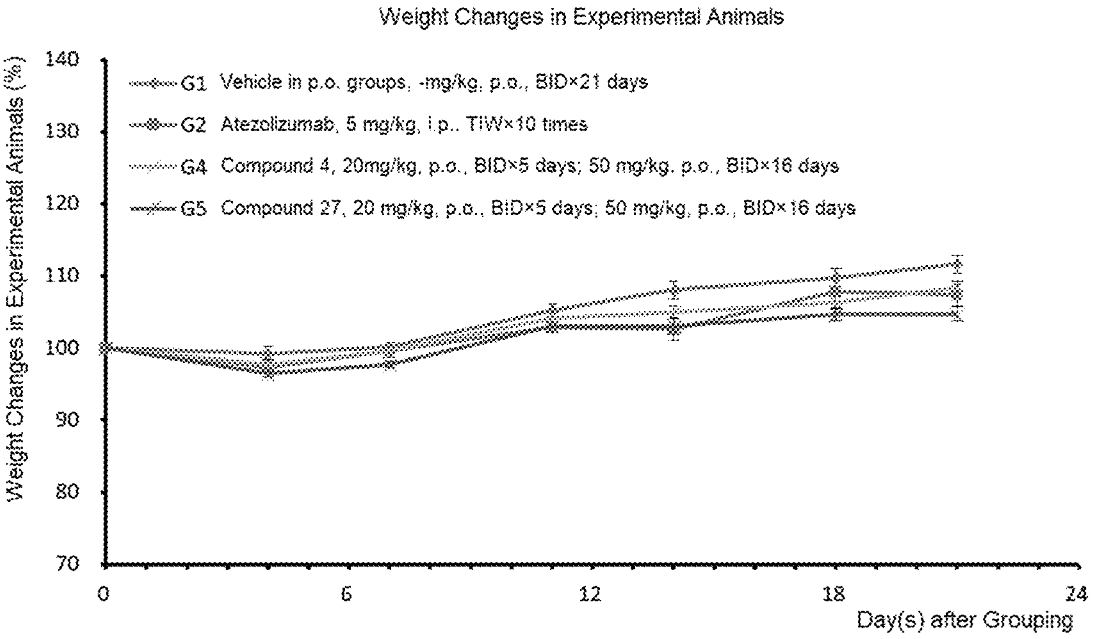
FIG. 3: Changes in body weight of experimental animals.
Figure 4:
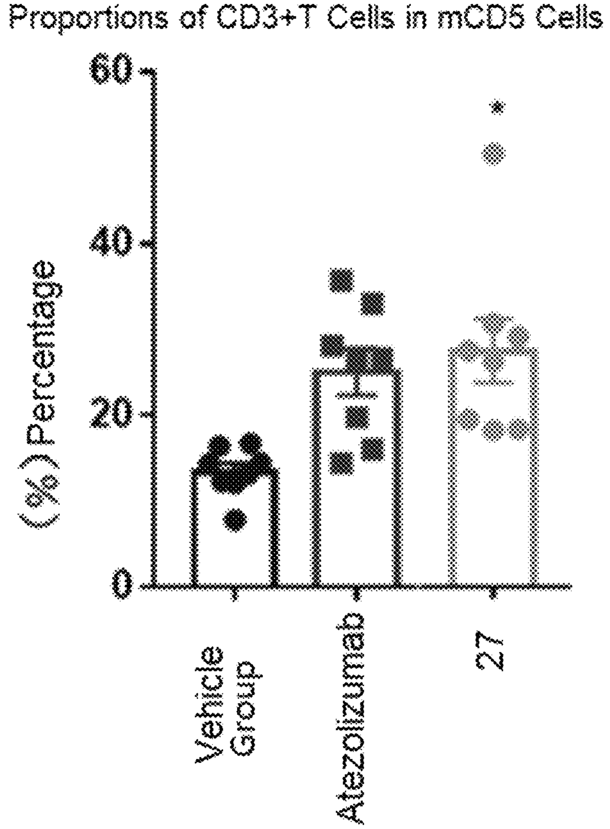
FIG. 4: Proportions of CD3+T cells in mCD5+ cells.
Figure 5:
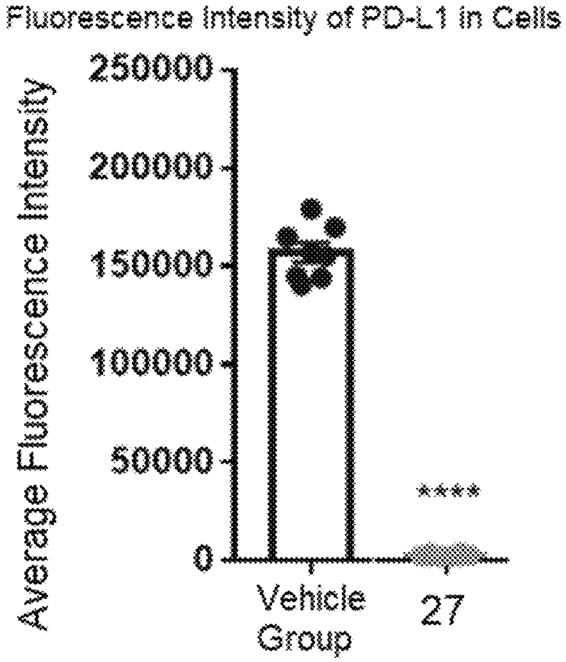
FIG. 5: Fluorescence intensity of PD-L1 in cells.

Experimental Results:

The $TGI_{TV}$ (%) for atezolizumab (group G2) was 88.4% ($p<0.0001$), the $TGI_{TV}$ (%) for compound 4 (group G4) was 86.1% ($p<0.0001$), and the $TGI_{TV}$ (%) for compound 27 (group G5) was 86.1% ($p<0.0001$). The changes in tumor-bearing volume and body weight of the experimental animals are shown in FIGS. 2 and 3, respectively. Four hours after the final administration, tumor tissues were collected from each group for tumor-infiltrating lymphocytes (TILs) detection. The results of the TILs detection are shown in FIGS. 4 and 5.

Experimental Conclusion:

The compounds of the present disclosure can significantly inhibit tumor PD-L1 expression in mice in vivo, effectively activate immunity, and inhibit the development of hPD-L1-positive MC38 tumors.

Experimental Example 5: Drug Efficacy Experiment of Humanized PBMC+A375 Co-Culture Model Experimental purpose: To evaluate the anti-tumor effect of the test drug in subcutaneous xenografted tumor model of human melanoma A375 mixed with peripheral blood mononuclear cells (PBMC).

Experimental Design:

1. Cell Culture:

A375 cells were cultured in DMEM medium supplemented with 10% fetal bovine serum (FBS). A375 cells in the exponential growth phase were collected, resuspended in HBSS to an appropriate concentration for subcutaneous tumor inoculation in NCG mice. The A375 cells used in the experiment were cultured with Mitomycin C, then washed with PBS.

2. Resuscitation and Co-Culture of Peripheral Blood Mononuclear Cells:

Frozen PBMCs were purchased, resuscitated and counted. The resulting PBMCs were added to A375 cells that have been treated with Mitomycin C for co-culture. The culture medium was RPMI 1640 culture medium containing IL-2 and 10% FBS.

3. Tumor Cell Inoculation:

After co-culture of PBMC and A375, PBMC and freshly digested A375 cells were harvested and inoculated subcutaneously on the right side of NCG mice. Subsequently, the mice were administrated according to randomized grouping based on the weight of the mice.

4. Assessment Indicators:

The inhibitory effect or complete curative ability of the test drug on the growth of A375 melanoma mixed PBMC xenograft tumor in vivo was detected and evaluated by tumor volume and tumor growth inhibition rate (TGI %).

What is claimed is:

1. A compound of formula (I) or a pharmaceutically acceptable salt thereof (I)

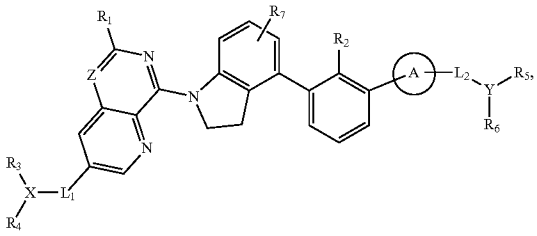

wherein ring A is selected from

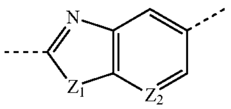

and

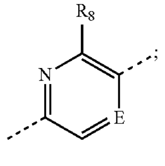

$L_1$ and $L_2$ are each independently selected from —$CH_2$— and —$CH_2$—NH—$CH_2$—;

Z and E are each independently selected from CH and N;

$Z_1$ selected from O and S;

$Z_2$ selected from N and $CR_9$;

X is selected from N and $CR_{14}$;

Y is selected from N and $CR_{15}$;

$R_1$ selected from H, $CH_3$, and $CHF_2$;

$R_2$ is selected from $CH_3$ and Cl;

$R_3$, $R_4$, $R_5$, and $R_6$ are each independently selected from H, $C_{1-6}$ alkyl, OH, COOH, and —$C_{1-3}$ alkyl-COOH;

alternatively, $R_3$, $R_4$ together with the atom to which they are attached form azetidinyl, pyrrolidinyl, oxazolidinyl, or piperidyl, and the azetidinyl, pyrrolidinyl, oxazolidinyl, and piperidyl are each independently and optionally substituted by 1, 2, or 3 $R_{16}$;

alternatively, $R_5$, $R_6$ together with the atom to which they are attached form azetidinyl, pyrrolidinyl, oxazolidinyl, or piperidyl, and the azetidinyl, pyrrolidinyl, oxazolidinyl, and piperidyl are each independently and optionally substituted by 1, 2, or 3 $R_{16}$;

$R_7$ is selected from H, F, Cl, $CH_3$, and $CHF_2$;

$R_8$ is selected from $—OCH_3$, $—O—CH_2—F$, and $—O—CH_2—CN$;

$R_9$ is selected from H, F, and CN;

$R_{14}$ and $R_{15}$ are each independently selected from H and $C_{1-6}$ alkyl;

each $R_{16}$ is independently selected from H, $C_{1-6}$ alkyl, OH, =O, COOH, and $—C_{1-3}$ alkyl-COOH.

2. The compound or the pharmaceutically acceptable salt thereof according to claim 1, wherein the compound is selected from (II)

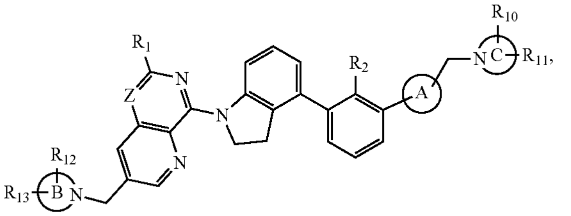

wherein ring B and ring C are each independently selected from azetidinyl, pyrrolidinyl, oxazolidinyl, and piperidyl;

$R_{10}$, $R_{11}$, $R_{12}$, and $R_{13}$ are each independently selected from H, $C_{1-4}$ alkyl, OH, =O, COOH, and $—C_{1-3}$ alkyl-COOH.

3. The compound or the pharmaceutically acceptable salt thereof according to claim 1, wherein the compound is selected from (I-1)

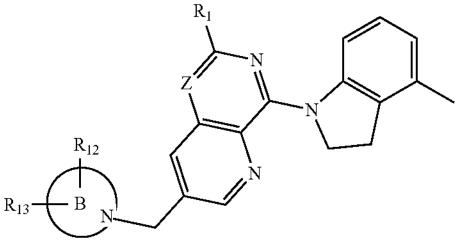

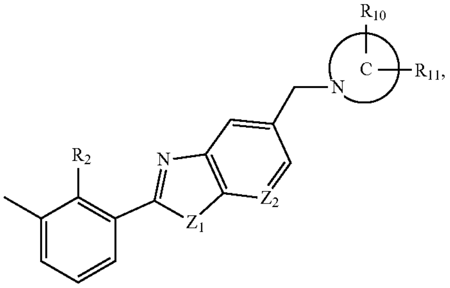

-continued (I-2)

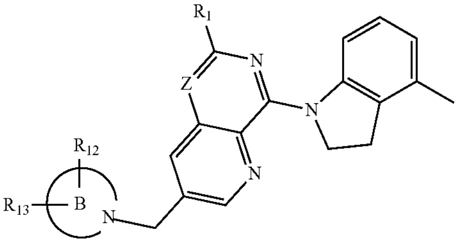

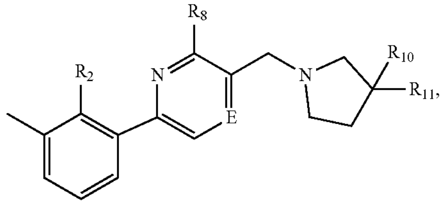

and (I-3)

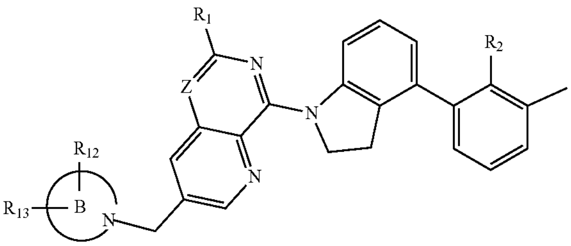

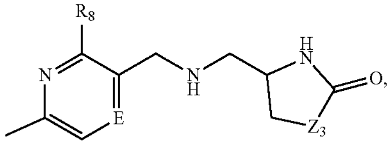

wherein ring B and ring C are each independently selected from azetidinyl, pyrrolidinyl, oxazolidinyl, and piperidyl;

$R_{10}$, $R_{11}$, $R_{12}$, and $R_{13}$ are each independently selected from H, $C_{1-4}$ alkyl, OH, =O, COOH, and $—C_{1-3}$ alkyl-COOH;

$Z_3$ is selected from $CH_2$ and O.

4. The compound or the pharmaceutically acceptable salt thereof according to claim 1, wherein the compound is selected from (I-1-a)

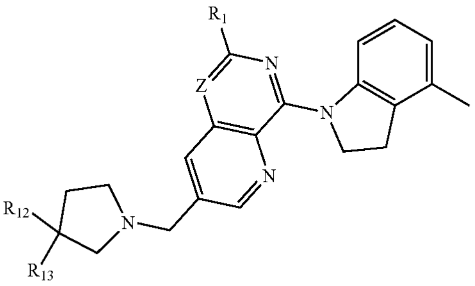

-continued

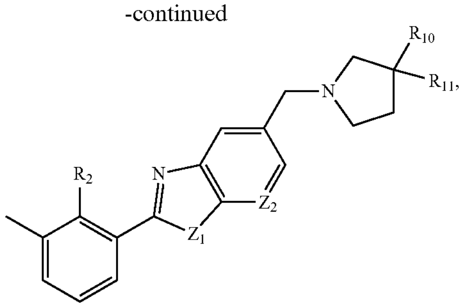

(I-2-a)

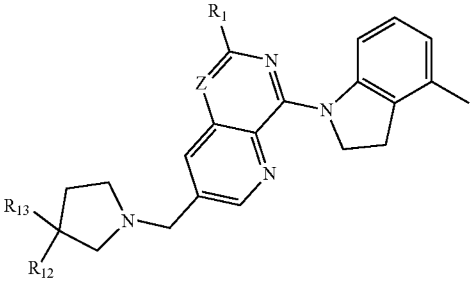

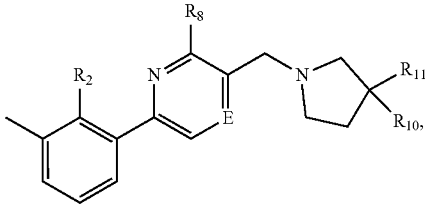

and (I-3-a)

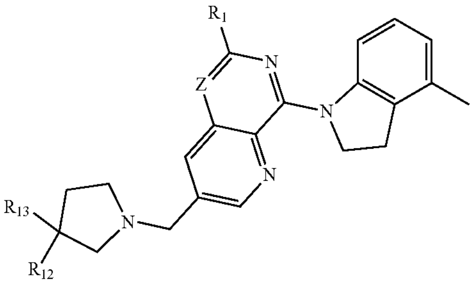

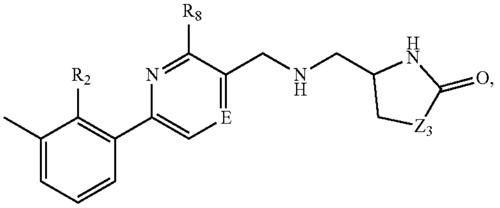

wherein $Z_3$ is selected from $CH_2$ and O, $R_{10}$, $R_{11}$, $R_{12}$, and $R_{13}$ are each independently selected from H, $C_{1-4}$ alkyl, OH, =O, COOH, and $-C_{1-3}$ alkyl-COOH.

5. The compound or the pharmaceutically acceptable salt thereof according to claim 1, wherein $Z_1$ is selected from O, $Z_2$ is selected from C(CN).

6. The compound or the pharmaceutically acceptable salt thereof according to claim 1, wherein X is selected from N.

7. The compound or the pharmaceutically acceptable salt thereof according to claim 1, wherein Y is selected from N.

8. The compound or the pharmaceutically acceptable salt thereof according to claim 1, wherein $R_1$ is selected from $CHF_2$.

9. The compound or the pharmaceutically acceptable salt thereof according to claim 1, wherein $R_3$, $R_4$, $R_5$, and $R_6$ are each independently selected from H, $CH_3$, isopropyl,

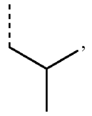

COOH, and $-C_{1-3}$ alkyl-COOH.

10. The compound or the pharmaceutically acceptable salt thereof according to claim 1, wherein $R_7$ is selected from H.

11. The compound or the pharmaceutically acceptable salt thereof according to claim 1, wherein ring A is selected from

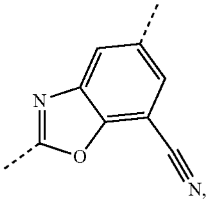

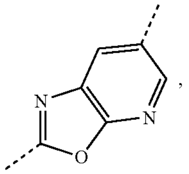

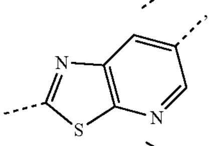

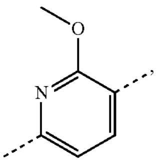

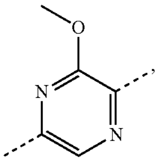

and

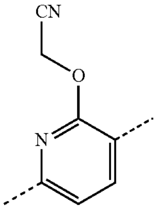

12. The compound or the pharmaceutically acceptable salt thereof according to claim 1, wherein the structural moieties

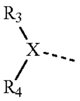

and

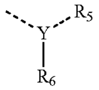

are each independently selected from

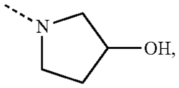

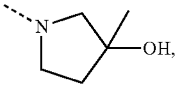

-continued
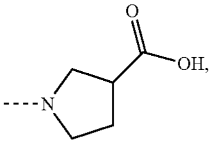
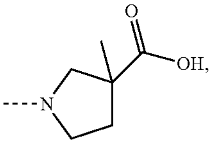
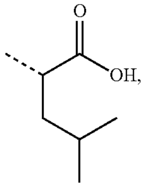
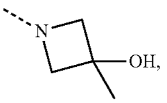
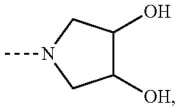
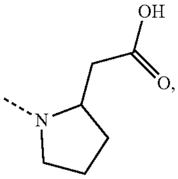
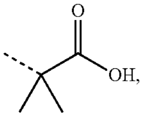
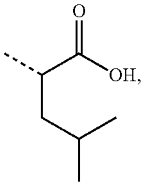
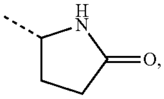
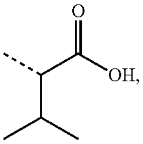
and
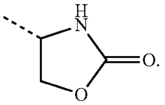
13. The compound or the pharmaceutically acceptable salt thereof according to claim 1, wherein the structural moieties
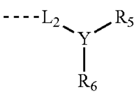
and
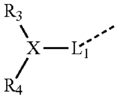
are each independently selected from
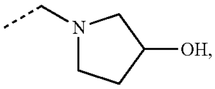
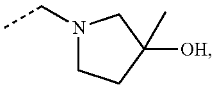
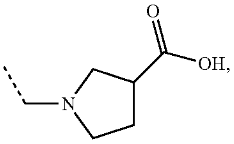
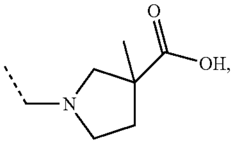
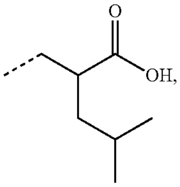
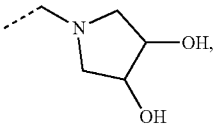
-continued
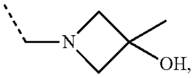
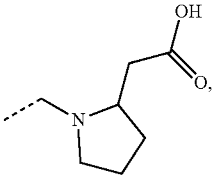
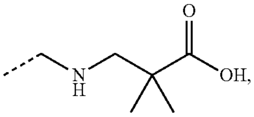
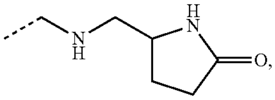
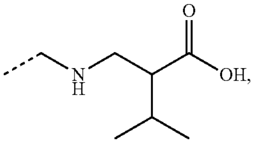
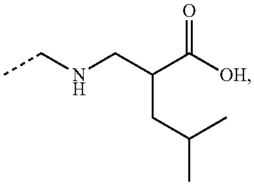
and
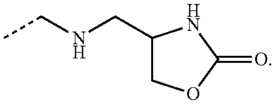
14. The compound or the pharmaceutically acceptable salt thereof according to claim 2, wherein the structural moieties
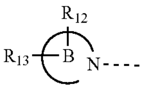
and
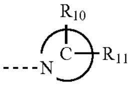
are each independently selected from
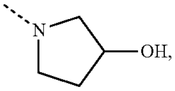
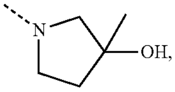
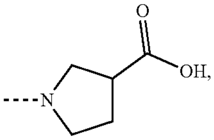
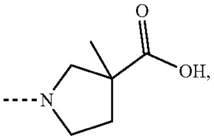
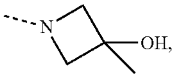
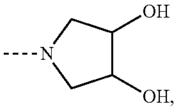
and
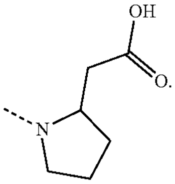

15. A compound of the following formula or a pharmaceutically acceptable salt thereof, selected from
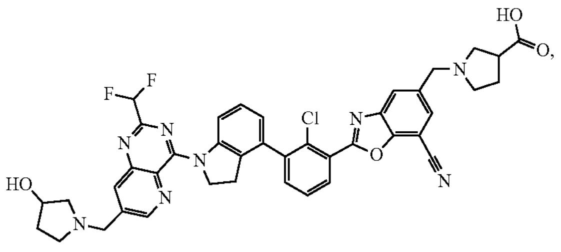 [SMILES: N#Cc1cc(CN2CCC(C(=O)O)C2)cc2nc(-c3cccc(-c4cccc5c4CCN5c4nc(C(F)F)nc5cc(CN6CCC(O)C6)cnc45)c3Cl)oc12]
,
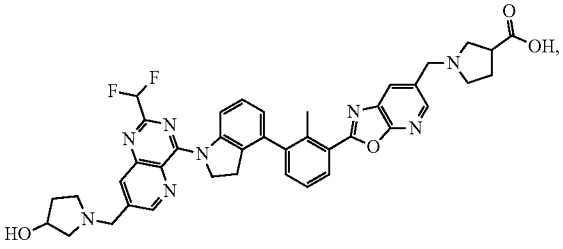
,
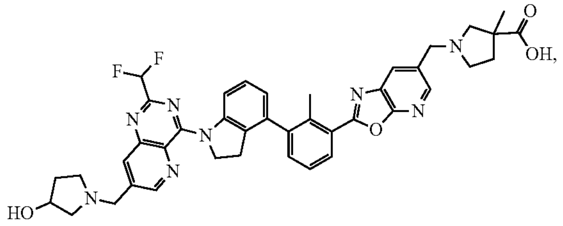
,
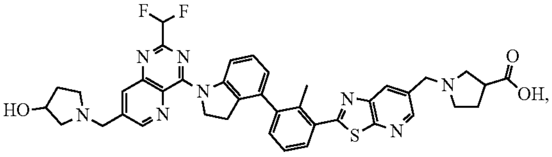
,
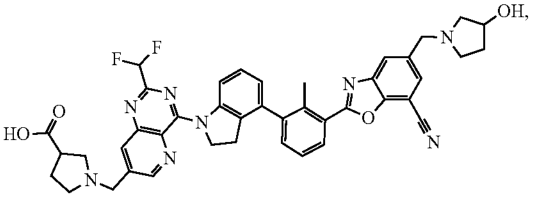
,
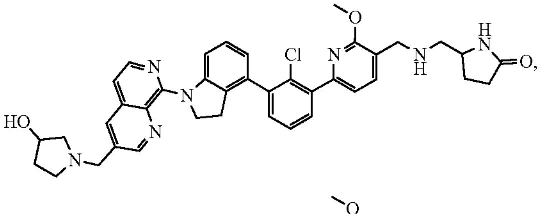
,
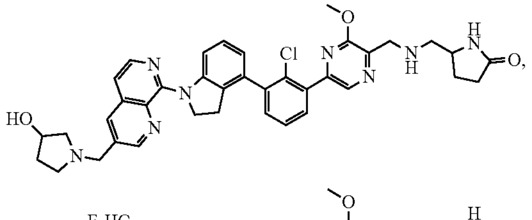
,
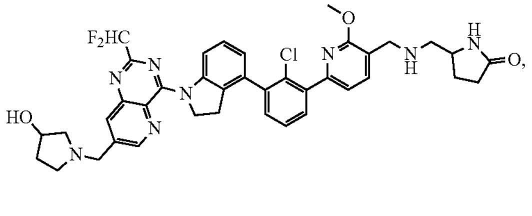
,
-continued
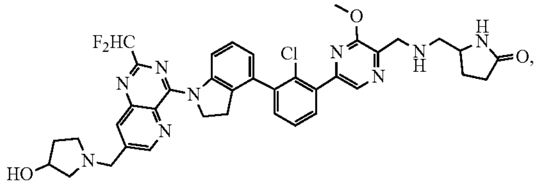
,
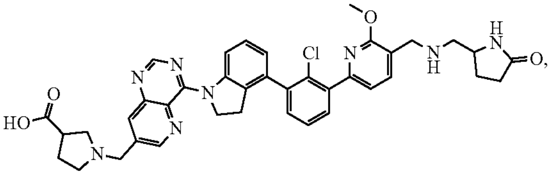
,
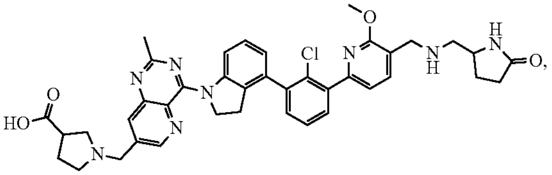
,
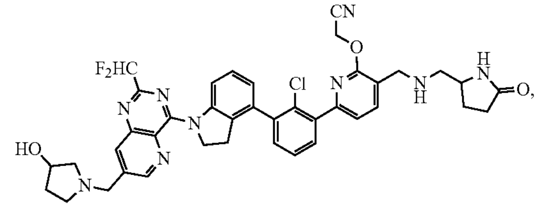
,
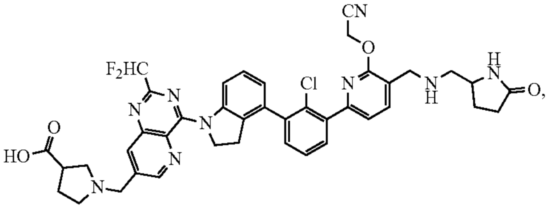
,
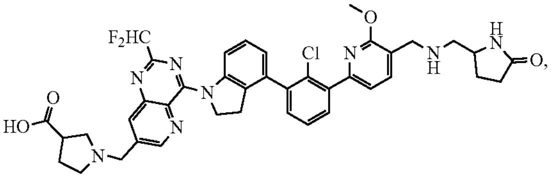
,
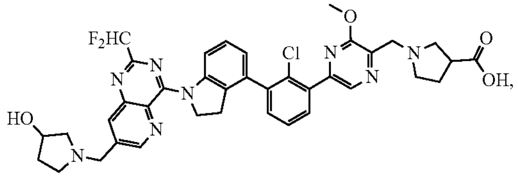
,
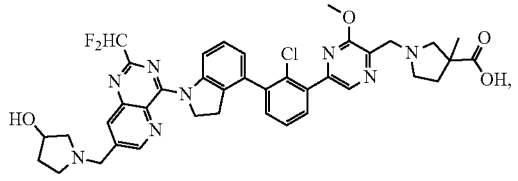
,
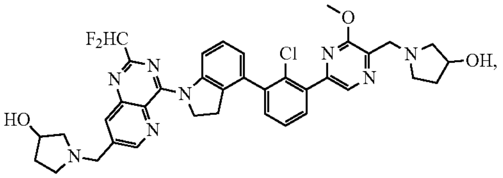
, -continued
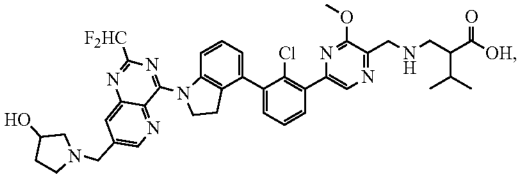
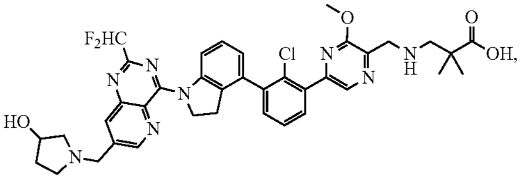
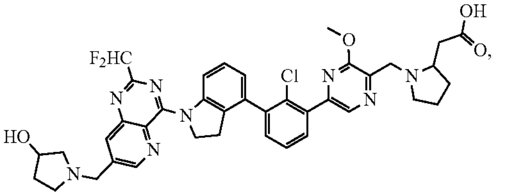
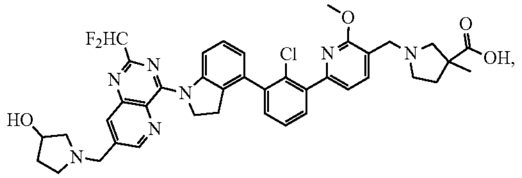
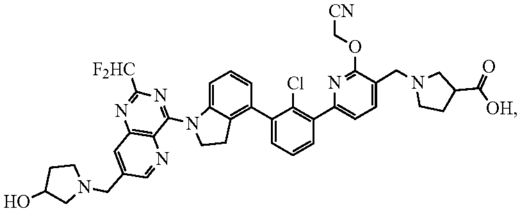
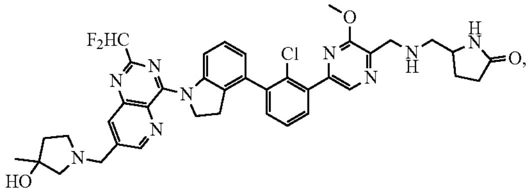
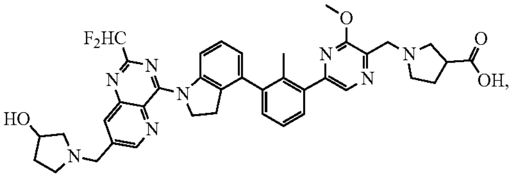
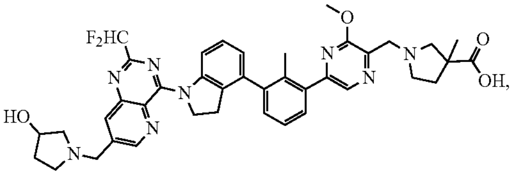
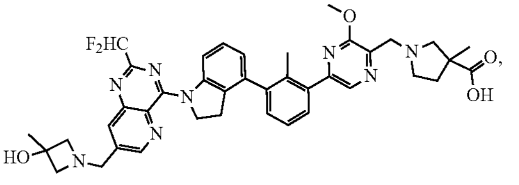
-continued
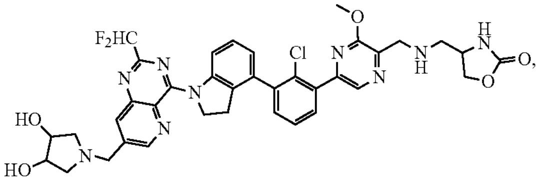
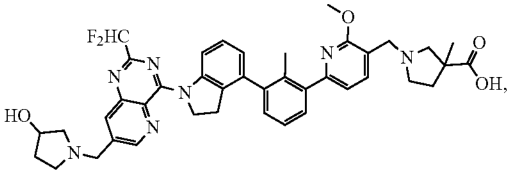
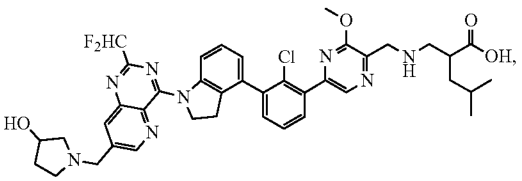
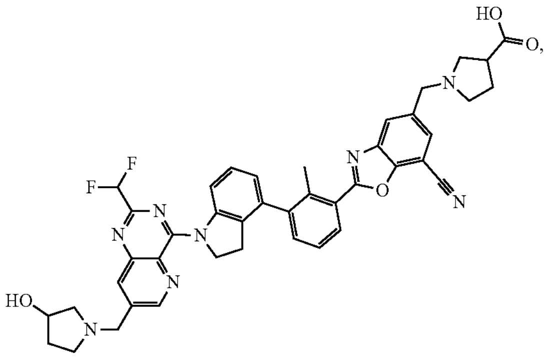
and
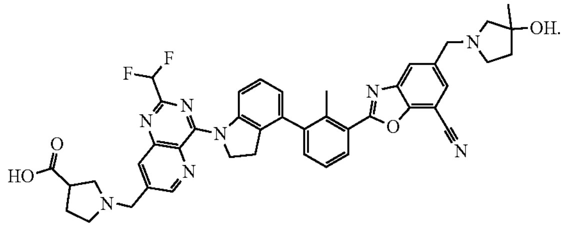
16. The compound or the pharmaceutically acceptable salt thereof according to claim 15, wherein the compound is selected from
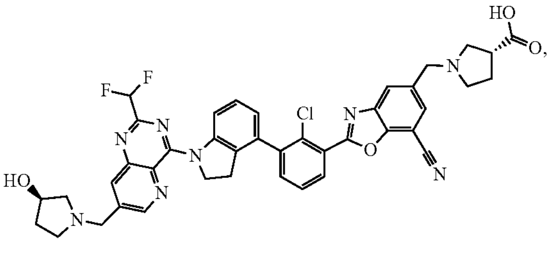

-continued
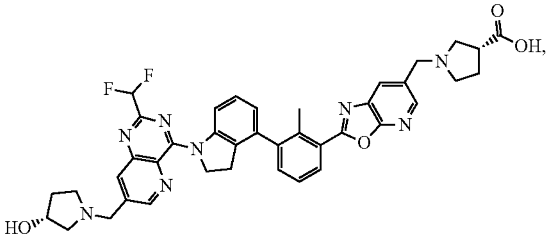,
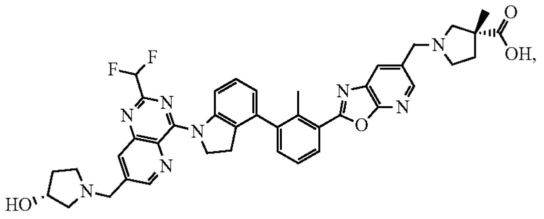,
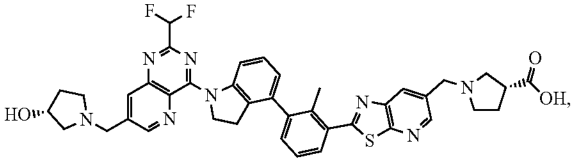,
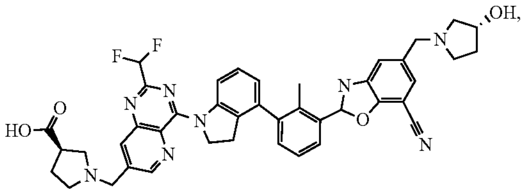,
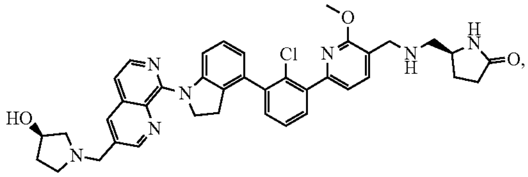,
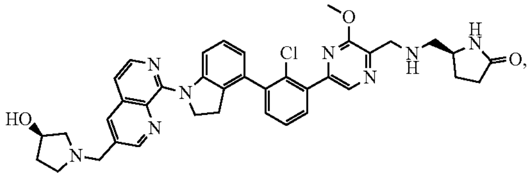,
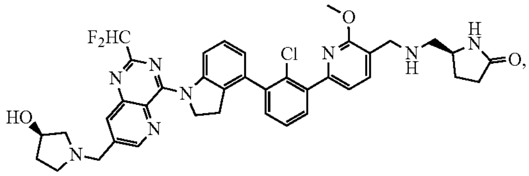,
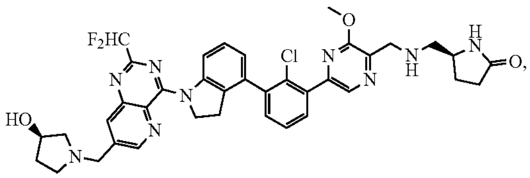,
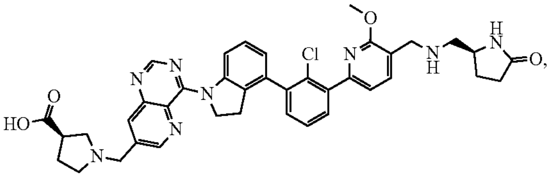,
-continued
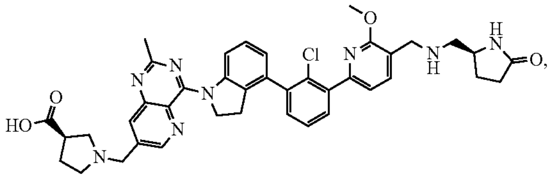,
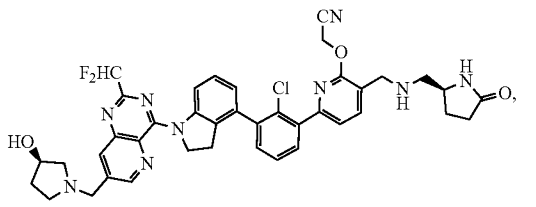,
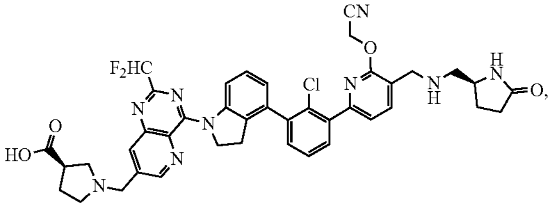,
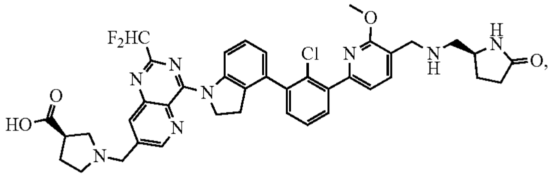,
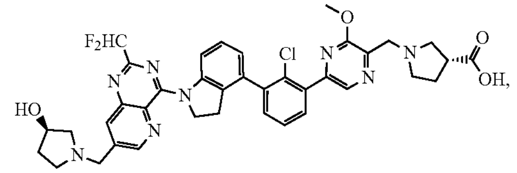,
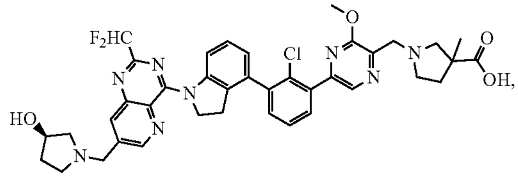,
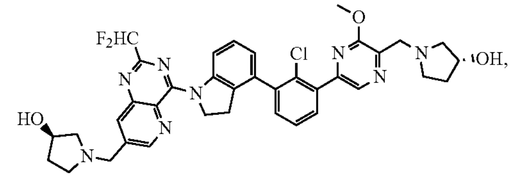,
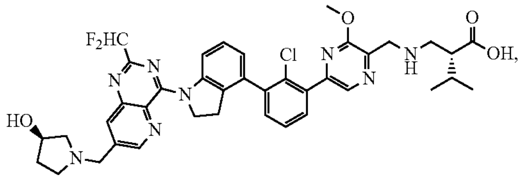,
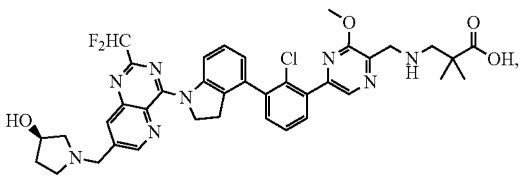, -continued
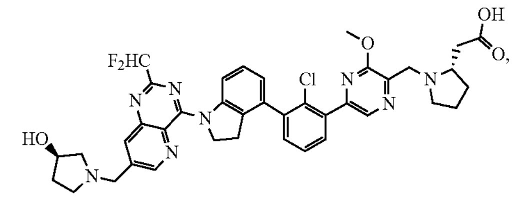
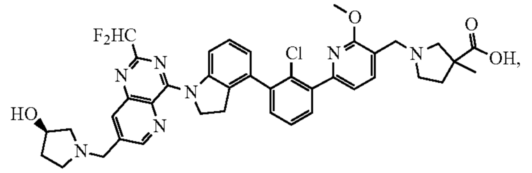
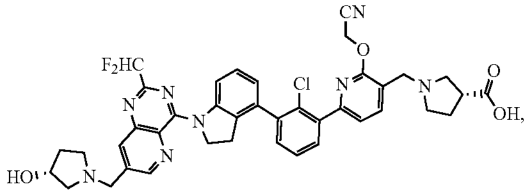
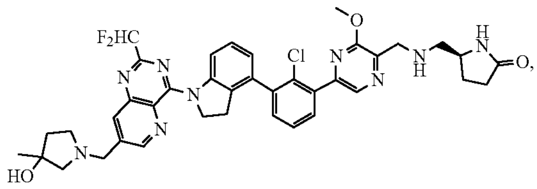
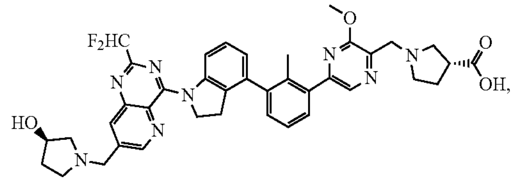
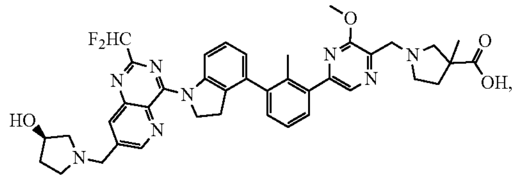
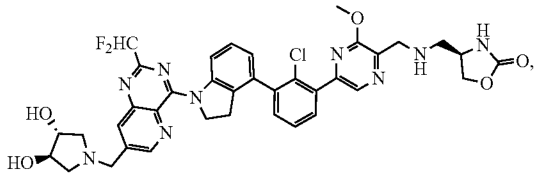
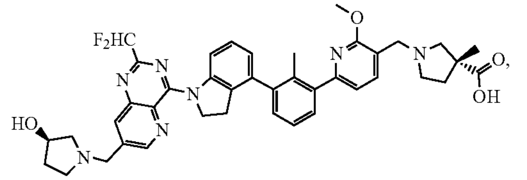
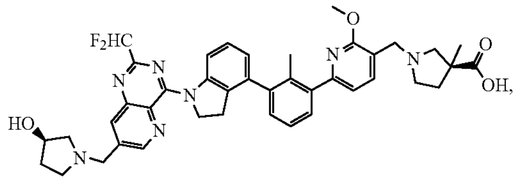
-continued
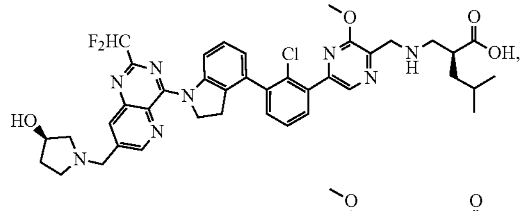
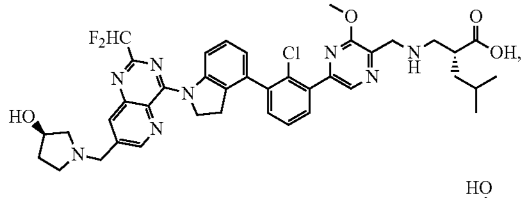
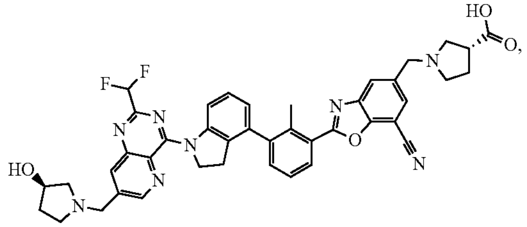
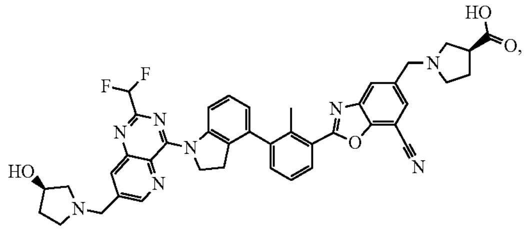
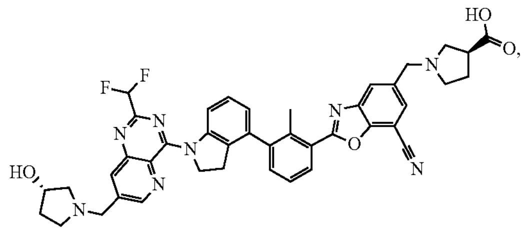
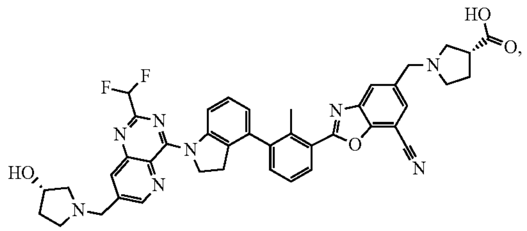
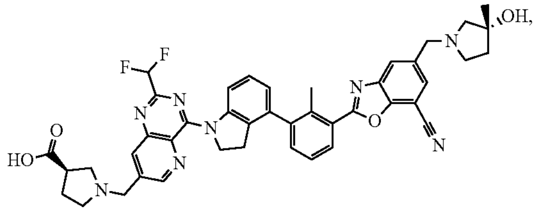
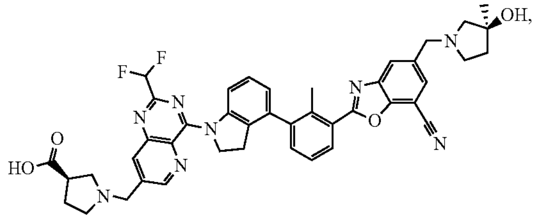

-continued

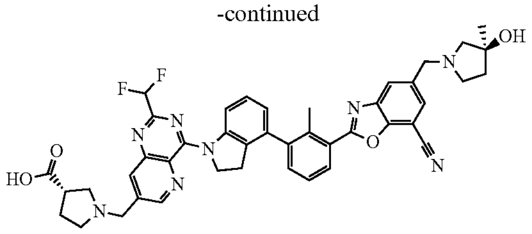

and

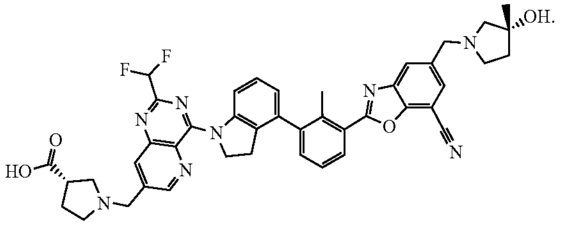 [SMILES: Cc1c(-c2nc3cc(CN4CC[C@@](C)(O)C4)cc(C#N)c3o2)cccc1-c1cccc2c1CCN2c1nc(C(F)F)nc2cc(CN3CC[C@H](C(=O)O)C3)cnc12]

17. A method for inhibiting PD-L1 in a subject in need thereof, comprising: administering the compound or the pharmaceutically acceptable salt thereof according to claim 1 to the subject.

18. A method for treating tumor in a subject in need thereof, comprising: administering the compound or the pharmaceutically acceptable salt thereof according to claim 1 to the subject.

19. The method according to claim 18, wherein the tumor is colon cancer, melanoma, non-small cell lung cancer, hepatocellular carcinoma, or renal cell carcinoma.

* * * * *